US012668627B2

(12) United States Patent
De Graaf et al.

(10) Patent No.: US 12,668,627 B2
(45) Date of Patent: *Jun. 30, 2026

(54) CYTOKINE-BASED THERAPIES AND METHODS

(71) Applicant: Reverb Therapeutics, Inc., Vancouver (CA)

(72) Inventors: David De Graaf, Vancouver (CA); Mark Fogg, Vancouver (CA); Surjit Bhimarao Dixit, Vancouver (CA); Stacey Tom-Yew, Vancouver (CA)

(73) Assignee: Reverb Therapeutics, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 19/205,170

(22) Filed: May 12, 2025

(65) Prior Publication Data

US 2025/0314662 A1     Oct. 9, 2025

Related U.S. Application Data

(63) Continuation of application No. PCT/US2024/018252, filed on Mar. 1, 2024.

(60) Provisional application No. 63/488,145, filed on Mar. 2, 2023.

(51) Int. Cl.
| | |
|---|---|
| C07K 16/24 | (2006.01) |
| A61P 37/02 | (2006.01) |
| C07K 16/28 | (2006.01) |
| G01N 33/50 | (2006.01) |
| G01N 33/68 | (2006.01) |
| A61K 39/00 | (2006.01) |

(52) U.S. Cl.
CPC ........... *C07K 16/246* (2013.01); *A61P 37/02* (2018.01); *C07K 16/244* (2013.01); *C07K 16/2827* (2013.01); *G01N 33/502* (2013.01); *G01N 33/6854* (2013.01); *G01N 33/6869* (2013.01); *A61K 2039/505* (2013.01); *A61K 2039/54* (2013.01); *C07K 2317/31* (2013.01); *C07K 2317/55* (2013.01); *C07K 2317/622* (2013.01); *C07K 2317/76* (2013.01); *C07K 2317/92* (2013.01); *G01N 2333/5406* (2013.01); *G01N 2333/5409* (2013.01); *G01N 2333/5412* (2013.01); *G01N 2333/5421* (2013.01); *G01N 2333/5434* (2013.01); *G01N 2333/5443* (2013.01); *G01N 2333/545* (2013.01); *G01N 2333/55* (2013.01); *G01N 2333/7155* (2013.01)

(58) Field of Classification Search
CPC ............ A61K 47/6851; A61K 47/6881; A61K 47/6845
See application file for complete search history.

(56) References Cited

U.S. PATENT DOCUMENTS

| | | |
|---|---|---|
| 2007/0071675 A1 | 3/2007 | Wu |
| 2011/0008326 A1 | 1/2011 | Hill |
| 2020/0399382 A1 | 12/2020 | Blanchetot |
| 2023/0112863 A1 | 4/2023 | Wu |
| 2023/0183379 A1 | 6/2023 | Poul |
| 2024/0425579 A1* | 12/2024 | Bedi .................... C07K 16/244 |
| 2025/0171531 A1 | 5/2025 | Kley |

FOREIGN PATENT DOCUMENTS

| | | |
|---|---|---|
| EP | 2420251 A2 | 2/2012 |
| WO | 2020077276 A2 | 4/2020 |

OTHER PUBLICATIONS

Shi et al. (bioRxiv, Mar. 17, 2022).*
Register et al, Int. J. Mol. Sci. 2021, 22(10).*
Banik, Soma SR, et al. "Breaking barriers in antibody discovery: harnessing divergent species for accessing difficult and conserved drug targets." MAbs. vol. 15. No. 1. Taylor & Francis, 2023.
Brinkmann, Ulrich, and Roland E. Kontermann. "The making of bispecific antibodies." MAbs. vol. 9. No. 2. Taylor & Francis, 2017.
Finch, D. K., et al. "Identification of a potent anti-IL-15 antibody with opposing mechanisms of action in vitro and in vivo." British journal of pharmacology 162.2 (2011): 480-490.
Grant, Joshuaine, et al. "Mechanistic PK/PD modeling to address early-stage biotherapeutic dosing feasibility questions." Mabs. vol. 15. No. 1. Taylor & Francis, 2023.
International Search Report issued Jul. 5, 2024 in PCT/US2024/018252.
Li, Aileen W., and Wendell A. Lim. "Engineering cytokines and cytokine circuits." Science 370.6520 (2020): 1034-1035.
Li, Yumei, et al. "A novel multifunctional anti-PD-L1-CD16a-IL15 induces potent cancer cell killing in PD-L1-positive tumour cells." Translational Oncology 21 (2022): 101424.
Liljeblad, Mathias, Arne Lundblad, and Peter Påhlsson. "Analysis of agalacto-IgG in rheumatoid arthritis using surface plasmon resonance." Glycoconjugate journal 17 (2000): 323-329.
Marks, James D., et al. "By-passing immunization: human antibodies from V-gene libraries displayed on phage." Journal of molecular biology 222.3 (1991): 581-597.
Martomo, Stella A., et al. "Single-dose anti-PD-L1/IL-15 fusion protein KD033 generates synergistic antitumor immunity with robust tumor-immune gene signatures and memory responses." Molecular Cancer Therapeutics 20.2 (2021): 347-356.

(Continued)

*Primary Examiner* — Gary B Nickol
(74) *Attorney, Agent, or Firm* — Greenberg Traurig, LLP

(57) ABSTRACT

The disclosure relates to methods for redirecting an active form of an endogenous cytokine to a target cell or target tissue of interest in a biological system or subject in need thereof by administering a multi-specific binding molecule comprising (a) a binding domain that specifically binds to an active form of a cytokine and (b) a binding domain that specifically binds to an epitope on a molecule that is a marker on a target cell or tissue, wherein the multi-specific binding molecule, when bound to the cytokine, does not block or only partially blocks, the ability of the cytokine to bind to and agonize a cognate receptor for the cytokine.

23 Claims, 48 Drawing Sheets

Specification includes a Sequence Listing.

(56)         References Cited

OTHER PUBLICATIONS

Morrison, Sherie L., et al. "Chimeric human antibody molecules: mouse antigen-binding domains with human constant region domains." Proceedings of the National Academy of Sciences 81.21 (1984): 6851-6855.

Mostbock, Sven. "Cytokine/Antibody complexes: an emerging class of immunostimulants." Current pharmaceutical design 15.7 (2009): 809-825.

Robert, Bruno, et al. "Cytokine targeting in tumors using a bispecific antibody directed against carcinoembryonic antigen and tumor necrosis factor α." Cancer research 56.20 (1996): 4758-4765.

Sestak, Karol, et al. "Beneficial effects of human anti-interleukin-15 antibody in gluten-sensitive rhesus macaques with celiac disease." Frontiers in Immunology 9 (2018): 1603.

Vicari, Alain P., et al. "Discovery and characterization of a novel humanized anti-IL-15 antibody and its relevance for the treatment of refractory celiac disease and eosinophilic esophagitis." MAbs. vol. 9. No. 6. Taylor & Francis, 2017.

Von Kreudenstein, Thomas Spreter, et al. "Improving biophysical properties of a bispecific antibody scaffold to aid developability: quality by molecular design." MAbs. vol. 5. No. 5. Taylor & Francis, 2013.

Waldmann, Thomas A., et al. "IL-15 in the combination immunotherapy of cancer." Frontiers in immunology 11 (2020): 868.

Wei, Yu-Ling, et al. "Strategies to evaluate potential effector function of glycan variants: A case study of ordesekimab (AMG 714 or PRV-015)." Journal of Immunotoxicology 19.1 (2022): 109-116.

Peluzzo, Amanda M., and Michael V. Autieri. "Challenging the paradigm: anti-inflammatory interleukins and angiogenesis." Cells 11.3 (2022): 587.

Wautier, Jean-Luc, and Marie-Paule Wautier. "Pro-and anti-inflammatory prostaglandins and cytokines in humans: a mini review." International journal of molecular sciences 24.11 (2023): 9647.

Clackson, Tim, et al. "Making antibody fragments using phage display libraries." Nature 352.6336 (1991): 624-628.

Heeley, Robert P., et al. "Mutations flanking the polyglutamine repeat in the modulatory domain of rat glucocorticoid receptor lead to an increase in affinity for hormone." Endocrine research 28.3 (2002): 217-229.

Köhler, Georges, and Cesar Milstein. "Continuous cultures of fused cells secreting antibody of predefined specificity." nature 256.5517 (1975): 495-497.

Ridgway, John BB, Leonard G. Presta, and Paul Carter. "'Knobs-into-holes' engineering of antibody CH3 domains for heavy chain heterodimerization." Protein Engineering, Design and Selection 9.7 (1996): 617-621.

Santollani, Luciano, and K. Dane Wittrup. "Spatiotemporally programming cytokine immunotherapies through protein engineering." Immunological Reviews 320.1 (2023): 10-28.

Schwartz, Rowena N., Lori Stover, and Janice P. Dutcher. "Managing toxicities of high-dose interleukin-2." Oncology (Williston Park, NY) 16.11 Suppl 13 (2002): 11-20.

Werkmeister, Richard, et al. "A clinical phase I/II trial of rhIL-4 applied topically in patients with oral squamous cell carcinomas to assess safety and therapeutic activity." Oncology reports 13.3 (2005): 449-452.

Xu, Yuanming, et al. "An engineered IL15 cytokine mutein fused to an anti-PD1 improves intratumoral T-cell function and antitumor immunity." Cancer Immunology Research 9.10 (2021): 1141-1157.

* cited by examiner

FIG. 3A                  FIG. 3B

(a) *cis* engagement               (b) *trans* engagement

FIG. 5A                    FIG. 5B
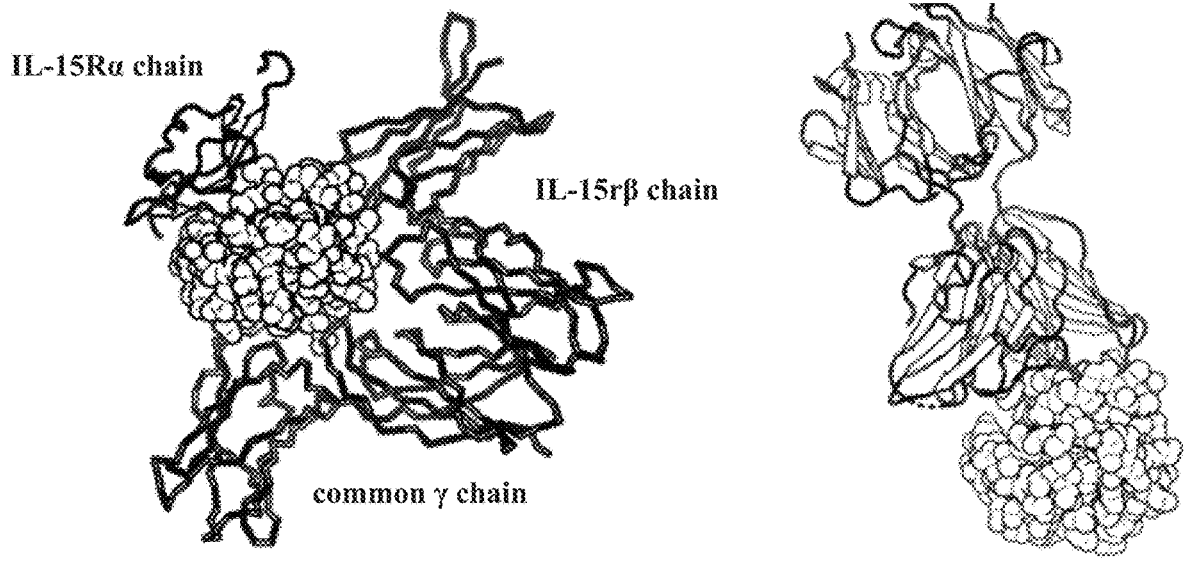
FIG. 5C
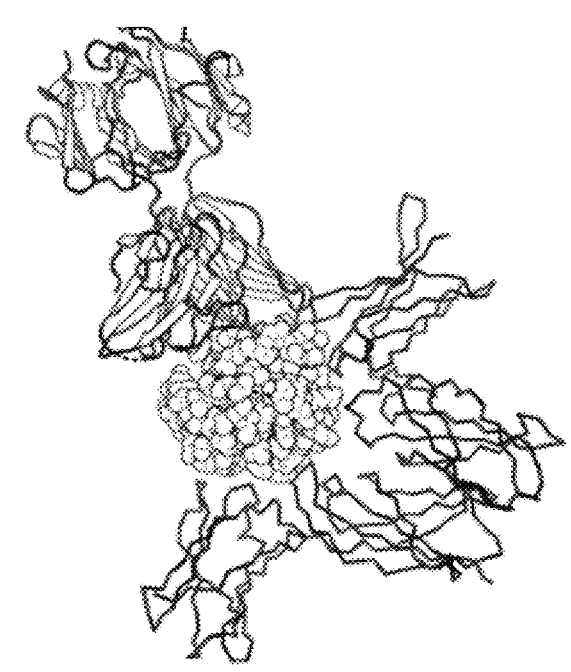

| Sample | Desired heterodimer species H1H2L1L2(%) | Mispaired species H1H2-L1L1 (%) | Half antibody species H1L1 (%) | Half antibody species H2L2 (%) |
|---|---|---|---|---|
| RV15 | 85 | 1 | 7.0 | 7 |

| Sample | Desired heterodimer species H1H2·L1L1(%) | Mispaired species H2H2L1L2 (%) | Half antibody species H1L1 (%) | Half antibody species H2L2 (%) |
|---|---|---|---|---|
| RV26 | 83* | 1 | 4.0 | 11 |

RV29 Mass Spectrum
I: 1900 - 4000 m/z

| Sample | H1H1L1L1(%) |
| --- | --- |
| RV29 | 100 |

FIG. 19A
FIG. 19B
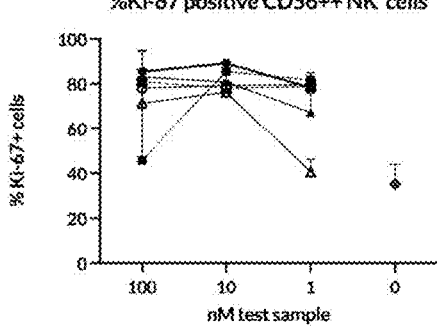
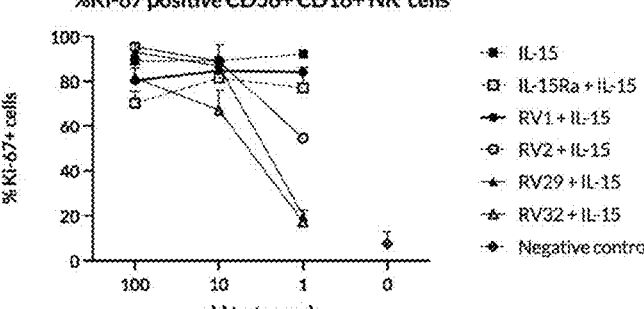

- ■ IL-15
- □ IL-15Ra + IL-15
- ● RV1 + IL-15
- ○ RV2 + IL-15
- ▲ RV29 + IL-15
- △ RV32 + IL-15
- ◇ Negative control

FIG. 21A
FIG. 21B
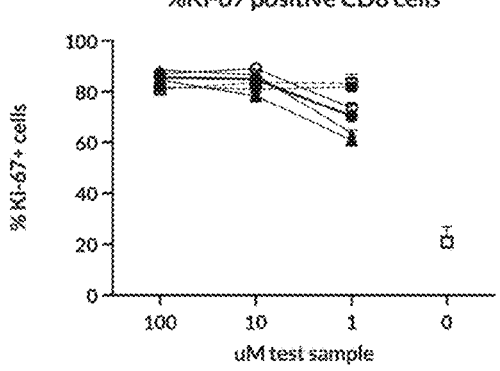
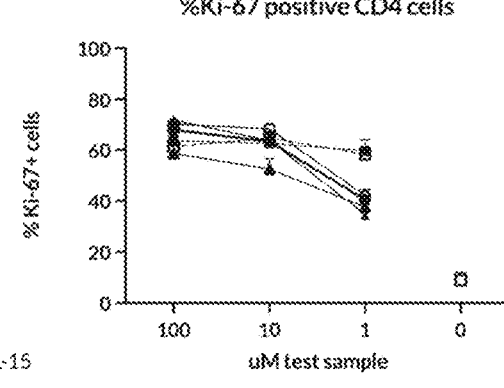

FIG. 22A
FIG. 22B
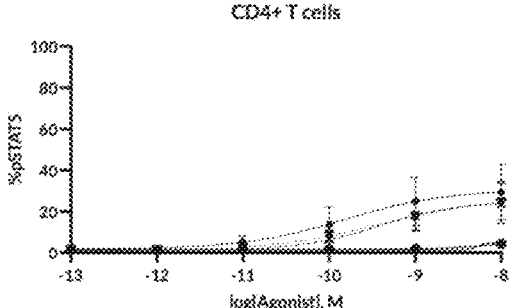
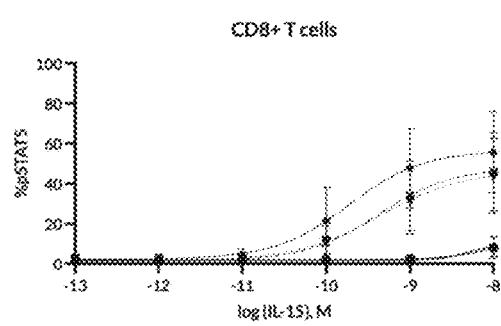
FIG. 22C
FIG. 22D
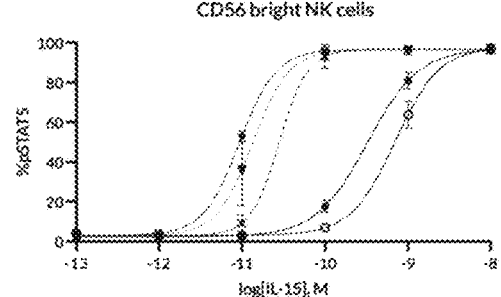
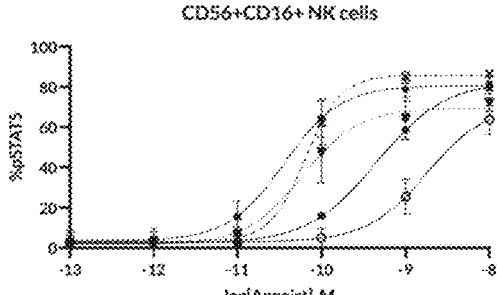

FIG. 24A

| Variant name | IgG subclass | Species | Format | Additional information |
|---|---|---|---|---|
| RV1 | IgG1 | human | | DISC0280 |
| RV2 | IgG1 | human | | DISC0280 with the LALAPG Fc null mutations |
| RV3 | IgG4 | human | | DISC0280, IgG4 format, with stabilizing S228P mutation |
| RV9 | IgG4 | human | | Pembrolizumab |
| RV10 | IgG1 | human | | Pembrolizumab with the LALAPG Fc null mutations |
| RV 15 | IgG1 | human | | Pembrolizumab Fab-DISC0280 Fab bispecific antibody, with the LALAPG Fc null mutations, with the LALAPG Fc null mutations. |

FIG. 24B

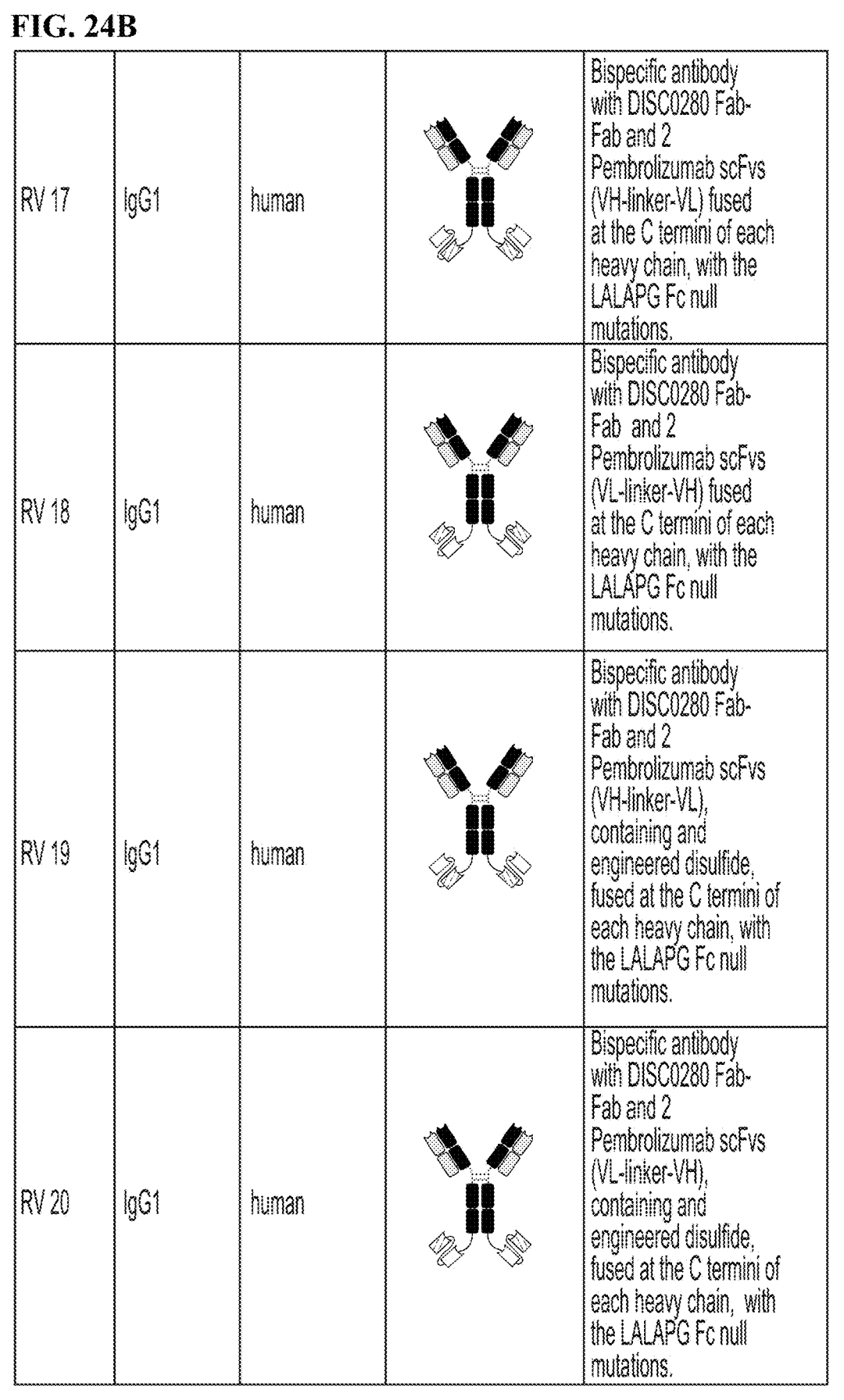

| | | | | |
|---|---|---|---|---|
| RV 17 | IgG1 | human | | Bispecific antibody with DISC0280 Fab-Fab and 2 Pembrolizumab scFvs (VH-linker-VL) fused at the C termini of each heavy chain, with the LALAPG Fc null mutations. |
| RV 18 | IgG1 | human | | Bispecific antibody with DISC0280 Fab-Fab  and 2 Pembrolizumab scFvs (VL-linker-VH) fused at the C termini of each heavy chain, with the LALAPG Fc null mutations. |
| RV 19 | IgG1 | human | | Bispecific antibody with DISC0280 Fab-Fab and 2 Pembrolizumab scFvs (VH-linker-VL), containing and engineered disulfide, fused at the C termini of each heavy chain, with the LALAPG Fc null mutations. |
| RV 20 | IgG1 | human | | Bispecific antibody with DISC0280 Fab-Fab and 2 Pembrolizumab scFvs (VL-linker-VH), containing and engineered disulfide, fused at the C termini of each heavy chain,  with the LALAPG Fc null mutations. |

FIG. 24C

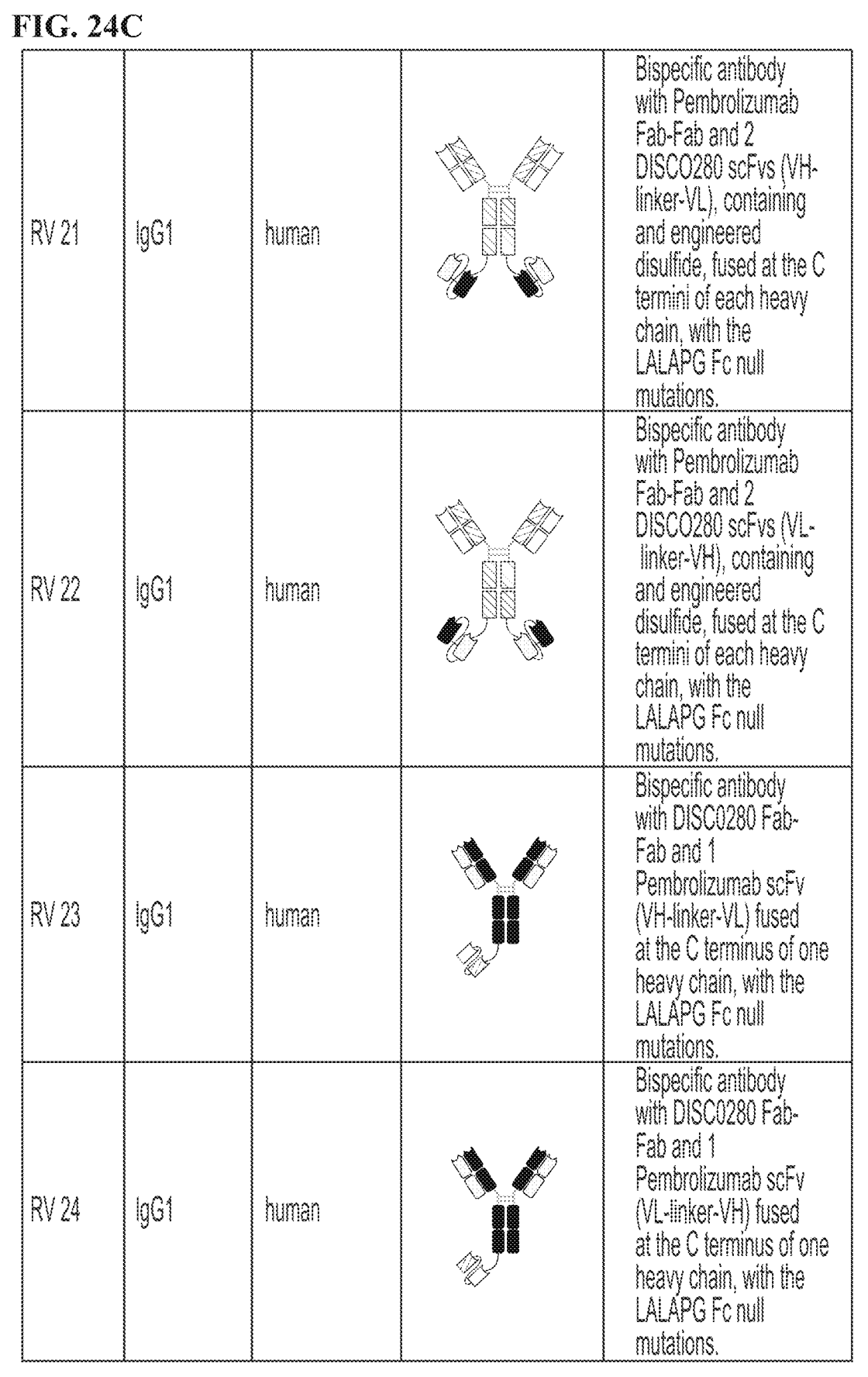

| | | | | |
|---|---|---|---|---|
| RV 21 | IgG1 | human | | Bispecific antibody with Pembrolizumab Fab-Fab and 2 DISCO280 scFvs (VH-linker-VL), containing and engineered disulfide, fused at the C termini of each heavy chain, with the LALAPG Fc null mutations. |
| RV 22 | IgG1 | human | | Bispecific antibody with Pembrolizumab Fab-Fab and 2 DISCO280 scFvs (VL-linker-VH), containing and engineered disulfide, fused at the C termini of each heavy chain, with the LALAPG Fc null mutations. |
| RV 23 | IgG1 | human | | Bispecific antibody with DISCO280 Fab-Fab and 1 Pembrolizumab scFv (VH-linker-VL) fused at the C terminus of one heavy chain, with the LALAPG Fc null mutations. |
| RV 24 | IgG1 | human | | Bispecific antibody with DISCO280 Fab-Fab and 1 Pembrolizumab scFv (VL-linker-VH) fused at the C terminus of one heavy chain, with the LALAPG Fc null mutations. |

FIG. 24D

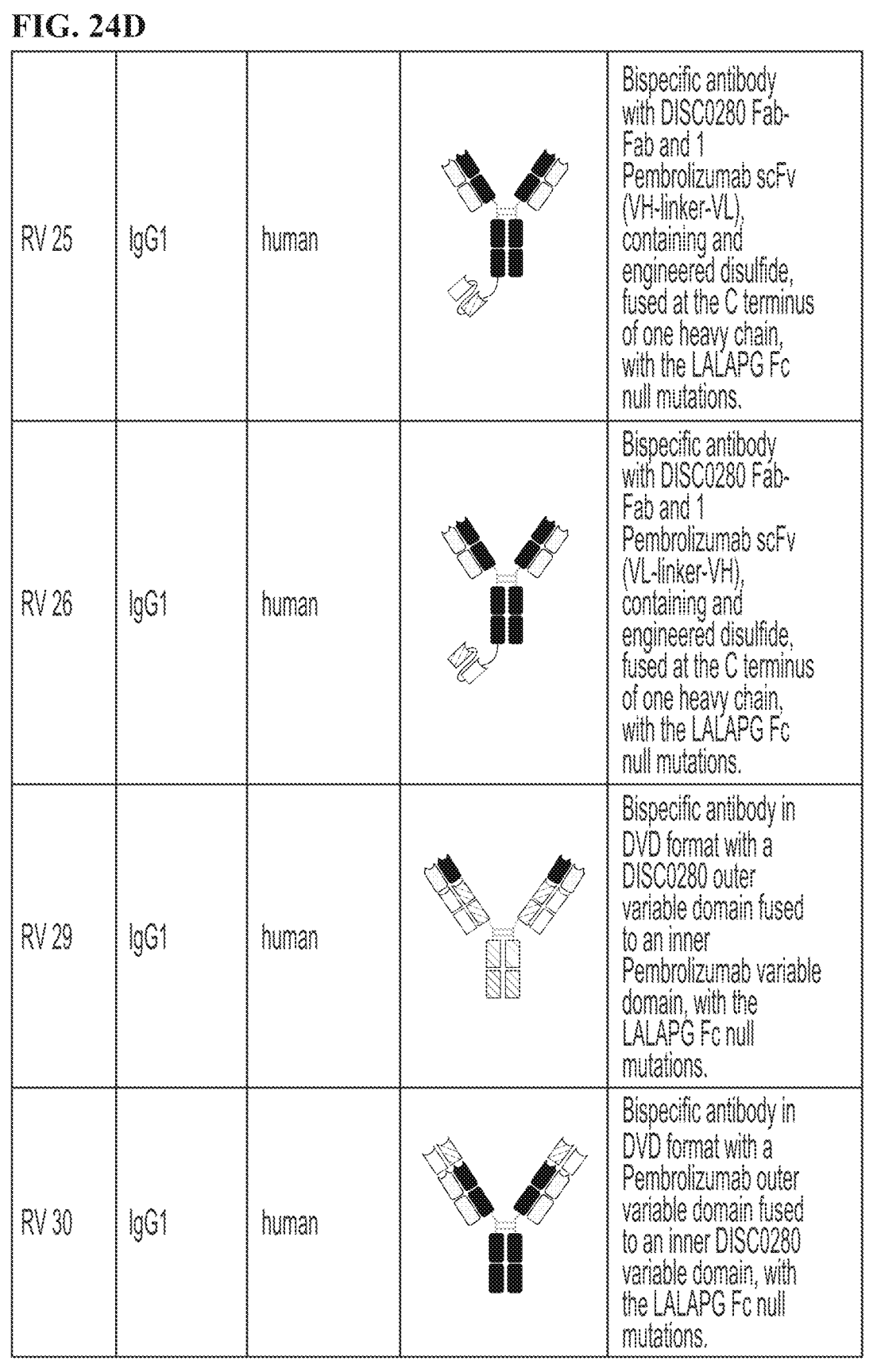

| | | | | |
|---|---|---|---|---|
| RV 25 | IgG1 | human | | Bispecific antibody with DISC0280 Fab-Fab and 1 Pembrolizumab scFv (VH-linker-VL), containing and engineered disulfide, fused at the C terminus of one heavy chain, with the LALAPG Fc null mutations. |
| RV 26 | IgG1 | human | | Bispecific antibody with DISC0280 Fab-Fab and 1 Pembrolizumab scFv (VL-linker-VH), containing and engineered disulfide, fused at the C terminus of one heavy chain, with the LALAPG Fc null mutations. |
| RV 29 | IgG1 | human | | Bispecific antibody in DVD format with a DISC0280 outer variable domain fused to an inner Pembrolizumab variable domain, with the LALAPG Fc null mutations. |
| RV 30 | IgG1 | human | | Bispecific antibody in DVD format with a Pembrolizumab outer variable domain fused to an inner DISC0280 variable domain, with the LALAPG Fc null mutations. |

FIG. 24E

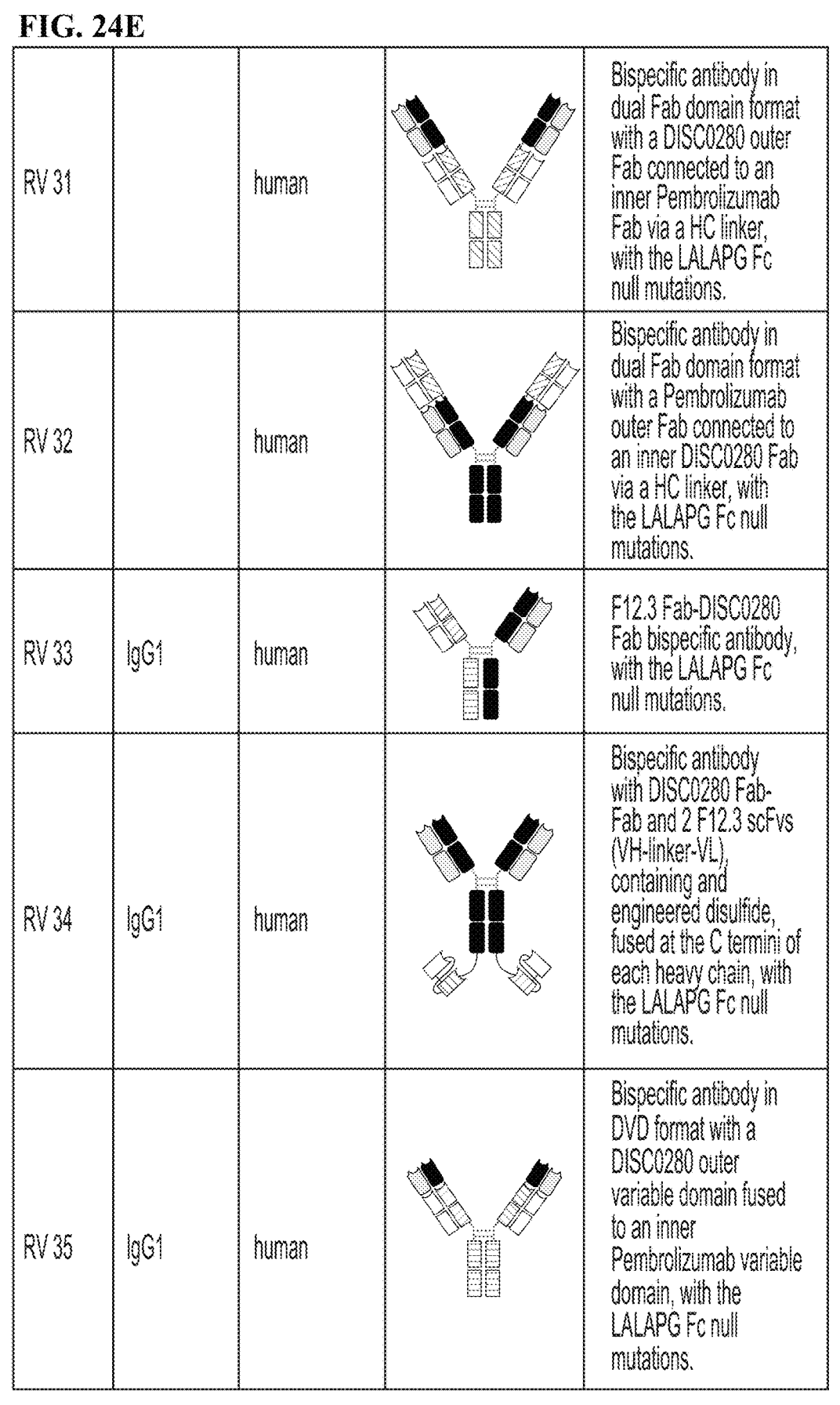

| | | | | |
|---|---|---|---|---|
| RV 31 | | human | | Bispecific antibody in dual Fab domain format with a DISC0280 outer Fab connected to an inner Pembrolizumab Fab via a HC linker, with the LALAPG Fc null mutations. |
| RV 32 | | human | | Bispecific antibody in dual Fab domain format with a Pembrolizumab outer Fab connected to an inner DISC0280 Fab via a HC linker, with the LALAPG Fc null mutations. |
| RV 33 | IgG1 | human | | F12.3 Fab-DISC0280 Fab bispecific antibody, with the LALAPG Fc null mutations. |
| RV 34 | IgG1 | human | | Bispecific antibody with DISC0280 Fab-Fab and 2 F12.3 scFvs (VH-linker-VL), containing and engineered disulfide, fused at the C termini of each heavy chain, with the LALAPG Fc null mutations. |
| RV 35 | IgG1 | human | | Bispecific antibody in DVD format with a DISC0280 outer variable domain fused to an inner Pembrolizumab variable domain, with the LALAPG Fc null mutations. |

FIG. 24F

| | | | | |
|---|---|---|---|---|
| RV 36 | IgG1 | human | | Bispecific antibody in DVD format with a DISC0280 outer variable domain fused via a longer linker to an inner Pembrolizumab variable domain, with the LALAPG Fc null mutations. |
| RV 37 | IgG1 | human | | Bispecific antibody in DVD format with a Pembrolizumab outer variable domain fused via a longer linker to an inner DISC0280 variable domain, with the LALAPG Fc null mutations. |

```
                          SEQUENCE LISTING

Sequence total quantity: 163
SEQ ID NO: 1             moltype = AA  length = 110
FEATURE                  Location/Qualifiers
source                   1..110
                         mol_type = protein
                         organism = synthetic construct
SEQUENCE: 1
QSVLTQPPSA SGTPGQRVTI SCSGSTSNLK RNYVYWYQQL PGTAPKLLIY RDRRRPSGVP   60
DRFSGSKSGT SASLAISGLR SEDEADYYCA WYDRELSEWV FGGGTKLTVL             110

SEQ ID NO: 2             moltype = AA  length = 110
FEATURE                  Location/Qualifiers
source                   1..110
                         mol_type = protein
                         organism = synthetic construct
SEQUENCE: 2
QSVLTQPPSA SGTPGQRVTI SCSGSTSNLK RNYVYWYQQL PGTAPKLLIY RDRRRPSGVP   60
DRFSGSKSGT SASLAISGLR SEDEADYYCA WYDRELSEWV FGCGTKLTVL             110

SEQ ID NO: 3             moltype = AA  length = 105
FEATURE                  Location/Qualifiers
source                   1..105
                         mol_type = protein
                         organism = synthetic construct
SEQUENCE: 3
QPKAAPSVTL FPPSSEELQA NKATLVCLIS DFYPGAVTVA WKADSSPVKA GVETTTPSKQ   60
SNNKYAASSY LSLTPEQWKS HRSYSCQVTH EGSTVEKTVA PTECS                 105

SEQ ID NO: 4             moltype = AA  length = 105
FEATURE                  Location/Qualifiers
source                   1..105
                         mol_type = protein
                         organism = synthetic construct
SEQUENCE: 4
QPKAAPSVTL FPPSDEELQA NTATLVCLIS DFYPGAVTVA WKADSSPVKA GVETTTPSKQ   60
SNNKYAAESE LSLTPEQWKS HRSYSCQVTH EGSTVEKTVA PTECS                 105

SEQ ID NO: 5             moltype = AA  length = 111
FEATURE                  Location/Qualifiers
source                   1..111
                         mol_type = protein
                         organism = synthetic construct
SEQUENCE: 5
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI K           111

SEQ ID NO: 6             moltype = AA  length = 110
FEATURE                  Location/Qualifiers
source                   1..110
                         mol_type = protein
                         organism = synthetic construct
SEQUENCE: 6
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI             110

SEQ ID NO: 7             moltype = AA  length = 111
FEATURE                  Location/Qualifiers
source                   1..111
                         mol_type = protein
                         organism = synthetic construct
SEQUENCE: 7
```

```
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGCGTKVEI K          111

SEQ ID NO: 8              moltype = AA   length = 110
FEATURE                   Location/Qualifiers
source                    1..110
                          mol_type = protein
                          organism = synthetic construct
SEQUENCE: 8
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGCGTKVEI           110

SEQ ID NO: 9              moltype = AA   length = 107
FEATURE                   Location/Qualifiers
source                    1..107
                          mol_type = protein
                          organism = synthetic construct
SEQUENCE: 9
RTVAAPSVFI FPPKDERLKS GTASVVCLLN NFYPREAKVQ WKVDNALQSG NSQESVTEQD  60
SKDSTYSLSS RLTLSKADYE KHKVYACEVT HQGLSSPVTK SFNRGEC              107

SEQ ID NO: 10             moltype = AA   length = 107
FEATURE                   Location/Qualifiers
source                    1..107
                          mol_type = protein
                          organism = synthetic construct
SEQUENCE: 10
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC              107

SEQ ID NO: 11             moltype = AA   length = 107
FEATURE                   Location/Qualifiers
source                    1..107
                          mol_type = protein
                          organism = synthetic construct
SEQUENCE: 11
DIVMTQSPSS LSVSAGDKVT MSCRASQGIS SWLAWYQQKP WQPPKLLIYK ASTLESGVPD  60
RFTGSGSGTD FTLTISSVQA EDLAVYYCQQ SYSTPWTFGG GTKLEIK              107

SEQ ID NO: 12             moltype = AA   length = 106
FEATURE                   Location/Qualifiers
source                    1..106
                          mol_type = protein
                          organism = synthetic construct
SEQUENCE: 12
DIVMTQSPSS LSVSAGDKVT MSCRASQGIS SWLAWYQQKP WQPPKLLIYK ASTLESGVPD  60
RFTGSGSGTD FTLTISSVQA EDLAVYYCQQ SYSTPWTFGC GTKLEI              106

SEQ ID NO: 13             moltype = AA   length = 107
FEATURE                   Location/Qualifiers
source                    1..107
                          mol_type = protein
                          organism = synthetic construct
SEQUENCE: 13
GTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC              107

SEQ ID NO: 14             moltype = AA   length = 107
FEATURE                   Location/Qualifiers
source                    1..107
                          mol_type = protein
                          organism = synthetic construct
SEQUENCE: 14
GTVAAPSVFI FPPKDERLKS GTASVVCLLN NFYPREAKVQ WKVDNALQSG NSQESVTEQD  60
SKDSTYSLSS RLTLSKADYE KHKVYACEVT HQGLSSPVTK SFNRGEC              107

SEQ ID NO: 15             moltype = AA   length = 118
FEATURE                   Location/Qualifiers
source                    1..118
                          mol_type = protein
                          organism = synthetic construct
SEQUENCE: 15
EVQLVESGGG LVKPGGSLEL SCAASGFTFS SYWMSWVRQA PEKCLEWVAA ISPSGGSTYY  60
ADSVKGRFTI SRDNAKNTLF LQMTSLRSED TAMYYCAKES WGAYYDLWGQ GTTVTVSS   118

SEQ ID NO: 16             moltype = AA   length = 118
FEATURE                   Location/Qualifiers
source                    1..118
                          mol_type = protein
```

```
                             organism = synthetic construct
SEQUENCE: 16
EVQLVESGGG LVKPGGSLEL SCAASGFTFS SYWMSWVRQA PEKGLEWVAA ISPSGGSTYY    60
ADSVKGRFTI SRDNAKNTLF LQMTSLRSED TAMYYCAKES WGAYYDLWGQ GTTVTVSS     118

SEQ ID NO: 17              moltype = AA  length = 125
FEATURE                    Location/Qualifiers
source                     1..125
                           mol_type = protein
                           organism = synthetic construct
SEQUENCE: 17
QVQLVQSGAE VKKPGASVKV SCKASGYSFS SFGISWVRQA PGQGLEWLGW ISAFNGYTKY    60
AQKFQDRVTM TTDTSTSTAY MELRSLRSDD TAVYYCARDP AAWPLQQSLA WFDPWGQGTM   120
VTVSS                                                              125

SEQ ID NO: 18              moltype = AA  length = 125
FEATURE                    Location/Qualifiers
source                     1..125
                           mol_type = protein
                           organism = synthetic construct
SEQUENCE: 18
QVQLVQSGAE VKKPGASVKV SCKASGYSFS SFGISWVRQA PGQCLEWLGW ISAFNGYTKY    60
AQKFQDRVTM TTDTSTSTAY MELRSLRSDD TAVYYCARDP AAWPLQQSLA WFDPWGQGTM   120
VTVSS                                                              125

SEQ ID NO: 19              moltype = AA  length = 120
FEATURE                    Location/Qualifiers
source                     1..120
                           mol_type = protein
                           organism = synthetic construct
SEQUENCE: 19
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120

SEQ ID NO: 20              moltype = AA  length = 120
FEATURE                    Location/Qualifiers
source                     1..120
                           mol_type = protein
                           organism = synthetic construct
SEQUENCE: 20
QVQLVQSGVE VKKPGASVKV SCKASGYTFT NYYMYWVRQA PGQCLEWMGG INPSNGGTNF    60
NEKFKNRVTL TTDSSTTTAY MELKSLQFDD TAVYYCARRD YRFDMGFDYW GQGTTVTVSS   120

SEQ ID NO: 21              moltype = AA  length = 98
FEATURE                    Location/Qualifiers
source                     1..98
                           mol_type = protein
                           organism = synthetic construct
SEQUENCE: 21
ASTKGPSVFP LRPSSKSTSG GTAALGCLVK DYFPEPVTVS WNSGALTSGV HTFPAVLQSS    60
GLYSLKSVVT VPSSSLGTQT YICNVNHKPS NTKVDKKV                           98

SEQ ID NO: 22              moltype = AA  length = 98
FEATURE                    Location/Qualifiers
source                     1..98
                           mol_type = protein
                           organism = synthetic construct
SEQUENCE: 22
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKV                           98

SEQ ID NO: 23              moltype = AA  length = 98
FEATURE                    Location/Qualifiers
source                     1..98
                           mol_type = protein
                           organism = synthetic construct
SEQUENCE: 23
ASTKGPSVFP LAPSSKSTSG GTAALGCEVT DYFPEPVTVS WNSGALTSGV HTFPAVLESS    60
GLYSLSSVVT VPSSSLGTQT YICNVNHKPS NTKVDKKV                           98

SEQ ID NO: 24              moltype = AA  length = 98
FEATURE                    Location/Qualifiers
source                     1..98
                           mol_type = protein
                           organism = synthetic construct
SEQUENCE: 24
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRV                           98
```

-continued

```
SEQ ID NO: 25              moltype = AA   length = 110
FEATURE                    Location/Qualifiers
source                     1..110
                           mol_type = protein
                           organism = synthetic construct
SEQUENCE: 25
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALGA PIEKTISKAK           110

SEQ ID NO: 26              moltype = AA   length = 110
FEATURE                    Location/Qualifiers
source                     1..110
                           mol_type = protein
                           organism = synthetic construct
SEQUENCE: 26
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK           110

SEQ ID NO: 27              moltype = AA   length = 110
FEATURE                    Location/Qualifiers
source                     1..110
                           mol_type = protein
                           organism = synthetic construct
SEQUENCE: 27
APEFLGGPSV FLFPPKPKDT LMISRTPEVT CVVVDVSQED PEVQFNWYVD GVEVHNAKTK  60
PREEQFNSTY RVVSVLTVLH QDWLNGKEYK CKVSNKGLPS SIEKTISKAK           110

SEQ ID NO: 28              moltype = AA   length = 15
FEATURE                    Location/Qualifiers
source                     1..15
                           mol_type = protein
                           organism = synthetic construct
SEQUENCE: 28
EPDSCDKTHT CPPCP                                                  15

SEQ ID NO: 29              moltype = AA   length = 15
FEATURE                    Location/Qualifiers
source                     1..15
                           mol_type = protein
                           organism = synthetic construct
SEQUENCE: 29
EPKSCDKTHT CPPCP                                                  15

SEQ ID NO: 30              moltype = AA   length = 12
FEATURE                    Location/Qualifiers
source                     1..12
                           mol_type = protein
                           organism = synthetic construct
SEQUENCE: 30
ESKYGPPCPP CP                                                     12

SEQ ID NO: 31              moltype = AA   length = 107
FEATURE                    Location/Qualifiers
source                     1..107
                           mol_type = protein
                           organism = synthetic construct
SEQUENCE: 31
GQPREPQVYT LPPSRDELTK NQVSLTCLVK GFYPSDIAVE WESNGQPENN YKTTPPVLDS  60
DGSFFLYSKL TVDKSRWQQG NVFSCSVMHE ALHNHYTQKS LSLSPGK              107

SEQ ID NO: 32              moltype = AA   length = 106
FEATURE                    Location/Qualifiers
source                     1..106
                           mol_type = protein
                           organism = synthetic construct
SEQUENCE: 32
GQPREPQVYT LPPSRDELTK NQVSLTCLVK GFYPSDIAVE WESNGQPENN YKTTPPVLDS  60
DGSFFLYSKL TVDKSRWQQG NVFSCSVMHE ALHNHYTQKS LSLSPG               106

SEQ ID NO: 33              moltype = AA   length = 106
FEATURE                    Location/Qualifiers
source                     1..106
                           mol_type = protein
                           organism = synthetic construct
SEQUENCE: 33
GQPREPQVYV YPPSRDELTK NQVSLTCLVK GFYPSDIAVE WESNGQPENN YKTTPPVLDS  60
DGSFALVSKL TVDKSRWQQG NVFSCSVMHE ALHNHYTQKS LSLSPG               106

SEQ ID NO: 34              moltype = AA   length = 107
```

```
FEATURE                   Location/Qualifiers
source                    1..107
                          mol_type = protein
                          organism = synthetic construct
SEQUENCE: 34
GQPREPQVYV YPPSRDELTK NQVSLTCLVK GFYPSDIAVE WESNGQPENN YKTTPPVLDS  60
DGSFALVSKL TVDKSRWQQG NVFSCSVMHE ALHNHYTQKS LSLSPGK             107

SEQ ID NO: 35            moltype = AA  length = 106
FEATURE                   Location/Qualifiers
source                    1..106
                          mol_type = protein
                          organism = synthetic construct
SEQUENCE: 35
GQPREPQVYV LPPSRDELTK NQVSLLCLVK GFYPSDIAVE WESNGQPENN YLTWPPVLDS  60
DGSFFLYSKL TVDKSRWQQG NVFSCSVMHE ALHNHYTQKS LSLSPG              106

SEQ ID NO: 36            moltype = AA  length = 106
FEATURE                   Location/Qualifiers
source                    1..106
                          mol_type = protein
                          organism = synthetic construct
SEQUENCE: 36
GQPREPQVYT LPPSQEEMTK NQVSLTCLVK GFYPSDIAVE WESNGQPENN YKTTPPVLDS  60
DGSFFLYSRL TVDKSRWQEG NVFSCSVMHE ALHNHYTQKS LSLSLG              106

SEQ ID NO: 37            moltype = AA  length = 20
FEATURE                   Location/Qualifiers
source                    1..20
                          mol_type = protein
                          organism = synthetic construct
SEQUENCE: 37
GGGGSGGGGS GGGGSGGGGS                                            20

SEQ ID NO: 38            moltype = AA  length = 20
FEATURE                   Location/Qualifiers
source                    1..20
                          mol_type = protein
                          organism = synthetic construct
SEQUENCE: 38
GGSGGGSGGG SGGGSGGGSG                                            20

SEQ ID NO: 39            moltype = AA  length = 10
FEATURE                   Location/Qualifiers
source                    1..10
                          mol_type = protein
                          organism = synthetic construct
SEQUENCE: 39
GGGGSGGGGS                                                       10

SEQ ID NO: 40            moltype = AA  length = 34
FEATURE                   Location/Qualifiers
source                    1..34
                          mol_type = protein
                          organism = synthetic construct
SEQUENCE: 40
EPDSCDKTHT SPPAPAPELL GGPAAPPAPA PAGG                            34

SEQ ID NO: 41            moltype = AA  length = 34
FEATURE                   Location/Qualifiers
source                    1..34
                          mol_type = protein
                          organism = synthetic construct
SEQUENCE: 41
EPKSCDKTHT SPPAPAPELL GGPAAPPAPA PAGG                            34

SEQ ID NO: 42            moltype =   length =
SEQUENCE: 42
000

SEQ ID NO: 43            moltype =   length =
SEQUENCE: 43
000

SEQ ID NO: 44            moltype =   length =
SEQUENCE: 44
000

SEQ ID NO: 45            moltype =   length =
```

```
SEQUENCE: 45
000

SEQ ID NO: 46            moltype =    length =
SEQUENCE: 46
000

SEQ ID NO: 47            moltype =    length =
SEQUENCE: 47
000

SEQ ID NO: 48            moltype =    length =
SEQUENCE: 48
000

SEQ ID NO: 49            moltype =    length =
SEQUENCE: 49
000

SEQ ID NO: 50            moltype =    length =
SEQUENCE: 50
000

SEQ ID NO: 51            moltype =    length =
SEQUENCE: 51
000

SEQ ID NO: 52            moltype = AA   length = 8
FEATURE                  Location/Qualifiers
source                   1..8
                         mol_type = protein
                         organism = synthetic construct
SEQUENCE: 52
GYSFSSFG                                                                  8

SEQ ID NO: 53            moltype = AA   length = 5
FEATURE                  Location/Qualifiers
source                   1..5
                         mol_type = protein
                         organism = synthetic construct
SEQUENCE: 53
SFGIS                                                                     5

SEQ ID NO: 54            moltype = AA   length = 7
FEATURE                  Location/Qualifiers
source                   1..7
                         mol_type = protein
                         organism = synthetic construct
SEQUENCE: 54
GYSFSSF                                                                   7

SEQ ID NO: 55            moltype = AA   length = 8
FEATURE                  Location/Qualifiers
source                   1..8
                         mol_type = protein
                         organism = synthetic construct
SEQUENCE: 55
ISAFNGYT                                                                  8

SEQ ID NO: 56            moltype = AA   length = 17
FEATURE                  Location/Qualifiers
source                   1..17
                         mol_type = protein
                         organism = synthetic construct
SEQUENCE: 56
WISAFNGYTK YAQKFQD                                                        17

SEQ ID NO: 57            moltype = AA   length = 6
FEATURE                  Location/Qualifiers
source                   1..6
                         mol_type = protein
                         organism = synthetic construct
SEQUENCE: 57
SAFNGY                                                                    6

SEQ ID NO: 58            moltype = AA   length = 18
FEATURE                  Location/Qualifiers
source                   1..18
                         mol_type = protein
```

```
                          organism = synthetic construct
SEQUENCE: 58
ARDPAAWPLQ QSLAWFDP                                                    18

SEQ ID NO: 59            moltype = AA  length = 16
FEATURE                  Location/Qualifiers
source                   1..16
                         mol_type = protein
                         organism = synthetic construct
SEQUENCE: 59
DPAAWPLQQS LAWFDP                                                      16

SEQ ID NO: 60            moltype = AA  length = 16
FEATURE                  Location/Qualifiers
source                   1..16
                         mol_type = protein
                         organism = synthetic construct
SEQUENCE: 60
DPAAWPLQQS LAWFDP                                                      16

SEQ ID NO: 61            moltype = AA  length = 8
FEATURE                  Location/Qualifiers
source                   1..8
                         mol_type = protein
                         organism = synthetic construct
SEQUENCE: 61
TSNLKRNY                                                               8

SEQ ID NO: 62            moltype = AA  length = 13
FEATURE                  Location/Qualifiers
source                   1..13
                         mol_type = protein
                         organism = synthetic construct
SEQUENCE: 62
SGSTSNLKRN YVY                                                         13

SEQ ID NO: 63            moltype = AA  length = 13
FEATURE                  Location/Qualifiers
source                   1..13
                         mol_type = protein
                         organism = synthetic construct
SEQUENCE: 63
SGSTSNLKRN YVY                                                         13

SEQ ID NO: 64            moltype =    length =
SEQUENCE: 64
000

SEQ ID NO: 65            moltype = AA  length = 7
FEATURE                  Location/Qualifiers
source                   1..7
                         mol_type = protein
                         organism = synthetic construct
SEQUENCE: 65
RDRRRPS                                                                7

SEQ ID NO: 66            moltype = AA  length = 7
FEATURE                  Location/Qualifiers
source                   1..7
                         mol_type = protein
                         organism = synthetic construct
SEQUENCE: 66
RDRRRPS                                                                7

SEQ ID NO: 67            moltype = AA  length = 11
FEATURE                  Location/Qualifiers
source                   1..11
                         mol_type = protein
                         organism = synthetic construct
SEQUENCE: 67
AWYDRELSEW V                                                           11

SEQ ID NO: 68            moltype = AA  length = 11
FEATURE                  Location/Qualifiers
source                   1..11
                         mol_type = protein
                         organism = synthetic construct
SEQUENCE: 68
AWYDRELSEW V                                                           11
```

-continued

```
SEQ ID NO: 69            moltype = AA   length = 11
FEATURE                  Location/Qualifiers
source                   1..11
                         mol_type = protein
                         organism = synthetic construct
SEQUENCE: 69
AWYDRELSEW V                                                           11

SEQ ID NO: 70            moltype = AA   length = 8
FEATURE                  Location/Qualifiers
source                   1..8
                         mol_type = protein
                         organism = synthetic construct
SEQUENCE: 70
GYTFTNYY                                                                8

SEQ ID NO: 71            moltype = AA   length = 5
FEATURE                  Location/Qualifiers
source                   1..5
                         mol_type = protein
                         organism = synthetic construct
SEQUENCE: 71
NYYMY                                                                   5

SEQ ID NO: 72            moltype = AA   length = 7
FEATURE                  Location/Qualifiers
source                   1..7
                         mol_type = protein
                         organism = synthetic construct
SEQUENCE: 72
GYTFTNY                                                                 7

SEQ ID NO: 73            moltype = AA   length = 8
FEATURE                  Location/Qualifiers
source                   1..8
                         mol_type = protein
                         organism = synthetic construct
SEQUENCE: 73
INPSNGGT                                                                8

SEQ ID NO: 74            moltype = AA   length = 17
FEATURE                  Location/Qualifiers
source                   1..17
                         mol_type = protein
                         organism = synthetic construct
SEQUENCE: 74
GINPSNGGTN FNEKFKN                                                     17

SEQ ID NO: 75            moltype = AA   length = 6
FEATURE                  Location/Qualifiers
source                   1..6
                         mol_type = protein
                         organism = synthetic construct
SEQUENCE: 75
NPSNGG                                                                  6

SEQ ID NO: 76            moltype = AA   length = 13
FEATURE                  Location/Qualifiers
source                   1..13
                         mol_type = protein
                         organism = synthetic construct
SEQUENCE: 76
ARRDYRFDMG FDY                                                         13

SEQ ID NO: 77            moltype = AA   length = 11
FEATURE                  Location/Qualifiers
source                   1..11
                         mol_type = protein
                         organism = synthetic construct
SEQUENCE: 77
RDYRFDMGFD Y                                                           11

SEQ ID NO: 78            moltype = AA   length = 11
FEATURE                  Location/Qualifiers
source                   1..11
                         mol_type = protein
                         organism = synthetic construct
SEQUENCE: 78
```

-continued

```
RDYRFDMGFD Y                                                    11

SEQ ID NO: 79         moltype = AA  length = 10
FEATURE               Location/Qualifiers
source                1..10
                      mol_type = protein
                      organism = synthetic construct
SEQUENCE: 79
KGVSTSGYSY                                                      10

SEQ ID NO: 80         moltype = AA  length = 15
FEATURE               Location/Qualifiers
source                1..15
                      mol_type = protein
                      organism = synthetic construct
SEQUENCE: 80
RASKGVSTSG YSYLH                                                15

SEQ ID NO: 81         moltype = AA  length = 15
FEATURE               Location/Qualifiers
source                1..15
                      mol_type = protein
                      organism = synthetic construct
SEQUENCE: 81
RASKGVSTSG YSYLH                                                15

SEQ ID NO: 82         moltype =    length =
SEQUENCE: 82
000

SEQ ID NO: 83         moltype = AA  length = 7
FEATURE               Location/Qualifiers
source                1..7
                      mol_type = protein
                      organism = synthetic construct
SEQUENCE: 83
LASYLES                                                         7

SEQ ID NO: 84         moltype = AA  length = 7
FEATURE               Location/Qualifiers
source                1..7
                      mol_type = protein
                      organism = synthetic construct
SEQUENCE: 84
LASYLES                                                         7

SEQ ID NO: 85         moltype = AA  length = 9
FEATURE               Location/Qualifiers
source                1..9
                      mol_type = protein
                      organism = synthetic construct
SEQUENCE: 85
QHSRDLPLT                                                       9

SEQ ID NO: 86         moltype = AA  length = 9
FEATURE               Location/Qualifiers
source                1..9
                      mol_type = protein
                      organism = synthetic construct
SEQUENCE: 86
QHSRDLPLT                                                       9

SEQ ID NO: 87         moltype = AA  length = 9
FEATURE               Location/Qualifiers
source                1..9
                      mol_type = protein
                      organism = synthetic construct
SEQUENCE: 87
QHSRDLPLT                                                       9

SEQ ID NO: 88         moltype = AA  length = 454
FEATURE               Location/Qualifiers
source                1..454
                      mol_type = protein
                      organism = synthetic construct
SEQUENCE: 88
QVQLVQSGAE VKKPGASVKV SCKASGYSFS SFGISWVRQA PGQGLEWLGW ISAFNGYTKY  60
AQKFQDRVTM TTDTSTSTAY MELRSLRSDD TAVYYCARDP AAWPLQQSLA WFDPWGQGTM  120
VTVSSASTKG PSVFPLAPSS KSTSGGTAAL GCLVKDYFPE PVTVSWNSGA LTSGVHTFPA  180
```

```
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454
```

SEQ ID NO: 89              moltype = DNA   length = 1368
FEATURE                    Location/Qualifiers
source                     1..1368
                           mol_type = other DNA
                           organism = synthetic construct
SEQUENCE: 89

```
caagtgcagc tggtgcagtc tggcgctgag gtgaagaaac caggcgcttc cgtgaaggta   60
tcctgcaagg cctctggcta ctctttcagc agcttcggta tctcctgggt gcgccaggcc  120
cctggacagg gcctggaatg gctgggctgg atctctgcct tcaacggcta taccaagtac  180
gcccagaaat tccaggacag agtgaccatg accaccgaca cctccaccag cacagcctac  240
atggaactga gatccctgcg gtctgacgac accgctgtgt actactgcgc cagagatcct  300
gctgcttggc ctctgcagca gtccctggcc tggttcgacc cttggggcca gggcaccatg  360
gtgaccgtgt cctccgctag cactaagggc ccctccgtgt tcctctggc  tccttcctct  420
aagtccacct ctggcggcac cgccgctctg ggctgcctgg tcaaggatta ctttccagaa  480
cctgtgaccg tgtcttggaa ctccggcgct ctgacctctg gagtgcatac cttccccgct  540
gtgctgcaga gctccggcct gtacagcctg tccagtgttg tcaccgtgcc tagctcttct  600
ctgggaacac agacctacat ctgcaacgtg aatcacaagc cctctaacac caaagtggac  660
aagaaggtgg aacctaagtc ttgcgacaaa acccacacct gtcctccttg tccggcgcct  720
gagctgctcg gcggaccttc tgtgtttctg ttcccaccta gcccaaggga tacccctgatg  780
atctccagaa cccctgaagt gacatgcgtg gtcgtggacg tgtctcacga ggaccccgag  840
gtgaagttca actggtacgt ggatggcgtg gaagtgcaca acgccaagac caagcctcgg  900
gaagagcagt acaactccac ctacagagtg gtgtctgtgc tcacagtgct gcatcaggat  960
tggctgaacg gcaaagagta caagtgcaag gtctccaaca aggccctgcc tgcccctatc 1020
gagaagacca tctccaaggc taagggccaa cctagagagc ctcaggtcta taccctgcca 1080
ccttctcggg acgagctgac caagaaccag gtgtctctga cctgtctggt gaaaggcttc 1140
taccttccg  acatcgccgt cgagtgggag tccaatggcc agcctgagaa caactacaag 1200
accacacctc ccgtgctgga ctccgacggc tctttcttct tgtactccaa gctgacagtg 1260
gacaagtcca gatggcagca aggcaacgtg ttctcctgct ccgtgatgca cgaggccctg 1320
cacaaccact acacgcagaa gagcctgtcc ctgtctcctg gataatga             1368
```

SEQ ID NO: 90              moltype = AA   length = 215
FEATURE                    Location/Qualifiers
source                     1..215
                           mol_type = protein
                           organism = synthetic construct
SEQUENCE: 90

```
QSVLTQPPSA SGTPGQRVTI SCSGSTSNLK RNYVYWYQQL PGTAPKLLIY RDRRRPSGVP   60
DRFSGSKSGT SASLAISGLR SEDEADYYCA WYDRELSEWV FGGGTKLTVL QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                             215
```

SEQ ID NO: 91              moltype = DNA   length = 651
FEATURE                    Location/Qualifiers
source                     1..651
                           mol_type = other DNA
                           organism = synthetic construct
SEQUENCE: 91

```
cagtctgtgc tgacccagcc tccttccgcc agcggcacac ccggacagag agtgaccatc   60
agctgttctg gctctaccag caacctgaag cggaactacg tgtactggta tcagcagctg  120
cctggcaccg ctcccaagct gctgatctac agagatagac ggagaccttc cggagtgccc  180
gaccggttct ccggctctaa atccggcacc tctgcttccc tggccatctc cggcctgaga  240
tctgaggacg aggccgacta ctactgcgct tggtacgacc gcgagctgtc cgagtgggtg  300
ttcggcggc  gaaccaagct caccgtgctg caacctaagg ctgctccatc cgtgaccctg  360
tttcctccaa gctccgaaga actgcaggcc aataaagcca ccctggtgtg cctgatctcc  420
gacttctacc ctggcgctgt gacagtggcc tggaaggccg atagctctcc tgtgaaggcc  480
ggcgtggaaa ccaccacacc ctccaagcag tccaacaaca gtacgccgc  ttcttcttac  540
ctgtctctga cccctgagca gtggaagtct cacagatcct actcctgcca ggtgacccac  600
gagggctcca cagtggaaaa gaccgtcgct cctaccgagt gctcctaatg a            651
```

SEQ ID NO: 92              moltype = AA   length = 454
FEATURE                    Location/Qualifiers
source                     1..454
                           mol_type = protein
                           organism = synthetic construct
SEQUENCE: 92

```
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALGAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPG                              454
```

```
SEQ ID NO: 93            moltype = DNA  length = 1368
FEATURE                  Location/Qualifiers
source                   1..1368
                         mol_type = other DNA
                         organism = synthetic construct
SEQUENCE: 93
caagtgcagc tggtgcagtc cggcgctgag gtgaagaagc ctggcgcttc cgtgaaggtg    60
tcctgcaagg cttctggcta ctctttttct agcttcggca tctcctgggt gcggcaggcc   120
ccaggccagg gcctggaatg gctgggctgg atctccgcct tcaacggcta taccaagtac   180
gcccagaagt tccaggacag agtcaccatg accaccgaca ccagcacctc taccgcctac   240
atggaactgc ggtctctgcg gtccgacgac accgccgtgt actactgcgc cagagatcct   300
gctgcttggc ctctgcaaca gtccctggcc tggttcgacc cttggggcca aggcaccatg   360
gtaaccgtga gctccgctag cacaaaagga ccttctgttt ttcctctgtc tccatcctcc   420
aagtccacat ccggcggaac cgctgccctc ggctgcctgg tcaaggacta cttccccgag   480
cctgtgaccg tgtcttggaa ctccggagca ctcacctccg gcgtgcatac cttccccgct   540
gtgctgcagt cttctggact gtactccctg tccagcgttg tgacagtgcc ttcttctagc   600
ctgggcacac agacctacat ctgcaacgtg aatcacaagc ccagcaacac caaagtggat   660
aagaaagtcg agcccaagtc ttgcgacaaa acccacacct gtccaccctg tccggcgcct   720
gaggccgctg gcgcgcccttc tgtgtttctg ttccctccta gcccaaagga tacctgatg    780
atctctcgga cccctgaggt gacctgcgtg gtggtggacg tgtctcacga ggaccctgaa    840
gtgaagttca actggtacgt ggacggcgtg gaagtgcaca acgccaagac caagcctagc    900
gaggaacagt acaactccac ctacagagtg gtgtcagtcc tgaccggtgct gcaccaggac    960
tggctgaacg gcaaagagta caagtgcaag gtgtccaaca aggccctggg cgctcctatc   1020
gagaagacaa tcagcaaggc caagggccag ccccgggaac ctcaggtgta caccctgcct   1080
ccctcccgcg acgaactgac caagaaccag gtgtccctga cctgtctggt gaagggcttc   1140
taccttctg acatcgccgt ggagtgggag tccaacggcc agcctgagaa caactacaag   1200
accacacctc ccgtgctgga ctctgatggc tccttcttcc tgtatagcaa gctgacagtc   1260
gacaagtcca gatggcagca gggcaacgtg ttctcctgct ccgtgatgca cgaggctctg   1320
cataaccact acacccagaa atctctgtcc ctgtctcctg gttaatga                1368

SEQ ID NO: 94            moltype = AA  length = 451
FEATURE                  Location/Qualifiers
source                   1..451
                         mol_type = protein
                         organism = synthetic construct
SEQUENCE: 94
QVQLVQSGAE VKKPGASVKV SCKASGYSFS SFGISWVRQA PGQGLEWLGW ISAFNGYTKY     60
AQKFQDRVTM TTDTSTSTAY MELRSLRSDD TAVYYCARDP AAWPLQQSLA WFDPWGQGTM    120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFL    240
GGPSVFLFPP KPKDTLMISR TPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
RWQEGNVFSC SVMHEALHNH YTQKSLSLSL G                                   451

SEQ ID NO: 95            moltype = DNA  length = 1359
FEATURE                  Location/Qualifiers
source                   1..1359
                         mol_type = other DNA
                         organism = synthetic construct
SEQUENCE: 95
caagtgcagc tggtccaatc tggcgctgag gtgaagaaac ctggtgcctc cgtgaaggtg    60
tcctgcaagg ccagcggcta ctctttctcc tccttcggca tctcttgggt cagacaggcc   120
cctggccagg gactggaatg gctgggctgg atctctgcct tcaacggcta taccaagtac   180
gcccagaagt tccaggacag agtgacaatg accaccgaca ccagcacctc taccgcctat   240
atggaactga gatctctgcg gtccgacgac acagccgtgt actactgcgc cagagatcct   300
gccgcttggc ctctgcagca gagcctggcc tggttcgacc catggggcca gggcaccatg   360
gtgacagtgt cttccgctag caccaagggc ccctccgtgt tccctctggc tccttgctcc   420
agatccacct ctgagtccac cgcagctctg ggctgcctgg tgaaggacta cttccccgag   480
cctgtgaccg tgtcctggaa ctccggcgct ctaacctctg gcgtgcacac cttccccgct   540
gtgctgcagt ctagcggcct gtactccctg tcctctgttg tgaccgtgcc ttcttcctcg   600
ctcggcacca agacctacac ctgtaacgtg gaccacaagc cttccaacac caaagtggat   660
aagcgggtcg agtctaagta cggccctcct tgcccacctt gtccgggccc agagttcctg   720
ggcggaccta gtgtgtttct gtttcctcct aagcccaagg ataccctgat gatctcccgc   780
accccctgagg tgacctgcgt ggtggtggat gtgtctcaag aggaccccga agtgcagttc   840
aactggtacg tggacggcgt ggaagtgcac aacgccaaaa ctaagcctag agaggaacag   900
tttaattcta catacagagt ggtctctgtg ctgaccgtcc tgcatcagga ctggctgaac   960
ggcaaagagt acaagtgcaa ggtgtccaac aagggcctcc ccagctccat cgagaagacc   1020
atctccaagg ctaagggaca gcctcgggaa cctcaggtgt acacactgcc tccatctcag   1080
gaagagatga ccaagaacca ggtgtccctg acctgtctgg tcaaaggctt ctaccttcc    1140
gacatcgccg tggagtggga gtccaatggc agcccgaga acaactacaa gacaaccca    1200
cctgctgctg actccgatgg ctccttcttc ctgtactccc ggctgaccgt ggacaagtct   1260
aggtggcagg aaggcaacgt gttcagttgc tctgtgatgc acgaggccct gcacaaccac   1320
tacacccaga agtccctgtc tctgagcctg ggctaatga                          1359

SEQ ID NO: 96            moltype = AA  length = 446
FEATURE                  Location/Qualifiers
source                   1..446
```

-continued

```
                        mol_type = protein
                        organism = synthetic construct
SEQUENCE: 96
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLG                                       446

SEQ ID NO: 97        moltype = DNA  length = 1344
FEATURE              Location/Qualifiers
source               1..1344
                     mol_type = other DNA
                     organism = synthetic construct
SEQUENCE: 97
caggtgcagc tggtgcagtc cggcgtggaa gtgaagaagc ctggcgcttc tgtgaaagtg    60
tcctgcaagg cctctggcta caccttcacc aattactaca tgtactgggt gcggcaggct   120
cctgacaag gcctcgagtg gatgggcggc atcaacccct ccaacggcgg aaccaacttc   180
aacgagaagt tcaagaacag agtgaccctg accaccgact ccagcaccac cacagcctac   240
atggagctga agtccctgca gttcgacgac accgccgtgt actactgtgc caggagagat   300
taccggtttg acatgggctt cgattattgg ggccagggca caacagtcac cgtgtcttct   360
gctagcacca agggcccctc cgtgttccct ctggctcctt gctccagatc cacctctgag   420
tccaccgcag ctctgggctg cctggtgaag gactacttcc ccgagcctgt gaccgtgtcc   480
tggaactccg gcgctctaac ctctggcgtg cacaccttcc ccgctgtgct gcagtctagc   540
ggcctgtact ccctgtcctc tgttgtgacc gtgccttctt cctcgctcgg caccaagacc   600
tacacctgta acgtggacca caagccttcc aacaccaaag tggataagcg ggtcgagtct   660
aagtacggcc ctccttgccc accttgtccg gcgccaagt tcctgggcgg acctagtgtg   720
tttctgtttc ctcctaagcc caaggatacc ctgatgatct cccgcacccc tgaggtgacc   780
tgcgtggtgg tggatgtgtc tcaagaggac cccgaagtgc agttcaactg gtacgtggac   840
ggcgtggaag tgcacaacgc caaaactaag cctagagagg aacagtttaa ttctacatac   900
agagtggtct ctgtgctgac cgtcctgcat caggactggc tgaacggcaa agagtacaag   960
tgcaaggtgt ccaacaaggg cctccccagc tccatcgaga agaccatctc caaggctaag  1020
ggacagcctc gggaacctca ggtgtacaca ctgcctccat ctcaggaaga gatgaccaag  1080
aaccaggtgt ccctgacctg tctggtcaaa ggcttctacc cttccgacat cgccgtggag  1140
tgggagtcca atggccagcc cgagaacaac tacaagacaa ccccacctgt gctggactcc  1200
gatggctcct tcttcctgta ctcccggctg accgtggaca gtctaggtg gcaggaaggc  1260
aacgtgttca gttgctctgt gatgcacgag gccctgcaca accactacac ccagaagtcc  1320
ctgtctctga gctgggcta atga                                         1344

SEQ ID NO: 98        moltype = AA  length = 218
FEATURE              Location/Qualifiers
source               1..218
                     mol_type = protein
                     organism = synthetic construct
SEQUENCE: 98
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 99        moltype = DNA  length = 660
FEATURE              Location/Qualifiers
source               1..660
                     mol_type = other DNA
                     organism = synthetic construct
SEQUENCE: 99
gagatcgtgc tgacccagtc ccctgctacc ctgtccctgt ctcctggcga gcgcgctaca    60
ctgagctgta gagcctctaa gggcgtgtcg acctctggct actcctatct gcactggtac   120
cagcagaagc ccgaggcgc ccctcggctc ctgatctacc tggcctccta cctggaaagc   180
ggagtccccg ctagattctc cggaagcggc tccggcaccg acttcaccct gaccatctcc   240
agcctggaac ccgaggattt tgccgtgtac tactgccagc actccagaga cctgcctctg   300
accttcggcg gcggaaacaa agtggaaatc aagcggaccg tggccgctcc ttctgtgttc   360
atctttcctc catccgacga gcagctgaag tctggcaccg cttccgtggt gtgcctgctg   420
aacaacttct accctagaga ggccaaggtg cagtggaagg tggacaacgc cctgcaatct   480
ggcaattctc aagagtctgt taccgagcag gactccaaag attctaccta ctctctgtcc   540
agcacattga ctctgtccaa ggccgactac gagaagcaca aggtctacgc ctgcgaggtg   600
acccatcagg gcctgtcctc tcctgtgacc aagtccttca cagaggcga atgctaatga   660

SEQ ID NO: 100       moltype = AA  length = 449
FEATURE              Location/Qualifiers
source               1..449
                     mol_type = protein
                     organism = synthetic construct
SEQUENCE: 100
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
```

-continued

```
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LGAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPG                                       449
```

```
SEQ ID NO: 101            moltype = DNA   length = 1353
FEATURE                   Location/Qualifiers
source                    1..1353
                          mol_type = other DNA
                          organism = synthetic construct
SEQUENCE: 101
caggtgcagc tggtgcagtc tggcgtggaa gtgaagaagc ctggcgcttc tgtgaaagtg    60
tcctgcaagg cctccggcta caccttcacc aactactaca tgtactgggt cagacaggcc    120
cctggacaag gcctcgagtg gatgggcggc atcaacccct ccaacggcgg aacaaatttc    180
aacgagaagt tcaagaacag agtgaccctg accacagact ccagcaccac caccgcctac    240
atggagctga gtccctgca gttcgacgac accgctgtgt actactgtgc cagacgcgat    300
taccggttcg acatgggctt tgattattgg ggccagggca ccacagtcac cgtgtctagc    360
gctagcacaa aaggaccttc tgttttcct ctggctccat cctccaagtc cacatccggc    420
ggaaccgctg ccctcggctg cctggtcaag gactacttcc ccgagcctgt gaccgtgtct    480
tggaactccg gagcactcac ctccggcgtg cataccttcc ctgccgtgct gcagtcttct    540
ggactgtact ccctgtccag cgttgtgaca gtgccttctt ctagcctggg cacacagacc    600
tacatctgca acgtgaatca caagcccagc aacaccaaag tggataagaa agtcgagccc    660
aagtcttgcg acaaaaccca cacctgtcca ccctgtccgg cgcctgaggc cgctggcggc    720
ccttctgtgt ttctgttccc tcctaagcca aaggataccc tgatgatctc tcggacccct    780
gaggtgacct gcgtggtggt ggacgtgtct cacgaggacc ctgaagtgaa gttcaactgg    840
tacgtggacg gcgtggaagt gcacaatgcc aagaccaagc ctagagagga acagtacaac    900
tccacctaca gtggtgtc agtcctgacg gtgctgcacc aggactggct gaacggcaaa    960
gagtacaagt gcaaggtgtc caacaaggcc ctgggcgctc ctatcgagaa gacaatcagt    1020
aaggccaagg gccagcccg ggaacctcag gtgtacaccc tgcctccctc ccgcgacgaa    1080
ctgaccaaga accaggtgtc cctgacctgt ctggtgaagg gcttctaccc ttctgacatc    1140
gccgtggagt gggagtccaa cggccagcct gagaacaact acaagaccac acctcccgtg    1200
ctggactctg atggctcctt cttcctgtat agcaagctga cagtcgacaa gtccagatgg    1260
cagcagggca cgtgttctc ctgctccgtg atgcacgagg ctctgcataa ccactacacc    1320
cagaaatctc tgtccctgtc cctggttaa tga                                 1353
```

```
SEQ ID NO: 102            moltype = AA   length = 215
FEATURE                   Location/Qualifiers
source                    1..215
                          mol_type = protein
                          organism = synthetic construct
SEQUENCE: 102
QSVLTQPPSA SGTPGQRVTI SCSGSTSNLK RNYVYWYQQL PGTAPKLLIY RDRRRPSGVP    60
DRFSGSKSGT SASLAISGLR SEDEADYYCA WYDRELSEWV FGGGTKLTVL QPKAAPSVTL    120
FPPSDEELQA NTATLVCLIS DFYPGAVTVA WKADSSPVKA GVETTTPSKQ SNNKYAAESE    180
LSLTPEQWKS HRSYSCQVTH EGSTVEKTVA PTECS                               215
```

```
SEQ ID NO: 103            moltype = DNA   length = 651
FEATURE                   Location/Qualifiers
source                    1..651
                          mol_type = other DNA
                          organism = synthetic construct
SEQUENCE: 103
cagtctgttc tgacacaacc tccttccgcc tctggtaccc caggccagag agtgaccatc    60
tcctgttctg gctccaccag caatctgaag cggaactacg tgtactggta tcagcagctg    120
cctggaactg ctcccaagct gctgatctac agagatcgga gacggccttc tggcgtgcct    180
gaccgctttt ctggctccaa aagcggcacc tctgcttcc tggccatcag cggactgaga    240
tctgaggatg aagctgacta ctactgcgct tggtacgaca gagagttgtc cgagtgggtg    300
ttcggcggcg gcaccaagct gacagtgctc cagcctaaag ctgctcctag cgtgacactg    360
ttccacccct ctgacgagga actgcaggcc aacaccgcca ccctggtgtg cctgatctcc    420
gacttctacc ccggcgctgt gaccgtcgcc tggaaggccg actcctctcc tgtgaaggcc    480
ggcgtcgaga caaccacccc ctccaagcag tccaacaaca gtacgccgc cgagtctgaa    540
ctgtctctga cccctgagca gtggaagtcc cacagatcct actcctgcca ggtgacccac    600
gagggcagca ccgtggaaaa gaccgtggcc ctaccgagt gctcctaatg a             651
```

```
SEQ ID NO: 104            moltype = AA   length = 449
FEATURE                   Location/Qualifiers
source                    1..449
                          mol_type = protein
                          organism = synthetic construct
SEQUENCE: 104
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS    120
ASTKGPSVFP LAPSSKSTSG GTAALGCEVT DYFPEPVTVS WNSGALTSGV HTFPAVLESS    180
GLYSLSSVVT VPSSSLGTQT YICNVNHKPS NTKVDKKVEP DSCDKTHTCP PCPAPEAAGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LGAPIEKTIS KAKGQPREPQ VYVYPPSRDE    360
LTKNQVSLTC LVKGFYPSDI AVEWESNGQP ENNYKTTPPV LDSDGSFALV SKLTVDKSRW    420
```

```
QQGNVFSCSV MHEALHNHYT QKSLSLSPG                                    449

SEQ ID NO: 105            moltype = DNA   length = 1353
FEATURE                   Location/Qualifiers
source                    1..1353
                          mol_type = other DNA
                          organism = synthetic construct
SEQUENCE: 105
caggtgcagc tggtacagtc cggcgtggaa gtgaagaaac ctggcgcttc agtgaaagtg   60
tcctgcaagg cttctggata taccttcacc aactactaca tgtactgggt gcggcaggct   120
cccggacagg gcctggaatg gatgggcggc atcaaccota gcaacggcgg caccaacttc   180
aacgaaaagt tcaagaaccg ggtgacactg accaccgact cttctaccac caccgcctac   240
atggagctga gagtctgca gttcgacgac acagccgtgt actactgcgc cagaagagat   300
taccggttcg acatgggctt tgactactgg ggccaggcca ccaccgtgac cgtgtcctcc   360
gctagcacca agggcccttc tgtcttcect ctggctccat cctccaaaag cacctctggc   420
ggaacagctg ctctgggctg cgaggtgacc gattacttcc ccgaaccagt gaccgtgagc   480
tggaactccg gtgccctgac cagcggcgtg catacatttc cagctgtgct ggagtcttct   540
ggcctgtact ctctgagcag cgtcgtgacc gtgcctccct ctagcctggg caccagacc   600
tacatctgca acgtgaacca caagccctct aacaccaagg tggacaagaa ggtgaaacct   660
gactcctgcg acaagacca cacctgtcct ccttgtccgg cgcctgaggc cgctggcgga   720
cctagcgtgt tcctgttccc ccccaagcct aaggacaccc tgatgatctc cagaaccct   780
gaggtgacct gcgtggtggt ggacgtgtcc cacgaggacc ctgaagttaa gttcaactgg   840
tatgtcgatg gcgtcgaagt gcacaacgcc aagacaaagc ctcgcgaaga gcagtacaac   900
tccacctaca gagttgtgtc tgtgctgaca gtgctgcacc aggactggct gaacggcaaa   960
gagtacaagt gcaaggtgtc caacaaggcc ctcggcgctc ctatcgagaa aaccatctct   1020
aaggccaaag gccaacctag agagcctcag gtgtacgtgt atcctccatc tcgggatgag   1080
ctgaccaaga atcaagtgtc actcacatgc ctggtgaagg gcttctaccc ctccgacatc   1140
gccgtggagt gggagtccaa tggccagcct gagaacaact acaagaccac ccctcctgtg   1200
ctggactctg acggctcctt cgccctggtg tccaagctaa cagtggataa gtctagatgg   1260
cagcagggca acgtgttctc ctgttccgtg atgcacgagg ctctgcataa tcactacacc   1320
cagaagtccc taagcttgtc tcctggataa tga                                1353

SEQ ID NO: 106            moltype = AA   length = 218
FEATURE                   Location/Qualifiers
source                    1..218
                          mol_type = protein
                          organism = synthetic construct
SEQUENCE: 106
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF   120
IFPPKDERLK SGTASVVCLL NNFYPREAKV QWKVDNALQS GNSQESVTEQ DSKDSTYSLS   180
SRLTLSKADY EKHKVYACEV THQGLSSPVT KSFNRGEC                           218

SEQ ID NO: 107            moltype = DNA   length = 660
FEATURE                   Location/Qualifiers
source                    1..660
                          mol_type = other DNA
                          organism = synthetic construct
SEQUENCE: 107
gagatcgtgc tgacacagtc tcctgctacc ctgtctctca gcccaggaga aagagctacc   60
ctgtcctgca gagcctccaa gggcgtctct acctctggct actcctacct gcactggtac   120
cagcagaagc ctggccaggc tcctagactg ctgatctacc tggcctccta tctggaaagc   180
ggcgtgcctg ctagattcag cggctccgga tctggcaccg attttacact gaccatctcc   240
agcctggaac tgaggacttt gccgtgtac tactgccagc actctcggga cctgcctctg   300
accttcggcg gcggaacaaa agtggaaatc aaacggaccg ttgctgcccc ttccgtgttc   360
atcttcccc ccaaggacga gcggctgaag tctggcaccg cttctgtggt gtgcctgctg   420
aacaacttct accccagaga ggccaaggtg cagtggaagg tggacaatgc tctgcagtcc   480
ggcaactccc aagagtccgt caccgagcag gactccaaag attccaccta ctctctgagc   540
tccaggctga ccttgtctaa ggccgactac gagaagcaca aggtttacgc ctgcgaggtg   600
acccatcagg gcctgtcctc tcctgtgacc aagtccttca cagaggcga gtgttaatga   660

SEQ ID NO: 108            moltype = AA   length = 454
FEATURE                   Location/Qualifiers
source                    1..454
                          mol_type = protein
                          organism = synthetic construct
SEQUENCE: 108
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM   120
VTVSSASTKG PSVFPLRPSS KSTSGGTAAL GCLVKDYFPE PVTVSWNSGA LTSGVHTFPA   180
VLQSSGLYSL KSVVTVPSSS LGTQTYICNV NHKPSNTKVD KKVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALGAPI EKTISKAKGQ PREPQVYVLP   360
PSRDELTKNQ VSLLCLVKGF YPSDIAVEWE SNGQPENNYL TWPPVLDSDG SFFLYSKLTV   420
DKSRWQQGNV FSCSVMHEAL HNHYTQKSLS LSPG                               454

SEQ ID NO: 109            moltype = DNA   length = 1368
FEATURE                   Location/Qualifiers
source                    1..1368
```

```
                         mol_type = other DNA
                         organism = synthetic construct
SEQUENCE: 109
caagtgcagc tggtgcagtc tggcgctgag gttaagaagc ctggcgcttc cgtgaaggtg    60
agctgcaagg cttctggcta tagtttctcc tccttcggca tctcttgggt cagacaggcc   120
cccggacagg gcctggaatg gctgggctgg atctccgcct tcaatggcta caccaagtac   180
gcccagaagt tccaggaccg cgtgaccatg accaccgaca catctacctc cacagcctac   240
atggagctga gatccctgcg gtctgacgac accgctgtgt actactgcgc cagagatcct   300
gctgcttggc tctgcagca gtctctggcc tggttcgacc cttggggcca aggcaccatg   360
gtgaccgtga gttctgctag caccaagggc ccatctgtct tccctctgcg gccttcttct   420
aagtccacct ccggcggcac cgccgctctg ggctgcctgg tcaaggacta cttcccggaa   480
cccgtgacac tgtcctggaa ctccggcgct ctgaccagcg gcgtgcacac cttccccgct   540
gtgctgcagt cctctggact gtacagcctg aagtccgtgg tcaccgtgcc ttccagctct   600
ctcggcaccc agacctacat ctgcaacgtg aaccacaagc cctccaacac caaagtggat   660
aagaaagtcg aacctaagtc ctgcgacaag acccacacat gccctccatg tccggcgcct   720
gaggccgccg gaggccctag tgtgtttctg ttccctccta agcctaagga caccctgatg   780
atctcccgga ccccctgaagt gacctgcgtg gtggtggatg tgtctcatga ggacccagag   840
gtgaagttca actggtatgt ggatggagtt gaagtgcaca acgccaaaac caagcctcgg   900
gaggaacagt acaactccac ctacagagtg gtgtctgtgc tgacagtgct gcaccaggat   960
tggctgaacg gcaaagagta caagtgcaag gtgtccaaca aggccctggg agctcctatc   1020
gagaagacca tcagcaaggc caagggccag cctagagagc tcaggtgta cgtgctgcct   1080
ccatctcggg acgagctgac caagaaccag gtgtccctcgt tgtgtctcgt gaaaggcttc   1140
taccttctg acatcgccgt ggaatggag tccaacggcc aacccgagaa caactacctg   1200
acctggcccc ccgtgctgga ttccgacggc tctttcttcc tgtactccaa gctgacagtg   1260
gacaagtcca gatggcagca gggcaacgtc ttttcctgtt ccgtgatgca cgaggctctg   1320
cataatcact acacccagaa aagcctaagc ttgtcccctg ctaatga              1368

SEQ ID NO: 110      moltype = AA  length = 454
FEATURE             Location/Qualifiers
source              1..454
                    mol_type = protein
                    organism = synthetic construct
SEQUENCE: 110
QVQLVQSGAE VKKPGASVKV SCKASGYSFS SFGISWVRQA PGQGLEWLGW ISAFNGYTKY    60
AQKFQDRVTM TTDTSTSTAY MELRSLRSDD TAVYYCARDP AAWPLQQSLA WFDPWGQGTM   120
VTVSSASTKG PSVFPLRPSS KSTSGGTAAL GCLVKDYFPE PVTVSWNSGA LTSGVHTFPA   180
VLQSSGLYSL KSVVTVPSSS LGTQTYICNV NHKPSNTKVD KKVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALGAPI EKTISKAKGQ PREPQVYVYP   360
PSRDELTKNQ VSLTCLVKGF YPSDIAVEWE SNGQPENNYK TTPPVLDSDG SFALVSKLTV   420
DKSRWQQGNV FSCSVMHEAL HNHYTQKSLS LSPG                              454

SEQ ID NO: 111      moltype = DNA  length = 1368
FEATURE             Location/Qualifiers
source              1..1368
                    mol_type = other DNA
                    organism = synthetic construct
SEQUENCE: 111
caagtgcagc tggtgcagtc cggcgctgag gtgaagaagc ctggtgcctc tgtgaaagtg    60
agctgtaagg cttccggata ttccttctcc tcctttggca tctcctgggt cggcagggct   120
cctggccaag gcctggaatg gctgggctgg atctctgcct tcaacggcta cactaagtac   180
gcccagaagt tccaggacag agtgaccatg accaccgaca cctctaccag cacagcttac   240
atggaactga gatccctgcg ctccgacgac accgccgtgt actactgcgc cagagatcct   300
gccgcctggc tctgcagca gtccctggct tggttcgacc cttggggcca gggcacaatg   360
gtgaccgtgt cctccgctag caccaagggc ccttctgtct tcccctgcg gccttcttct   420
aagtccacct ccggcggcac cgctgctctg ggctgcctgg tgaaggacta cttccctgaa   480
cccgtgactg tgtcttggaa ctctggagct ctcacatccg gcgtgcacac cttccctgcc   540
gtgctgcaat cttctggcct gtactccctg aagtctgtcg tgaccgtgcc ttctagcagc   600
ctcggcaccc agacctacat ctgcaacgtg aaccacaagc cttcaaacac caaggtggac   660
aagaaagtgg aacctaagtc ctgcgacaag acccatacct gccccccttg tccggcgcct   720
gaggccgctg gcggaccttc tgtgttcctg ttcccccaa agcccaagga taccctgatg   780
atcagcagaa cccctgaggt gacctgcgtg gtcgtcgacg tgtctcacga ggaccctgaa   840
gtgaagttca actggtacgt ggacggcgtg gaagtgcaca cgccaaaac caagcctcgg   900
gaggaacagt acaactccac ctaccgggtg gtgagcgtgc tgaccgtcct gcaccaggat   960
tggctgaacg gcaaagagta caagtgcaag gtgtccaaca aggccctggg cgctcctatc   1020
gagaagacca tctccaaggc caagggcacg cccagagagc tcaggtgta tgtgtaccct   1080
ccttctcggg acgagctgac aaagaatcag gtgagcctga cctgtctggt caagggcttc   1140
tacccctctg acatcgccgt ggagtgggag tccaatggcc agcccgagaa caactacaag   1200
accacacctc ctgtgctgga ctccgatggc tccttcgccc tggtctccaa gctgaccgtg   1260
gataaatcta gatggcagca gggcaacgtg ttttcttgct ccgtgatgca cgaggctctg   1320
cataatcact acacacagaa aagcctaagc ttgtccccag ctaatga              1368

SEQ ID NO: 112      moltype = AA  length = 725
FEATURE             Location/Qualifiers
source              1..725
                    mol_type = protein
                    organism = synthetic construct
SEQUENCE: 112
QVQLVQSGAE VKKPGASVKV SCKASGYSFS SFGISWVRQA PGQGLEWLGW ISAFNGYTKY    60
```

-continued

```
AQKFQDRVTM TTDTSTSTAY MELRSLRSDD TAVYYCARDP AAWPLQQSLA WFDPWGQGTM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALGAPI EKTISKAKGQ PREPQVYTLP   360
PSRDELTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGKGGGGS GGGGSGGGGS GGGGSQVQLV   480
QSGVEVKKPG ASVKVSCKAS GYTFTNYYMY WVRQAPGQGL EWMGGINPSN GGTNFNEKFK   540
NRVTLTTDSS TTTAYMELKS LQFDDTAVYY CARRDYRFDM GFDYWGQGTT VTVSSGGSGG   600
GSGGGGSGGGS GGGSGEIVLT QSPATLSLSP GERATLSCRA SKGVSTSGYS YLHWYQQKPG   660
QAPRLLIYLA SYLESGVPAR FSGSGSGTDF TLTISSLEPE DFAVYYCQHS RDLPLTFGGG   720
TKVEI                                                              725
```

SEQ ID NO: 113            moltype = DNA   length = 2181
FEATURE                   Location/Qualifiers
source                    1..2181
                          mol_type = other DNA
                          organism = synthetic construct
SEQUENCE: 113

```
caggtgcagc tggtgcagtc cggcgctgag gtcaaaaagc ctggcgcttc tgtgaaagtg   60
tcttgcaagg cctctggcta ttccttctcc agcttcggca tctcctgggt gcggcaggct   120
cccggccaag gcctggaatg gctgggctgg atctctgcct tcaacggcta tacaaagtac   180
gcccagaagt tccaggatag agtgacaatg accaccgaca cctcgacctc aaccgcctat   240
atggaactga gatccctgcg gtctgacgac accgctgtgt actactgcgc ccgcgaccct   300
gccgcctggc ctctgcaaca gtccctggct tggttcgatc cttggggaca gggcactatg   360
gtgaccgttt cttctgctag cactaaaggc ccttctgtgt tccccctggc cccttcttcc   420
aaatccacct ccggaggcac agctgccctg ggctgcctgg tgaaggacta ctttccagag   480
cccgtgacag tttcttggaa tagcggcgct ctcacctctg gtgtgcacac ctttcccgca   540
gtgctgcagt cctccggcct gtacagcctg agctccgtgg tgaccgtgcc ttcctcttct   600
ctgggcaccc agacctacat ctgcaacgta aaccacaagc cttccaacac caaggtggac   660
aagaaggtgg aacctaagtc ctgcgacaag acccacacct gcccttccatg tccggcgcct   720
gaggctgcag gcgggaccttc tgtgtttctg ttccctccca agcctaagga caccctgatg   780
atctcccgga cccctgaggt gacatgcgtg gtggtggacg tgtcccatga ggaccctgag   840
gtgaagttca attggtacgt ggacggagtg gaagtgcata acgccaagac aaagcctaga   900
gaagagcagt acaacagcac ctacagagtg gtgagtgttc tgactgtgct gcaccaggac   960
tggctgaatg gcaaagagta caagtgcaag gtgtctaaca aggctctggg cgctcctatt   1020
gagaaaacca tctctaaagc caagggccag cctagagagc cccaggtgta caccctgcct   1080
ccatctcggg acgagctgac caagaaccag gtctccctga cctgtctggt caagggcttc   1140
tacccttccg acatcgccgt ggagtgggag tccaacggtc agccagagaa caactacaag   1200
accaccctc ctgtgctgga ctccgatggc tctttcttcc tgtactctaa gctgaccgtg   1260
gataagtcca gatggcagca gggcaacgtg ttctcctgct ccgtgatgca cgaggccctg   1320
cacaaccact acacccagaa gtccctaagc ttgtcccctg gcaagggcgg aggtggctct   1380
ggaggcggtg gatctggtgg tggcggatca ggtggaggcg gagccaggt cagctggtg   1440
caatctggcg tggaagtgaa gaagccaggg gcctccgtga aggtgtcctg taaggcctct   1500
ggatacacct tcaccaacta ctatatgtac tgggtcagac aggcccctgg ccagggcctg   1560
gagtggatgg gcggcatcaa ccctccaat ggcggcacca acttcaacga gaagttcaag   1620
aacagagtga ccctgaccac cgactcttct accacaacga cttacatgga actgaagtct   1680
ttacagttcg acgataccgc cgtgtactac tgtgccagaa gagattaccg attcgacatg   1740
ggctttgact actggggcca gggcaccacc gtgaccgtct cgtccggagg atcgggcggc   1800
ggtagtggag gaggctctgg tggtggaagc ggcggcggat ctggcgagat cgtgctgacc   1860
caaagccctg ctacactgtc tctctctcct ggcgaacggg ctacactgtc ttgcagagcc   1920
agcaaaggcg tgtccaccag cggctactcc tacctgcact ggtaccaaca gaagcccggc   1980
caggctcctc ggctgctgat ctacctggcc tcctacctgg aatccggcgt gccagctaga   2040
ttctccgggt ctggctccgg caccgatttc accctgacca tcagcagttt ggagcctgaa   2100
gacttcgccg tgtactactg ccagcactcc cgggattac ctctgacctt cggcggcggt   2160
acaaaagtcg agatctaatg a                                            2181
```

SEQ ID NO: 114            moltype = AA   length = 726
FEATURE                   Location/Qualifiers
source                    1..726
                          mol_type = protein
                          organism = synthetic construct
SEQUENCE: 114

```
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALGAPI EKTISKAKGQ PREPQVYTLP   360
PSRDELTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGKGGGGS GGGGSGGGGS GGGGSEIVLT   480
QSPATLSLSP GERATLSCRA SKGVSTSGYS YLHWYQQKPG QAPRLLIYLA SYLESGVPAR   540
FSGSGSGTDF TLTISSLEPE DFAVYYCQHS RDLPLTFGGG TKVEIKGGSG GGSGGGGSGG   600
SGGGSGQVQL VQSGVEVKKP GASVKVSCKA SGYTFTNYYM YWVRQAPGQG LEWMGGINPS   660
NGGTNFNEKF KNRVTLTTDS STTTAYMELK SLQFDDTAVY YCARRDYRFD MGFDYWGQGT   720
TVTVSS                                                             726
```

SEQ ID NO: 115            moltype = DNA   length = 2184
FEATURE                   Location/Qualifiers

```
source                  1..2184
                        mol_type = other DNA
                        organism = synthetic construct
SEQUENCE: 115
caggtccagc tggtgcagtc aggcgctgag gtgaaaaagc ccggtgcctc cgtgaaagtg   60
tcttgcaagg cttctggcta ctccttttcc tcttttggca tctcctgggt gcggcaggcc  120
cctggccagg gcctggaatg gctgggctgg atctccgcct tcaatggcta tacaaagtac  180
gcccagaagt tccaggaccg ggtgaccatg accacagaca cgtccaccag cactgcctac  240
atggaactgc ggagcctgag atctgatgac accgccgtgt actactgcgc cagagatcct  300
gctgcgtggc ctctgcaaca atctctggct tggttcgacc cttgggggaca gggcaccatg  360
gtgaccgtgt cctccgctag caccaaggggc ccttccgtgt ttcctctggc tccttcttca  420
aagtctacaa gcggcggcac cgctgctctc ggctgcctgg tcaaggacta cttccccgag  480
cccgtgaccg tgtcgtggaa ctccggcgct ctgacctcag gcgtgcacac cttccccgcc  540
gttctgcagt cctctggcct gtacagcctg agctccgtga ccaccgtgcc ttccagcagc  600
ttgggaaccc agacctacat ctgcaatgtg aaccacaagc cttctaacac caaagtggat  660
aagaaagtgg aaccgaagtc ctgcgacaag acccatacct gccctccttg tccggcgcct  720
gaggccgctg gcggccccttc tgtgtttctg ttccctccaa agcctaagga caccctgatg  780
atctctcgga cccctgaggt gacatgcgtg gtggtgacg tgtctcatga ggacccccga  840
gtgaagttca actggtacgt ggatggcgta gaagtgcaca acgccaagac caagcccagg  900
gaggaacagt acaactctac ctacagagtg gtgagcgtgc tgacagttct gcaccaggac  960
tggctgaacg gcaaagagta caagtgcaag gtgagcaaca aggccctggg cgctcctatc 1020
gagaaaacca tttctaaggc caaagtgtcag cctagagaac ctcaggtata tacactgcct 1080
ccttctagag acgagctgac caagaaccag gtgtcactga cctgtctggt gaagggcttc 1140
tacccctctg acatcgccgt ggagtgggag tccaatggac agcccgagaa caactacaag 1200
accacccccac ctgtgctgga ctccgacggc agcttcttcc tgtactccaa gctgaccgtg 1260
gacaagtcta gatggcagca gggcaacgtg ttctcctgct ccgtgatgca cgaggccctg 1320
cacaaccact acacccagaa gtctctaagc ttgtctcctg gcaagggcgg aggtggctct 1380
ggaggcggtg gatctggtgg tggcggatca ggtggaggcg ggagcgagat cgtgctgaca 1440
cagtctccag ctaccctgtc cctgtcccct ggcgagcggg ccacccctgag ctgcagagc 1500
tccaaggggg tgtccacctc tggctactcc tatctccact atgatcagca gaaacctgga 1560
caggcccctc ggctgctgat ctacctggcc tcttacctgg aatctggggt gcctgctcgc 1620
ttctccggct ctggcagcgg caccgacttc accctgacca tctcctccct ggagcctgag 1680
gatttcgccg tgtactactg ccagcactcc cgggacctgc ctctgacctt cggcggcgga 1740
acaaaggtgg agatcaaggg cggatctggc ggcggtagtg gaggaggctc tggtggtgga 1800
agcggcggcg gatctggcca agtgcagctg gtgcagtctg gcgtgaagt gaagaagcct 1860
ggcgcttccg tcaaagtctc ctgtaaggca tctggctaca cctttaccaa ctactacatg 1920
tactgggtca gacaggctcc cggccaaggc ctggagtgga tgggcggcat caatccatcc 1980
aacggcggga ccaacttcaa cgagaagttc aagaacagag tgacactgac caccgactct 2040
tccaccacca ccgcttacat ggaactgaag tccctgcagt cgacgatac cgctgtgtac 2100
tactgtgcca gacgggacta ccggttcgac atgggctttg attactgggg ccaggaaca 2160
acagtgaccg tgtcctctta atga                                        2184

SEQ ID NO: 116        moltype = AA  length = 725
FEATURE               Location/Qualifiers
source                1..725
                      mol_type = protein
                      organism = synthetic construct
SEQUENCE: 116
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALGAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGKGGGGS GGGGSGGGGS GGGGSQVQLV  480
QSGVEVKKPG ASVKVSCKAS GYTFTNYYMY WVRQAPGQCL EWMGGINPSN GGTNFNEKFK  540
NRVTLTTDSS TTTAYMELKS LQFDDTAVYY CARRDYRFDM GFDYWGQGTT VTVSSGGSGG  600
GSGGGSGGGS GGGSGEIVLT QSPATLSLSP GERATLSCRA SKGVSTSGYS YLHWYQQKPG  660
QAPRLLIYLA SYLESGVPAR FSGSGSGTDF TLTISSLEPE DFAVYYCQHS RDLPLTFGCG  720
TKVEI                                                              725

SEQ ID NO: 117        moltype = DNA  length = 2181
FEATURE               Location/Qualifiers
source                1..2181
                      mol_type = other DNA
                      organism = synthetic construct
SEQUENCE: 117
caggtgcagc tggtgcaatc cggcgctgag gttaagaaac ctggcgcttc cgtgaaggtg   60
tcctgcaagg ccagcggcta ctctttctcc tcctttggca tctcttgggt gcggcaggct  120
cctggccagg gcctggagtg gctgggctgg atctccgcct tcaatggcta caccaagtac  180
gctcagaagt tccaggacag agtgaccatg accaccgata tatctacttc taccgcctac  240
atggaactga gatctctgcg tctgacgat accgctgtgt actactgcgc cagagatcct  300
gctgcgtggc ctctgcagca atctctggct tggttcgacc cctgggggca aggcaccatg  360
gtgaccgtgt cctctgctag cacaaagggc cctagcgtgt tccctctggc cccttcttct  420
aagtctacct ccggcggcac cgccgccctg ggctgcctgg tgaaggacta cttccctgag  480
cccgtgaccg tgtcctggaa ctccggcgct ctcacctccg gcgtgcatac ctttccagct  540
gtgctgcagt cctccggcct gtactccctg tcctccgtgg tcaccgtgcc cagctcctcc  600
ctgggcacac agacctacat ctgcaacgtg aaccacaagc cttctaacac caaagtggac  660
```

```
aagaaggtgg aacctaagtc atgcgacaag acccacacat gccctccttg tccggcgcct    720
gaggccgctg gcggaccttc tgtgtttctg ttccctccta agcccaagga cacgctgatg    780
atctccagaa cacctgaggt gacctgcgtc gtcgtggacg tgtctcacga ggaccccgag    840
gtcaagttca actggtacgt ggatggcgtg gaagtgcaca acgccaagac caagcctagg    900
gaagagcagt acaactctac ctaccgggtg gtgtccgtgc tgaccgtgct gcaccaggat    960
tggctgaacg gcaaagagta caagtgcaag gtttccaaca aggccctggg agctcccatc   1020
gagaaaacca tttccaaggc caagggccag cccagagagc ctcaggttta cactgcct     1080
ccatctcggg acgagttgac caagaaccag gtgagtctga cctgtctggt gaaaggcttc   1140
tacccttctg acatcgccgt cgagtgggag tccaacggcc agcctgagaa caactacaag   1200
accacccctc ctgtgctgga ctccgacggc agcttcttcc tgtattccaa gctgaccgtg   1260
gacaagtcca gatggcagca gggcaacgtg ttctcctgtt ctgtgatgca cgaggctctg   1320
cataatcact acacccagaa gtccctaagc ttgtctcctg caagggcgg aggtggctct    1380
ggaggcggtg gatctggtgg tggcggatca ggtggaggcg ggagccaagt gcagctggtg   1440
caatcaggcg tggaagtgaa gaagcccggc gcttcggtga aggtgtcctg taaggcttct   1500
ggctatacct tcaccaacta ctacatgtac tgggtgcagc aggctcctgg acagtgcctg   1560
gaatggatgg gaggcatcaa cccttccaat ggcggaacca acttcaacga gaaattcaag   1620
aacagagtga cattaacaac cgactccagc accacaaccg cctacatgga actgaagtcc   1680
ctgcagttcg acgacactgc cgtgtactac tgtgccagac aggattacag attcgacatg   1740
ggctttgact actggggcca gggaaccacc gtgacagtgt ctagcggcgg ctctggcggc   1800
ggtagtggag gaggctctgg tggtggaagc ggcggcggat ctggcgagat cgtgctgacc   1860
cagtcccctg ccaccctgtc cctgagccct ggcgagcggg ctaccctctc ttgcagagcc   1920
tccaagggag tgtccaccag cggctactcc tacctgcact ggtaccagca gaaacccggc   1980
caggcccctc ggctgctgat ctacctggcc tcttacctgg aatctggcgt gcctgcccgg   2040
ttcagcggct ccggctctgg caccgacttt accctgacca tctcgagcct ggaaccagaa   2100
gatttcgccg tgtactactg ccagcactct agagacctgc cactgacctt cggctgcggc   2160
accaaggtgg agatctaatg a                                            2181
```

SEQ ID NO: 118          moltype = AA   length = 726
FEATURE                 Location/Qualifiers
source                  1..726
                        mol_type = protein
                        organism = synthetic construct
SEQUENCE: 118

```
QVQLVQSGAE VKKPGASVKV SCKASGYSFS SFGISWVRQA PGQGLEWLGW ISAFNGYTKY    60
AQKFQDRVTM TTDTSTSTAY MELRSLRSDD TAVYYCARDP AAWPLQQSLA WFDPWGQGTM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALGAPI EKTISKAKGQ PREPQVYTLP   360
PSRDELTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGKGGGGS GGGGSGGGGS GGGGSEIVLT   480
QSPATLSLSP GERATLSCRA SKGVSTSGYS YLHWYQQKPG QAPRLLIYLA SYLESGVPAR   540
FSGSGSGTDF TLTISSLEPE DFAVYYCQHS RDLPLTFGCG TKVEIKGGSG GGSGGGSGGG   600
SGGGSGQVQL VQSGVEVKKP GASVKVSCKA SGYTFTNYYM YWVRQAPGQC LEWMGGINPS   660
NGGTNFNEKF KNRVTLTTDS STTAYMELK SLQFDDTAVY YCARRDYRFD MGFDYWGQGT   720
TVTVSS                                                             726
```

SEQ ID NO: 119          moltype = DNA   length = 2184
FEATURE                 Location/Qualifiers
source                  1..2184
                        mol_type = other DNA
                        organism = synthetic construct
SEQUENCE: 119

```
caggtgcagc tggtgcagtc cggcgctgag gtgaagaagc ctggagccag cgtaaaggtg    60
tcctgcaagg cctctgggta tagcttttct agcttcggca tctcctgggt gcggcaggcc   120
cctggccaag gactggaatg gctgggctgg atctccgcct tcaacggcta cacaaagtac   180
gctcagaagt tccaggacag agtgaccatg accaccgaca cctccaccag caccgcctac   240
atggaactgc ggtccctgcg gtccgatgac accgctgtgt actactgtgc tagagatccc   300
gctgcttggc ctctccagca atccctcgcc tggttcgatc cttggggaca gggcaccatg   360
gtgaccgtga gctctgctag caccaagggc cctagcgtgt tcctctggc tccatcctct   420
aaatctacct ctggcggcac cgccgccctg ggatgcttgg tcaaggacta cttccctgag   480
cccgtgaccg tgtcttggaa ctccggcgct ctgacctctg gcgtgcatac cttccctgcc   540
gtgctgcagt ccagcggcct gtacagtctg tccagcgtgg tgaccgtgcc ttcatcctct   600
ctgggcaccc agacctacat ctgcaacgtg aaccacaagc catctaacac caaagtggat   660
aagaaagtcg aacctaagtc ctgcgacaag acccacacct gtcctccttg cccggcgcct   720
gaggccgctg gcggaccttc tgtgttcctg ttcccaccta gcccaagga taccctgatg   780
atctctagaa cacctgaggt gacctgcgtg gtcgtggacg tgtcccacga ggaccctgaa   840
gtgaagttca actggtacgt ggacggcgtg gaagtgcaca acgccaagac caaacccaga   900
gaggagcagt acaactccac ttatagagtg gtgtcagttc tgacagtgct gcaccaggac   960
tggctgaacg gcaaagagta caagtgcaag gtgtccaaca aggctctggg cgctcctatc   1020
gagaaaacca tttccaaggc caaaggccag ccccgggaac tcaagtgta caccttacct   1080
ccttcccggg acgagctgac caagaaccag gtgtccctca catgtctggt gaaaggcttc   1140
tacccctccg acatcgccgt ggagtgggag tccaatggcc agcctgagaa caactacaag   1200
accacccctc ctgtgctgga ctccgatggc tccttcttcc tgtacagcaa gctgacggtg   1260
gacaagtcta gatggcagca gggcaatgtg ttctcttgct ccgtgatgca cgaggctctg   1320
cataatcact acacacagaa atctctaagc ttgtcccctg caagggcgg aggtggctct   1380
ggaggcggtg gatctggtgg tggcggatca ggtggaggcg ggagcgagat cgtgctgacc   1440
cagtctcctg ctacactgag cctgtctccg ggcgagagag ccaccctgtc ttgcagagcc   1500
tccaaggggcg tttctacatc cggctacagc tacctgcact ggtaccagca gaagcctggc   1560
```

```
caggctccaa gactgctgat ctacctggcc tcttatctgg aatctggagt gcccgccaga    1620
ttctcaggct ccggcagcgg caccgatttc accctcacca tcagcagcct ggaacccgag    1680
gacttcgccg tgtactactg ccagcactcc cgggacctgc ctctgacctt tggctgcggc    1740
accaaggtgg aaatcaaggg cggctccggc ggcggtagtg gaggaggctc tggtggtgga    1800
agcggcggcg gatctggtca agtgcagctg gtccagtctg gcgtggaagt gaagaagcct    1860
ggagcttccg tgaaggtctc ttgtaaggcc tctggctaca ccttcaccaa ttactacatg    1920
tactgggtca gacaggctcc cggccaatgc ctggagtgga tgggcggcat caacccttcc    1980
aacggcggca ccaacttcaa cgagaagttc aagaaccgcg tgactctgac caccgactct    2040
agcacaacca cagcttacat ggaactgaag tccctgcagt tcgacgacac cgccgtctac    2100
tattgcgccc ggagagatta ccggtttgac atgggctttg actactgggg ccagggcaca    2160
accgtgactg tgtcttccta atga                                           2184
```

SEQ ID NO: 120          moltype = AA   length = 725
FEATURE                 Location/Qualifiers
source                  1..725
                        mol_type = protein
                        organism = synthetic construct
SEQUENCE: 120

```
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LGAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK GGGGSGGGGS GGGGSGGGGS QVQLVQSGAE    480
VKKPGASVKV SCKASGYSFS SFGISWVRQA PGQCLEWLGW ISAFNGYTKY AQKFQDRVTM    540
TTDTSTSTAY MELRSLRSDD TAVYYCARDP AAWPLQQSLA WFDPWGQGTM VTVSSGGSGG    600
GSGGGSGGGS GGGSGQSVLT QPPSASGTPG QRVTISCSGS TSNLKRNYVY WYQQLPGTAP    660
KLLIYRDRRR PSGVPDRFSG SKSGTSASLA ISGLRSEDEA DYYCAWYDRE LSEWVFGCGT    720
KLTVL                                                                725
```

SEQ ID NO: 121          moltype = DNA   length = 2181
FEATURE                 Location/Qualifiers
source                  1..2181
                        mol_type = other DNA
                        organism = synthetic construct
SEQUENCE: 121

```
caggtgcagc tggtacagag cggagtggaa gtgaaaaagc caggagcctc cgtgaaagtg    60
tcctgcaagg cctctggata caccttcacc aattactaca tgtactgggt gagacaggct    120
cctggacagg gcctggaatg gatgggcgga atcaacccca gcaacggcgg gaccaacttc    180
aacgagaagt tcaagaacag agtgacgctg accacagact cttctacaac caccgcttat    240
atggaactga agtccctgca gttcgacgat accgctgtgt actactgcgc ccggcgggac    300
tatcggttcg acatgggctt cgactactgg ggccaaggca ccaccgtgac cgtctcctcc    360
gctagcacca agggcccctc cgtctttcct ctggcccctt ctagcaagtc taccagcggc    420
ggcaccgccg ccctgggctg tctggtgaag gattacttcc ccgagcctgt taccgtatct    480
tggaactccg gcgctctgac ctctggcgtg cacacatttc ctgctgtgct gcaatcttcc    540
ggcctgtact ccctgtcctc ggtggtgaca gtgccaagct cttctctggg cacacagacc    600
tacatctgca acgtgaacca caagccctcc aacaccaagg tggacaagaa ggtgaaaccc    660
aagtcctgcg acaagaccca cacctgtcca ccatgtccgg cgcctgaggc cgctggcggc    720
ccctctgtgt tcctgttccc tcccaagcct aaggacacac tgatgatctc ccggacccct    780
gaagtgacat gcgtggtggt cgacgtgtct catgaggacc ctgaagtgaa gttcaactgg    840
tacgtggatg gcgtggaagt gcataacgcc aagaccaagc ctcgggaaga gcagtacaac    900
tccacctaca gtggtgtgtc tgtgctgacc gtgctgcacc aggactggct gaacgggaaa    960
gagtacaagt gcaaggtttc taataaggcc tccggcgctc ctatcgagaa gaccatctcc    1020
aaggctaagg gccagcctag agaacctcag gtttacaccc tgcctccgtc tcgcgacgag    1080
ctgacaaaga accaggtgtc tctgacctgc ctggtgaaag gcttctaccc ttccgacatc    1140
gccgtggagt gggagtccaa tgggcagcct gagaacaact ataaaactac ccctcctgtc    1200
ttggactccg acggctcctt cttcctgtac tccaagctga ccgtggataa gtctagatgg    1260
cagcagggca acgtgttttc ctgctccgtg atgcacgagg ccctgcacaa tcactacacc    1320
cagaaatccc taagcttgtc ccctggcaag ggcggaggtg gctctggagg cggtggatct    1380
ggtggtggcg atcaggtgg aggcgggagc caggtgcaac tggtgcaatc cggcgctgag    1440
gtgaagaagc ccggcgcttc cgtgaaggtg tcctgcaagg cctccggtta ctcattcagc    1500
tccttcggca tctcctgggt ccggcaggcc cctggccagt gcctggaatg gctgggctgg    1560
atctctgcct tcaacggcta cacaaagtac gcccagaagt tcaggatag agtgaccatg    1620
accaccgaca ccagcacctc aaccgcctac atggaactga atctctgag atccgacgac    1680
acagctgtgt actactgtgc cagagatccc gctgcttggc ctctgcagca aagcctggct    1740
tggttcgatc cttggggcca aggaaccatg gtgaccgtgt cttctggcgg ctctggcggc    1800
ggtagtggag gaggctctgg tggtggaagc ggcggcagtc ctggcagctc cgtgctgacc    1860
cagcctccct ccgcctccgg caccctggc cagagagtca caatttcttg ctctggctct    1920
acctccaacc tgaagcggaa ctacgtgtat tggtaccagc agctgcctgg cacagctcct    1980
aagctgctga tctaccggga cagaagacgc ccttcgggcg tgcctgacag gttctccggc    2040
tccaaatctg gcaccagcgc ctctctggcc atctctggat tgcggtccga ggatgaggcc    2100
gactactact gcgcttggta cgacagagag ctgtctgagt gggtgttcgg atgtggtacc    2160
aaactgaccg tgctgtaatg a                                               2181
```

SEQ ID NO: 122          moltype = AA   length = 725
FEATURE                 Location/Qualifiers
source                  1..725

```
                        mol_type = protein
                        organism = synthetic construct
SEQUENCE: 122
QVQLVQSGVE VKKPGASVKV SCKASGYTFT NYYMYWVRQA PGQGLEWMGG INPSNGGTNF     60
NEKFKNRVTL TTDSSTTTAY MELKSLQFDD TAVYYCARRD YRFDMGFDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LGAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK GGGGSGGGGS GGGGSGGGGS QSVLTQPPSA    480
SGTPGQRVTI SCSGSTSNLK RNYVYWYQQL PGTAPKLLIY RDRRRPSGVP DRFSGSKSGT    540
SASLAISGLR SEDEADYYCA WYDRELSEWV FGCGTKLTVL GGSGGGSGGG SGGGSGGGGS    600
QVQLVQSGAE VKKPGASVKV SCKASGYSFS SFGISWVRQA PGQCLEWLGW ISAFNGYTKY    660
AQKFQDRVTM TTDTSTSTAY MELRSLRSDD TAVYYCARDP AAWPLQQSLA WFDPWGQGTM    720
VTVSS                                                                725

SEQ ID NO: 123         moltype = DNA   length = 2181
FEATURE                Location/Qualifiers
source                 1..2181
                       mol_type = other DNA
                       organism = synthetic construct
SEQUENCE: 123
caggttcagc tcgtgcagtc cggcgtggaa gtgaagaagc ccggcgcttc cgtgaaagtg     60
agctgtaagg cctccggcta taccttcacc aattactaca tgtactgggt cagacaggct    120
cccggccagg gcctggagtg gatgggcggc atcaaccctt ccaatggcgg caccaacttc    180
aacgagaagt tcaagaacag agtgaccctg accaccgaca gctccaccac aaccgcctac    240
atggaactga gagcctgca gttcgacgac accgccgtgt actactgcgc cagacgggac    300
taccggttcg acatgggctt cgattactgg ggccaaggca ccaccgtgac cgtgtcttct    360
gctagcacca agggacctag cgtgtttccg ttggcacctt cctctaagtc tacatctggc    420
ggaaccgctg ctctgggctg tctggttaag gactacttcc ctgaaccgt aacagtgtct    480
tggaactccg gagctctgac atccggcgtg catacctttc ctgctgtgtt gcaatcctca    540
ggcctgtact ctttatcctc tgttgtcaca gtgccctcct catcactcgg tacacagacc    600
tacatctgca acgtgaacca caagccttcc aacaccaagg tggacaagaa agtggagcgc    660
aaatcttgcg acaaaaccca cacctgtcct ccttgcccgg cgcctgaggc tgctggcggc    720
cctagcgtat tcctgttccc cccaaagccc aaggacaccc tgatgatctc ccggacccct    780
gaggtgacct gcgtggtggt ggacgtgtct cacgaggacc ctgaagtgaa gttcaactgg    840
tatgtggacg gcgtggaagt gcacaacgcc aagaccaagc cccgggaaga gcagtacaac    900
tctacctaca gtggtgtc cgtgctgaca gtgctgcaca ggactggct gaacggtaaa    960
gagtataagt gcaaggtgtc taacaaggcc ctgggcgctc ctatcgagaa aaccatctcc   1020
aaggctaagg gccaacctag agagcctcag gtgtacaccc tgccaccttc cagggacgag   1080
ctgaccaaga accaggtgtc tctgacttgc ctggtcaagg gcttctaccc ttccgacatc   1140
gccgtggaat gggagtccaa tggccagccc gagaacaact acaagaccac ccctcctgtc   1200
ctggactccg atggcagctt cttcctgtac tccaaactga ccgtggataa atccagatgg   1260
cagcaaggca acgtgttctc ctgctctgtg atgcacgagg ccctgcataa ccactacacc   1320
cagaaatccc taagcttgtc tcccggaaag ggcgaggtg gctctggagg cggtggatct   1380
ggtggtggcg gatcaggtgg aggcggggac cagtccggtc gacccagcc tccaagcgcc   1440
agcggcaccc caggccagag agtgacaatc agctgctccg gctccacctc caacctgaag   1500
cggaactacg tgtactggta ccagcagctg cctggaacag ctcctaagct gctgatctac   1560
agagaccgga gaagacctag cggcgtgcca gatagattct ctggtccaa gtccggcacc   1620
tctgcctccc tggccatctc cggcctgcgg tccgaagacg aggccgacta ctactgcgcc   1680
tggtacgaca gagaactgtc tgagtgggtg tttggctgcg gcacaaagct gaccgtgctg   1740
ggcggctccg gcgcggtag tggaggagc tctggtggtg gaagcggcgg cggatctggc   1800
caggtgcaac tggtgcagtc cggagccgag gtgaagaagc ctggcgcttc cgtcaaggtg   1860
tcctgtaagg cttctggcta ctcttttct tctttcggca tttcctgggt gcggcaggcc   1920
cctggccagt gcctggaatg gctgggctgg atcagcgcct tcaacggcta caccaagtac   1980
gcccagaagt tccaggatcg cgtcaccatg accaccgaca cgtcgacatc caccgcttac   2040
atggaactga gatccctgcg gtctgacgat accgccgtgt attactgcgc cagagatcct   2100
gccgcttggc ctctgcagca gtctctggcc tggttcgacc cttggggaca gggcaccatg   2160
gtgaccgtct cctcctaatg a                                             2181

SEQ ID NO: 124         moltype = AA   length = 725
FEATURE                Location/Qualifiers
source                 1..725
                       mol_type = protein
                       organism = synthetic construct
SEQUENCE: 124
QVQLVQSGAE VKKPGASVKV SCKASGYSFS SFGISWVRQA PGQGLEWLGW ISAFNGYTKY     60
AQKFQDRVTM TTDTSTSTAY MELRSLRSDD TAVYYCARDP AAWPLQQSLA WFDPWGQGTM    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSNTKVD KKVEPKSCDK THTCPPCPAP    240
EAAGGPSVFL FPPKPKDTLM ISRTPEVTCV VVDVSHEDPE VKFNWYVDGV EVHNAKTKPR    300
EEQYNSTYRV VSVLTVLHQD WLNGKEYKCK VSNKALGAPI EKTISKAKGQ PREPQVYVYP    360
PSRDELTKNQ VSLTCLVKGF YPSDIAVEWE SNGQPENNYK TTPPVLDSDG SFALVSKLTV    420
DKSRWQQGNV FSCSVMHEAL HNHYTQKSLS LSPGKGGGGS GGGGSGGGGS GGGGSQVQLV    480
QSGVEVKKPG ASVKVSCKAS GYTFTNYYMY WVRQAPGQGL EWMGGINPSN GGTNFNEKFK    540
NRVTLTTDSS TTTAYMELKS LQFDDTAVYY CARRDYRFDM GFDYWGQGTT VTVSSGGSGG    600
GSGGGGSGGG GSGEIVLTQ SPATLSLSP GERATLSCRA SKGVSTSGYS YLHWYQQKPG    660
QAPRLLIYLA SYLESGVPAR FSGSGSGTDF TLTISSLEPE DFAVYYCQHS RDLPLTFGGG    720
```

-continued

```
TKVEI                                                                   725

SEQ ID NO: 125          moltype = DNA   length = 2181
FEATURE                 Location/Qualifiers
source                  1..2181
                        mol_type = other DNA
                        organism = synthetic construct
SEQUENCE: 125
caggtgcagc tggtgcagag cggagccgag gtgaaaaagc ccggcgcttc tgtgaaggtg   60
tcctgcaagg cttccggcta ctccttctcc tctttcggca tctcctgggt cagacaggcc  120
cctggccaag gcctggagtg gctgggctgg atctctgcct tcaatggcta taccaagtac  180
gcccagaagt tccaggacag agtgaccatg accaccgaca cctccaccag caccgcctac  240
atggaactgc ggtccctgag atccgacgac accgccgtgt actactgcgc cagagaccct  300
gcagcctggc ctctgcagca atctctggct tggttcgatc cttggggcca aggcaccatg  360
gtgaccgtca gtagcgctag caccaaggga ccttcggtgt tccctctggc cccaagctcc  420
aagtccacat caggcggtac cgctgctctc ggctgcctgg tgaaggacta cttccccgag  480
cccgtgaccg tgtcttggaa ctccggcgct ctgacctccg gcgtgcatac atttcctgcc  540
gtgctgcagt cctctgggct gtacagtctg agctccgtgg tgacggtgcc ctcctcctct  600
ctgggcaccc agacctacat ctgcaacgtg aaccacaagc ctagcaacac caaggtggac  660
aagaaagtgg agcctaagtc ttgcgacaag acccacacct gccctccttg tccggcgcct  720
gaggccgctg gcgggccttc cgtgttcctg ttccccccca agccaaagga cactctgatg  780
atcagcagga cacctgaagt gacctgtgtg gtggtggacg tgtcccacga agatcctgaa  840
gtgaagttta actggtacgt ggacggcgtg gaggtgcaca acgccaagac caagcctcgc  900
gaggagcagt acaactccac ctaccgggtg gtctctgtgc tgaccgtgct gcaccaggat  960
tggctgaacg gcaaagagta caagtgcaag gtgtccaaca aggccctggg cgctcctatc  1020
gagaaaacca tctccaaagc taaggccagc cctagagcc ctcaggtgta cgtgtatcca  1080
ccttcccggg acgagctgac aaagaaccag gtcagcctga catgtctggt caagggcttc  1140
tacccctctg acatcgccgt ggaatgggag tctaatggcc aacctgagaa caactacaag  1200
accacccctc ctgtgctgga ctccgatggc agtttcgccc tggtctccaa gctgaccgtg  1260
gataagtcta gatggcagca gggcaacgtc ttctcctgct ccgtgatgca cgaggctctg  1320
cataatcact acacccagaa gtctctaagc ttgtctcctg gaaaaggcgg aggtggctct  1380
ggaggcggtg gatctggtgg tggcggatca ggtggaggcg ggagccaggt gcagctggtg  1440
cagtctggtg tagaagtgaa gaagcccggc gcttctgtta aagtctcctg caaagcctcc  1500
ggctacacct tcaccaacta ctacatgtac tgggtgcggc aggcccctgg ccaggcttg  1560
gaatggatgg gcggcatcaa cccttccaac ggcggcacca acttcaacga gaagttcaag  1620
aaccgggtta cactgaccac agatagctct accaccactg cctacatgga actgaagtcc  1680
ctgcagttcg acgataccgc tgtgtactac tgtgctagaa gagattatcg gtttgacatg  1740
ggcttcgact actggggcca gggcaccacc gtgacagttt cctccggtgg ctctggcggc  1800
ggtagtggag gaggctgtgg tggtggaagc ggcggcggat ctggcgaagt cgtgctgacc  1860
cagtctccag ctaccctgag cctgtcccct ggcgaaaagg ccaccctgag ctgcagagcc  1920
tctaagggcg tgtctacctc aggctactcc tacctgcact ggtaccagca gaaacctggc  1980
caggctccta gactgctgat ctacctggcc tcttatctcg agtccggcgt gcctgcccgg  2040
ttctctggct ctggctccgg caccgacttc accctgacca ttagctctct ggaaccggag  2100
gactttgccg tgtactactg ccagcactcc agagacctgc ctctgacctt tggcgggggc  2160
accaaggtgg aaatctaatg a                                             2181

SEQ ID NO: 126          moltype = AA   length = 454
FEATURE                 Location/Qualifiers
source                  1..454
                        mol_type = protein
                        organism = synthetic construct
SEQUENCE: 126
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALGAPI EKTISKAKGQ PREPQVYVLP  360
PSRDELTKNQ VSLLCLVKGF YPSDIAVEWE SNGQPENNYL TWPPVLDSDG SFFLYSKLTV  420
DKSRWQQGNV FSCSVMHEAL HNHYTQKSLS LSPG                               454

SEQ ID NO: 127          moltype = DNA   length = 1368
FEATURE                 Location/Qualifiers
source                  1..1368
                        mol_type = other DNA
                        organism = synthetic construct
SEQUENCE: 127
caagtgcagc tggtgcagag cggcgctgag gtgaagaagc ctggcgcttc tgtgaaagtg   60
tcctgcaagg cctccggcta ttccttctcc tctttcggca tcagctgggt cagacaggcc  120
cccggccaag gcctggaatg gctgggctgg atctctgcct tcaacggcta tacaaagtac  180
gcccagaagt tccaggatcg ggtgaccatg accaccgaca cctccaccag caccgcctac  240
atggaactga atccctgcg tccgacgac accgctgtgt actactgcgc cagagatcct  300
gctgcttggc cctgcagca gtctctggcc tggttcgacc cttggggcca gggcaccatg  360
gtgacagttt cctctgctag cacaaagggc ccttccggtg tcttccagc  420
aagtctacct tggtggaac agccgccctg ggctgtctgg tcaaggacta cttcccagag  480
cctgtgacag tgtcttggaa ctctggcgct ctgacatccg gagtgcatac cttccctgcc  540
gtgctgcagt cttccggact gtactccctg tcctccgtgg tcaccgtgcc ttccagctct  600
ttgggaaccc agacctacat ctgcaacgtg aaccacaagc catctaacac caaggtggac  660
aagaaggtgg aacctaagtc ctgtgataaa acccacacgt gccctccttg cccggcgcct  720
```

```
gaggctgctg gcggcccaag cgtgttcctc ttcccccca agcctaagga taccctgatg      780
atctccagaa cccctgaggt gacctgtgtg gtggtggacg tgtcgcacga ggaccccgaa      840
gtgaagttta actggtacgt cgacggcgtg gaagtgcaca acgccaagac caagcccaga      900
gaggaacagt acaactccac ctacagagtg gtgtctgtgc tgaccgtgct gcaccaggac      960
tggctgaacg gcaaagagta caagtgcaaa gtctccaaa aggctctcgg cgctcccatc     1020
gagaagacca tcagcaaggc caagggccag cctcgggaac cacaggtgta cgtgctgcct     1080
ccttctcgcg acgagctgac caagaaccag gtgtccctgc tgtgcctggt caaaggcttc     1140
tacccctctg acatcgccgt ggagtgggag tccaatggcc agcctgagaa caactacctg     1200
acctggcctc ctgtgctgga ctccgatggc agcttctttc tgtactccaa gctgaccgtg     1260
gacaagtcta gatggcagca aggcaacgtg ttctcttgct ccgtgatgca cgaggctctg     1320
cataatcact acacccagaa atccctaagc ttgtctcctg gataatga               1368
```

SEQ ID NO: 128          moltype = AA   length = 726
FEATURE                 Location/Qualifiers
source                  1..726
                        mol_type = protein
                        organism = synthetic construct
SEQUENCE: 128
```
QVQLVQSGAE VKKPGASVKV SCKASGYSFS SFGISWVRQA PGQGLEWLGW ISAFNGYTKY       60
AQKFQDRVTM TTDTSTSTAY MELRSLRSDD TAVYYCARDP AAWPLQQSLA WFDPWGQGTM      120
VTVSSASTKG PSVFPLAPSS KSTSGGTAAL GCLVKDYFPE PVTVSWNSGA LTSGVHTFPA      180
VLQSSGLYSL SSVVTVPSSS LGTQTYICNV NHKPSNTKVD THTCPPCPAP              240
EAAGGPSVFL FPPKPKDTLM ISRTPEVTCV VVDVSHEDPE VKFNWYVDGV EVHNAKTKPR      300
EEQYNSTYRV VSVLTVLHQD WLNGKEYKCK VSNKALGAPI EKTISKAKGQ PREPQVYVYP      360
PSRDELTKNQ VSLTCLVKGF YPSDIAVEWE SNGQPENNYK TTPPVLDSDG SFALVSKLTV      420
DKSRWQQGNV FSCSVMHEAL HNHYTQKSLS LSPGKGGGGS GGGGSGGGGS GGGGSEIVLT      480
QSPATLSLSP GERATLSCRA SKGVSTSGYS YLHWYQQKPG QAPRLLIYLA SYLESGVPAR      540
FSGSGSGTDF TLTISSLEPE DFAVYYCQHS RDLPLTFGGG TKVEIKGGSG GGGSGGGSGGGG      600
SGGGGSGQVQL VQSGVEVKKP GASVKVSCKA SGYTFTNYYM YWVRQAPGQG LEWMGGINPS      660
NGGTNFNEKF KNRVTLTTDS STTAYMELK SLQFDDTAVY YCARRDYRFD MGFDYWGQGT      720
TVTVSS                                                            726
```

SEQ ID NO: 129          moltype = DNA   length = 2184
FEATURE                 Location/Qualifiers
source                  1..2184
                        mol_type = other DNA
                        organism = synthetic construct
SEQUENCE: 129
```
caggtgcagc tggtccagag cggagccgag gtcaagaagc ccggagcttc tgtgaaggtg       60
tcttgcaagg cctccggcta ctccttctcc tcctttggaa tctcctgggt gcggcaggcc      120
cctggccagg gcctggaatg gctgggctgg atctccgcct tcaacggcta taccaagtac      180
gcccagaagt tccaggacag agtaacaatg accaccgata cctctacctc taccgcctac      240
atggaactgc ggtccctgag atctgatgac accgccgtgt actactgcgc cagggaccct      300
gcagcttggc ctctgcagca gtctctggcc tggttcgatc cttggggaca aggaaccatg      360
gtgaccgtga gttccgctag caccaaaggc ccttccgtgt tcccctggc cctagctcc      420
aaatccacct ccgaggaac tgctgccctg ggctgcctgg tgaaggacta cttccccgag      480
cccgtgacag tctcctggaa ctctggcgct ctgacatctg gtgtgcacac ctttccagct      540
gtcctgcaaa gctctggact gtactccctg tcctccgtgg tgaccgtgcc tagctcttct      600
ctgggcaccc agacctacat ctgcaacgtg aaccacaagc cttccaacac caaagtggac      660
aagaaagtgg aacccaagtc ctgcgacaaa acccacacct gtccaccctg tccggcgcct      720
gaggctgctg gcggcccctc cgtgttcctg ttccctccta agcctaagga caccctgatg      780
atcagccgga cccctgaggt gacctgcgtg gtggtcgacg tgtcccacga ggaccctgag      840
gtgaagttca ctggtatgt ggacggcgtg gaagtgcata cgccaagac caagcctcgg      900
gaagagcagt acaactccac atacagagtc gtgtccgtgc tgaccgtgct gcaccaggat      960
tggctgaacg gcaaagagta caagtgcaag gtgtccaaa aggccctggg cgctcctatt     1020
gagaagacca tctccaaagc caagggccag cctagagagc ctcaggtcta cgtctaccct     1080
ccttctcggg acgagctgac caagaaccag gtgtctctga cctgtctggt gaagggcttc     1140
tacccatctg acatcgccgt ggagtgggag tccaacggcc agcccgagaa caattacaag     1200
accacacctc ctgtgctgga ctccgatggc tccttcgcc tcgtgagcaa gctgaccgtg     1260
gacaagtcta gatggcagca aggcaacgtg ttctcctgct ccgtgatgca cgaggccctg     1320
cacaaccact acacccagaa gtctctaagc ttgtctcccg gcaagggcgg aggtggctct     1380
ggaggcggtg gatctggtgg tggcggatca ggtggaggcg ggagcgagat cgtgctgaca     1440
cagtcccctg ctacactgag cctgagccct ggcgagcggg ctaccctgag ctgcagagcc     1500
tccaagggcg tttccacctc tggctactct tacctccagg ataccagca gaaacctgga     1560
caggcccca gactgctgat ctacctggcc tcctacctgg aatctggagt gcccgctcgc     1620
ttttctggca gcggctccgg caccgacttc acactgacaa tctcctccct ggaacctgag     1680
gactttgctg tgtactactg ccagcactct agagacctgc ctctgacctt cggcggcggc     1740
accaaggtgg aaatcaaggg cggctcgggc ggcggtagtg gaggaggctc tggtggtgga     1800
agcggcggcg gatctggcca agtgcagctg gtgcagtctg gagtggaagt gaagaagcca     1860
ggcgcttctg ttaaggtgtc ctgcaaggcc tctggctata ccttcaccaa ttattacatg     1920
tactgggtca gacaggctcc tggccaggc ctcgagtgga tgggcggcat caacccttct     1980
aatggcggca ccaacttcaa cgagaagttc aagaacagtg tgaccctgac caccgactcc     2040
agcaccacca cggcctatat ggaactgaag tctctgcagt tcgacgacac agctgtgtac     2100
tactgtgcca ggagagatta ccggttcgac atgggctttg attactgggg ccagggcacc     2160
acagtgaccg tgtcctctta atga                                        2184
```

SEQ ID NO: 130          moltype = AA   length = 725
FEATURE                 Location/Qualifiers
source                  1..725

-continued

```
                         mol_type = protein
                         organism = synthetic construct
SEQUENCE: 130
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALGAPI EKTISKAKGQ PREPQVYVYP  360
PSRDELTKNQ VSLTCLVKGF YPSDIAVEWE SNGQPENNYK TTPPVLDSDG SFALVSKLTV  420
DKSRWQQGNV FSCSVMHEAL HNHYTQKSLS LSPGKGGGGS GGGGSGGGGS GGGGSQVQLV  480
QSGVEVKKPG ASVKVSCKAS GYTFTNYYMY WVRQAPGQCL EWMGGINPSN GGTNFNEKFK  540
NRVTLTTDSS TTTAYMELKS LQFDDTAVYY CARRDYRFDM GFDYWGQGTT VTVSSGGSGG  600
GSGGGGSGGG GGGSGEIVLT QSPATLSLSP GERATLSCRA SKGVSTSGYS YLHWYQQKPG  660
QAPRLLIYLA SYLESGVPAR FSGSGSGTDF TLTISSLEPE DFAVYYCQHS RDLPLTFGCG  720
TKVEI                                                              725

SEQ ID NO: 131          moltype = DNA  length = 2181
FEATURE                 Location/Qualifiers
source                  1..2181
                        mol_type = other DNA
                        organism = synthetic construct
SEQUENCE: 131
caggtgcagc tggtgcagag cggcgctgag gtgaagaagc ctggagcttc cgtcaaggtg   60
tcctgcaagg cctccggcta ctccttctcc agcttcggaa tttcctgggt cagacaggcc  120
ccaggccaag gcctggagtg gctgggctgg atctccgcct tcaacggcta caccaagtac  180
gcccagaagt tccaggacag agttaccatg accaccgaca ccagcacctc taccgcatac  240
atggaactga gatctctcag atctgacgat acagctgtgt actactgcgc cagagacccc  300
gccgcctggc ctctgcagca gtctctggcc tggttcgatc catggggcca gggcaccatg  360
gtcaccgtga gttctgctag caccaaaggc ccatccgtct tccccctggc cccatcttcc  420
aagtccacct ctggcggcac cgctgctctg ggcgtgtctgg tcaaggacta cttccctgag  480
cccgtgaccg tgtcttggaa ctccggcgct ctcacctctg gcgtgcatac ctttcctgcc  540
gtgctgcaat cctccggcct gtactccctg agctctgtgg tgaccgtgcc ttctagctca  600
ctgggcaccc agacctacat ctgcaacgtg aaccacaagc ctagcaacac caaggtggac  660
aagaaagtgg aacctaagtc ctgcgacaag acacacacct gtcctccttg cccggcgcct  720
gaggctgctg gcggaccttc agtgttcctg ttccccccta gcccaaggga taccctgatg  780
atctctagaa cccctgaagt gacctgcgtg gttgtggacg tgagccatga agatcccgag  840
gtgaagttca actggtacgt ggatggcgtc gaggtgcaca acgccaagac caagcctaga  900
gaggaacagt acaactctac ctacagagtg gtgtccgtgc tgacagtgct gcaccaggac  960
tggctgaacg gcaaagagta caagtgcaag gtcagcaaca aggctctggg cgctcctatc 1020
gagaaaacca tcagcaaggc caagggccaa cctcgcgagc ctcaggtcta cgtgtatcct 1080
ccatcacggg acgagctgac caagaaccag gtatcactga catgcctggt gaagggcttc 1140
tacccctccg acatcgccgt ggaatgggag tccaatgcc agctgagaa caactacaag 1200
acaacccctc ctgtgctgga ctctgacggc tcttttgccc tggtgtccaa gctgacggtg 1260
gataagtcca gatggcagca gggcaacgtg ttcagctgtt ctgtaatgca cgaagccctg 1320
cacaatcact acacccagaa atctctaagc ttgtctcctg gcaagggcgg aggtggctct 1380
ggaggcggtg gatctggtgg tggcggatca ggtggaggcg ggagccaggt gcagctggtg 1440
caatctggcg ttgaggtgaa aaagcctggc gcatccgtga aggtgtcctg taaagccagt 1500
ggctacacct tcaccaatta ctacatgtac tgggtgcggc aggccccgg ccagtgcctg 1560
gaatggatgg gaggcatcaa cccctccaac ggcggcacca acttcaacga gaagttcaag 1620
aacagagtga ccctgacgac cgactcctcc accaccgcct cttacatgga actgaagtcc 1680
ctgcagttcg acgacaccgc tgtgtactac tgtgctcggc gggattaccg gttcgacatg 1740
ggctttgact attggggcca gggcacaacc gtgaccgtgt cctctggcgg ctctggcggc 1800
ggtagtggag gaggctctgg tggtggaagc ggcggcggat ctggcgagat cgtgctgacc 1860
cagagccctg ccaccctgag cctgtcccct ggcgagcgg ccacactgtc ttgcagagcc 1920
tctaagggcg tctccacatc tggctattct tacctgcact ggtaccagca aaagcctgga 1980
caggctcctc ggctgctgat ctacctggct tcctatctgg aatccggcgt gcccgccaga 2040
ttctccggtt ccggctctgg caccgatttc acactgacaa tctcctctct ggagcctgag 2100
gacttcgccg tgtactactg ccagcactcc agggacctgc ctctgacctt cggctgcggc 2160
acgaaagtgg aaatctaatg a                                           2181

SEQ ID NO: 132          moltype = AA  length = 726
FEATURE                 Location/Qualifiers
source                  1..726
                        mol_type = protein
                        organism = synthetic construct
SEQUENCE: 132
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALGAPI EKTISKAKGQ PREPQVYVYP  360
PSRDELTKNQ VSLTCLVKGF YPSDIAVEWE SNGQPENNYK TTPPVLDSDG SFALVSKLTV  420
DKSRWQQGNV FSCSVMHEAL HNHYTQKSLS LSPGKGGGGS GGGGSGGGGS GGGGSEIVLT  480
QSPATLSLSP GERATLSCRA SKGVSTSGYS YLHWYQQKPG QAPRLLIYLA SYLESGVPAR  540
FSGSGSGTDF TLTISSLEPE DFAVYYCQHS RDLPLTFGCG TKVEIKGGSG GGSGGGGSGG  600
SGGGGSGVQL VQSGVEVKKP GASVKVSCKA SGYTFTNYYM YWVRQAPGQC LEWMGGINPS  660
NGGTNFNEKF KNRVTLTTDS STTTAYMELK SLQFDDTAVY YCARRDYRFD MGFDYWGQGT  720
```

-continued

```
TVTVSS                                                            726

SEQ ID NO: 133        moltype = DNA   length = 2184
FEATURE               Location/Qualifiers
source                1..2184
                      mol_type = other DNA
                      organism = synthetic construct
SEQUENCE: 133
caggtgcagc tggtgcagtc cggcgctgaa gtgaagaagc ccggcgcttc cgtgaaggtg    60
tcttgcaagg cctcaggcta cagcttctcc tcctttggca tctcttgggt gcggcaggcc   120
cctggccagg gcctggaatg gctgggctgg atctccgcct tcaatggcta taccaagtac   180
gcccagaagt ccaagacag agtgaccatg accaccgaca cctctaccag cacggcctac   240
atggaactga gatctctgcg gtccgacgat accgccgtgt actattgtgc cagagatccc   300
gcagcttggc ctctgcagca gagcctggcc tggttcgatc cttggggcca aggcaccatg   360
gtgaccgtgt cttctgctag caccaaagga ccttccgtgt tcctctcgc tccctcctcc   420
aagtccactt ccggcggcac cgctgctctg ggctgcctgg tcaaggacta cttccctgag   480
cctgtgaccg tgtcttggaa ctctggcgct ctgaccagcg gcgtgcatac cttccccgcc   540
gtgctgcagt cttccggcct gtactccctg tcctccgtgg tgaccgtgcc ctcctcctct   600
cttggcaccc agacctacat ctgcaacgtg aaccacaagc ccagcaacac caaagtggat   660
aagaaagtgg aacctaaatc ttgcgacaag acccacacct gcctcctgg tccggcgcct   720
gaggccgctg gcggcccttc tgtgttcctg ttccctccta gcctaagga caccctgatg   780
atcagtcgga cacctgaggt cacctgtgtg gtagtgacga tgtcgcatga ggaccccgaa   840
gtgaagttca actggtacgt ggatggcgtg gaagtgcaca acgccaagac caagcctaga   900
gaagagcagt acaactccac ctacagtgt gtctccgtgc tgactgtgtt acaccaggat   960
tggctgaacg gcaaagagta caagtgcaag gtgtccaaca aggccctggg cgctcctatc  1020
gagaagacca tctccaaggc caaggacag cctagagacg ctcaggttta cgtgtaccct  1080
ccatcgcgcg acgagctgac caagaaccag gtgtcgctga cctgtctggt caaaggcttc  1140
tacccccagcg acatcgccgt ggagtgggag tccaacggcc aacctgagaa caactacaag  1200
acaaccccac ctgtgctgga ctctgacggc tccttcgcc tggtgtccaa gctgacagtg  1260
gacaagtcca gatggcagca gggcaacgtg ttctcctgct ccgtgatgca cgaggctctg  1320
cacaatcact acacccagaa gtccctaagc ttgtctcctg gcaagggcgg aggtggctct  1380
ggaggcggtg gatctggtgg tggcggatca ggtggaggcg ggagcgagat cgtgctgaca  1440
cagtcgcctg ctaccctgtc tctgtcccca ggcgagagag ccaccctgtc ttgcagagcc  1500
tccaaggcg tgtccaccag cggatactcc tacctggct ggtaccagca aaagcccggc  1560
caggcccctc ggctgctgat ctacctggct tcttacctgg aatccggcgt gcctgctaga  1620
ttcagcggct ccgggagtgg caccgatttt acactgacca tttctagcct ggaaccggag  1680
gactttgccg tctattactg ccagcactcc cgggacctgc ctctcacatt cggctgtggc  1740
accaaggtgg agatcaaagg cggaagcggc ggcggtagtg gaggaggctc tggtggtgga  1800
agcggcggcg gatctggcca agtgcagctg gtacagtctg gcgtggaagt gaagaagcct  1860
ggagcctccg tgaaagtgtc ctgcaaggcc tctggctaca ccttcaccaa ctactacatg  1920
tactgggtca gacaggctcc tggacagtgc ctggagtgga tgggcggcat caacccttct  1980
aatgcggaa ccaacttcaa cgagaagttc aagaaccggg tcacgctgac cacagactcc  2040
tctaccacaa cagcctatat ggaactgaag tctctgcagt tcgacgacac cgctgtgtac  2100
tactgcgccc ggagagatta ccggttcgac atgggctttg actactgggg ccagggcaca  2160
accgtgaccg tctcctccta atga                                        2184

SEQ ID NO: 134        moltype = AA    length = 584
FEATURE               Location/Qualifiers
source                1..584
                      mol_type = protein
                      organism = synthetic construct
SEQUENCE: 134
QVQLVQSGAE VKKPGASVKV SCKASGYSFS SFGISWVRQA PGQGLEWLGW ISAFNGYTKY    60
AQKFQDRVTM TTDTSTSTAY MELRSLRSDD TAVYYCARDP AAWPLQQSLA WFDPWGQGTM   120
VTVSSGGGGS GGGGSQVQLV QSGVEVKKPG ASVKVSCKAS GYTFTNYYMY WVRQAPGQGL   180
EWMGGINPSN GGTNFNEKFK NRVTLTTDSS TTTAYMELKS LQFDDTAVYY CARRDYRFDM   240
GFDYWGQGTT VTVSSASTKG PSVFPLAPSS KSTSGGTAAL GCLVKDYFPE PVTVSWNSGA   300
LTSGVHTFPA VLQSSGLYSL SSVVTVPSSS LGTQTYICNV NHKPSNTKVD KKVEPKSCDK   360
THTCPPCPAP EAAGGPSVFL FPPKPKDTLM ISRTPEVTCV VVDVSHEDPE VKFNWYVDGV   420
EVHNAKTKPR EEQYNSTYRV VSVLTVLHQD WLNGKEYKCK VSNKALGAPI EKTISKAKGQ   480
PREPQVYTLP PSRDELTKNQ VSLTCLVKGF YPSDIAVEWE SNGQPENNYK TTPPVLDSDG   540
SFFLYSKLTV DKSRWQQGNV FSCSVMHEAL HNHYTQKSLS LSPG                   584

SEQ ID NO: 135        moltype = DNA   length = 1758
FEATURE               Location/Qualifiers
source                1..1758
                      mol_type = other DNA
                      organism = synthetic construct
SEQUENCE: 135
caggttcagc tggtgcagtc tggtgccgag gtgaagaaac ccggcgcttc cgtcaaggtg    60
tcttgcaagg cttctggcta ctccttctct agctttggca tctcctgggt cagacaggct   120
cctggccagg gcctcgagtg gctgggctgg atcagcgctt ttaatggcta caccaagtac   180
gcccagaagt ccaggacag agtgaccatg accaccgata cctctacctc cacagcttat   240
atggagctga gatctctgcg gtccgacgac accgccgtgt actactgcgc cagagatcct   300
gccgcctggc ctctgcagca gagcctggct tggttcgacc cttggggcca gggcaccatg   360
gtgacagtgt cttctggagg aggcggctcc ggcggaggcg ctctcaggt gcaactggtc   420
cagtccggcg tggaagtgaa gaagcccggc gcttccgtga agtgtcctg caaggcctcc   480
ggctatacct tcaccaacta ctacatgtac tgggtgcggc aggcccccag ccaaggcctg   540
gagtggatgg gcggcatcaa ccctagcaac ggcggaacaa acttcaacga gaagttcaag   600
```

-continued

```
aaccgggtga ccctgaccac cgactcctcc accacaactg cctacatgga actgaagtcc   660
ctgcagttcg atgacaccgc tgtgtactac tgtgccagac gggactacag attcgacatg   720
ggcttcgact actggggaca aggcaccacc gtgaccgtgt cctctgctag cacaaaagga   780
ccttctgttt ttcctctggc tccatcctcc aagtccacat ccggcggaac cgctgccctc   840
ggctgcctgg tcaaggacta cttccccgag cctgtgaccg tgtcttggaa ctccggagca   900
ctcacctccg gcgtgcatac cttccccgct gtgctgcagt cttctggact gtactccctg   960
tccagcgttg tgacagtgcc ttcttctagc ctgggcacac agacctacat ctgcaacgtg  1020
aatcacaagc ccagcaacac caaagtggat aagaaagtcg agcccaagtc ttgcgacaaa  1080
acccacacct gtccaccctg tccggcgcct gaggccgctg gcggcccttc tgtgtttctg  1140
ttccctccta gcccaaagga taccctgatg atctctcgga cccctgaggt gacctgcgtg  1200
gtggtggacg tgtctcacga ggaccctgaa gtgaagttca actggtacgt ggacggcgtg  1260
gaagtgcaca atgccaagac caagcctaga gaggaacagt acaactccac ctacagagtg  1320
gtgtcagtcc tgacggtgct gcaccaggac tggctgaacg gcaaagagta caagtgcaag  1380
gtgtccaaca aggccctggg cgctcctatc gagaagacaa tcagcaaggc caaggggcaa  1440
ccccgggaac ctcaggtgta caccctgcct ccctcccgcg acgaactgac caagaaccag  1500
gtgtccctga cctgtctggt gaagggcttc taccttctg acatcgccgt ggagtgggag  1560
tccaacggcc agcctgagaa caactacaag accacacctc ccgtgctgga ctctgatggc  1620
tccttcttcc tgtatagcaa gctgacagtc gacaagtcca gatggcagca gggcaacgtg  1680
ttctcctgct ccgtgatgca cgaggctctg cataaccact acacccagaa atctctgtcc  1740
ctgtctcctg gttaatga                                                1758
```

SEQ ID NO: 136          moltype = AA   length = 338
FEATURE                 Location/Qualifiers
source                  1..338
                        mol_type = protein
                        organism = synthetic construct
SEQUENCE: 136
```
QSVLTQPPSA SGTPGQRVTI SCSGSTSNLK RNYVYWYQQL PGTAPKLLIY RDRRRPSGVP   60
DRFSGSKSGT SASLAISGLR SEDEADYYCA WYDRELSEWV FGGGTKLTVL GGGGSGGGGS  120
EIVLTQSPAT LSLSPGERAT LSCRASKGVS TSGYSYLHWY QQKPGQAPRL LIYLASYLES  180
GVPARFSGSG SGTDFTLTIS SLEPEDFAVY YCQHSRDLPL TFGGGTKVEI KRTVAAPSVF  240
IFPPSDEQLK SGTASVVCLL NNFYPREAKV QWKVDNALQS GNSQESVTEQ DSKDSTYSLS  300
STLTLSKADY EKHKVYACEV THQGLSSPVT KSFNRGEC                          338
```

SEQ ID NO: 137          moltype = DNA   length = 1020
FEATURE                 Location/Qualifiers
source                  1..1020
                        mol_type = other DNA
                        organism = synthetic construct
SEQUENCE: 137
```
cagtctgtgc tgacccagcc tccttctgct tctggcaccc ctggccagcg ggtgaccatc   60
tcctgttccg gctctacctc caacctgaaa cggaactatg tgtactggta ccagcagctg  120
cctggaaccg cccctaagct gctgatctac agagatcgcc ggcgtcc ggcgtgccc  180
gaccggttct ccggaagcaa gtccggcacc tccgccagcc tggccatctc tggcctgaga  240
tctgaggatg aggctgatta ctactgcgcc tggtacgaca gagaactgag cgagtgggtg  300
ttcggcggcg gaaccaagct gaccgtcctg ggcggcggcg gctctggcgg cggaggctcc  360
gagatcgtgc tcacccaatc tcctgccaca ctgtctctct ctcccggcga aagagccacc  420
ctgtcctgca gagcctctaa gggcgtgtcc acctccggct actcctacct gcactggtat  480
cagcagaagc ccggccaagc tcctagactg ctgatctacc tggcttctta cctggaatca  540
ggcgtgcctg ctagattcag cggctccggc agcggaaccg acttcaccct gacaatctcc  600
tctctggagc ctgaggactt cgccgtgtac tactgccagc attctaggga cctgcccctg  660
acctttggcg gtggcaccaa agtggaaatc aagcggaccg tggctgcccc atccgtgttc  720
atcttccctc catccgacga gcagctgaag tccggcacag ccagcgtggt ctgcctgctg  780
aacaacttct accccagaga ggctaaggtg cagtggaagg tggacaacgc cctgcagtca  840
ggcaattccc aagaatccgt tacggaacag gactccaaag attccaccta ctctctgtcg  900
tctacactga ccctgtccaa ggccgactac gagaagcaca aggtgtacgc ctgcgaggtg  960
acccaccagg gcttgtccag tcctgtgaca aagagcttta cagaggcgca gtgttaatga 1020
```

SEQ ID NO: 138          moltype = AA   length = 584
FEATURE                 Location/Qualifiers
source                  1..584
                        mol_type = protein
                        organism = synthetic construct
SEQUENCE: 138
```
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
GGGGSGGGGS QVQLVQSGAE VKKPGASVKV SCKASGYSFS SFGISWVRQA PGQGLEWLGW  180
ISAFNGYTKY AQKFQDRVTM TTDTSTSTAY MELRSLRSDD TAVYYCARDP AAWPLQQSLA  240
WFDPWGQGTM VTVSSASTKG PSVFPLAPSS KSTSGGTAAL GCLVKDYFPE PVTVSWNSGA  300
LTSGVHTFPA VLQSSGLYSL SSVVTVPSSS LGTQTYICNV NHKPSNTKVD KKVEPKSCDK  360
THTCPPCPAP EAAGGPSVFL FPPKPKDTLM ISRTPEVTCV VVDVSHEDPE VKFNWYVDGV  420
EVHNAKTKPR EEQYNSTYRV VSVLTVLHQD WLNGKEYKCK VSNKALGAPI EKTISKAKGQ  480
PREPQVYTLP PSRDELTKNQ VSLTCLVKGF YPSDIAVEWE SNGQPENNYK TTPPVLDSDG  540
SFFLYSKLTV DKSRWQQGNV FSCSVMHEAL HNHYTQKSLS LSPG                   584
```

SEQ ID NO: 139          moltype = DNA   length = 1758
FEATURE                 Location/Qualifiers
source                  1..1758
                        mol_type = other DNA

```
                             organism = synthetic construct
SEQUENCE: 139
caagtgcagc tggtgcaatc tggtgttgaa gtgaagaagc ctggcgcttc cgtgaaggtc   60
agctgtaagg cctctggcta taccttcacc aactactaca tgtactgggt acggcaggcc  120
cccggacagg gcctggaatg gatgggcggc atcaacccca gcaatggcgg aaccaacttc  180
aacgagaagt tcaagaaccg ggtgaccctg acaacagact ccagcacaac aaccgcctac  240
atggaactga gtctctgca gttcgacgat accgctgtgt actactgtgc tagacgggac  300
tacagattcg acatgggctt tgattattgg ggccagggca ccaccgtgac cgtgtcctct  360
ggcggaggcg gctccggtgg tggcggctct caggtgcagc tggtgcagtc cggcgctgag  420
gtgaagaagc ccggagcctc cgtgaaggtg tcttgcaagg cctccggcta ctccttctcc  480
tccttcggca tctcctgggt cagacaggcc ccaggccaag gcctggagtg gctgggctgg  540
atctccgcct tcaatggcta taccaagtac gcccagaagt tccaggatag agtgaccatg  600
accaccgaca cctctactag caccgcgtac atggaactgc ggtccctgag atccgacgac  660
accgctgtgt actactgcgc cagagatcct gctgcttggc ctctgcagca gtccctggcc  720
tggttcgacc cttggggaca aggcaccatg gtcaccgtgt cctctgctag cacaaaagga  780
ccttctgttt ttcctctggc tccatcctcc aagtccacat ccggcggaac cgctgccctc  840
ggctgcctgg tcaaggacta cttccccgag cctgtgaccg tgtcttggaa ctccggagca  900
ctcacctccg gcgtgcatac cttccccgct gtgctgcagt cttctggact gtactcctgg  960
tccagcgttg tgacagtgcc ttcttctagc ctgggcacac agacctacat ctgcaacgtg 1020
aatcacaagc ccagcaacac caaagtggat aagaaagtcg agcccaagtc ttgcgacaaa 1080
acccacacct gtccaccctg tccggcgcct gaggccgctg cgggccctc tgtgtttctg  1140
ttccctccta agccaaagga taccctgatg atctctcgga ccctgaggt gacctgcgtg 1200
gtggtggacg tgtctcacga ggaccctgaa gtgaagttca actggtacgt ggacggcgtg 1260
gaagtgcaca tgccaagac caagcctaga gaggaacagt acaactccac ctacagagtg 1320
gtgtcagtcc tgacggtgct gcaccaggac tggctgaacg gcaaagagta caagtgcaag 1380
gtgtccaaca aggccctggg cgctcctatc gagaagacaa tcaagaaggc caagggccag 1440
ccccgggaac ctcaggtgta caccctgcct ccctcccgcg acgaactgac caagaaccag 1500
gtgtccctga cctgtctggt gaagggcttc taccttctg acatcgccgt ggagtgggag 1560
tccaacggcc agcctgagaa caactacaag accacacctc ccgtgctgga ctctgatggc 1620
tccttcttcc tgtatagcaa gctgacagtc gacaagtcca gatggcagca gggcaacgtg 1680
ttctcctgct ccgtgatgca cgaggctctg cataaccact acacccagaa gtctctgtcc 1740
ctgtctcctg gttaatga                                                1758

SEQ ID NO: 140      moltype = AA   length = 336
FEATURE             Location/Qualifiers
source              1..336
                    mol_type = protein
                    organism = synthetic construct
SEQUENCE: 140
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KGGGGSGGGG  120
SQSVLTQPPS ASGTPGQRVT ISCSGSTSNL KRNYVYWYQQ LPGTAPKLLI YRDRRRPSGV  180
PDRFSGSKSG TSASLAISGL RSEDEADYYC AWYDRELSEW VFGGGTKLTV LQPKAAPSVT  240
LFPPSSEELQ ANKATLVCLI SDFYPGAVTV AWKADSSPVK AGVETTTPSK QSNNKYAASS  300
YLSLTPEQWK SHRSYSCQVT HEGSTVEKTV APTECS                            336

SEQ ID NO: 141      moltype = DNA   length = 1014
FEATURE             Location/Qualifiers
source              1..1014
                    mol_type = other DNA
                    organism = synthetic construct
SEQUENCE: 141
gagatcgtgc tgacacagtc cccagccacc ctgtctctgt ctcccggcga gcgggctacc   60
ctgtcttgca gagcttctaa aggagtgtcc acatccggct actcctatct gcactggtac  120
cagcagaaac ccggccaggc tccaaggcta ctgatctacc tcgcctccta cctggaaagc  180
ggcgtccctg ccagattttc tggctccggc tctggcaccg acttcaccct gacaatctct  240
tcactcgagc ccgaggactt cgccgtgtac tactgccagc attcccggga cctgcctctg  300
acatttggcg gcggcaccaa agtggaaatc aagggcggag gcggatctgg cggtggcggc  360
tctcagtccg tgctgaccca gcctcctagt gcttctggca cactggcca gagagtgacc  420
atctcctgca gcggctccac ctctaatctg aagcggaact acgtgtactg gtaccagcaa  480
ctgcctggaa ccgctcctaa gctgctgatc tacagagatc ggagacggcc ttcgggcgtg  540
cctgaccggt ctctggctc caagagcggc acctccgcct ccctggccat ctccggcctg  600
agatccgaag acgaggccga ctactactgc gcctggtatg atagagagct gtccgaatgg  660
gtgttcggcg gcggaaccaa gctgaccgtg ctgcaaccca gctctgtgacc  720
ctgttccctc cttcttctga ggaactgcag gctaacaagg ctaccctggt gtgcctgatc  780
tccgatttct accctggcgc agtcaccgtg gcctggaagg ccgactccag ccctgtgaag  840
gctgcgttga gacaaccac ccccagcaag cagtccaaca caagtacgc cgccagctcc  900
tacctgtctc tgacccctga gcagtggaag tcccacagat cttactcctg tcaggtcacc  960
cacgagggca gcaccgtgga aaagaccgtg gctcaactg agtgttctta atga          1014

SEQ ID NO: 142      moltype = AA   length = 706
FEATURE             Location/Qualifiers
source              1..706
                    mol_type = protein
                    organism = synthetic construct
SEQUENCE: 142
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM  120
VTVSSASTKG PSVFPLRPSS KSTSGGTAAL GCLVKDYFPE PVTVSWNSGA LTSGVHTFPA  180
```

-continued

```
VLQSSGLYSL KSVVTVPSSS LGTQTYICNV NHKPSNTKVD KKVEPKSCDK THTSPPAPAP  240
ELLGGPAAPP APAPAGGQVQ LVQSGVEVKK PGASVKVSCK ASGYTFTNYY MYWVRQAPGQ  300
GLEWMGGINP SNGGTNFNEK FKNRVTLTTD SSTTTAYMEL KSLQFDDTAV YYCARRDYRF  360
DMGFDYWGQG TTVTVSSAST KGPSVFPLAP SSKSTSGGTA ALGCEVTDYF PEPVTVSWNS  420
GALTSGVHTF PAVLESSGLY SLSSVVTVPS SSLGTQTYIC NVNHKPSNTK VDKKVEPDSC  480
DKTHTCPPCP APEAAGGPSV FLFPPKPKDT LMISRTPEVT CVVVDVSHED PEVKFNWYVD  540
GVEVHNAKTK PREEQYNSTY RVVSVLTVLH QDWLNGKEYK CKVSNKALGA PIEKTISKAK  600
GQPREPQVYT LPPSRDELTK NQVSLTCLVK GFYPSDIAVE WESNGQPENN YKTTPPVLDS  660
DGSFFLYSKL TVDKSRWQQG NVFSCSVMHE ALHNHYTQKS LSLSPG           706

SEQ ID NO: 143          moltype = DNA  length = 2124
FEATURE                 Location/Qualifiers
source                  1..2124
                        mol_type = other DNA
                        organism = synthetic construct
SEQUENCE: 143
caagtgcagc tggtgcagtc tggcgctgag gtgaagaagc ccggcgcttc agtcaaagtt  60
tcttgcaagg cctccggcta cagcttctcc tccttcggca tctcctgggt cagacaggcc  120
cccggccaag gactggaatg gctgggctgg atcagcgcct tcaacggcta caccaagtac  180
gcccagaaat ccaggacag agtgaccatg accaccgaca cctccacctc caccgcctac  240
atggaactga gatccctgag atctgacgac accgctgtgt actactgtgc tagagatcct  300
gccgcttggc ccctgcagca gtctctggcc tggttcgatc cttggggcca gggcaccatg  360
gtgaccgtga gctctgctag caccaagggg cccagcgtgt tcccactgcg gccttcctcc  420
aagtctacat ccggcggaac cgccgccctg ggctgcctgg tgaaggacta ctttcctgag  480
cccgtaaccg tgtcttggaa ctccggcgct ctcacctctg gggtgcacac ctttcctgct  540
gtcctgcaaa gctccggcct gtactctttg aagtccgtgg tgactgtgcc ttcctcctcc  600
ctgggcacgc agacctacat ctgtaacgtg aaccacaagc cttctaacac taaggtggac  660
aagaaagtgg agcccaagtc ttgcgataaa acccatacca gccctcctgc acctgctcct  720
gagctgctgg gcggacctgc tgctcctccc gccccagccc ctgccggcgg ccaggtccag  780
ctggtgcagt ccggcgtgga ggttaagaaa cctggcgctt ccgtgaaagt gagctgcaag  840
gcctctggct acaccttcac caactactac atgtactggg tgcggcaggc tcctggccaa  900
ggcctggaat ggatgggcgg catcaacccc tccaacggcg gcacgaactt caacgagaag  960
ttcaagaacc gggtgacact gaccaccgac tcctctacaa ccacagctta catggaactc 1020
aagtctctgc agttcgacga caccgccgtg tactactgcg ccagacggga ttatagattc 1080
gacatgggct cgactactg gggacagggc acaacagtca ccgtgagttc tgcctctacc 1140
aaaggcccta gcgtgtttcc tctcgctcct tcttccaagt ctacctctgg cggcaccgcc 1200
gctctgggat gtgaagtgac cgattacttc ccagaacctg tgaccgtttc ctggaactcc 1260
ggagctctga cctctggcgt gcacaccttt ccagccgtgc tggaatcttc cggcctgtac 1320
tctctgtctt ctgtggtgac cgtgccttcc tcatctctgg gcacccagac ctatatctgc 1380
aacgtgaacc acaagccaag caataccaag gtggacaaga aggtcgagcc tgattcctgc 1440
gacaagaccc acacctgtcc tccttgcccg gcgcctgagg ccgctggcgg cccttctgtg 1500
tttctgttcc ctcctaagcc aaaggatacc ctgatgatct ctcggacccc tgaggtgacc 1560
tgcgtggtgg tggacgtgtc tcacgaggac cctgaagtga agttcaactg gtacgtggac 1620
ggcgtggaag tgcacaatgc caagaccaag cctagagagg aacagtacaa ctccacctac 1680
agagtggtgt cagtcctgac ggtgctgcac caggactggc tgaacggcaa agagtacaag 1740
tgcaaggtgt ccaacaaggc cctgggcgct cctatcgaga gacaatcag caaggccaag 1800
ggccagcccc gggaacctca ggtgtacacc ctgcctccc cccgcgacga actgaccaag 1860
aaccaggtgt ccctgacctg tctggtgaag ggcttctacc cttctgacat cgccgtggag 1920
tgggagtcca acggccagcc tgagaacaac tacaagacca cacctccgt gctggactct 1980
gatggctcct tcttcctgta tagcaagctg acagtcgaca gtccagatg gcagcagggc 2040
aacgtgttct cctgctccgt gatgcacgag gctctgcata accactacac ccagaaatct 2100
ctgtccctgt ctcctggtta atga                                   2124

SEQ ID NO: 144          moltype = AA  length = 706
FEATURE                 Location/Qualifiers
source                  1..706
                        mol_type = protein
                        organism = synthetic construct
SEQUENCE: 144
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
ASTKGPSVFP LAPSSKSTSG GTAALGCEVT DYFPEPVTVS WNSGALTSGV HTFPAVLESS  180
GLYSLSSVVT VPSSSLGTQT YICNVNHKPS NTKVDKKVEP DSCDKTHTSP PAPAPELLGG  240
PAAPPAPAPA GGQVQLVQSG AEVKKPGASV KVSCKASGYS FSSFGISWVR QAPGQGLEWL  300
GWISAFNGYT KYAQKFQDRV TMTTDTSTST AYMELRSLRS DDTAVYYCAR DPAAWPLQQS  360
LAWFDPWGQG TMVTVSSAST KGPSVFPLRP SSKSTSGGTA ALGCLVKDYF PEPVTVSWNS  420
GALTSGVHTF PAVLQSSGLY SLKSVVTVPS SSLGTQTYIC NVNHKPSNTK VDKKVEPKSC  480
DKTHTCPPCP APEAAGGPSV FLFPPKPKDT LMISRTPEVT CVVVDVSHED PEVKFNWYVD  540
GVEVHNAKTK PREEQYNSTY RVVSVLTVLH QDWLNGKEYK CKVSNKALGA PIEKTISKAK  600
GQPREPQVYT LPPSRDELTK NQVSLTCLVK GFYPSDIAVE WESNGQPENN YKTTPPVLDS  660
DGSFFLYSKL TVDKSRWQQG NVFSCSVMHE ALHNHYTQKS LSLSPG           706

SEQ ID NO: 145          moltype = DNA  length = 2124
FEATURE                 Location/Qualifiers
source                  1..2124
                        mol_type = other DNA
                        organism = synthetic construct
SEQUENCE: 145
caggtgcaac tcgtgcagtc cggcgtggaa gtgaaaaagc ccggcgcttc tgtgaaggtg   60
```

```
tcttgcaagg ccagcggcta caccttcacc aactattaca tgtactgggt ccggcaggcc  120
cctggccaag gcctggaatg gatgggcggc atcaacccct ccaatggcgg caccaacttc  180
aacgagaagt tcaagaacag agtgaccctg acgaccgatt cctctacaac cacagcctat  240
atggaactga agtccctgca gttcgacgac acagctgtgt actactgtgc ccggcgggac  300
tacagattcg acatgggctt cgattactgg ggccaaggca ccaccgtgac cgtcagctcc  360
gcctccacaa agggaccctc cgtgtttcct ctggcccctt cttccaagag cacctctggc  420
ggcaccgccg ctctgggctg cgaggtgacc gactacttcc ctgagccgt caccgtgtct  480
tggaacagcg gtgccctgac ctccggcgtg cacacctttc ccgcggttct ggagtcttcc  540
ggactgtact ctctttccag cgtcgtgacc gtgccctct catccctggg cacccagacc  600
tacatctgta atgtgaatca caagccttct aataccaagg tggataagaa ggtggaacct  660
gactcctgcg acaagaccca cacctctcct cccgccctg ctccagagct gctgggagga  720
cctgctgctc ctccagcccc agctcctgct ggcggacaag tgcagctggt acagtccggc  780
gctgaggtca agaagcctgg cgcttccgtg aaggtgtcct gcaaggcctc tggctactcc  840
ttctcctctt tcggcatctc ctgggtgaga caggcccctg gccaggcct ggaatggctg  900
ggctggatca gcgccttcaa cggatataca aagtacgccc agaagttcca ggacagagtg  960
accatgacca ccgacacctc cacatccacc gcttacatgg aactccgctc tctgcggtct  1020
gacgataccg ccgtgtacta ctgcgccaga gatcctgccg cctggcctct gcagcagtct  1080
ctggcttggt tcgacccttg gggccagggc accatggtga ctgtgtcttc tgctagcacc  1140
aagggaccct ccgtgttccc tctgagacct cctccaagt ccacctctgg cggaaccgct  1200
gctctgggct gtctggttaa ggactacttt cccgagcctg tgacagtgtc ttggaactcc  1260
ggtgctctga cctccggcgt tcataccttt ccagctgtgc tgcagagctc gggcctgtac  1320
agcctgagct ctgtcgtgac cgtgcctagc tcctctctgg gaacacagac ctacatctgc  1380
aacgtgaacc acaagccttc taacaccaaa gtggacaaga agtggaacc caagagctgt  1440
gacaagaccc atacttgccc gccttgcccg gcgcctgagg ccgctggcgg cccttctgtg  1500
tttctgttcc ctcctaagcc aaaggatacc ctgatgatct ctcggacccc tgaggtgacc  1560
tgcgtggtgg tggacgtgtc tcacgaggac cctgaagtga agttcaactg gtacgtggac  1620
ggcgtggaag tgcacaatgc caagaccaag cctagagagg aacagtacaa ctccacctac  1680
agagtggtgt cagtcctgac ggtgctgcac caggactggc tgaacggcaa agagtacaag  1740
tgcaaggtgt ccaacaaggc cctgggcgct cctatcgaga gacaatcag caaggccaag  1800
ggccagcccc gggaacctca ggtgtacacc ctgcctccct cccgcgacga actgaccaag  1860
aaccaggtgt ccctgacctg tctggtgaag ggcttctacc cttctgacat cgccgtggag  1920
tgggagtcca acggccagcc tgagaacaac tacaagacca cacctcccgt gctggactct  1980
gatggctcct tcttcctgta tagcaagctg acagtcgaca agtccagatg gcagcagggc  2040
aacgtgttct cctgctccgt gatgcacgag gctctgcata accactacac ccagaaatct  2100
ctgtccctgt ctcctggtta atga  2124
```

```
SEQ ID NO: 146            moltype = AA  length = 447
FEATURE                   Location/Qualifiers
source                    1..447
                          mol_type = protein
                          organism = synthetic construct
SEQUENCE: 146
EVQLVESGGG LVKPGGSLEL SCAASGFTFS SYWMSWVRQA PEKGLEWVAA ISPSGGSTYY  60
ADSVKGRFTI SRDNAKNTLF LQMTSLRSED TAMYYCAKES WGAYYDLWGQ GTTVTVSSAS  120
TKGPSVFPLA PSSKSTSGGT AALGCEVTDY FPEPVTVSWN SGALTSGVHT FPAVLESSGL  180
YSLSSVVTVP SSSLGTQTYI CNVNHKPSNT KVDKKVEPDS CDKTHTCPPC PAPEAAGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALG APIEKTISKA KGQPREPQVY VLPPSRDELT  360
KNQVSLLCLV KGFYPSDIAV EWESNGQPEN NYLTWPPVLD SDGSFFLYSK LTVDKSRWQQ  420
GNVFSCSVMH EALHNHYTQK SLSLSPG  447
```

```
SEQ ID NO: 147            moltype = DNA  length = 1347
FEATURE                   Location/Qualifiers
source                    1..1347
                          mol_type = other DNA
                          organism = synthetic construct
SEQUENCE: 147
gaggtgcagc tggtcgagtc cggcggcggc ctggtgaagc ctggcggttc tctggaactg  60
tcctgtgctg cttccggctt taccttctcc tcctactgga tgtcctgggt gcggcaggcc  120
cccgagaagg gcctggagtg ggtggccgct atcagccct ctggtggctc tacctactac  180
gccgactccg tgaaaggcag attcaccatc tcccgggaca cgccaagaa caccctgttc  240
ctgcagatga ccagcctgag atccgaggat accgccatgt actactgcgc caaagaatcc  300
tggggcgctt actacgacct gtggggccag ggcaccacgt gaccgtgtc ctccgctagc  360
accaagggac catccgtctt cctctggcc ccagcagta agtctacatc cggaggaacc  420
gctgctctgg gctgcgaggt gaccgactac ttcccagagc ccgtgaccgt ttcttggaac  480
agcggcgctc tgacctctgg agtgcacacc ttccccgctg tgctgaaag cagcggcctg  540
tactctctgt cctctgtggt gaccgtgcct tcctcttctc tcggcacaca gacctacatc  600
tgcaatgtga atcacaagcc aagcaacacc aaggtggaca gaaggtgga gcctgattct  660
tgcgacaaga cccacacctg tccccccttgt cctgctcctg aggccgccgg cggcccttct  720
gtgtttctgt tccctcctaa gcccaaggac accctgatga tctctcggac acctgaagtg  780
acttgcgtgg ttgtggacgt cagccacgag gaccctgaag tcaagttcaa ctggtatgtg  840
gatggcgtgg aagtgcataa tgccaaaacc aaacctagag gaacagta caactctaca  900
tatagagtgg tctccgtgct gacagtgctg caccaggact ggctgaacgg caaagagtac  960
aagtgcaagg tgtctaacaa ggccctgggc gcgcctatcg agaagaccat ctccaaggcc  1020
aagggccagc ctagagagcc tcaggtgtac gtgctgcctc cctctcggga cgagctgacc  1080
aagaaccaag tgtccctgct gtgcctggtg aagggcttct acccttctga catcgccgtg  1140
gaatgggagt ctaacggcca acctgagaac aactacctga cctggcctcc agtgctggac  1200
tccgacggct ccttcttcct gtactccaag ttgaccgtag ataagtccag atggcagcag  1260
ggcaacgtgt tctcctgctc tgtgatgcac gaggctctgc ataaccacta cacccagaag  1320
```

-continued

```
tccctgtctc tgtctcctgg ataatga                                       1347

SEQ ID NO: 148          moltype = AA   length = 214
FEATURE                 Location/Qualifiers
source                  1..214
                        mol_type = protein
                        organism = synthetic construct
SEQUENCE: 148
DIVMTQSPSS LSVSAGDKVT MSCRASQGIS SWLAWYQQKP WQPPKLLIYK ASTLESGVPD    60
RFTGSGSGTD FTLTISSVQA EDLAVYYCQQ SYSTPWTFGG GTKLEIKGTV AAPSVFIFPP    120
KDERLKSGTA SVVCLLNNFY PREAKVQWKV DNALQSGNSQ ESVTEQDSKD STYSLSSRLT    180
LSKADYEKHK VYACEVTHQG LSSPVTKSFN RGEC                                214

SEQ ID NO: 149          moltype = DNA   length = 648
FEATURE                 Location/Qualifiers
source                  1..648
                        mol_type = other DNA
                        organism = synthetic construct
SEQUENCE: 149
gacatcgtga tgacccaaag cccttctagc ctgtccgtgt ccgctggtga caaggtgacc    60
atgtcctgca gagcctctca gggcatctcc tcttggctgg cttggtacca gcagaagcct    120
tggcagcctc ctaagctgct gatctacaag gcttccaccc tggaatctgg cgtgcccgat    180
cggtttaccg gctccggctc tggaaccgac ttcaccttga ccatctcttc tgtgcaggcc    240
gaggatctgg ccgtgtacta ctgccagcag tcctacagta cacccttggac cttcggcggc    300
ggaaccaagc tggaaatcaa gggcacagtg gccgctccta cgttttcat cttcccaccc    360
aaggacgagc ggctgaagtc tggcaccgcc tcagtggtgt gcctgctgaa caacttctac    420
cccagagagg ctaaagtcca gtggaaagtg gacaacgccc tgcagtctgg caattcccaa    480
gagtccgtca ccgagcagga ctccaaagat tctacctact ccctgtcctc cagactgaca    540
ctcagcaagg ccgactacga gaagcacaag gtgtatgcct gcgaagtgac ccaccagggc    600
ctgtcctctc ctgtgactaa gtccttcaac agaggcgagt gttaatga               648

SEQ ID NO: 150          moltype = AA   length = 719
FEATURE                 Location/Qualifiers
source                  1..719
                        mol_type = protein
                        organism = synthetic construct
SEQUENCE: 150
QVQLVQSGAE VKKPGASVKV SCKASGYSFS SFGISWVRQA PGQGLEWLGW ISAFNGYTKY    60
AQKFQDRVTM TTDTSTSTAY MELRSLRSDD TAVYYCARDP AAWPLQQSLA WFDPWGQGTM    120
VTVSSASTKG PSVFPLAPSS KSTSGGTAAL GCLVKDYFPE PVTVSWNSGA LTSGVHTFPA    180
VLQSSGLYSL SSVVTVPSSS LGTQTYICNV NHKPSNTKVD KKVEPKSCDK THTCPPCPAP    240
EAAGGPSVFL FPPKPKDTLM ISRTPEVTCV VVDVSHEDPE VKFNWYVDGV EVHNAKTKPR    300
EEQYNSTYRV VSVLTVLHQD WLNGKEYKCK VSNKALGAPI EKTISKAKGQ PREPQVYTLP    360
PSRDELTKNQ VSLTCLVKGF YPSDIAVEWE SNGQPENNYK TTPPVLDSDG SFFLYSKLTV    420
DKSRWQQGNV FSCSVMHEAL HNHYTQKSLS LSPGKGGGGS GGGGSGGGGS GGGGSEVQLV    480
ESGGGLVKPG GSLELSCAAS GFTFSSYWMS WVRQAPEKCL EWVAAISPSG GSTYYADSVK    540
GRFTISRDNA KNTLFLQMTS LRSEDTAMYY CAKESWGAPY DLWGQGTTVT VSSGGSGGGS    600
GGGSGGGSGG GSGDIVMTQS PSSLSVSAGD KVTMSCRASQ GISSWLAWYQ QKPWQPPKLL    660
IYKASTLESG VPDRFTGSGS GTDFTLTISS VQAEDLAVYY CQQSYSTPWT FGCGTKLEI     719

SEQ ID NO: 151          moltype = DNA   length = 2163
FEATURE                 Location/Qualifiers
source                  1..2163
                        mol_type = other DNA
                        organism = synthetic construct
SEQUENCE: 151
caagtgcaat tagttcagtc tggcgctgag gtcaagaagc ctggcgcttc tgtgaaggtg    60
tcttgcaagg cttccggcta cagtttcagc tcctttggca tttcttgggt cagacaggct    120
cctggccagg gcctggaatg gctgggctgg atctccgcct tcaacggcta caccaagtac    180
gcccagaagt tccaggacag agtgaccatg accaccgaca cctccacctc taccgcctac    240
atggaactgc ggtccctgag atccgacgac accgctgtgt actactgcgc cagagatccc    300
gctgcttggc ctctgcagca gtctctggcc tggttcgacc cttggggcca gggcaccatg    360
gtcacagtgt cctctgctag caccaaggga ccttctgtgt tcccactggc cccatcgagc    420
aagtccacct ccggcggcac cgctgctctc ggctgtctga tgaaggacta cttcccggaa    480
cccgtgaccg tgtcctggaa ctccggcgct ctgacatcag gcgtgcatac ctttcctgcc    540
gtgctgcagt cctccggact gtacagcctg tccagcgtgg ttactgtgcc ctcctccagt    600
ctgggcaccc agacctacat ctgcaacgtg aaccacaagc cttccaacac caaggtggat    660
aagaaagtgg aacccaagtc atgcgacaag acccatacat gccctccttg tccggcgcct    720
gaggccgcag gtggccccca cgtgttcctg tttccaccca gcctaagga taccctgatg    780
atctctcgga cccctgaggt gacctgtgtt gtggtggacg tgtctcacga ggaccctgaa    840
gtgaagttca ctggtacgt ggacggcgtg gaggtgcaca tgccaaaac aaagccacga    900
gaagaacagt acaactctac ctacagagtg gtgtccgtgc tcactgtgct gcaccaggac    960
tggctgaacg gcaaagagta caagtgcaag gtgtccaaca aggctctggg agccctatc    1020
gagaagacag tctctaaggc caaggacag cctagagagc ctcaggtgta caactgccc    1080
ccttcccgcg acgagctcac caagaaccag gtgtccctga cctgcctggt caagggcttc    1140
tacccttctg acatcgccgt tgagtgggag tctaatggc agctgagaa caactacaaa    1200
accacacccc ctgtgctgga ctccgatggc tctttcttct tgtattccaa gctgaccgtc    1260
gataaatcaa ggtggcagca gggcaacgtg ttctcctgct ccgtcatgca cgaagctctg    1320
cacaatcact acacccagaa gagcctaagc ttgtctccag gaaagggcgg aggtggctct    1380
```

```
ggaggcggtg gatctggtgg tggcggatca ggtggaggcg ggagcgaggt gcagctggtg   1440
gaatctggag gcggcctggt gaagcccggc ggctctctgg agctgtcctg tgccgcgagc   1500
ggctttacct tctcctccta ctggatgtcc tgggtgcggc aagctcctga gaagtgcctg   1560
gaatgggtgg ccgccatctc ccctagtggt ggctccacct attacgccga ctccgtcaaa   1620
ggccggttca caatctccag agacaacgcc aagaacaccc tgttcctgca gatgacctcc   1680
ctgagatctg aggataccgc catgtactac tgtgctaaag agtcttgggg cgcttactac   1740
gacctgtggg gacaggggac caccgtgaca gtgtcttctg gaggtccggg cggcggtagt   1800
ggaggaggct ctggtggtgg aagcggcggc ggatctggcg atatcgtgat gacccaatcc   1860
cctagcagcc tgagcgtctc tgctggcgac aaggtgacca tgtcctgcag agcttcccaa   1920
ggcatctctt cttggctggc ttggtatcag cagaaacctt ggcagcctcc aaagctgctg   1980
atctacaagg cctctacact ggaatccggc gtgcctgacc ggttcaccgg ctccggatcg   2040
ggaaccgact tcaccctgac catctcgtct gtgcaggccg aggacctggc cgtgtactac   2100
tgccagcaga gttacagcac accttggacc ttcggctgcg gcaccaagct ggagatctaa   2160
tga                                                                  2163

SEQ ID NO: 152          moltype = AA  length = 582
FEATURE                 Location/Qualifiers
source                  1..582
                        mol_type = protein
                        organism = synthetic construct
SEQUENCE: 152
QVQLVQSGAE VKKPGASVKV SCKASGYSFS SFGISWVRQA PGQGLEWLGW ISAFNGYTKY   60
AQKFQDRVTM TTDTSTSTAY MELRSLRSDD TAVYYCARDP AAWPLQQSLA WFDPWGQGTM   120
VTVSSGGGGS GGGGSEVQLV ESGGGLVKPG GSLELSCAAS GFTFSSYWMS WVRQAPEKGL   180
EWVAAISPSG GSTYYADSVK GRFTISRDNA KNTLFLQMTS LRSEDTAMYY CAKESWGAYY   240
DLWGQGTTVT VSSASTKGPS VFPLAPSSKS TSGGTAALGC LVKDYFPEPV TVSWNSGALT   300
SGVHTFPAVL QSSGLYSLSS VVTVPSSSLG TQTYICNVNH KPSNTKVDKK VEPKSCDKTH   360
TCPPCPAPEA AGGPSVFLFP PKPKDTLMIS RTPEVTCVVV DVSHEDPEVK FNWYVDGVEV   420
HNAKTKPREE QYNSTYRVVS VLTVLHQDWL NGKEYKCKVS NKALGAPIEK TISKAKGQPR   480
EPQVYTLPPS RDELTKNQVS LTCLVKGFYP SDIAVEWESN GQPENNYKTT PPVLDSDGSF   540
FLYSKLTVDK SRWQQGNVFS CSVMHEALHN HYTQKSLSLS PG                      582

SEQ ID NO: 153          moltype = DNA  length = 1752
FEATURE                 Location/Qualifiers
source                  1..1752
                        mol_type = other DNA
                        organism = synthetic construct
SEQUENCE: 153
caggtgcagc tggtccaatc tggcgctgag gtgaagaagc ccggcgcttc tgtgaaggtg   60
tcctgcaagg ccagcggcta ctccttctct tcttttggca tcagctgggt gcggcaggcc   120
cccggccagg gctggaatg gctgggctgg atctccgcct tcaacggcta caccaagtac   180
gctcagaagt tccaggacag agtgaccatg accaccgata cctctacctc caccgcctac   240
atggaactgc ggagcctgcg ctccgacgat accgctgtgt actactgtgc cagagatcct   300
gctgcttggc ctctgcagca gtccctggcc tggttcgacc cttggggcca aggcactatg   360
gtgaccgtgt cctctggcgg cggcggctct ggcggaggcg gcagcgaagt gcagctggtg   420
gaatccggcg gcggactggt gaagcctggc ggctctctcg agctgtcctg cgccgcttcc   480
ggcttcacct tctcctccta ctggatgtcc tgggtcagac aggtccctga gaagggcctg   540
gagtgggtgg ccgccatctc tccatctgga ggaagcacct actacgccga ctccgtgaaa   600
ggcagattta ccatctcccg ggacaacgcc aagaacaccc tgttcctgca gatgacatct   660
ctgagatccg aggacaccgc catgtactac tgcgctaaag agtcttgggg tgcttattac   720
gacctgtggg gccagggaac aaccgtgaca gtttcctctg ctagcacaaa aggaccttct   780
gttttttcctc tggctccatc ctccaagtcc acatccggcg gaaccgctgc cctcggctgc   840
ctggtcaagg actacttccc cgagcctgtg accgtgtctt ggaactccgg agcactcacc   900
tccggcgtgc ataccttccc cgctgtgctg cagtcttctg gactgtactc cctgtccagc   960
gttgtgacag tgccttcttc tagcctgggc acacagacct acatctgcaa cgtgaatcac   1020
aagcccagca cacccaaagt ggataagaaa gtcgagccca agtcttgcga caaaacccac   1080
acctgtccac cctgtccggc gcctgaggcc gctggcggcc cttctgtgtt tctgttccct   1140
cctaagccaa aggataccct gatgatctct cggacccctg aggtgacctg cgtggtggtg   1200
gacgtgtctc acgaggacc tgaagtgaag ttcaactggt acgtggacgg cgtggaagtg   1260
cacaatgcca agaccaagcc tagagaggaa cagtacaact ccacctacag agtggtgtca   1320
gtcctgacgg tgctgcacca ggactggctg aacggcaaag agtacaagtg caaggtgtcc   1380
aacaaggccc tgggcgctcc tatcgagaag acaatcagca aggccaaggg ccagccccgg   1440
gaacctcagg tgtacaccct gcctccctcc cgcgacgaac tgaccaagaa ccaggtgtcc   1500
ctgacctgtc tggtgaaggg cttctacccc tctgacatcg ccgtggagtg ggagtccaac   1560
ggccagcctg agaacaacta caagaccaca cctcccgtgc tggactctga tggctccttc   1620
ttcctgtata gcaagctgac agtcgacaag tccagatggc agcagggcaa cgtgttctcc   1680
tgctccgtga tgcacgaggc tctgcataac cactacaccc agaaatctct gtccctgtct   1740
cctggttaat ga                                                       1752

SEQ ID NO: 154          moltype = AA  length = 334
FEATURE                 Location/Qualifiers
source                  1..334
                        mol_type = protein
                        organism = synthetic construct
SEQUENCE: 154
QSVLTQPPSA SGTPGQRVTI SCSGSTSNLK RNYVYWYQQL PGTAPKLLIY RDRRRPSGVP   60
DRFSGSKSGT SASLAISGLR SEDEADYYCA WYDRELSEWV FGGGTKLTVL GGGGSGGGGS   120
DIVMTQSPSS LSVSAGDKVT MSCRASQGIS SWLAWYQQKP WQPPKLLIYK ASTLESGVPD   180
RFTGSGSGTD FTLTISSVQA EDLAVYYCQQ SYSTPWTFGG GTKLEIKGTV AAPSVFIFPP   240
```

```
SDEQLKSGTA SVVCLLNNFY PREAKVQWKV DNALQSGNSQ ESVTEQDSKD STYSLSSTLT  300
LSKADYEKHK VYACEVTHQG LSSPVTKSFN RGEC                              334

SEQ ID NO: 155          moltype = DNA  length = 1008
FEATURE                 Location/Qualifiers
source                  1..1008
                        mol_type = other DNA
                        organism = synthetic construct
SEQUENCE: 155
cagtccgtgc tgacccagcc tccttctgcc tctggcaccc ctggccagag ggtgaccatc  60
tcctgttctg gctctacatc caacctgaag agaaactacg tgtactggta tcagcagctg  120
cctggcaccg cccctaagct gctgatctac agagatcggc ggagacccag cggagtccct  180
gatagattct ccggatctaa aagtggcacc tccgcttccc tggccatctc cggcctgaga  240
tccgaagatg aagctgacta ctactgcgcc tggtacgaca gagagctgtc cgagtgggtc  300
tttggcggag gcaccaaact gaccgttctg ggcggcggcg gctccggcgg cggcggatca  360
gacatcgtga tgacccaatc tccatcctct ctgtctgtgt ctgctggcga caaggtgacc  420
atgagctgca gagcctccca aggcatctca agttggctgg cttggtacca gcagaagcct  480
tggcagcccc ccaagctgct gatttacaag gcttccaccc tggaatccgg cgtgcccgac  540
cggttcaccg gttctggaag cggcaccgac ttcacactga ccatctcctc tgtgcaggcc  600
gaggacctgg ccgtgtacta ttgccagcag tcctactcta caccttggac ctttgggggc  660
ggcaccaagt ggagatcaa gggcaccgtg gctgctccta gcgtgttcat cttccctcca  720
agcgatgagc agctgaagtc cggcaccgct tctgtggtgt gcctgctgaa caacttctac  780
cctcgggagg ccaaggtgca gtggaaagtg gacaacgccc tgcagtctgg caattcccaa  840
gaatctgtca ccgaacagga ctccaaggac tccacctact ccctcagctc tacactcacc  900
ctgagcaagg ccgactacga gaagcacaag gtgtacgcct gcgaggtgac ccaccagggc  960
ctgtcctctc ctgtgacaaa gtccttcaac agaggcgagt gttaatga             1008

SEQ ID NO: 156          moltype = AA  length = 594
FEATURE                 Location/Qualifiers
source                  1..594
                        mol_type = protein
                        organism = synthetic construct
SEQUENCE: 156
QVQLVQSGAE VKKPGASVKV SCKASGYSFS SFGISWVRQA PGQGLEWLGW ISAFNGYTKY  60
AQKFQDRVTM TTDTSTSTAY MELRSLRSDD TAVYYCARDP AAWPLQQSLA WFDPWGQGTM  120
VTVSSGGGGS GGGGSGGGGS GGGGSQVQLV QSGVEVKKPG ASVKVSCKAS GYTFTNYYMY  180
WVRQAPGQGL EWMGGINPSN GGTNFNEKFK NRVTLTTDSS TTTAYMELKS LQFDDTAVYY  240
CARRDYRFDM GFDYWGQGTT VTVSSASTKG PSVFPLAPSS KSTSGGTAAL GCLVKDYFPE  300
PVTVSWNSGA LTSGVHTFPA VLQSSGLYSL SSVVTVPSSS LGTQTYICNV NHKPSNTKVD  360
KKVEPKSCDK THTCPPCPAP EAAGGPSVFL FPPKPKDTLM ISRTPEVTCV VVDVSHEDPE  420
VKFNWYVDGV EVHNAKTKPR EEQYNSTYRV VSVLTVLHQD WLNGKEYKCK VSNKALGAPI  480
EKTISKAKGQ PREPQVYTLP PSRDELTKNQ VSLTCLVKGF YPSDIAVEWE SNGQPENNYK  540
TTPPVLDSDG SFFLYSKLTV DKSRWQQGNV FSCSVMHEAL HNHYTQKSLS LSPG        594

SEQ ID NO: 157          moltype = DNA  length = 1788
FEATURE                 Location/Qualifiers
source                  1..1788
                        mol_type = other DNA
                        organism = synthetic construct
SEQUENCE: 157
caagtgcaac tcgtccagtc cggcgctgag gtgaaaaagc ccggcgcttc cgtgaaggtg  60
tcttgcaagg cctctggcta ctccttctcc agcttcggca tctcctgggt gcggcaggcc  120
ccaggccagg gcctggagtg gctgggctgg atctccgcct tcaacggcta taccaagtac  180
gcccagaagt tcaggacag agtcacaatg acgaccgata cctctaccag caccgcctac  240
atggaactgc ggtccctgag atccgacgac accgccgtgt actactgcgc cagagaccct  300
gctgcttggc ctctgcagca gtctctggcc tggttcgatc cttggggaca gggcaccatg  360
gtgaccgttt cctctggcgg aggtggctct ggaggcggtg gatctggtgg tggcggatca  420
ggtggaggcg ggagccaggt gcagctggtg cagtccggcg tggaagtgaa gaagcctggc  480
gcttctgtga aagtgagctg caaggcctct ggctacacct tcaccaacta ctacatgtac  540
tgggtcagac aggctcctgg ccagggcctg gagtggatgg gcggcatcaa cccttccaat  600
ggcggcacca acttcaacga gaagttcaag aaccgggtga ccctgacaac cgactcctcc  660
accaccacac cttacatgga gctgaagtcc ctgcagttcg acgacaccgc tgtgtactat  720
tgtgctcgcg agagattacag attcgacatg ggctttgact actggggcca gggaaccacc  780
gtgacagtga gctctgctag cacaaaagga ccttctgttt ttcctctggc tccatcctcc  840
aagtccacat ccggcggaac cgctgccctc ggctgcctgg tcaaggacta cttccccgag  900
cctgtgaccg tgtcttggaa ctccggagca ctcacctccg gcgtgcatac cttccccgct  960
gtgctgcagt cttctggact gtactccctg tccagcgttg tgacagtgcc ttcttctagc  1020
ctgggcacac agacctacat ctgcaacgtg aatcacaagc ccagcaacac caaagtggat  1080
aagaaagtcg agcccaagtc ttgcgacaaa acccacacct gtccggcgcgt tccggcgcctt  1140
gaggccgctg gcggccccttc tgtgtttctg ttccctccta gcccaaagga tacccctgatg  1200
atctctcgga cccctgaggt gacctgcgtg gtggtggacg tgtctcacga ggaccctgaa  1260
gtgaagttca ctggtacgt ggacggcgtg gaagtgcaca tgccaagac caagcctaga  1320
gaggaacagt acaactccac ctacagagtg gtgtcagtcc tgacggtgct gcaccaggac  1380
tggctgaacg gcaaagagta caagtgcaag gtgtccaaca aggccctggg cgctcctatc  1440
gagaagacaa tcagcaaggc caagggccag ccccgggaac tcaggtgta caccctgcct  1500
ccctcccgcg acgaactgac caagaaccag gtgtccctga cctgtctggt gaagggcttc  1560
tacccttctg acatcgccgt gggagtggag tccaacggcc agcctgagaa caactacaag  1620
accacacctc ccgtgctgga ctctgatggc tccttcttcc tgtatagcaa gctgacagtc  1680
gacaagtcca gatggcagca gggcaacgtg ttctcctgct ccgtgatgca cgaggctctg  1740
```

-continued

```
cataaccact acacccagaa atctctgtcc ctgtctcctg gttaatga              1788

SEQ ID NO: 158          moltype = AA   length = 348
FEATURE                 Location/Qualifiers
source                  1..348
                        mol_type = protein
                        organism = synthetic construct
SEQUENCE: 158
QSVLTQPPSA SGTPGQRVTI SCSGSTSNLK RNYVYWYQQL PGTAPKLLIY RDRRRPSGVP    60
DRFSGSKSGT SASLAISGLR SEDEADYYCA WYDRELSEWV FGGGTKLTVL GGGGSGGGGS   120
GGGGSGGGGS EIVLTQSPAT LSLSPGERAT LSCRASKGVS TSGYSYLHWY QQKPGQAPRL   180
LIYLASYLES GVPARFSGSG SGTDFTLTIS SLEPEDFAVY YCQHSRDLPL TFGGGTKVEI   240
KRTVAAPSVF IFPPSDEQLK SGTASVVCLL NNFYPREAKV QWKVDNALQS GNSQESVTEQ   300
DSKDSTYSLS STLTLSKADY EKHKVYACEV THQGLSSPVT KSFNRGEC                348

SEQ ID NO: 159          moltype = DNA   length = 1050
FEATURE                 Location/Qualifiers
source                  1..1050
                        mol_type = other DNA
                        organism = synthetic construct
SEQUENCE: 159
cagtctgtgc tgactcagcc tccttccgcc agcggcacac ctggccagag agtgaccatc    60
tcttgctccg gctccacctc caacctgaag cggaactacg tgtactggta ccagcagctg   120
cccggcaccg ctcctaagct gctgatctac agagatcggc ggcggccttc tggcgtccct   180
gaccggtttt ccgaagcaa atctggcacc tctgcttccc tggccatctc tggcctgaga   240
tccgaagatg aggccgacta ctactgcgcc tggtacgaca gagagctgtc cgaatgggtg   300
ttcggcggcg gcaccaagct gaccgtgctg ggcggaggtg gctctggagg cggtggatct   360
ggtggtggcg gatcaggtgg aggcgggagc gagatcgtgc tgacccaatc ccccgctacc   420
ctgagcctga gtccaggcga gcgggctacc ctgtcctgta gagcttctaa gggcgtgtct   480
acatccggct actcctacct gcactggtat cagcagaagc ccggacaggc ccctcggctg   540
ctgatctacc tggcttctta tctggaatcc ggcgtgcccg ctagattctc tggctccggc   600
tccggcaccg acttcaccct gaccatcagc tccctggagc ctgaggactt cgccgtgtac   660
tactgccagc acagcagaga cctgcctctg accttTggcg gcggcacaaa agtggaaatc   720
aagagaacag tggccgctcc ctccgtcttc atcttccctc catccgacga acagctgaag   780
tctggcaccg cctctgtggt gtgcctgctc aacaacttct accctagaga agctaaagtg   840
cagtggaagg tggacaacgc cctgcagtcc ggaaatagcc aagagtccgt gaccgagcag   900
gactccaagg attctaccta ctctctgagc tctaccctga ccctctccaa ggccgattac   960
gagaagcaca aggtgtacgc ctgcgaggtg acccatcagg gcttgtctag ccctgtgacc  1020
aagtccttca acagaggcga gtgttaatga                                   1050

SEQ ID NO: 160          moltype = AA   length = 594
FEATURE                 Location/Qualifiers
source                  1..594
                        mol_type = protein
                        organism = synthetic construct
SEQUENCE: 160
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
GGGGSGGGGS GGGGSGGGGS QVQLVQSGAE VKKPGASVKV SCKASGYSFS SFGISWVRQA   180
PGQGLEWLGW ISAFNGYTKY AQKFQDRVTM TTDTSTSTAY MELRSLRSDD TAVYYCARDP   240
AAWPLQQSLA WFDPWGQGTM VTVSSASTKG PSVFPLAPSS KSTSGGTAAL GCLVKDYFPE   300
PVTVSWNSGA LTSGVHTFPA VLQSSGLYSL SSVVTVPSSS LGTQTYICNV NHKPSNTKVD   360
KKVEPKSCDK THTCPPCPAP EAAGGPSVFL FPPKPKDTLM ISRTPEVTCV VVDVSHEDPE   420
VKFNWYVDGV EVHNAKTKPR EEQYNSTYRV VSVLTVLHQD WLNGKEYKCK VSNKALGAPI   480
EKTISKAKGQ PREPQVYTLP PSRDELTKNQ VSLTCLVKGF YPSDIAVEWE SNGQPENNYK   540
TTPPVLDSDG SFFLYSKLTV DKSRWQQGNV FSCSVMHEAL HNHYTQKSLS LSPG          594

SEQ ID NO: 161          moltype = DNA   length = 1788
FEATURE                 Location/Qualifiers
source                  1..1788
                        mol_type = other DNA
                        organism = synthetic construct
SEQUENCE: 161
caggttcaac tcgtgcagag cggagtggaa gtgaagaaac caggcgcttc tgtgaaagtg    60
tcctgcaagg cctccggata caccttcacc aactactaca tgtactgggt caggcaggct   120
cctggccagg gcctggagtg gatgggcggc atcaaccca gcaacggcgg caccaacttc   180
aacgagaagt tcaagaacag agtgaccctg accacagact cctctaccac cacagcctac   240
atggagctga gtccctgca gttcgacgat accgccgtgt actattgcgc tagacgggac   300
tacagattcg acatgggctt cgattactgg ggtcaaggca caaccgtgac agtgtcgtct   360
ggcggaggtg gctctggagg cggtggatct ggtggtggcg gatcaggtgg aggcgggagc   420
caggtgcagc tggtccagtc cggcgctgag gtgaagaagc ctggcgcttc cgtgaaggtg   480
tcttgcaagg cctccggcta ctccttctcc tcctttggca tctcctgggt gcggcaggcc   540
cccggacagg gcctggaatg gctgggctgg atctccgcct caatggcta caccaagtac   600
gcccaagagt ttcaggacag agtgaccatg accactgaca ccagcacctc taccgcctat   660
atggagctgc ggagcctgag atccgacgac accgctgtgt actactgtgc cagagatcct   720
gctgcctggc ctctgcagca gtctctggct tggttcgacc cttggggcca gggcaccatg   780
gtcaccgtga gctctgctag cacaaaagga ccttctgttt ttcctctggc tccatcctcc   840
aagtccacat ccggcggaac cgctgccctc ggctgcctgg tcaaggacta cttccccgag   900
cctgtgaccg tgtcttggaa ctccggagca ctcacctccg gcgtgcatac cttccccgct   960
```

-continued

```
gtgctgcagt cttctggact gtactccctg tccagcgttg tgacagtgcc ttcttctagc   1020
ctgggcacac agacctacat ctgcaacgtg aatcacaagc ccagcaacac caaagtggat   1080
aagaaagtcg agcccaagtc ttgcgacaaa acccacacct gtccaccctg tccggcgcct   1140
gaggccgctg gcggcccttc tgtgtttctg ttccctccta agccaaagga taccctgatg   1200
atctctcgga cccctgaggt gacctgcgtg gtggtggacg tgtctcacga ggaccctgaa   1260
gtgaagttca actggtacgt ggacggcgtg gaagtgcaca atgccaagac caagcctaga   1320
gaggaacagt acaactccac ctacagagtg gtgtcagtcc tgacggtgct gcaccaggac   1380
tggctgaacg gcaaagagta caagtgcaag gtgtccaaca aggccctggg cgctcctatc   1440
gagaagacaa tcagcaaggc caagggccag ccccgggaac ctcaggtgta caccctgcct   1500
ccctcccgcg acgaactgac caagaaccag gtgtccctga cctgtctggt gaagggcttc   1560
tacccttctg acatcgccgt ggagtgggag tccaacggcc agcctgagaa caactacaag   1620
accacacctc ccgtgctgga ctctgatggc tccttcttcc tgtatagcaa gctgacagtc   1680
gacaagtcca gatggcagca gggcaacgtg ttctcctgct ccgtgatgca cgaggctctg   1740
cataaccact acacccagaa atctctgtcc ctgtctcctg gttaatga             1788
```

```
SEQ ID NO: 162            moltype = AA   length = 346
FEATURE                   Location/Qualifiers
source                    1..346
                          mol_type = protein
                          organism = synthetic construct
SEQUENCE: 162
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KGGGGSGGGG   120
SGGGGSGGGG SQSVLTQPPS ASGTPGQRVT ISCSGSTSNL KRNYVYWYQQ LPGTAPKLLI   180
YRDRRRPSGV PDRFSGSKSG TSASLAISGL RSEDEADYYC AWYDRELSEW VFGGGTKLTV   240
LQPKAAPSVT LFPPSSEELQ ANKATLVCLI SDFYPGAVTV AWKADSSPVK AGVETTTPSK   300
QSNNKYAASS YLSLTPEQWK SHRSYSCQVT HEGSTVEKTV APTECS                  346
```

```
SEQ ID NO: 163            moltype = DNA   length = 1044
FEATURE                   Location/Qualifiers
source                    1..1044
                          mol_type = other DNA
                          organism = synthetic construct
SEQUENCE: 163
gagatcgtgc tgacccagtc tcctgctacc ctgagcctgt cccctggcga gagagccact    60
ctctcttgta gagcttctaa aggcgtgtcc accagcggct acagctacct gcactggtac   120
cagcagaaac ccggccaggc tcctagactg ctgatctacc tggcctccta cctggaatcc   180
ggcgtgcccg ccaggttctc cggctccggc tctggaaccg acttcaccct gaccatctcc   240
tccctggaac ccgaggattt cgccgtgtac tactgccagc actccagaga cctgcctctg   300
acctttggag gcggcacaaa agtggaaatc aagggcggag gtggctctgg aggcggtgga   360
tctggtggtg gcggatcagg tggaggcggg agccagtccg tgctgacaca gcctccttcc   420
gcctccggca caccaggcca gagagtgacc atctcttgct ccggctccac ctccaacctg   480
aagcggaact acgtgtactg gtatcagcag ctgcccggca ccgctcccaa gctgctgatc   540
taccgggatc gcagacggcc ttctggcgtg cctgaccggt tttctggctc caagtccggc   600
acctctgcct ctctcgccat cagcggcctg cggtccgagg acgaggccga ctactactgt   660
gcttggtacg acagagagct gtctgagtgg gtgttcggcg gaggcaccaa gctgacagtg   720
ctgcagccta aggctgctcc atctgtcacc ctgttccctc caagcagcga agaactgcaa   780
gccaataagg ccacactggt gtgcctgatc tccgacttct accctggcgc tgttacagtg   840
gcctggaagg ccgattcctc tcctgtgaag gctggcgtgg aaaccaccac ccctagcaag   900
cagagcaaca acaagtacgc cgcctcctca tatctgtccc tgacccctga gcagtggaag   960
tctcatagat cctactcctg ccaagtgacc cacgagggct ctaccgtcga gaagaccgtg   1020
gctcctaccg agtgctctta atga                                        1044
```

CYTOKINE-BASED THERAPIES AND METHODS

RELATED APPLICATIONS

This application is a continuation of International Application No. PCT/US24/18252, filed Mar. 1, 2024, which claims the benefit of U.S. Provisional Application No. 63/488,145 filed on Mar. 2, 2023, which are incorporated by reference in their entirety.

SEQUENCE LISTING

The instant application contains a Sequence Listing which has been submitted electronically in ST.26 xml format and is hereby incorporated by reference in its entirety. Said xml copy, created on Feb. 29, 2024, is named 780675_000005_SL.xml and is 215,958 bytes in size.

BACKGROUND

Cytokines have far-reaching effects on the behavior of immune cells. However, there are several problems that severely limit the therapeutic use of cytokines, including their pleiotropic actions and systemic toxicity (Li & Lim (2020) Science 370, 1034). Systemic toxicity limits cytokine utility across a variety of cytokines (e.g., IL-15, IL-2, and IL-4). rhIL-15 proved too difficult to administer as an intravenous bolus dose because of clinical toxicities produced by intense cytokine secretion that occurred following administration (Waldmann et al. (2020) Front Immunol 11, 10.3389/fimmu.2020.00868). Recombinant human IL-2 (rhIL-2) is now rarely used to treat patients with cancer because it too often causes severe toxicities (Schwartz et al. (2002) Oncology 16, 11). The observation of limiting toxicity occurring as local pain at the injection site, led to termination of rhIL-4 trial in oral squamous cell carcinoma (Werkmeister et al. (2005) Oncology Reports 13, 449).

Recognizing the limitations of therapeutic use of recombinant cytokines, others in the field have engineered potential solutions that have unfortunately created new issues. Pegylation was introduced to solve problems with half-life, however the solution has instead introduced diminished activity, heterogenous product, manufacturing challenges, PEG inclusions in the liver, and limited half-life extension (See, clinical research products by Nektar and Ascendis pharma). Fc fusions were intended to solve the half-life challenges, but introduced other challenges including altered activity, dose limiting toxicity, manufacturing challenges, increased immunogenicity, and limited half-life extension (See, clinical research products by ImmunityBio and Xencor). Site specifically engineered cytokines referred to as muteins were intended to overcome pleiotropic action, yet they resulted in increased immunogenicity and made for difficult clinical translation of novel biology.

To spatially limit the delivery of cytokines, there have been efforts to create genetic fusion of cytokines with antibodies, the antibodies functioning to localize the cytokine to desired target. Xu et al. (Xu et al. (2021) Cancer Immunology Research 9, 1141) describe the design and use of PD1 targeting antibody genetically fused to an engineered IL-15 mutein. Martomo et al. (Martomo et al. (2021) Molecular Cancer Therapeutics 20, 347) describe the development of an anti PD-L1 antibody genetically linked to the sushi domain of the human IL-15/IL-15 receptor alpha complex. The group at Anaveon AG describe a ANV600 comprising of a PD1 binding moiety and a fusion protein comprising of the cytokine IL-2 fused to an anti IL-2 protein. Thus, all these solutions comprise genetic fusions of a cytokine to other antibodies and such engineered cytokines pose development risk and challenges mentioned above.

See the review article by Santollani and Wittrup (Santollani et al. (2023) Immunological Reviews 320, 10) which lists the challenges and several approaches adopted by the community to solve the challenges associated with development of cytokine therapies. All of these solutions comprise complex engineered cytokines, cytokine receptors, and/or their fusion molecules (WO 2022/036079).

Thus, there is a need for new compositions and differentiated methods that can amplify the action of natural cytokines, specifically in a tumor or tissue, and overcome the dosing challenges and systemic toxicity of presently available approaches. In particular, it is desirable to develop methods to redirect and localize the effect of cytokines without having to design and dose fusion proteins comprising the cytokines or their receptors in engineered forms.

SUMMARY

This disclosure relates to novel cytokine-based therapies and methods of amplifying the action of the natural cytokine, specifically in desired tumor or tissue, to overcome dosing challenges and systemic toxicity.

In one aspect, the disclosure relates to methods for redirecting an active form of a cytokine to a target cell or target tissue of interest in a biological system, the biological system comprising (i) the active form of the cytokine; (ii) a cell bearing a cognate receptor for the active form of the cytokine on its surface; (ii) one or more target cells or tissues of interest to which the cytokine is to be redirected; the method comprising exposing the biological system to a multi-specific binding molecule comprising (a) at least one first binding domain that specifically binds to an epitope on the active form of the cytokine (a cytokine-binding domain); and (b) at least one second binding domain that specifically binds to an epitope on a molecule that is not the cognate receptor on the target cell or tissue (a target-binding domain), wherein the cytokine, when complexed with the multi-specific binding molecule, retains its ability to bind to and agonize its cognate receptor; thereby redirecting the active form of the cytokine to the target cell or tissue. The biological system can be an in vitro culture, an animal model or a human subject.

In another aspect, the disclosure relates to methods for redirecting an active form of a cytokine to a target cell or target tissue of interest in a subject comprising administering to the subject a sufficient amount of a multi-specific binding molecule comprising (a) a binding domain that specifically binds to the active form of the cytokine (a cytokine-binding domain) and (b) a binding domain that specifically binds to a molecule that is a marker on the target cell or tissue (a target-binding domain), wherein the cytokine, when complexed with the multi-specific binding molecule, retains its ability to bind to and agonize a cognate receptor for the cytokine; thereby redirecting the active form of the cytokine to the target cell or tissue. Administration of the multi-specific binding molecule to the subject can prolong the half-life of the cytokine in the subject. Administration of the multi-specific binding molecule to the subject can increase the amount of the cytokine in the serum of the subject.

In some embodiments the multi-specific binding molecule causes accumulation of the cytokine at or around the target cell or tissue.

In one aspect of the disclosure, the cytokine is endogenous to the system.

In another aspect of the disclosure, the cytokine is exogenous to the system obtained by introducing a recombinant version of the cytokine into the system.

In another aspect of the disclosure, the cytokine could be either endogenous or exogenous or a mixture of both in the system.

In some embodiments, the active form of the cytokine, when redirected, exerts an agonistic effect on the cell bearing its cognate receptor.

In some embodiments, the multi-specific binding molecule, when bound to the cytokine, reduces but does not completely block, the ability of the cytokine to bind to and/or agonize its cognate receptor.

In some embodiments, the multi-specific binding molecule, when bound to the cytokine, attenuates the ability of the cytokine to bind to and/or agonize its cognate receptor. In some embodiments, the multi-specific binding molecule, when bound to the cytokine, alters the cognate receptor mediated clearance characteristics of the cytokine.

In another aspect, the disclosure relates to methods for redirecting an active form of a cytokine to a target cell or target tissue of interest comprising: (a) selecting a cytokine of interest; (b) selecting a target molecule that is a marker on a target cell or in a target tissue of interest; (c) generating a panel of binding domains that bind to the cytokine; (d) generating a panel of binding domains that bind the target molecule; (e) screening the cytokine-binding domains using an assay that measures the ability of the cytokine, when complexed with the cytokine-binding domain, to bind to and/or agonize its cognate receptor compared to the ability of unbound cytokine to bind to and/or agonize its cognate receptor; (f) screening the target-binding domains for binding to an appropriate epitope on the target molecule; (g) selecting cytokine-binding domains that do not block or only partially block, the ability of the cytokine to bind to and/or agonize its cognate receptor; (h) generating a panel of multi-specific binding molecules comprising one or more of the selected cytokine-binding domains and one or more selected target-binding domains; and (i) screening the multi-specific binding molecules in an in vitro cell-based assay that measures the ability of the cytokine to bind to and agonize its cognate receptor in the presence of varying amounts of the multi-specific binding molecule. The method can also include screening the multi-specific binding molecules in an in vivo assay in a non-human subject that measures the ability of the cytokine to bind to and agonize its cognate receptor when administered to the subject. The method can further involve performing an epitope binning assay in conjunction with the cytokine-binding domain screening step to identify a region or regions on the cytokine that, when bound to the cytokine-binding domain in the multi-specific binding molecule, retain or partially retain the ability of the cytokine to bind to and agonize its cognate receptor.

In some embodiments the multi-specific binding molecule comprises (a) one cytokine-binding domain and one target-binding domain; (b) one cytokine-binding domain and two identical or non-identical target-binding domains; (c) two identical or non-identical cytokine-binding domains and one target-binding domain; or (d) two identical or non-identical cytokine-binding domains and two identical or non-identical target-binding domains.

In some embodiments, the multi-specific binding molecule comprises a cytokine-binding domain that specifically binds to IL-15 or to IL-15 complexed with IL-15 receptor alpha. The cytokine-binding domain can bind to an IL-15 with an affinity of less than 100 nM, less than 10 nM, less than 1 nM or less than 0.1 nM as measured by surface plasmon resonance (SPR).

In an embodiment of the multi-specific molecule, the specific binding of the cytokine binding domain to the cytokine is non-covalent in nature.

In some embodiments, the multi-specific binding molecule comprises a target-binding domain that specifically binds to a protein expressed in a tumor microenvironment (TME).

In some embodiments, the multi-specific binding molecule comprises a target-binding domain that specifically binds to a tumor-associated antigen (TAA) expressed on the surface of a tumor cell, and the agonistic effect of the cytokine is redirected to the location of the tumor cell.

In some embodiments, the multi-specific binding molecule comprises a target-binding domain that specifically binds to a receptor on an immune cell, optionally a T cell, a macrophage, a dendritic cell or a NK-cell.

In some embodiments, the multi-specific binding molecule comprises a cytokine-binding domain and a target-binding domain that bind to epitopes that are on the same cell (cis binding).

In some embodiments, the multi-specific binding molecule comprises a cytokine-binding domain and a target-binding domain that directly or indirectly bind to receptors that are on different cells (trans binding).

In some embodiments, the multi-specific binding molecule comprises a scaffold, optionally an albumin-based scaffold, a fibronectin-based scaffold or an immunoglobin-based scaffold. The immunoglobulin-based scaffold can be derived from an IgG1, an IgG2, an IgG4, an IgM, or an IgA. The albumin-based or immunoglobulin-based scaffold can be capable of binding to the neonatal Fc receptor (FcRn).

In some embodiments, the multi-specific binding molecule comprises a scaffold, optionally an albumin-based scaffold, a fibronectin-based scaffold or an immunoglobin-based scaffold to which the cytokine binding domain and target binding domain are fused. The multi-specific binding molecule can comprise a cytokine binding domain, target binding domain and scaffold. The immunoglobulin-based scaffold can be derived from an IgG1, an IgG2, an IgG4, an IgM, or an IgA. The albumin-based or immunoglobulin-based scaffold can be capable of binding to the neonatal Fc receptor (FcRn).

In some embodiments, the multi-specific binding molecule comprises a first cytokine binding domain, a second target binding domain and a third Fc domain which can interact with Fcγ receptors.

In some embodiments, the multi-specific binding molecule is a bi-specific antibody comprising a binding domain that specifically binds to an epitope on the active form of the cytokine and a binding domain that specifically binds to an epitope on a receptor molecule on the target cell or tissue.

In another aspect, the disclosure relates to a method for redirecting the agonistic effect of an active form of an endogenous cytokine using a multi-specific molecule, wherein specificity of the multi-specific molecule is against an active form of an endogenous cytokine, engagement of the active form of the endogenous cytokine by the multi-specific molecule is non-blocking, engagement of the active form of the endogenous cytokine by the multi-specific molecule allows the endogenous cytokine to retain its agonistic effect, at least one other specificity of the multi-specific molecule is against a non-cytokine molecule, and the multi-specific molecule sequesters the endogenous cytokine and redirects its agonistic effects by binding to the cell surface receptor molecule. The endogenous cytokine can be in soluble form or in in cell surface form. The cell surface receptor molecule can also be a molecule in the extra-cellular matrix of the target cell. The active form of the endogenous cytokine can be a cytokine, cytokine complex or isoform of cytokine.

In another aspect, the disclosure relates to a method for redirecting the agonistic effect of an active form of a cytokine using a multi-specific molecule, wherein specificity of the multi-specific molecule is against an active form of a cytokine, engagement of the active form of the cytokine by the multi-specific molecule is non-blocking, engagement of the active form of the cytokine by the multi-specific molecule allows the cytokine to retain its agonistic effect, at least one other specificity of the multi-specific molecule is against a non-cytokine molecule, and the multi-specific molecule sequesters the cytokine and redirects its agonistic effects by binding to the cell surface receptor molecule. The cytokine can be in soluble form or in in cell surface form. The cell surface receptor molecule can also be a molecule in the extra-cellular matrix of the target cell. The active form of the cytokine can be a cytokine, cytokine complex or isoform of cytokine.

In some embodiments, the cell surface receptor molecule targeted by the multi-specific molecule of the present invention could be a molecule in the lymph node, in a tumor draining lymph node or in the spleen.

In some embodiments, the agonistic effect is redirected to a desired tissue or cell surface. The desired tissue or cell surface can be immune cells, tumor cells, stromal cells, cells in the tumor micro environment, cells in the bone marrow, cells in the lymph nodes, epithelial cells, endothelial cells, blood cells, skin cells, stem cells, bone cells, nerve cells, adipocytes, or myocytes.

In some embodiments, the cell surface receptor molecule targeted by the multi-specific molecule of the present invention could be a molecule in tissue associated with an auto-immune disease condition.

In some embodiments, the agonistic effect is redirected to a desired tissue to allow for cis or trans presentation of the endogenous cytokine in a targeted environment.

In some embodiments, the agonistic effect is redirected to a desired tissue to allow for cis or trans presentation of the cytokine in a targeted environment.

In some embodiments, the agonistic effect of the endogenous cytokine is preferentially localized to a desired tissue to allow for cis or trans presentation in the targeted environment.

In some embodiments, the agonistic effect of the cytokine is preferentially localized to a desired tissue to allow for cis or trans presentation in the targeted environment.

In another aspect, the disclosure relates to a method for developing a non-blocking multispecific binding molecule, comprising selecting an immune signaling molecule; selecting a target molecule; testing separately the multispecific binding molecules for binding to either the immune signaling molecule or target molecule; testing the multispecific binding molecules for binding to the immune signaling molecule and also agonizing a cognate receptor; and testing the multispecific binding molecules for non-blocking binding to the immune signaling molecule that allows for immune signaling agonistic activity. Optionally, the method can further include modeling a complex between an endogenous cytokine receptor and the immune signaling molecule to define an epitope on the immune signaling molecule that maintains endogenous cytokine receptor specificity and signaling characteristics upon binding of the monospecific binding molecule, thereby developing a non-blocking multispecific binding molecule that binds to an immune signaling molecule and a target molecule. The multispecific binding molecule can be a bispecific binding molecule.

In another aspect, the disclosure relates to a method for developing a non-blocking multispecific binding molecule, comprising selecting an immune signaling molecule; selecting a target molecule; testing separately the multispecific binding molecules for binding to either the immune signaling molecule or target molecule; testing the multispecific binding molecules for binding to the immune signaling molecule and also agonizing a cognate receptor; and testing the multispecific binding molecules for non-blocking binding to the immune signaling molecule that allows for immune signaling agonistic activity. Optionally, the method can further include modeling a complex between an endogenous cytokine receptor and the immune signaling molecule to define an epitope on the immune signaling molecule that maintains endogenous cytokine receptor specificity and signaling characteristics upon binding of the monospecific binding molecule, using this information to design a cytokine binding domain that binds the defined epitope, thereby developing a non-blocking multispecific binding molecule that binds to an immune signaling molecule and a target molecule. The multispecific binding molecule can be a bispecific binding molecule.

In another aspect, the disclosure relates to a method for developing a non-blocking multispecific binding molecule, comprising selecting an immune signaling molecule; selecting a target molecule; testing separately the multispecific binding molecules for binding to either the immune signaling molecule or target molecule; testing the multispecific binding molecules for binding to the immune signaling molecule and also agonizing a cognate receptor; and testing the multispecific binding molecules for non-blocking binding to the immune signaling molecule that allows for immune signaling agonistic activity. Optionally, the method can further include modeling a complex between a cytokine receptor and the immune signaling molecule to define an epitope on the immune signaling molecule that maintains cytokine receptor specificity and signaling characteristics upon binding of the monospecific binding molecule, using this information to design a cytokine binding domain that binds the defined epitope, thereby developing a non-blocking multispecific binding molecule that binds to an immune signaling molecule and a target molecule. The multispecific binding molecule can be a bispecific binding molecule.

In an aspect of this disclosure, the multi-specific binding molecule bound cytokine only shows agonistic activity upon engagement of the receptor target by the multi-specific binding molecule. In another aspect of this disclosure, the multi-specific binding molecule bound cytokine shows stronger agonistic activity upon engagement of the receptor target by the multi-specific binding molecule relative to a monospecific cytokine binding domain which cannot engage the receptor target.

In another aspect, the disclosure relates to a method for developing a non-blocking multispecific binding molecule, comprising selecting an immune signaling molecule; selecting a target molecule; testing separately a monospecific binding molecule for binding to either the immune signaling molecule or target molecule; testing the monospecific binding molecule for binding to the immune signaling molecule and also agonizing a cognate receptor; testing the monospecific binding molecules for non-blocking binding to the immune signaling molecule that allows for immune signaling agonistic activity; and designing the non-blocking multispecific binding molecule as comprising of the monospecific binding molecule of the immune signaling molecule and the monospecific binding molecule binding the target molecule. The immune signaling molecule can be an endogenous cytokine, chemokine, growth factor or hormone. The method can optionally include a step of modeling pharmacological properties of the endogenous cytokine or endogenous cytokine complex. The method can optionally include a step of modeling pharmacological properties of the target molecule. The method can optionally include a step of determining a competitive binding profile of the monospecific binding molecules. Determining a competitive binding profile can be done by epitope binning.

In another aspect, the disclosure relates to a method for developing a non-blocking multispecific binding molecule, comprising selecting an immune signaling molecule; selecting a target molecule; testing separately a monospecific binding molecule for binding to either the immune signaling molecule or target molecule; testing the monospecific binding molecule for binding to the immune signaling molecule and also agonizing a cognate receptor; testing the monospecific binding molecules for non-blocking binding to the immune signaling molecule that allows for immune signaling agonist activity; and designing the non-blocking multispecific binding molecule as comprising of the monospecific binding molecule of the immune signaling molecule and the monospecific binding molecule binding the target molecule. The immune signaling molecule can be a cytokine (e.g., endogenous cytokine), chemokine, growth factor or hormone. The method can optionally include a step of modeling pharmacological properties of the cytokine (e.g., endogenous cytokine) or cytokine complex. The method can optionally include a step of modeling pharmacological properties of the target molecule. The method can optionally include a step of determining a competitive binding profile of the monospecific binding molecules. Determining a competitive binding profile can be done by epitope binning.

In another aspect, the disclosure relates to a method for developing a non-blocking multispecific binding molecule, comprising the steps of selecting an endogenous cytokine or an endogenous cytokine complex, further comprising modeling pharmacological properties of the endogenous cytokine or the endogenous cytokine complex; selecting a target molecule, further comprising modeling the pharmacological properties of the target molecule; testing separate monospecific binding molecules for binding to either the endogenous cytokine, endogenous cytokine complex, or target molecule; testing the monospecific binding molecules for non-blocking binding to the endogenous cytokine or the endogenous cytokine complex, further comprising determining a competitive binding profile of the monospecific binding molecules by epitope binning; modeling a complex between a cytokine receptor and the endogenous cytokine or endogenous cytokine complex to define an epitope on the endogenous cytokine or endogenous cytokine complex that maintains endogenous cytokine receptor specificity and signaling characteristics upon binding of the monospecific binding molecule, thereby developing a non-blocking bispecific binding molecule that binds to an endogenous cytokine and a target molecule; designing a multispecific binding molecule as comprising of monospecific binding molecule for the endogenous cytokine and the monospecific binding molecule for the target molecule. Optionally, the method can further comprise validating the non-blocking multispecific binding molecules for binding to both the endogenous cytokine and the target molecule by in vitro cell-based receptor signaling screen for cytokine activity and target molecule specificity. The method can further comprise evaluating efficacy of the non-blocking multispecific binding molecules in vivo. The method can also include evaluating pharmacokinetic and pharmacodynamic properties of the non-blocking multispecific binding molecules in vivo. Selecting an endogenous cytokine for the method can include determining an endogenous expression level of the endogenous cytokine in a subject, determining an amount of the endogenous cytokine existing in an active state in circulation or at a tissue of interest in the subject, determining a distribution profile of the endogenous cytokine receptor in the subject, and/or determining a clearance and a metabolism mechanism of the endogenous cytokine in the subject. Selecting a target molecule can include examining an expression level, tissue-specificity, localization on a cell surface, molecule internalization dynamics, and/or molecule recycling dynamics of the target molecule in the subject. Modeling pharmacological properties of the endogenous cytokine or endogenous cytokine complex can determine a desirable affinity range for a non-blocking bispecific binding molecule-endogenous cytokine or endogenous cytokine complex interaction, predict differential pharmacokinetics and biodistribution of free endogenous cytokine or endogenous cytokine complex, and/or predict differential pharmacokinetics and biodistribution of non-blocking bispecific binding molecule-bound endogenous cytokine or endogenous cytokine complex. Modeling of pharmacological properties of the target molecule can determine a desirable affinity range for a non-blocking bispecific binding molecule-targeting molecule interaction, and/or predict a differential biodistribution of the target molecule with and without a non-blocking bispecific binding molecule binding. Testing can utilize an in vitro sandwich assay test for bridging of the monospecific binding molecule and the endogenous cytokine receptor via binding of the endogenous cytokine or endogenous cytokine complex. Modeling can determine a non-blocking bispecific binding molecule scaffold geometry that maintains an endogenous cytokine receptor specificity and/or signaling characteristics while binding to the target molecule.

In another aspect, the disclosure relates to a method for developing a non-blocking multispecific binding molecule, comprising the steps of selecting a cytokine or a cytokine complex, further comprising modeling pharmacological properties of the cytokine or the cytokine complex; selecting a target molecule, further comprising modeling the pharmacological properties of the target molecule; testing separate monospecific binding molecules for binding to either the cytokine, cytokine complex, or target molecule; testing the monospecific binding molecules for non-blocking binding to the cytokine or the cytokine complex, further comprising determining a competitive binding profile of the monospecific binding molecules by epitope binning; modeling a complex between a cytokine receptor and the cytokine or cytokine complex to define an epitope on the cytokine or cytokine complex that maintains cytokine receptor specificity and signaling characteristics upon binding of the monospecific binding molecule, thereby developing a non-blocking bispecific binding molecule that binds to an cytokine and a target molecule; designing a multispecific binding molecule as comprising of the monospecific binding molecule for the cytokine and the monospecific binding molecule for the target molecule. Optionally, the method can further comprise validating the non-blocking multispecific binding molecules for binding to both the cytokine and the target molecule by in vitro cell-based receptor signaling screen for cytokine activity and target molecule specificity. The method can further comprise evaluating efficacy of the non-blocking multispecific binding molecules in vivo. The method can also include evaluating pharmacokinetic and pharmacodynamic properties of the non-blocking multispecific binding molecules in vivo. Selecting a cytokine for the method can include determining an expression level of the cytokine in a subject, determining the amount of exogenous cytokine to be introduced in the subject, determining an amount of the cytokine existing in an active state in circulation or at a tissue of interest in the subject, determining a distribution profile of the cytokine receptor in the subject, and/or determining a clearance and a metabolism mechanism of the cytokine in the subject. Selecting a target molecule can include examining an expression level, tissue-specificity, localization on a cell surface, molecule internalization dynamics, and/or molecule recycling dynamics of the target molecule in the subject. Modeling pharmacological properties of the cytokine or cytokine complex can determine a desirable affinity range for a non-blocking bispecific binding molecule-cytokine or cytokine complex interaction, predict the amount of exogenous cytokine that may be introduced in the system or subject to increase the total amount of cytokine, predict differential pharmacokinetics and biodistribution of free cytokine or cytokine complex, and/or predict differential pharmacokinetics and biodistribution of non-blocking bispecific binding molecule-bound cytokine or cytokine complex. Modeling of pharmacological properties of the target molecule can determine a desirable affinity range for a non-blocking bispecific binding molecule-targeting molecule interaction, and/or predict a differential biodistribution of the target molecule with and without a non-blocking bispecific binding molecule binding. Testing can utilize an in vitro sandwich assay test for bridging of the monospecific binding molecule and the cytokine receptor via binding of the cytokine or cytokine complex. Structural modeling can determine a non-blocking bispecific binding molecule scaffold geometry that maintains a cytokine receptor specificity and/or signaling characteristics while binding to the target molecule.

In some embodiments, the methods further comprise performing a competition assay between the monospecific binding molecules for the endogenous cytokine or endogenous cytokine complex that is bound to the endogenous cytokine receptor.

In some embodiments, the methods further comprise performing a competition assay between the monospecific binding molecules for the cytokine or cytokine complex bound to the cytokine or cytokine complex and the free cytokine or cytokine complex, as they bind to the cytokine receptor.

In some embodiments, the endogenous cytokine complex is an IL-15SA complex comprising IL-15 and IL-15 receptor alpha. The non-blocking bispecific binding molecules can bind to an epitope of IL-15 receptor alpha. The non-blocking bispecific binding molecules can bind to an epitope of IL-15. The endogenous cytokine can be IL-15 or IL-2. The non-blocking bispecific binding molecules can bind to IL-15 with a greater affinity than IL-15 receptor alpha. The non-blocking bispecific binding molecules have an affinity to IL-15 that is at least about 10× higher than the non-specific binding molecules affinity to IL-15. In another embodiment, the non-blocking bispecific binding molecules can bind to IL-15 with a weaker affinity than IL-15 receptor alpha. In another embodiment, the non-blocking bispecific binding molecules can bind to IL-15 with an affinity comparable to that of IL-15 receptor alpha.

In some embodiments, the target molecule is programmed cell death protein 1 (PD1), CD33, CD16, programmed death-ligand 1 (PD-L1), an integrin, disialoganglioside (GD2), CD20, fibroblast activation protein (FAP), carcinoembryonic antigen receptor (CEAR), or carcinoembryonic antigen (CEA).

In some embodiments, the non-blocking multispecific binding molecule comprises a bispecific molecule scaffold selected from the group consisting of a homodimeric Fc, a heterodimeric Fc, an albumin-based bispecific scaffold, an affibody, an asymmetric antibody, a bispecific T cell engager (BiTE), a diabody, a dual-affinity retargeting molecule (DART), an immunoglobulin domain crossover (CrossMAb), a minibody, a tandem diabody (TandAb), a fibronectin-based scaffold, or a FynomAb, an antibody fusion construct, an albumin fusion construct. In some embodiments the Fc can be derived from any of the naturally observed antibody isoforms such as IgG1, IgG2, IgG3, IgG4, IgA, IgD, IgE or IgM isoforms or with some site-specific mutations.

In some embodiments, the non-blocking multispecific binding molecule is an engineered fusion protein comprising a (e.g., one or more) monospecific binding molecule or molecules for binding to the immune signaling molecule and another (e.g., one or more) monospecific binding molecule or molecules for binding to the target molecule. The monospecific binding molecules can be antibodies, divalent antibody fragments, fragment antigen-binding (Fab) regions, minibodies, monovalent antibodies, single-chain variable fragments (scFv), reduced immunoglobulins, disulfide-stabilized variable fragments, Fab fragments, nanobodies, immunoglobulin domain antibodies, variable light (VL) constructs, variable heavy (VH) constructs, fynomers, or darpins.

In another aspect, the disclosure relates to a method for developing a non-blocking multispecific binding molecule comprising the steps of selecting an endogenous cytokine of interest to be amplified; obtaining data pertaining to the systems level characteristics of the endogenous cytokine; obtaining data pertaining to target receptors; modeling and simulation of the endogenous cytokine in its native state an upon association with an antibody; modeling and simulation of the receptor targeting of the endogenous cytokine; identifying binders to the endogenous cytokine and the target receptor; performing binding screens and/or competition assays; performing epitope binning of antibodies; defining the desired epitope on the endogenous cytokine; and performing mixed cell-based receptor signaling screen, wherein non-blocking multispecific binding molecules that engage the endogenous cytokine and retain cytokine receptor binding and signaling characteristics of the endogenous cytokine.

In another aspect, the disclosure relates to a method for developing a non-blocking multispecific binding molecule comprising the steps of selecting a cytokine of interest to be amplified; obtaining data pertaining to the systems level characteristics of the cytokine; obtaining data pertaining to target receptors; modeling and simulation of the cytokine in its native state upon association with an antibody; modeling and simulation of the receptor targeting of the cytokine; identifying binders to the cytokine and the target receptor; performing binding screens and/or competition assays; performing epitope binning of antibodies; defining the desired epitope on the cytokine; and performing mixed cell-based receptor signaling screen, wherein non-blocking multispecific binding molecules that engage the cytokine and retain cytokine receptor binding and signaling characteristics of the cytokine.

In another aspect, the disclosure relates to a multi-specific binding molecule comprising: (a) a binding domain that specifically binds to an active form of a cytokine and (b) a binding domain that specifically binds to an epitope on a molecule that is a marker on a target cell or tissue, wherein the multi-specific binding molecule, when bound to the cytokine, does not block or only partially blocks, the ability of the cytokine to bind to and agonize a cognate receptor for the cytokine.

In another aspect, the disclosure relates to a non-blocking antibody complex comprising an antibody and a cytokine, wherein the antibody is capable of presenting the cytokine to its cognate receptor. The antibody complex can be multi-specific. The antibody can be capable of localizing the cytokine to desired tissue or target cell surface receptor. The half-life of the complex can be the same as that of the antibody. In another aspect, the half-life of the complex can be shorter than that of an unbound antibody.

In another aspect, the disclosure relates to a method of multispecific targeting comprising the steps of generating a non-blocking multispecific binding molecule using a method described herein and administering the non-blocking multispecific binding molecule to a subject in need thereof, wherein the multispecific binding molecule targets an endogenous cytokine in serum of the subject and activates and/or proliferates tumor specific effector cells; thereby inducing tumor cell killing.

In another aspect, the disclosure relates to a method of multispecific targeting comprising the steps of generating a non-blocking multispecific binding molecule using a method described herein and administering the non-blocking multispecific binding molecule to a subject in need thereof, wherein the multispecific binding molecule targets a cytokine in serum of the subject and activates and/or proliferates tumor specific effector cells; thereby inducing tumor cell killing.

In another aspect, the disclosure relates to methods for redirecting an active form of an endogenous cytokine to a target cell or tissue of interest in a biological system, wherein the biological system comprises (i) the active form of the cytokine; (ii) (ii) a cell bearing a cognate receptor for the active form of the cytokine on its surface; (iii) one or more target cells or tissues of interest to which the cytokine is to be redirected; the method comprising exposing the biological system to a multi-specific binding molecule comprising (a) a binding domain that specifically binds to an epitope on the active form of the cytokine (a cytokine-binding domain), wherein the cytokine, when complexed with the multi-specific binding molecule, retains its ability to bind to and agonize its cognate receptor; and (b) a binding domain that specifically binds to an epitope on a molecule that is not a cytokine receptor on the target cell or tissue (a target-binding domain), wherein the cytokine, when complexed with the multi-specific binding molecule, retains its ability to bind to and agonize its cognate receptor; thereby redirecting the active form of the cytokine to the target cell or tissue.

In another aspect, the disclosure relates to a multi-specific binding molecule that binds PD-1 and IL-15 comprising one binding domain specific for PD-1 and a second binding domain specific for IL-15, wherein (a) the binding domain specific for PD-1 comprises CDR H1 (SEQ ID NO: 70, SEQ ID NO: 71, or SEQ ID NO:72), CDR H2 (SEQ ID NO: 73, SEQ ID NO: 74, or SEQ ID NO: 75), CDR H3 (SEQ ID NO:

76, SEQ ID NO: 77, or SEQ ID NO: 78), CDR L1 (SEQ ID NO:79, SEQ ID NO: 80, or SEQ ID NO:81), CDR L2 (SEQ ID NO: 82, SEQ ID NO: 83, or SEQ ID NO: 84), and L3 (SEQ ID NO: 85, SEQ ID NO: 86, or SEQ ID NO: 87); and (b) the binding domain specific for IL-15 comprises CDR H1 (SEQ ID NO: 52, SEQ ID NO: 53, or SEQ ID NO: 54), CDR H2 (SEQ ID NO: 55, SEQ ID NO: 56, or SEQ ID NO: 57), CDR H3 (SEQ ID NO: 58, SEQ ID NO: 59, or SEQ ID NO: 60) CDR L1 (SEQ ID NO: 61, SEQ ID NO: 62, or SEQ ID NO: 63), CDR L2 (SEQ ID NO: 64, SEQ ID NO: 65, or SEQ ID NO: 66), and L3 (SEQ ID NO: 67, SEQ ID NO: 68, or SEQ ID NO: 69).

In another aspect, the disclosure relates to a multi-specific binding molecule that binds PD-1 and IL-15, wherein the binding domain is specific for PD-1 comprises a variable fragment light chain (VL) selected from the group consisting of SEQ ID NO: 5, SEQ ID NO:6, SEQ ID NO: 7, and SEQ ID NO: 8.

In another aspect, the disclosure related to a multi-specific binding molecule that binds PD-1 and IL-15, wherein the binding domain specific for IL-15 comprises a variable fragment light chain (VL) selected from the group consisting of SEQ ID NO: 1 and SEQ ID NO: 2.

In another aspect, the disclosure relates to a multi-specific binding molecule that binds PD-1 and IL-15, wherein the binding domain specific for PD-1 comprises a VL selected from the group consisting of SEQ ID NO: 5, SEQ ID NO:6, SEQ ID NO: 7, and SEQ ID NO: 8; and the binding domain specific for IL-15 comprises a VL selected from the group consisting of SEQ ID NO: 1 and SEQ ID NO: 2.

In another aspect, the disclosure relates to a multi-specific binding molecule that binds PD-1 and IL-15, wherein the binding domain specific for PD-1 comprises a variable fragment heavy chain (VH) selected from the group consisting of SEQ ID NO: 19 and SEQ ID NO: 20.

In another aspect, the disclosure relates to a multi-specific binding molecule that binds PD-1 and IL-15, wherein the binding domain specific for IL-15 comprises a variable fragment heavy chain (VH) selected from the group consisting of SEQ ID NO: 17 and SEQ ID NO: 18.

In another aspect, the disclosure relates to a multi-specific binding molecule that binds PD-1 and IL-15, wherein (a) the binding domain specific for PD-1 comprises a VH selected from the group consisting of SEQ ID NO: 19 and SEQ ID NO: 20; and (b) the binding domain specific for IL-15 comprises a variable fragment heavy chain (VH) selected from the group consisting of SEQ ID NO: 17 and SEQ ID NO: 18.

In another aspect, the disclosure relates to a multi-specific binding molecule that binds PD-1 and IL-15, wherein the binding domain specific for PD-1 comprises a constant fragment light chain (CL) selected from the group consisting of SEQ ID NO: 9 and SEQ ID NO: 10.

In another aspect, the disclosure relates to a multi-specific binding molecule that binds PD-1 and IL-15, wherein the binding domain specific for IL-15 comprises a CL selected from the group consisting of SEQ ID NO: 3 and SEQ ID NO: 4.

In another aspect, the disclosure relates to a multi-specific binding molecule that binds PD-1 and IL-15, comprising a constant fragment heavy chain 1 (CH1) selected from the group consisting of SEQ ID NO: 21, SEQ ID NO: 22, SEQ ID NO: 23, SEQ ID NO: 24; a constant fragment heavy chain 2 (CH2) selected from the group consisting of SEQ ID NO: 25, SEQ ID NO: 26, and SEQ ID NO: 27; and a constant fragment heavy chain 3 (CH3) selected from the group consisting of SEQ ID NO: 31, SEQ ID NO: 32, SEQ ID NO: 33, SEQ ID NO: 34, SEQ ID NO: 35, and SEQ ID NO: 36.

In another aspect, the disclosure relates to a multi-specific binding molecule that binds PD-1 and IL-15, wherein said binding molecule is an antibody in a Fab-Fab format. In another aspect, the disclosure relates to a multi-specific binding molecule that binds PD-1 and IL-15, further comprising at least one scFv fused to the C terminus of a heavy chain.

In another aspect, the disclosure relates to a multi-specific binding molecule that binds PD-1 and IL-15, wherein one Fab is specific for PD-1, and the scFv is specific for IL-15.

In another aspect, the disclosure relates to a multi-specific binding molecule that binds PD-1 and IL-15, wherein one Fab is specific for IL-15, and the scFv is specific for PD-1.

In another aspect, the disclosure relates to a multi-specific binding molecule that binds PD-1 and IL-15, wherein said binding molecule is an antibody in a dual variable domain (DVD) format.

In another aspect, the disclosure relates to a multi-specific binding molecule that binds PD-1 and IL-15, wherein said binding molecule is an antibody in a dual variable domain (DVD) format. In a further aspect, the VH domain comprising specificity to PD-1 is fused to the N terminus of the VH domain comprising specificity to IL-15, and wherein the VL domain comprising specificity to PD-1 is fused to the N terminus of the VL domain with specificity to IL-15.

In another aspect, the disclosure relates to a multi-specific binding molecule that binds PD-1 and IL-15, wherein said binding molecule is an antibody in a dual variable domain (DVD) format, wherein the VH domain comprising specificity to PD-1 is fused to the N terminus of the VH domain comprising specificity to IL-15, and wherein the VL domain comprising specificity to PD-1 is fused to the N terminus of the VL domain with specificity to IL-15, and wherein outermost Fabs are specific for PD-1 and the inner Fabs are specific for IL-15.

In another aspect, the disclosure relates to a multi-specific binding molecule that binds PD-1 and IL-15, wherein said binding molecule is an antibody in a dual variable domain (DVD) format, wherein the VH domain comprising specificity to IL-15 is fused to the N terminus of the VH domain comprising specificity to PD-1, and wherein the VL domain comprising specificity to IL-15 is fused to the N terminus of the VL domain with specificity to PD-1, and wherein outermost Fabs are specific for IL-15 and the inner Fabs are specific for PD-1.

In another aspect, the disclosure relates to a multi-specific binding molecule that binds PD-1 and IL-15, wherein said binding molecule is an antibody in a dual variable domain (DVD) format, wherein the DVD comprises a linker connecting the VH domain comprising specificity to PD-1 to the VH domain comprising specificity to IL-15, and a linker connecting the VL domain comprising specificity to PD-1 to the VL comprising specificity to IL-15. In a further aspect, the linker is selected from the group consisting of SEQ ID NO: 37, SEQ ID NO: 38, and SEQ ID NO: 39. In yet another aspect, the linker is selected from the group consisting of SEQ ID NO: 40 and SEQ ID NO: 41.

In another aspect, the disclosure relates to a multi-specific binding molecule that binds PD-1 and IL-15, wherein said binding molecule is a fusion protein. In another aspect, the disclosure relates to a multi-specific binding molecule that binds PD-1 and IL-15, wherein said binding molecule comprises more than one PD-1 binding domain, more than one IL-15 binding domain, or more than one PD-1 binding domain and more than one IL-15 binding domain.

In another aspect, the disclosure relates to methods for redirecting an active form of a cytokine to a target cell or target tissue of interest in a subject comprising administering to the subject a sufficient amount of a multi-specific binding molecule comprising (a) a binding domain that specifically binds to the active form of the cytokine (a cytokine-binding domain) and (b) a binding domain that specifically binds to a molecule that is a marker on the target cell or tissue (a target-binding domain), wherein the cytokine, when complexed with the multi-specific binding molecule, retains its ability to bind to and agonize a cognate receptor for the cytokine; thereby redirecting the active form of the cytokine to the target cell or tissue. In another aspect, the active form of the cytokine is endogenous to the system or the subject. In another aspect, the active form of the cytokine is an exogenous cytokine, and wherein the exogenous cytokine is added to the biological system or administered to the subject. In another aspect, the active form of the cytokine is a mixture of endogenous and exogenous cytokine.

In another aspect, the disclosure relates to a method for redirecting the agonistic effect of an active form of an endogenous cytokine using a multi-specific molecule, wherein specificity of the multi-specific molecule is against an active form of an endogenous cytokine, engagement of the active form of the endogenous cytokine by the multi-specific molecule is non-blocking, engagement of the active form of the endogenous cytokine by the multi-specific molecule allows the endogenous cytokine to retain its agonistic effect, at least one other specificity of the multi-specific molecule is against a non-cytokine molecule, and the multi-specific molecule sequesters the endogenous cytokine and redirects its agonistic effects by binding to the cell surface receptor molecule. The endogenous cytokine can be in soluble form or in in cell surface form. In another aspect, the non-blocking multi-specific molecules bind to IL-15 with affinity less than IL-15Rα and the affinity is at least about 10×, about 100×, or lower. In another aspect, a non-blocking antibody complex is shorter than that of the antibody but longer than that of the free cytokine.

BRIEF DESCRIPTION OF THE DRAWINGS

To better understand the present disclosure, it will now be described by way of examples, with reference to the accompanying drawings in which embodiments of the disclosures are illustrated and, together with the description below, explain the principles of the disclosure.

FIGS. 5A-5C show model structures and predicted model structures of an antibody Fab and IL-15 in complex with its cognate receptor chains. FIG. 5A shows the quaternary structure of IL-15 bound to its cognate receptor chains IL-15Rα, IL-15Rβ, and the common gamma chain (model based on the crystal structure pdb id 4gs7). FIG. 5B shows a model structure of an antibody Fab (shown as ribbon) bound to the cytokine IL-15 (shown as space filling) based on crystal structure pdb id 2xqb.

FIG. 5C shows a predicted model structure of Fab (shown as ribbon) bound IL-15 (shown as space filling) bound to it cognate receptor chains, the IL-15Rβ and common gamma chains (shown as wire frame). Model based on pdb id structure 2xqb and 4gs7.

FIG. 6A depicts the structure of a bispecific antibody in a Fab-Fab format, with one Fab arm specific for PD1 and the other Fab arm specific for IL-15. FIGS. 6B and 6C depict the structure of possible versions of a bispecific antibody in Fab-Fab format with one or two scFvs fused to the C terminus of heavy chains. In the embodiments, the Fabs are specific for one antigen, whereas the scFvs are specific for the other antigen. FIG. 6D depicts the structure of a bispecific antibody in dual variable domain (DVD) format, where the VH domain with specificity to one antigen is fused to the N terminus of the VH domain with specificity to the other antigen, and the VL domain with specificity to one antigen is fused to the N terminus of the VL domain with specificity to the other antigen. FIG. 6E depicts the structure of a bispecific antibody in dual Fab domain format, where the outermost Fabs are specific for one antigen and the inner Fabs are specific for the other antigen.

In FIG. 7A, RV18 and RV20 each showed predominantly two bands, with the higher molecular weight band indicative of intact H chain with scFv attached (H+ scFv) and the lower molecular weight band indicative of the L chain. Comparison with RV17 and RV19 also showed two predominant bands, with the lower molecular weight band matching the L chain band of RV18 and RV20; however, the H chains of RV17 and RV19 showed lower molecular weight bands vs RV18 and RV20, consistent with the loss of the scFv. In FIG. 7B, RV24 and RV26 each showed predominantly three bands with the highest molecular weight band indicative of H chain with scFv attached (H+ scFv), the intermediate band indicative of H chain and the lower molecular weight band indicative of the L chain. For RV23 and RV25, only the bands corresponding to H and L chains were observed. Overall, for the variants with the anti-PD1 scFv designed with the VL-linker-VH orientation (RV20 and RV26), the engineered disulfides seemed to stabilize the scFv, as evidenced by the stronger H+ scFv bands vs variants that lacked the engineered disulfides (RV18, RV24).

FIG. 8A shows a bispecific antibody in a Fab-Fab format (RV15), FIG. 8B shows a fusion of 1 scFv to a HC of a bispecific antibody in Fab-Fab format (RV26), FIG. 8C shows a bispecific antibody in DVD format (RV29), FIG. 8D shows a bispecific antibody in dual Fab domain format (RV32) and FIG. 8E shows fusions of 2 scFvs to the HCs of a bispecific antibody in Fab-Fab format (RV34).

FIG. 9A depicts results from LC-MS analysis of a bispecific antibody in a Fab-Fab format (RV15). FIG. 9B depicts results from LC-MS analysis of fusion of 1 scFv to a HC of a bispecific antibody in Fab-Fab format (RV26). FIG. 9C depicts results from LC-MS analysis of a bispecific antibody in DVD format (RV29). FIG. 9D depicts results from LC-MS analysis of a bispecific antibody in dual Fab domain format (RV32). FIG. 9E depicts results from LC-MS analysis of fusions of 2 scFvs to the HCs of a bispecific antibody in Fab-Fab format (RV34).

FIG. 11A shows results from using the Fab-Fab format (RV15), FIG. 11B shows results from using a bispecific antibody in dual Fab domain format (RV32), FIG. 11C shows results from using a bispecific antibody in DVD format (RV29) and FIG. 11D shows results from using a fusion of 1 scFv to a HC of a bispecific antibody in Fab-Fab format (RV26).

FIG. 12A shows the SPR sensorgram using the anti-PD1 capture surface. FIG. 12B shows the SPR sensorgram using the anti-human Fc capture surface. For both figures, the baselines were set to zero for the start of the RV capture step. The arrows indicate when either ligands or analyte were injected. The lower curve shows the response to the injections of ligands only, with a final injection of PBST instead of IL-15 βγ receptor, resulting in the formation of RV30:PD1:IL-15 complex. The upper curve shows the response to the injections of ligands and analyte resulting in the formation of the RV30:PD1:IL-15:IL-15 βγ receptor complex. With subsequent injections of higher concentrations of IL-15 βγ receptor, corresponding responses in the upper curve showed increased formation of the RV30:PD1:IL-15:IL-15 βγ receptor complex.

FIGS. 19A and 19B show the frequency of Ki-67 positive CD56++ NK (FIG. 19A) and CD56+CD16+ NK (FIG. 19B) cells in human PBMC after 4 days of in vitro culture with 100 nM, 10 nM, or 1 nM of IL-15 precomplexed with either RV1, RV2, RV29, RV32 or IL-15Rα-Fc, IL-15 alone or no treatment.

FIGS. 21A and 21B show the frequency of Ki-67 positive CD3+CD8+ (FIG. 21A) and CD3+CD4+ (FIG. 21B) cells in in vitro activated human T cells after 4 days of in vitro culture with 100 nM, 10 nM, or 1 nM of IL-15 precomplexed with either RV1, RV2, RV29, RV32 or IL-15Rα-Fc, IL-15 alone or no treatment.

FIGS. 22A-22D show induction of STAT5 phosphorylation on CD4+ T cells (FIG. 22A) on CD8+ T cells (FIG. 22B), CD56 bright NK cells (FIG. 22C) and on CD56+ CD16+ NK cells (FIG. 22D) by IL-15 alone, and IL-15 complexed with IL-15Rα, a Fc, RV1, RV3 or an isotype control (anti-RSV) antibody.

FIG. 23A shows simulation based on an antibody with 0.1 nM affinity (Kd) for IL-15 and an assumption of 1 day half-life of the antibody-cytokine complex. Scan of IL-15 concentration change in serum predicted at different dose of antibody treatment is shown. FIG. 23B shows simulation based on an antibody with 0.1 nM affinity (Kd) for IL-15 and an assumption of 3 day half-life of the antibody-cytokine complex. Scan of IL-15 concentration change in serum predicted at different dose of antibody treatment is shown. FIG. 23C shows simulation based on an antibody with 1 nM affinity (Kd) for IL-15 and an assumption of 3 day half-life of the antibody-cytokine complex. Scan of IL-15 concentration change in serum predicted at different dose of antibody treatment is shown.

FIGS. 24A-24F show the structure and a brief description of the bispecific variants produced (RV15, RV17, RV18, RV19, RV20, RV21, RV22, RV23, RV24, RV25, RV26, RV29, RV30, RV31, RV32, RV33, RV34, RV35, RV36 and RV37) and the monospecific parent antibodies produced (RV1, RV2, RV3, RV9 and RV10).

DETAILED DESCRIPTION

Figure 1:
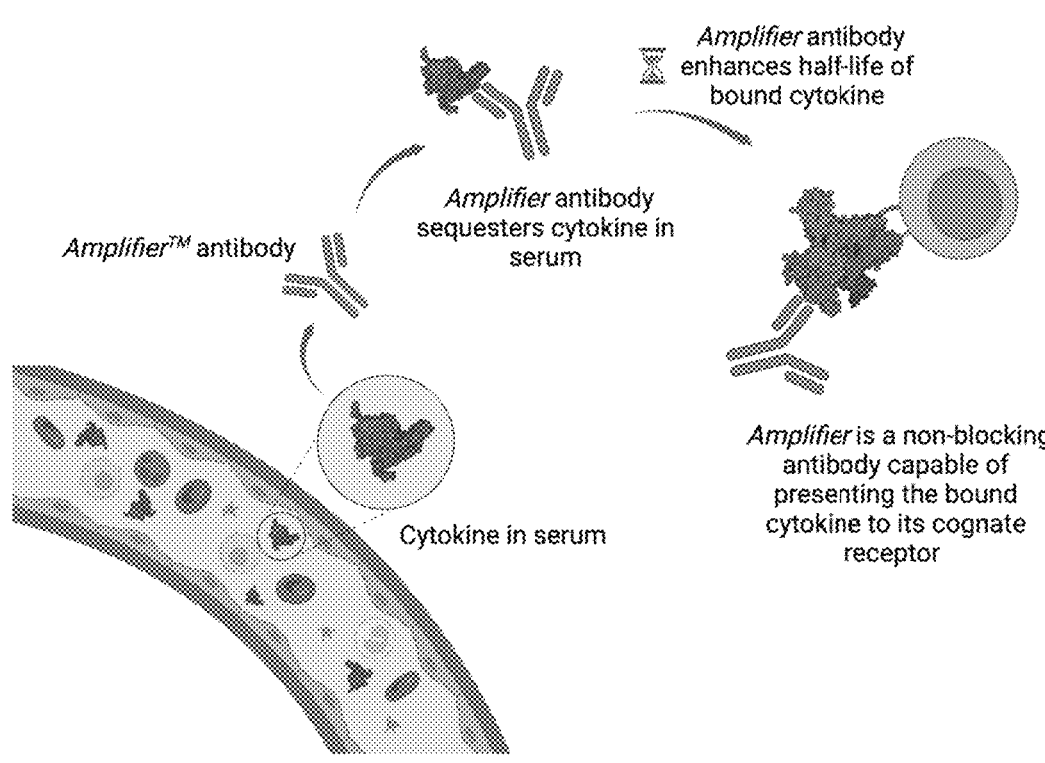
FIG. 1 is a schematic of a cytokine binding antibody (labelled as Amplifier antibody in figure) action. The antibody sequesters the active form of the cytokine molecules in serum of the biological system. The antibody bound cytokine may have an improved half-life in the biological system as it is protected from different modes of elimination, unlike the unbound cytokines which typically have a short half-life in serum. The antibody bound cytokine can agonize its cognate receptor. The engagement of the cytokine by the antibody is non-blocking i.e. the antibody bound cytokine is in its active form and can be presented to it is cognate receptor on a cell surface such as an immune cell surface and induce signaling.

The present disclosure is directed toward systems and methods of amplifying the action of the natural cytokine, specifically in tumor or tissue and overcome dosing challenges and systemic toxicity. The technology disclosed herein overcomes the limitations of existing cytokine therapies.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments", as defined herein, comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. In certain embodiments, the antibody fragments retain at least part of the hinge and optionally the CH1 region of an IgG heavy chain. In some embodiments the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal," indicates the character of the antibody as being obtained from a substantially homogeneous population of antibodies, and is not to be construed as requiring production of the antibody by any particular method. In certain embodiments the monoclonal antibodies to be used in accordance with the present disclosure are made by the hybridoma method first described by Kohler et al., Nature 256:495 (1975), or may be made by recombinant DNA methods (see, e.g., U.S. Pat. No. 4,816,567). In some embodiments "monoclonal antibodies" are isolated from phage antibody libraries using the techniques described in Clackson et al., Nature 352:624-628 (1991) and Marks et al., J. Mol. Biol. 222:581-597 (1991), for example.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "binding domain" refers to the region of a polypeptide that binds to another molecule.

The term "bispecific" is intended to include any agent which has two antigen binding moieties (e.g. antigen binding polypeptide constructs), each with a unique binding specificity. For example, a first antigen binding moiety binds to an epitope on a first antigen, and a second antigen binding moiety binds to an epitope on a second antigen.

The term "cytokine" as used herein is meant a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

"Endogenous cytokines" as used herein encompasses a cytokine, cytokine complex or isoforms of cytokine produced inside an organism or cell. The endogenous cytokine can be in soluble form or cell surface (membrane anchored) form.

"Exogenous cytokines" as used here encompass a cytokine, cytokine complex or isoforms of cytokine, or engineered mutant of a wildtype cytokine produced recombinantly. The exogenous cytokine can be introduced into a system or organism as part of treatment.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic .quadrature.-sandwich folding topology. The known Ig domains in the IgG class of antibodies are VH, Cγ1, Cγ2, Cγ3, VL, and CL.

The term "immune signaling molecule" when used herein refers to an endogenous cytokine, chemokine, growth factor, or hormone.

"Specifically binds" or "specific binding" means that the binding is selective for the antigen and can be discriminated from unwanted or non-specific interactions. The ability of a binding molecule to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al, Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding construct to the antigen as measured, e.g., by SPR. In certain embodiments, an antigen binding construct that binds to the antigen, or an antigen binding molecule comprising that antigen binding moiety, has a dissociation constant (KD) of <1 μM, <100 nM, <10 nM, <1 nM, <0.1 nM, <0.01 nM, or <0.001 nM (e.g. 10-8 M or less, e.g. from 10-8 M to 10-13 M, e.g., from 10-9 M to 10-13 M).

The term "target," "target antigen," or "target receptor" as used herein is meant the molecule that is bound specifically by the variable region of a given antibody. A target antigen or target receptor may be a protein, carbohydrate, lipid, or other chemical compound. The molecule may be, for example, programmed cell death protein 1 (PD1), CD33, CD16, programmed death-ligand 1 (PD-L1), an integrin, disialoganglioside (GD2), CD20, fibroblast activation protein (FAP), carcinoembryonic antigen receptor (CEAR), and carcinoembryonic antigen (CEA).

The term "target cell" as used herein is meant a cell that expresses a target antigen.

Multi-Specific Binding Molecules

The multi-specific binding molecules disclosed herein can include one cytokine-binding domain and one target-binding domain; one cytokine-binding domain and two identical or non-identical target-binding domains; two identical or non-identical cytokine-binding domains and one target-binding domain; or two identical or non-identical cytokine-binding domains and two identical or non-identical target-binding domains.

In one embodiment, the multi-specific binding molecule may include a binding domain that specifically binds to an active form of a cytokine and a binding domain that specifically binds to an epitope on a molecule that is a marker on a target cell or tissue, wherein the multi-specific binding molecule, when bound to the cytokine, does not block or only partially blocks, the ability of the cytokine to bind to and agonize a cognate receptor for the cytokine.

In some embodiments, the multi-specific binding molecule is a bispecific antibody. The bispecific antibody can include a binding domain that specifically binds to an epitope on the active form of a cytokine and a binding domain that specifically binds to an epitope on a molecule that is not a cytokine receptor on the target cell or tissue. For example, the bispecific antibody can bind to an epitope IL-15 and the second specificity can be for an epitope on the checkpoint receptor PD1.

The cytokine-binding domain may specifically bind any cytokine, for example, but not limited to IL-2, IL-15, or IL-15 complexed with IL-15 receptor alpha. In certain embodiments, the cytokine-binding domain binds to an IL-15-IL:15 receptor alpha complex with an affinity of less than 100 nM, less than 10 nM, less than 1 nM or less than 0.1 nM as measured by surface plasmon resonance (SPR). In certain embodiments, the cytokine-binding domain binds to an IL-2-IL:2R complex with an affinity of less than 100 nM, less than 10 nM, less than 1 nM or less than 0.1 nM as measured by SPR.

The multi-specific (e.g., bispecific) binding molecules can have an affinity to IL-15 that is at least about 10× higher than the non-specific binding molecules affinity to IL-15. The affinity may be, for example, at least about 10×, 15×, 20×, 30×, 40×, or 50× higher than the non-specific binding molecules affinity to IL-15.

The multi-specific binding molecule can include a target-binding domain that specifically binds to a protein expressed in a tumor microenvironment (TME); a tumor-associated antigen (TAA) expressed on the surface of a tumor cell, and the agonistic effect of the cytokine is redirected to the location of the tumor cell; and/or a receptor on an immune cell (e.g., a T cell, a macrophage, an NK-cell). In some embodiments, the target is selected from the group consisting of programmed cell death protein 1 (PD1), CD33, CD16, programmed death-ligand 1 (PD-L1), an integrin, disialoganglioside (GD2), CD20, fibroblast activation protein (FAP), carcinoembryonic antigen receptor (CEAR), and carcinoembryonic antigen (CEA).

The multi-specific binding molecule can comprise a cytokine-binding domain and a target-binding domain that bind to cytokine receptor and target receptor that are on the same cell (cis binding) or to receptors that are on different cells (trans binding).

The multi-specific binding molecule can include a scaffold (e.g., an albumin-based scaffold, a fibronectin-based scaffold, immunoglobin-based scaffold). The scaffold can be, for example, an albumin-based bispecific scaffold, an affibody, an asymmetric antibody, a bispecific T cell engager (BiTE), a diabody, an immunoglobulin domain crossover (CrossMAb), a minibody, a tandem diabody (TandAb), a fibronectin-based scaffold, a dual variable domain (DVD) antibody, or a FynomAb, an antibody fusion construct, an albumin fusion construct. The scaffold can be, for example, a dual-affinity retargeting molecule (DART). The scaffold can be, for example, an albumin-based scaffold, a fibronectin-based scaffold, or an immunoglobin-based scaffold. An immunoglobulin-based scaffold can be derived from an IgG1, an IgG2, an IgG4, an IgM, or an IgA. The albumin-based or immunoglobulin-based scaffold can be capable of binding to the neonatal Fc receptor (FcRn). FcRn is structurally similar to major histocompatibility complex (MHC) and consists of an α-chain noncovalently bound to β2-microglobulin.

The multispecific binding molecule can be a fusion protein comprising a monospecific binding molecule for binding to the immune signaling molecule and another monospecific binding molecule for binding to the target molecule. Examples of monospecific binding molecules, include, but are not limited to antibodies, divalent antibody fragments, fragment antigen-binding regions, minibodies, monovalent antibodies, single-chain variable fragments (scFv), reduced immunoglobulins, and disulfide-stabilized variable fragments, Fab fragments, nanobodies, immunoglobulin domain antibodies, fynomers, and darpins. In another aspect of this disclosure, the non-blocking cytokine binding domain is not the native receptor of the cytokine, such as IL-15Rα for IL-15 or IL-2Rα for IL-2.

In another aspect, the disclosure relates to a non-blocking antibody complex that comprises an antibody and a cytokine, wherein the antibody is capable of presenting the cytokine to its cognate receptor. The antibody complex can be multispecific, for example the antibody complex can be bispecific, tri-specific, or specific for at least 4, 5, 6, 7, 8, 9, 10 or more targets. The antibody can be capable of localizing the cytokine to a desired tissue or target cell surface receptor. The half-life of the non-blocking antibody complex can be the same as that of the antibody. The half-life of the non-blocking antibody complex can be greater than the half-life of the antibody alone or shorter than the half-life of the antibody alone.

In another aspect, the disclosure relates to a multi-specific binding molecule that binds PD-1 and IL-15, comprising one binding domain specific for PD-1 and a second binding domain specific for IL-14, wherein the binding domain specific for PD-1 and comprises CDR H1 (SEQ ID NO: 70, SEQ ID NO: 71, or SEQ ID NO:72), CDR H2 (SEQ ID NO: 73, SEQ ID NO: 74, or SEQ ID NO: 75), CDR H3 (SEQ ID NO: 76, SEQ ID NO: 77, or SEQ ID NO: 78), CDR L1 (SEQ ID NO:79, SEQ ID NO: 80, or SEQ ID NO:81), CDR L2 (SEQ ID NO: 82, SEQ ID NO: 83, or SEQ ID NO: 84), and CDR L3 (SEQ ID NO: 85, SEQ ID NO: 86, or SEQ ID NO: 87); and the binding domain specific for IL-15 and comprises CDR H1 (SEQ ID NO: 52, SEQ ID NO: 53, or SEQ ID NO: 54), CDR H2 (SEQ ID NO: 55, SEQ ID NO: 56, or SEQ ID NO: 57), CDR H3 (SEQ ID NO: 58, SEQ ID NO: 59, or SEQ ID NO: 60) CDR L1 (SEQ ID NO: 61, SEQ ID NO: 62, or SEQ ID NO: 63), CDR L2 (SEQ ID NO: 64, SEQ ID NO: 65, or SEQ ID NO: 66), and CDR L3 (SEQ ID NO: 67, SEQ ID NO: 68, or SEQ ID NO: 69).

In another aspect, the multi-specific binding molecule that binds PD-1 and IL-15 comprises a binding domain specific for PD-1 comprising a variable fragment light chain (VL) selected from the group consisting of SEQ ID NO: 5, SEQ ID NO:6, SEQ ID NO: 7, and SEQ ID NO: 8.

In another aspect, the multi-specific binding molecule that binds PD-1 and IL-15 comprises a binding domain specific for PD-1 comprising a heavy chain (VH) selected from the group consisting of SEQ ID NO: 19 and SEQ ID NO: 20.

In another aspect, the multi-specific binding molecule that binds PD-1 and IL-15 comprises a binding domain specific for IL-15 comprising a variable light chain (VL) selected from the group consisting of SEQ ID NO: 1 and SEQ ID NO: 2.

In another aspect, the multi-specific binding molecule that binds PD-1 and IL-15 comprises a binding domain specific for IL-15 comprising a heavy chain (VH) selected from the group consisting of SEQ ID NO: 17 and SEQ ID NO: 18.

In another aspect, the multi-specific binding molecule that binds PD-1 and IL-15 comprises a binding domain specific for PD-1 comprising a VL selected from the group consisting of SEQ ID NO: 5, SEQ ID NO:6, SEQ ID NO: 7, and SEQ ID NO: 8; and the Fab arm specific for IL-15 comprises a VL selected from the group consisting of SEQ ID NO: 1 and SEQ ID NO: 2.

In another aspect, the multi-specific binding molecule that binds PD-1 and IL-15 comprises a binding domain specific for PD-1 comprising a VH selected from the group consisting of SEQ ID NO: 19 and SEQ ID NO: 20; and a binding domain specific for IL-15 comprising a variable fragment heavy chain (VH) selected from the group consisting of SEQ ID NO: 17 and SEQ ID NO: 18.

In some aspects, the multi-specific binding molecule that binds PD-1 and IL-15 is in a Fab-Fab format can comprise a light chain variable region. In another aspect, the multi-specific binding molecule that binds PD-1 and IL-15 comprises a binding molecule further comprising at least one scFV fused to the C-terminus of ta heavy chain.

In another aspect, the disclosure relates to a multi-specific binding molecule that binds PD-1 and IL-15, wherein one binding domain is specific for PD-1 and comprises a CDR H1 that can include the amino acid sequence of SEQ ID NO: 70, or a sequence approximately at least 90% identical thereto, a CDR H1 that can include the amino acid sequence of SEQ ID NO: 71, or a sequence approximately at least 90% identical thereto, or a CDRH1 that can include the amino acid sequence of SEQ ID NO:72, or a sequence approximately at least 90% identical thereto, a CDR H2 that can include the amino acid sequence of SEQ ID NO: 73, or a sequence approximately at least 90% identical thereto, a CDR H2 that can include the amino acid sequence of SEQ ID NO: 74, or a sequence approximately at least 90% identical thereto, or CDR H2 that can include the amino acid sequence of SEQ ID NO: 75, or a sequence approximately at least 90% identical thereto, and a CDR H3 that can include the amino acid sequence of SEQ ID NO: 76, or a sequence approximately at least 90% identical thereto, a CDR-H3 that can include the amino acid sequence of SEQ ID NO: 77, or a sequence approximately at least 90% identical thereto, or a CDRH3 that can include the amino acid sequence of SEQ ID NO: 78, or a sequence approximately at least 90% identical thereto, a CDR L1 that can include the amino acid sequence of SEQ ID NO: 79, or a sequence approximately at least 90% identical thereto, a CDR L1 that can include the amino acid sequence of SEQ ID NO: 80, or a sequence approximately at least 90% identical thereto, or a CDR L1 that can include the amino acid sequence of SEQ ID NO:81, or a sequence approximately at least 90% identical thereto, a CDR L2 that can include the amino acid sequence of SEQ ID NO: 82, or a sequence approximately at least 90% identical thereto, a CDR L2 that can include the amino acid sequence of SEQ ID NO: 83, or a sequence approximately at least 90% identical thereto, or a CDR L2 that can include the amino acid sequence of SEQ ID NO: 84, or a sequence approximately at least 90% identical thereto, and a CDR-L3 that can include the amino acid sequence of SEQ ID NO: 85, or a sequence approximately at least 90% identical thereto, a CDR-L3 that can include the amino acid sequence of SEQ ID NO: 86, or a sequence approximately at least 90% identical thereto, or a CDR-L3 that can include the amino acid sequence of SEQ ID NO: 87, or a sequence approximately at least 90% identical thereto; and the other binding domain is specific for IL-15 and comprises a CDR H1 that can include the amino acid sequence of SEQ ID NO: 52, or a sequence approximately at least 90% identical thereto, a CDR H1 that can include the amino acid sequence of SEQ ID NO: 53, or a sequence approximately at least 90% identical thereto, or a CDR H1 that can include the amino acid sequence of SEQ ID NO: 54, or a sequence approximately at least 90% identical thereto, a CDR H2 that can include the amino acid sequence of SEQ ID NO: 55, or a sequence approximately at least 90% identical thereto, a CDR H2 that can include the amino acid sequence of SEQ ID NO: 56, or a sequence approximately at least 90% identical thereto, or a CDR H2 that can include the amino acid sequence of SEQ ID NO: 57, or a sequence approximately at least 90% identical thereto, and a CDR H3 that can include the amino acid sequence of SEQ ID NO: 58, or a sequence approximately at least 90% identical thereto, a CDR H3 that can include the amino acid sequence of SEQ ID NO: 59, or a sequence approximately at least 90% identical thereto, or a CDR H3 that can include the amino acid sequence of SEQ ID NO: 60, or a sequence approximately at least 90% identical thereto, a CDR L1 that can include the amino acid sequence of SEQ ID NO: 61, or a sequence approximately at least 90% identical thereto, a CDR L1 that can include the amino acid sequence of SEQ ID NO: 62, or a sequence approximately at least 90% identical thereto, or a CDR L1 that can include the amino acid sequence of SEQ ID NO: 63, or a sequence approximately at least 90% identical thereto, a CDR L2 that can include the amino acid sequence of SEQ ID NO: 64, or a sequence approximately at least 90% identical thereto, a CDR L2 that can include the amino acid sequence of SEQ ID NO: 65, or a sequence approximately at least 90% identical thereto, or a CDR L2 that can include the amino acid sequence of SEQ ID NO: 66, or a sequence approximately at least 90% identical thereto, and a CDR L3 that can include the amino acid sequence of SEQ ID NO: 67, or a sequence approximately at least 90% identical thereto, a CDR L3 that can include the amino acid sequence of SEQ ID NO: 68, or a sequence approximately at least 90% identical thereto, or a CDR L3 that can include the amino acid sequence of SEQ ID NO: 69, or a sequence approximately at least 90% identical thereto.

In another aspect the multi-specific binding molecule is in a dual variable domain (DVD) format.

In another aspect, the disclosure relates to methods for redirecting an active form of a cytokine to a target, wherein the active form of the cytokine is endogenous to the system or the subject.

In another aspect, the disclosure relates to methods for redirecting an active form of a cytokine to a target wherein the active form of the cytokine is exogenous cytokine, and wherein the exogenous cytokine is added to the biological system or administered to the subject.

In another aspect, the disclosure relates to methods for redirecting an active form of a cytokine to a target, wherein the active form of the cytokine is a mixture of endogenous and exogenous cytokine in the biological system or subject.

In another aspect, the disclosure relates to methods for redirecting an active form of a cytokine to a target, wherein the non-blocking bispecific binding molecules bind to IL-15 with affinity less than IL-15Rα and the affinity is at least about 10×, 100×, or lower.

Methods for Redirecting an Active Form of a Cytokine to a Target Cell or Tissue

In one aspect, the disclosure relates to methods for redirecting an active form of a cytokine (e.g., endogenous cytokine, exogenous cytokine) to a target cell or target tissue of interest.

In one embodiment, the method redirects an active form of a cytokine (e.g., endogenous cytokine, exogenous cytokine) to a target cell or target tissue of interest in a biological system (e.g., in vitro culture, animal model, human subject). The biological system can include (i) the active form of the cytokine; (ii) a cell bearing a cognate receptor for the active form of the cytokine on its surface; and/or (iii) one or more target cells or tissues of interest to which the cytokine is to be redirected. The method can include exposing the biological system to a multi-specific binding molecule comprising (a) a binding domain that specifically binds to an epitope on the active form of the cytokine (a cytokine-binding domain); and (b) a binding domain that specifically binds to an epitope on a molecule that is not a cytokine receptor on the target cell or tissue (a target-binding domain), wherein the cytokine, when complexed with the multi-specific binding molecule, retains its ability to bind to and agonize its cognate receptor; thereby redirecting the active form of the cytokine to the target cell or tissue.

In another embodiment, the method redirects the agonistic effect of an active form of a cytokine using a multi-specific molecule, wherein specificity of the multi-specific molecule is against an active form of a cytokine, engagement of the active form of the cytokine by the multi-specific molecule is non-blocking, engagement of the active form of the cytokine by the multi-specific molecule allows the cytokine to retain its agonistic effect, at least one other specificity of the multi-specific molecule is against a non-cytokine molecule, and the multi-specific molecule sequesters the cytokine and redirects its agonistic effects by binding to the non-cytokine cell surface target receptor molecule.

The agonistic effect can be redirected to a desired tissue or cell surface. For example, the agonistic effect can be redirected to a desired stroma to allow for cis or trans presentation of the endogenous cytokine in a targeted environment.

The cytokine (e.g., endogenous cytokine, exogenous cytokine) can be in soluble form or in cell surface form.

The non-cytokine target molecule can be a cell surface receptor molecule.

The target tissue (e.g., desired tissue) or cell surface includes, for example, immune cells, tumor cells, stromal cells, cells in the tumor micro environment, cells in the bone marrow, cells in the lymph nodes, epithelial cells, endothelial cells, blood cells, skin cells, stem cells, bone cells, nerve cells, adipocytes, and myocytes.

The target cell can be any cell that expresses a target antigen. Virtually any antigen may be targeted by the proteins and polypeptides described herein, including but not limited to the following list of proteins, subunits, domains, motifs, and epitopes belonging to the following list of proteins: CD2; CD3, CD3E, CD4, CD11, CD11a, CD14, CD16, CD18, CD19, CD20, CD22, CD23, CD25, CD28, CD29, CD30, CD32, CD33 (p67 protein), CD38, CD40, CD40L, CD52, CD54, CD56, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma; TNF-alpha, TNFbeta2, TNFc, TNFalphabeta, TNF-RI, TNF-RII, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TALI, BAFF-R, EPO; LFA-3, ICAM-1, ICAM-3, EpCAM, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, VLA-1, VLA-4, L-selectin, anti-Id, E-selectin, HLA, HLA-DR, CTLA-4, T cell receptor, B7-1, B7-2, VNRintegrin, TGFbeta1, TGFbeta2, eotaxin1, BLyS (B-lymphocyte Stimulator), complement C5, IgE, factor VII, CD64, CBL, NCA 90, EGFR (ErbB-1), Her2/neu (ErbB-2), Her3 (ErbB-3), Her4 (ErbB-4), Tissue Factor, VEGF, VEGFR, endothelin receptor, VLA-4, Hapten NP-cap or NIP-cap, T cell receptor alpha/beta, E-selectin, digoxin, placental alkaline phosphatase (PLAP) and testicular PLAP-like alkaline phosphatase, transferrin receptor, Carcinoembryonic antigen (CEA), CEACAM5, HMFG PEM, mucin MUC1, MUC18, Heparanase 1, human cardiac myosin, tumor-associated glycoprotein-72 (TAG-72), tumor-associated antigen CA 125, Prostate specific membrane antigen (PSMA), High molecular weight melanoma-associated antigen (HMW-MAA), carcinoma-associated antigen, Geoprotein IIb/IIIa (GPIIb/IIIa), tumor-associated antigen expressing Lewis Y related carbohydrate, human cytomegalovirus (HCMV) gH envelope glycoprotein, HIV gp120, HCMV, respiratory syncital virus RSV F, RSVF Fgp, VNRintegrin, IL-8, cytokeratin tumor-associated antigen, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, and *Clostridium perfringens* toxin. One skilled in the art will appreciate that the aforementioned list of targets refers not only to specific proteins and biomolecules, but the biochemical pathway or pathways that comprise them.

The "active form" of a cytokine (e.g., endogenous cytokine, exogenous cytokine) can be a complex. The active form of the cytokine (e.g., endogenous cytokine, exogenous cytokine) is a state in which, when redirected, it can exert an agonistic effect on the cell bearing its cognate receptor. The active form of the cytokine (e.g., endogenous cytokine, exogenous cytokine) in some embodiments is as a single chain poly-peptide. In other embodiments the active form of the cytokine (e.g., endogenous cytokine, exogenous cytokine) can be more complex comprising of two or more chains, a homodimer, heterodimer or in multimeric form. Some cytokine chains can be associated with other protein chains to form a complex, for example IL-15 can associate with IL-15Ra for a complex that is referred to the IL-15 super agonist complex (IL-15SA). The active form of the cytokine (e.g., endogenous cytokine, exogenous cytokine) can be glycosylated, aglycosolated, or may have other forms of post-translational modification. The active form of a cytokine (e.g., endogenous cytokine, exogenous cytokine) can be an isoform of the cytokine or a mutant of the cytokine.

In an embodiment, cytokine (e.g., endogenous cytokine, exogenous cytokine) means the broad family of soluble proteins available in the biological system has a natural function, and the function involves interacting with its cognate receptor to engage in a cell signaling function. The family of soluble proteins can be signaling proteins and belong to the class of cytokines, chemokines, growth factors, enzymes, endogenous regulatory peptides and proteins or other biologically active proteins present in soluble form.

In another embodiment, the active form of the cytokine (e.g., endogenous cytokine, exogenous cytokine) is anchored directly to the cell surface. In an embodiment, the active form of the endogenous cytokine is anchored to a cell surface indirectly by being bound to another protein that is anchored on the cell surface. In another embodiment, the active form of the exogenous cytokine is anchored to a cell surface indirectly by being bound to another protein that is anchored on the cell surface.

In another embodiment, the method redirects an active form of an endogenous cytokine to a target cell or target tissue of interest in a subject by administering to the subject a sufficient amount of a multi-specific binding molecule comprising (a) a binding domain that specifically binds to the active form of the cytokine (a cytokine-binding domain) and (b) a binding domain that specifically binds to a molecule that is a marker on the target cell or tissue (a target-binding domain), wherein the cytokine, when complexed with the multi-specific binding molecule, retains its ability to bind to and agonize a cognate receptor for the cytokine; thereby redirecting the active form of the cytokine to the target cell or tissue. Administration of the multi-specific binding molecule to a subject can prolongs the half-life of the cytokine in the subject. For example, the half-life of the cytokine can be prolonged by at least about 1.5×, 2×, 2.5×, 3×, 3.5×, 4×, 4.5×, 5×, 5.5×. 6×, 6.5×, 7×, 7.5×, 8×, 8.5×, 9×, 9.5×, 10×, 15×, 20×, 30×, 100×, 1000× the original half-life of the cytokine.

In another embodiment, the method redirects an active form of an exogenous cytokine to a target cell or target tissue of interest in a subject by administering to the subject a sufficient amount of a multi-specific binding molecule comprising (a) a binding domain that specifically binds to the active form of the cytokine (a cytokine-binding domain) and (b) a binding domain that specifically binds to a molecule that is a marker on the target cell or tissue (a target-binding domain), wherein the cytokine, when complexed with the multi-specific binding molecule, retains its ability to bind to and agonize a cognate receptor for the cytokine; thereby redirecting the active form of the cytokine to the target cell or tissue. Administration of the multi-specific binding molecule to a subject can prolongs the half-life of the cytokine in the subject. For example, the half-life of the cytokine can be prolonged by at least about 1.5×, 2×, 2.5×, 3×, 3.5×, 4×, 4.5×, 5×, 5.5×. 6×, 6.5×, 7×, 7.5×, 8×, 8.5×, 9×, 9.5×, 10×, 15×, 20×, 30×, 100×, 1000× the original half-life of the cytokine.

Administration of the multi-specific binding molecule to a subject can increase the amount of the cytokine (e.g., endogenous cytokine, exogenous cytokine) in the serum of the subject. The amount of cytokine in the serum a subject can be increased by at least about 5%, 10%, 15%, 20%, 25%, 30%, 35%, 40%, 45%, 50%, 55%, 60%, 65%, 70%, 75%, 80%, 85%, 90%, 95%, or 100%. In other embodiments, the amount of cytokine in the subject can be increased 5-fold, 10-fold, 15-fold, 20-fold, 30-fold, 40-fold, 50-fold relative to the cytokine level prior to the administration of the multi-specific binding molecule.

The multi-specific binding molecule can cause accumulation of the endogenous cytokine at or around the target cell or tissue.

The multi-specific binding molecule can cause accumulation of the exogenous cytokine at or around the target cell or tissue.

The multi-specific binding molecule, when bound to the cytokine, can reduce but not completely block (e.g., reduces ability to bind by about 0-90%, 0-75%, 0-60%, 0-50%, 0-40%, 0-30%, 0-20%), the ability of the cytokine to bind to and/or agonize its cognate receptor. The ability of the cytokine to bind to and/or agonize its cognate receptor may be reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99%.

The multi-specific binding molecule described in wherein the ability of the cytokine to bind it cognate receptor is recovered or enhanced when the multi-specific binding molecule also engages with the target molecule using the target binding domain.

In an embodiment, antibodies developed against cytokines with the goal of neutralizing the cytokine, which could not be ultimately developed as neutralizing antibodies for various reasons is the cytokine binding molecule of the multispecific binding molecule of the current invention. In a specific embodiment, this antibody increases the serum concentration of the cytokine upon treatment of a biological system. In another embodiment, this antibody induces an agonistic effect of the cytokine upon treatment of a biological system.

In another aspect, the method relates to redirecting an active form of a cytokine (e.g., endogenous cytokine, exogenous cytokine) to a target cell or target tissue of interest comprising the steps of (a) selecting a cytokine of interest; (b) selecting a target molecule that is a marker on a target cell or in target tissue of interest; (c) generating a panel of binding domains that bind to the cytokine; (d) generating a panel of binding domains that bind to the target molecule; (e) screening the cytokine-binding domains using an assay that measures the ability of the cytokine, when complexed with the cytokine-binding domain, to bind to and/or agonize its cognate receptor compared to the ability of unbound cytokine to bind to and/or agonize its cognate receptor; (f) screening the target-binding domains for binding to an appropriate epitope on to the target molecule; (g) selecting cytokine-binding domains that do not block or partially block, the ability of the cytokine to bind to and/or agonize its cognate receptor; (h) generating a panel of multi-specific binding molecules comprising one or more of the selected cytokine-binding domains and one or more selected target-binding domains; and (i) screening the multi-specific binding molecules in an in vitro cell-based assay that measures the ability of cytokine to bind to and agonize its cognate receptor in the presence of varying amounts of the multi-specific binding molecule. Optionally, the method can further include a step for screening the multi-specific binding molecules in an in vivo assay in a non-human subject that measures the ability of the cytokine to bind to and agonize its cognate receptor when administered to the subject. In addition to, or alternatively, the method can include performing an epitope binning assay in conjunction with the cytokine-binding domain screening step to identify a region or regions on the cytokine that, when bound to the cytokine-binding domain, retain or partially retain the ability of the cytokine to bind to and agonize its cognate receptor.

Any suitable assay can be used for screening, including, but not limited to, label-based approach such as ELISA or a label free approach such as Surface plasmon resonance (SPR). Flow cytometry based techniques can be employed to determine binding of the multi-specific molecule and cytokine to its cognate cytokine receptor or the cell surface target. Bridging or sandwich binding screens can be employed to evaluate co-engagement of the cognate cytokine receptor and the cell surface target. Western blot or alternate techniques can be used to evaluate signaling effects such as phosphorylation induced in the cognate cytokine receptor. Various RNASeq based techniques or protein expression tracking approaches can also be employed to observe the effects of cognate cytokine receptor signaling. Histochemistry approaches can also be employed to observe the effect of cognate cytokine receptor signaling.

Methods for Multispecific Targeting

In one aspect, the disclosure relates to methods of multispecific targeting. In a particular aspect, the method of multispecific targeting includes the steps of generating a non-blocking multispecific binding molecule using a method disclosed herein below and administering the non-blocking multispecific binding molecule to a subject in need thereof, wherein the multispecific binding molecule targets a cytokine (e.g., endogenous cytokine, exogenous cytokine) in serum of the subject and activates and/or proliferates tumor specific effector cells; thereby inducing tumor cell killing.

The disclosure encompasses administering a non-blocking multispecific binding molecule (e.g., bispecific antibody) to an animal, in particular a mammal, specifically, a human, for preventing, treating, or ameliorating one or more symptoms associated with a disease, disorder, or infection.

In one embodiment, the non-blocking multispecific binding molecules described herein are used for the treatment or prevention of a disease or disorder where an altered efficacy of effector cell function (e.g., ADCC, CDC) is desired. The non-blocking multispecific binding molecules and compositions thereof are particularly useful for the treatment or prevention of primary or metastatic neoplastic disease (i.e., cancer), and infectious diseases. Molecules of the invention may be provided in pharmaceutically acceptable compositions as known in the art or as described herein. As detailed below, the molecules of the invention can be used in methods of treating or preventing cancer, autoimmune disease, inflammatory disorders or infectious diseases.

The non-blocking multispecific binding molecules described herein may also be advantageously utilized in combination with other therapeutic agents known in the art for the treatment or prevention of a cancer, autoimmune disease, inflammatory disorders or infectious diseases. The non-blocking multispecific binding molecules disclosed herein may also be advantageously utilized in combination with one or more drugs used to treat a disease, disorder, or infection such as, for example anticancer agents, anti-inflammatory agents or anti-viral agents.

Accordingly, the present disclosure provides methods for preventing, treating, or ameliorating one or more symptoms associated with cancer and related conditions by administering one or more non-blocking multispecific binding molecules. Although not intending to be bound by any mechanism of actions, a non-blocking multispecific binding molecule that binds with a greater affinity than a comparable molecule will result in the selective targeting and efficient destruction of cancer cells.

The disclosure further encompasses administering one or more non-blocking multispecific binding molecules in combination with other therapies known to those skilled in the art for the treatment or prevention of cancer, including but not limited to, current standard and experimental chemotherapies, hormonal therapies, biological therapies, immunotherapies, radiation therapies, or surgery. In some embodiments, the molecules of the invention may be administered in combination with a therapeutically or prophylactically effective amount of one or more anti-cancer agents, therapeutic antibodies or other agents known to those skilled in the art for the treatment and/or prevention of cancer. Examples of dosing regimens and therapies which can be used in combination with the non-blocking multispecific binding molecules disclosed herein are well known in the art.

Cancers and related disorders that can be treated or prevented by methods and compositions of the present invention include, but are not limited to, the following: Leukemias, lymphomas, multiple myelomas, bone and connective tissue sarcomas, brain tumors, breast cancer, adrenal cancer, thyroid cancer, pancreatic cancer, pituitary cancers, eye cancers, vaginal cancers, vulvar cancer, cervical cancers, uterine cancers, ovarian cancers, esophageal cancers, stomach cancers, colon cancers, rectal cancers, liver cancers, gallbladder cancers, cholangiocarcinomas, lung cancers, testicular cancers, prostate cancers, penal cancers; oral cancers, salivary gland cancers pharynx cancers, skin cancers, kidney cancers, and bladder cancers.

In a specific embodiment, a molecule of the invention (e.g., a bispecific antibody) inhibits or reduces the growth of primary tumor or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of primary tumor or metastasis in the absence of said molecule disclosed herein.

In a specific embodiment, the cytokine in the presence of the multispecific molecule of the invention induces proliferation of a variety of immune effector cells including NK cells and T-cells by at least 2 fold, at least 3-fold, at least 5 fold, at least 10 fold relative to the absence of the multispecific molecule.

In an embodiment, a cytokine in the presence of a multispecific binding molecule induces selective proliferation of a subset of T or NK cells. In a specific embodiment, there is selective proliferation in CD8+ T cells.

The present disclosure encompasses the use of one or more non-blocking multispecific binding molecules disclosed herein for preventing, treating, or managing one or more symptoms associated with an inflammatory disorder in a subject. The disclosure further encompasses administering the non-blocking multispecific binding molecules in combination with a therapeutically or prophylactically effective amount of one or more anti-inflammatory agents. The disclosure also provides methods for preventing, treating, or managing one or more symptoms associated with an autoimmune disease further comprising, administering to said subject a non-blocking multispecific binding molecules in combination with a therapeutically or prophylactically effective amount of one or more immunomodulatory agents. Examples of autoimmune disorders that may be treated by administering the non-blocking multispecific binding molecules of the invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephalitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections. Some autoimmune disorders are associated with an inflammatory condition, thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephalitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

Non-blocking multispecific binding molecules of the invention can also be used to reduce the inflammation experienced by animals, particularly mammals, with inflammatory disorders. In a specific embodiment, a non-blocking multispecific binding molecule disclosed herein reduces the inflammation in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an subject, which is not administered the said molecule.

The disclosure provides methods and pharmaceutical compositions comprising non-blocking multispecific binding molecules (e.g., bispecific antibodies). The disclosure also provides methods of treatment, prophylaxis, and amelioration of one or more symptoms associated with a disease, disorder or infection by administering to a subject an effective amount of at least one non-blocking multispecific binding molecule, or a pharmaceutical composition comprising at least one non-blocking multispecific binding molecule. In a specific embodiment, the subject is an animal, such as a mammal including non-primates (e.g., cows, pigs, horses, cats, dogs, rats etc.) and primates (e.g., monkey such as, a cynomolgus monkey and a human). In a specific embodiment, the subject is a human. In yet another specific embodiment, the non-blocking multispecific binding molecule is from the same species as the subject.

The disclosure provides methods and pharmaceutical compositions comprising non-blocking multispecific binding molecules (e.g., bispecific antibodies). The disclosure also provides approach for developing complementary diagnostics which will aid in recognizing patients who may be most suited for treatment with the multispecific binding molecule. In a specific embodiment, the complementary diagnostic approach would involve screening for the level of endogenous cytokine or other relevant factors in the patient to be treated. In another specific embodiment, the diagnostic information can be used in modeling and planning the dosing strategy for the multispecific binding molecule as a drug.

The route of administration of the composition depends on the condition to be treated. For example, intravenous injection may be preferred for treatment of a systemic disorder such as a lymphatic cancer or a tumor that has metastasized. Alternately, subcutaneous injection may be the preferred route of administration. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual subject, and the severity of the subject's symptoms. Depending on the condition, the composition can be administered orally, parenterally, intranasally, intravesically, vaginally, rectally, lingually, sublingually, buccally, intrabuccally and/or transdermally to the subject.

The pharmaceutical compositions of the present invention can be administered parenterally, such as, for example, by intravenous, intramuscular, intrathecal and/or subcutaneous injection. Parenteral administration can be accomplished by incorporating the compositions of the present invention into a solution or suspension. Such solutions or suspensions may also include sterile diluents, such as water for injection, saline solution, fixed oils, polyethylene glycols, glycerine, propylene glycol and/or other synthetic solvents. Parenteral formulations may also include antibacterial agents, such as, for example, benzyl alcohol and/or methyl parabens, antioxidants, such as, for example, ascorbic acid and/or sodium bisulfite, and chelating agents, such as EDTA. Buffers, such as acetates, citrates and phosphates, and agents for the adjustment of tonicity, such as sodium chloride and dextrose, may also be added. The parenteral preparation can be enclosed in ampules, disposable syringes and/or multiple dose vials made of glass or plastic. Rectal administration includes administering the composition into the rectum and/or large intestine. This can be accomplished using suppositories and/or enemas. Suppository formulations can be made by methods known in the art. Transdermal administration includes percutaneous absorption of the composition through the skin. Transdermal formulations include patches, ointments, creams, gels, salves, and the like. The compositions of the present invention can be administered nasally to a patient. As used herein, nasally administering or nasal administration includes administering the compositions to the mucous membranes of the nasal passage and/or nasal cavity of the patient.

The pharmaceutical compositions of the disclosure may be used in accordance with the methods described herein for preventing, treating, or ameliorating one or more symptoms associated with a disease, disorder, or infection. It is contemplated that the pharmaceutical compositions of the invention are sterile and in suitable form for administration to a subject.

The present invention also encompasses protocols for preventing, treating, or ameliorating one or more symptoms associated with a disease, disorder, or infection which a non-blocking multispecific binding molecule is used in combination with a therapy (e.g., prophylactic or therapeutic agent) other than a non-blocking multispecific binding molecule. The invention is based, in part, on the recognition that the non-blocking multispecific binding molecules potentiate and synergize with, enhance the effectiveness of, improve the tolerance of, and/or reduce the side effects caused by, other cancer therapies, including current standard and experimental chemotherapies. The combination therapies of the invention have additive potency, an additive therapeutic effect or a synergistic effect. The combination therapies of the invention enable lower dosages of the therapy (e.g., prophylactic or therapeutic agents) utilized in conjunction with non-blocking multispecific binding molecules for preventing, treating, or ameliorating one or more symptoms associated with a disease, disorder, or infection and/or less frequent administration of such prophylactic or therapeutic agents to a subject with a disease disorder, or infection to improve the quality of life of said subject and/or to achieve a prophylactic or therapeutic effect. Further, the combination therapies of the invention reduce or avoid unwanted or adverse side effects associated with the administration of current single agent therapies and/or existing combination therapies, which in turn improves patient compliance with the treatment protocol. Numerous molecules which can be utilized in combination with the non-blocking multispecific binding molecules of the disclosure are well known in the art.

Methods for Developing a Non-Blocking Multispecific Binding Molecule

In one aspect, the disclosure relates to methods for developing non-blocking multispecific binding molecules disclosed herein. In one embodiment, the method for developing non-blocking multispecific binding molecules comprises the steps of (a) selecting an immune signaling molecule; (b) selecting a target molecule; (c) testing separately the multispecific binding molecules for binding to either the immune signaling molecule or target molecule, (d) testing the multispecific binding molecules for binding to the immune signaling molecule and also agonizing a cognate receptor; and (e) testing the multispecific binding molecules for non-blocking binding to the immune signaling molecule that allows for immune signaling agonistic activity. Optionally, the method can further include a step (f) modeling a complex between a cytokine (e.g., endogenous cytokine, exogenous cytokine) receptor and the immune signaling molecule to define an epitope on the immune signaling molecule that maintains the cytokine receptor specificity and signaling characteristics upon binding of the monospecific binding molecule bound cytokine (e.g., endogenous cytokine, exogenous cytokine), thereby developing a non-blocking multispecific binding molecule that binds to an immune signaling molecule and a target molecule. The multispecific binding molecule can be, for example, a bispecific antibody.

In another embodiment, the method for developing non-blocking multispecific binding molecules comprises the steps of (a) selecting an immune signaling molecule; (b) selecting a target molecule; (c) testing separately a monospecific binding molecule for binding to either the immune signaling molecule or target molecule; (d) testing the monospecific binding molecule for binding to the immune signaling molecule and also agonizing a cognate receptor; (e) testing the monospecific binding molecules for non-blocking binding to the immune signaling molecule that allows for immune signaling agonistic activity; and (f) designing the non-blocking multispecific binding molecule as comprising of the monospecific binding molecule of the immune signaling molecule and the monospecific binding molecule binding the target molecule. The active form of the cytokine (e.g., endogenous cytokine, exogenous cytokine) can be, for example, a cytokine, cytokine complex or isoform of cytokine. The immune signaling molecule can be, for example, a cytokine (e.g., endogenous cytokine, exogenous cytokine), chemokine, growth factor, or hormone. The immune signaling molecule can be, for example, a signaling peptide.

The methods disclosed herein can also include modeling pharmacological properties of the cytokine (e.g., endogenous cytokine, exogenous cytokine) or cytokine (e.g., endogenous cytokine, exogenous cytokine) complex, modeling pharmacological properties of the target molecule, or determining a competitive binding profile of the monospecific binding molecules. In a specific embodiment, parameters such as the steady state level of the active form of cytokine, the rates of clearance of the cytokines from different routes of elimination, the expression level of the target molecule in system, expression pattern of the cytokine and the target receptor in different compartments of the biological system, the affinity of the multispecific molecule for the cytokine and the target can be used to simulate scenarios. Using this modeling and simulation one can estimate the range of desirable features of the multispecific molecule, such as affinity for the cytokine or extent of blocking desired and the exposure of the cytokine achievable in the biological system. Such simulations can be employed to model a variety of pharmacodynamic and pharmacokinetic features of the multispecific molecule in the biological system of interest. In an embodiment, the simulations are based on solving partial differential equations. Epitope binning can be used to determine the competitive binding profile. In an embodiment, this information can be used with structural models of protein and its complexes or with other experimental site directed mutagenesis approaches to engineer the multispecific molecules for optimal features.

In another embodiment, the method for developing a non-blocking multispecific binding molecule comprises the steps of (a) selecting a cytokine (e.g., endogenous cytokine, exogenous cytokine) or a cytokine (e.g., endogenous cytokine, exogenous cytokine) complex, further comprising modeling pharmacological properties of the cytokine (e.g., endogenous cytokine, exogenous cytokine) or the cytokine (e.g., endogenous cytokine, exogenous cytokine) complex; (b) selecting a target molecule, further comprising modeling the pharmacological properties of the target molecule; (c) testing separate monospecific binding molecules for binding to either the cytokine (e.g., endogenous cytokine, exogenous cytokine), cytokine (e.g., endogenous cytokine, exogenous cytokine) complex, or target molecule; (d) testing the monospecific binding molecules for non-blocking binding to the cytokine (e.g., endogenous cytokine, exogenous cytokine) or the cytokine (e.g., endogenous cytokine, exogenous cytokine) complex, further comprising determining a competitive binding profile of the monospecific binding molecules by epitope binning; (e) modeling a complex between a cytokine receptor and the cytokine (e.g., endogenous cytokine, exogenous cytokine) or cytokine (e.g., endogenous cytokine, exogenous cytokine) complex to define an epitope on the cytokine (e.g., endogenous cytokine, exogenous cytokine) or cytokine (e.g., endogenous cytokine, exogenous cytokine) complex that maintains cytokine receptor specificity and signaling characteristics upon binding of the monospecific binding molecule, thereby developing a non-blocking bispecific binding molecule that binds to a cytokine (e.g., endogenous cytokine, exogenous cytokine) and a target molecule; and (f) designing a multispecific binding molecule as comprising of monospecific binding molecule for the cytokine (e.g., endogenous cytokine, exogenous cytokine) and the monospecific binding molecule for the target molecule. The method can also optionally include validating the non-blocking multispecific binding molecules for binding to both the cytokine (e.g., endogenous cytokine, exogenous cytokine) and the target molecule by an in vitro cell-based receptor signaling screen for cytokine (e.g., endogenous cytokine, exogenous cytokine) activity and target molecule specificity. The methods can also include evaluating efficacy of the non-blocking multispecific binding molecules and/or evaluating pharmacokinetic and pharmacodynamic properties of the non-blocking multispecific binding molecules in vivo.

A cytokine (e.g., endogenous cytokine, exogenous cytokine) or a cytokine (e.g., endogenous cytokine, exogenous cytokine) complex can be selected by determining an expression level of the cytokine in a subject, determining an amount of the cytokine (e.g., endogenous cytokine, exogenous cytokine) existing in an active state in circulation or at a tissue of interest in the subject, determining a distribution profile of the cytokine receptor in the subject, determining the effect of administering additional cytokine (e.g., endogenous cytokine, exogenous cytokine) to the subject, and/or determining a clearance and a metabolism mechanism of the cytokine in the subject.

A target molecule can be selected by examining an expression level, tissue-specificity, localization on a cell surface, molecule internalization dynamics, and/or molecule recycling dynamics of the target molecule in the subject.

Pharmacological properties of the cytokine (e.g., endogenous cytokine, exogenous cytokine) or cytokine (e.g., endogenous cytokine, exogenous cytokine) complex can be modeled by determining a desirable affinity range for a non-blocking bispecific binding molecule cytokine (e.g., endogenous cytokine, exogenous cytokine) or cytokine (e.g., endogenous cytokine, exogenous cytokine) complex interaction, predicting differential pharmacokinetics and biodistribution of free cytokine or cytokine complex, and/or predicting differential pharmacokinetics and biodistribution of non-blocking bispecific binding molecule-bound cytokine (e.g., endogenous cytokine, exogenous cytokine) or cytokine (e.g., endogenous cytokine, exogenous cytokine) complex.

Modeling of pharmacological properties of the target molecule can determine a desirable affinity range for a non-blocking bispecific binding molecule-targeting molecule interaction, and/or predicting a differential biodistribution of the target molecule with and without a non-blocking bispecific binding molecule binding.

The monospecific binding molecules can be tested for non-blocking binding to the cytokine (e.g., endogenous cytokine, exogenous cytokine) or the cytokine (e.g., endogenous cytokine, exogenous cytokine) complex by, for example, an in vitro sandwich assay testing for bridging of the monospecific binding molecule and the cytokine receptor via binding of the cytokine (e.g., endogenous cytokine, exogenous cytokine) or cytokine (e.g., endogenous cytokine, exogenous cytokine) complex.

The methods disclosed herein can further include performing a competition assay between the monospecific binding molecules for the cytokine (e.g., endogenous cytokine, exogenous cytokine) or cytokine (e.g., endogenous cytokine, exogenous cytokine) complex that is bound to the cytokine receptor.

The modeling of a complex between a cytokine receptor and the cytokine (e.g., endogenous cytokine, exogenous cytokine) or cytokine (e.g., endogenous cytokine, exogenous cytokine) complex can determine, for example, a non-blocking bispecific binding molecule scaffold geometry that maintains a cytokine receptor specificity and/or signaling characteristics while binding to the target molecule.

In another embodiment, a method for developing a non-blocking multispecific binding molecule includes the steps of (a) selecting a cytokine (e.g., endogenous cytokine, exogenous cytokine) of interest whose effect needs to be amplified in the system for desired biological or therapeutic effect; (b) obtaining data pertaining to the systems level characteristics of the cytokine (e.g., endogenous cytokine, exogenous cytokine); (c) obtaining data pertaining to target receptors; (d) modeling and simulation of the cytokine (e.g., endogenous cytokine, exogenous cytokine) in its native state an upon association with an antibody; (e) modeling and simulation of the receptor targeting of the cytokine (e.g., endogenous cytokine, exogenous cytokine); (f) identifying binders to the cytokine (e.g., endogenous cytokine, exogenous cytokine) and the target receptor; (g) performing binding screens and/or competition assays; (h) performing epitope binning of antibodies; (i) defining the desired epitope on the cytokine (e.g., endogenous cytokine, exogenous cytokine); and (j) performing mixed cell-based receptor signaling screen, wherein non-blocking multispecific binding molecules that engage the cytokine (e.g., endogenous cytokine, exogenous cytokine) and retain cytokine receptor binding and signaling characteristics of the cytokine (e.g., endogenous cytokine, exogenous cytokine).

Method for Creating and Characterizing Antibodies Functioning as Cytokine Capture Binding Domains in Amplifier Antibody.

A generalized schematic of a cytokine capture antibody action to be employed in a non-blocking bispecific binding antibody molecule of the present invention is presented in FIG. 1. The methods employed in creating and characterizing antibodies having binding domains targeting the cytokine IL-15 with such action is described below.

An antibody discovery campaign is carried out using either a display technique such as phage display or the immunization of a live animal such as mouse or rabbit with human IL-15 or a fragment thereof, followed by selection to generate a panel of antibodies capable of binding human IL-15. Such antibody discovery technologies are well established in the field. A person of skill in the art can use one such discovery campaign or any other discovery approach to find a panel of antibodies or polypeptides capable of binding the cytokine IL-15. Antibodies described in the literature such as DISC0280 [Finch et al. Brit J Pharma (2011) 162, 480], B-E29, MOB-1254Z, PABZ-081, MOB-0784CT, HPAB-0238-YC, HPAB-0359-WJ, MOM-18387 etc., which are capable of binding IL-15 have been discovered using such approaches and find utility in the context of the multispecific antibody described in this invention.

Binding affinities of the antibodies for IL-15 can be estimated using a technique such as ELISA or label free approaches such as surface plasmon resonance. Binding characteristics of the IL-15: antibody complex to cognate receptor of IL-15 such as IL-15Rβγ can be determined to estimate the level of blocking or non-blocking nature of the antibody engagement. Antibodies which do not block or partially block receptor engagement relative to binding of free IL-15 can find application in the amplifier antibodies described herein. The anti IL-15 antibodies listed above can be evaluated for their ability to bind IL-15 and yet not block or only partially block IL-15 receptor engagement (IL-15Rβγ) relative to binding of free IL-15 in an SPR assay.

To determine the impact of IL-15: antibody complex on the capacity of IL-15 to bind its receptor and induce functionally relevant effect on target cells which express the receptor on their cell surface, receptor signaling based assay can be employed. The assay can be based on evaluation of phosphorylation of associated intracellular proteins such as STAT5. Alternately, proliferation of the target cells observed as change in number of cells or changes in intracellular markers of cell proliferation such as Ki-67 can be evaluated. Induction of cytokine release following treatment with IL-15:antibody complex is another alternate indicator of function. IL-15 is mixed with the IL-15 antibody at different ratios (e.g. 1:1, 2:1, 1:10, 10:1, 1:100, 100:1 or another ratio) and the complex mixture is screened for binding to cells expressing one or more of the IL-15 receptor chains, namely IL-15Ralpha (IL-15Rα), IL-15/2Rbeta (IL-15Rβ) and common gamma chain (γ). Examples of such cells include CTLL-2, KIT225 or M-07e. Alternately, binding can be evaluated using an engineered cell line such as U2OS kit #93-0998c3 from Discoverx. Alternately, PBMC isolated from human blood sample, or T or NK cells may be used to evaluate the functional signaling effect. An antibody not capable of binding IL-15, such as the RSV targeting antibody palivizumab, may be used as a control to quantify the effect of free IL-15 engagement in these receptor expressing cells.

The antibody bound IL-15 with the panel of antibodies is able to induce signaling in its cognate receptor over a range of levels, from being fully non-blocking to blocking. Antibodies involved in antibody:IL-15 mixtures which induce receptor signaling comparable to the free IL-15 are referred to as non-blocking antibodies. For some of the antibodies, antibody bound IL-15 shows reduced signaling upon receptor engagement and these are referred to as partially blocking antibodies. The third class of blocking antibodies appear to completely block the interaction and signal of IL-15 via its cognate receptor.

Further, the blocking, partially blocking, or non-blocking characteristics of the cytokine capture antibody can be evaluated in vivo in a live animal such as mouse or a non-human primate. Upon treatment of the animal with a human IL-15 cytokine and an antibody which can bind and engage the cytokine, the effect of cytokine-antibody complex can be observed in vivo in terms of proliferation of certain immune cells in the animal. One could also observe changes in levels of other cytokines such as IFNγ (interferon-gamma) in the animal because of the cytokine: capture antibody complex action in vivo. In some embodiments, the IL-15:antibody complex may present the ability to engage the receptor complex (IL-15Rβγ) in a particular assay format and thus present as a non-blocking complex, while limiting activity via the receptor complex and acting as a blocking complex in another assay. In another embodiment, the IL-15: capture antibody complex may show non-blocking action with certain cell types but appear to be blocking with other cells. In an embodiment the blocking or partially blocked behavior of the complex can be induced to function as a non-blocking complex in the context of a bispecific antibody composition.

Figure 2:
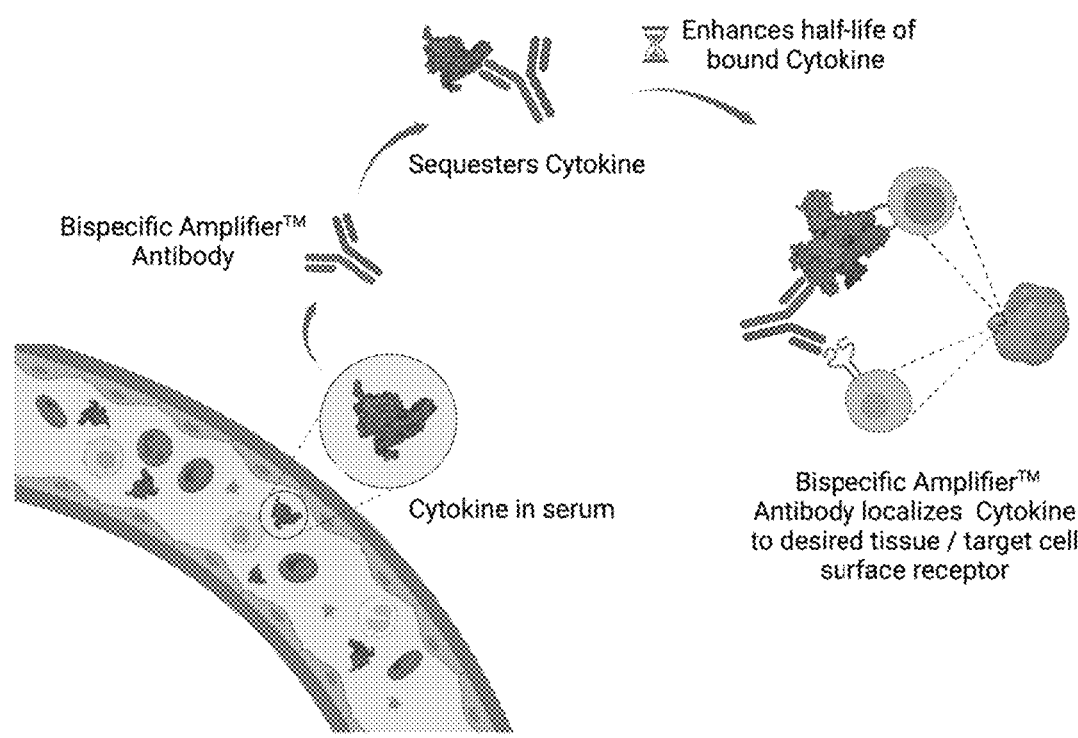
FIG. 2 is a schematic of the bispecific antibody comprising a cytokine binding domain and a target binding domain (labelled as Bispecific Amplifier Antibody) and its action. The bispecific amplifier antibody is an example of the multi-specific binding molecule of this disclosure. The bispecific amplifier antibody has two specificities, an arm with specificity for an epitope on the active form of the cytokine and a second specificity for an epitope on the target cell surface receptor. Localization of cytokine bound bispecific antibody on the designated target cell surface receptor presents the cytokine for interaction with its cognate receptor in that local environment of the target cell.
Figure 4:
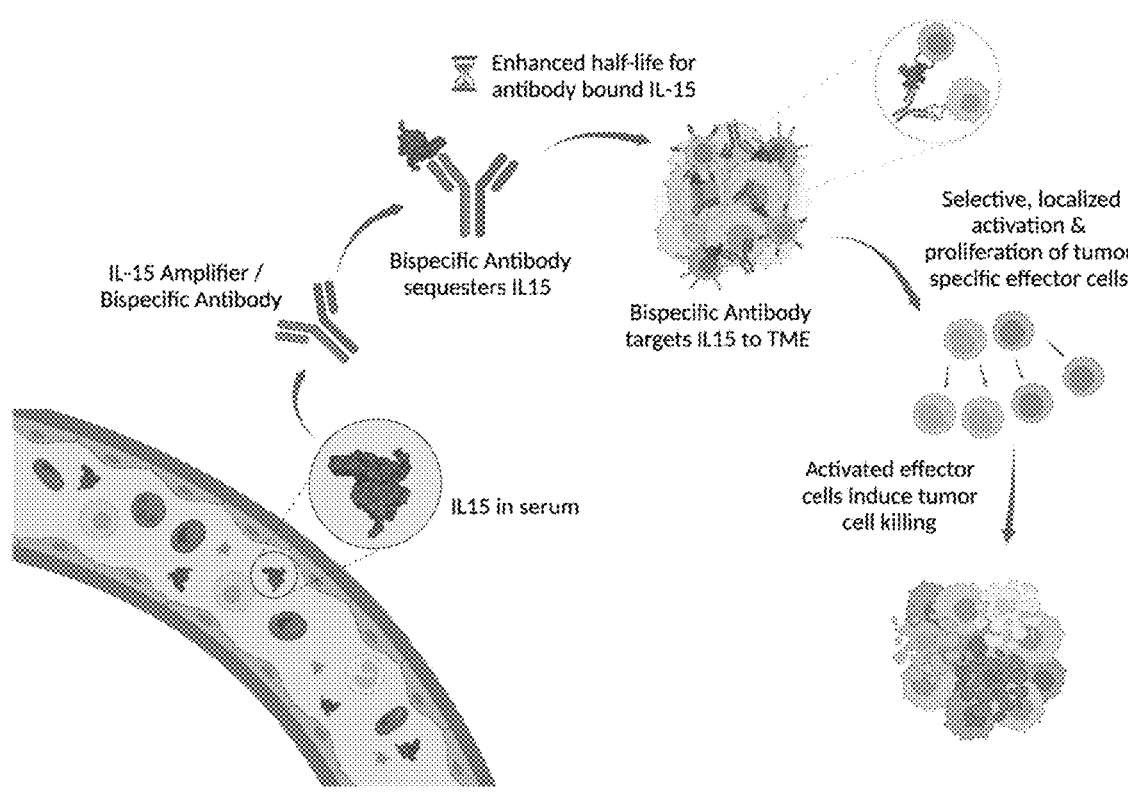
FIG. 4 is a schematic of an IL-15 bispecific binding (amplifier) antibody and its mode of action. The Bispecific amplifier antibody sequesters the active form of IL-15 in serum and redirects it to the tumor microenvironment (TME). The target receptor in the TME can be a cell surface receptor on an immune cell such as PD1, or it could be a tumor cell surface receptor such as HER2 or it could be a molecule in the tumor stroma such as collagen. Such localized and redirected IL-15 engagement can result in selective, localized activation and proliferation of tumor specific effector cells for targeted tumor cell killing.

Bispecific Antibodies Comprising an IL-15 Binding Domain and Target Binding Domain A generalized schematic of the mechanism of action of a bispecific antibody (amplifier) targeting a cytokine and a second receptor target is presented in FIG. 2 and a schematic for IL-15 redirection is shown in FIG. 4. The method employed in creating and characterizing antibodies having binding domains for the cytokine IL-15 and a second binding domain for a receptor target is described below.

Amplifier antibodies being described herein are a new class of antibodies, which can engage cytokines, either endogenous to the system or exogenous cytokine administered to the system, and also bind a second target, a cell surface receptor. As a result of this dual engagement, the antibodies can increase the local concentration of the cytokine in sites which present the second target, thereby spatially modulating the effect of the cytokine. Such antibodies can engage the cytokine and amplify the effect of the cytokine, relative to the action of cytokine by itself. Amplifier antibodies can be designed as bispecific antibodies comprising a cytokine capture arm and a second target binding arm, the second target typically being a cell surface receptor or part of the extracellular matrix. The bispecific antibody can comprise one, or more than one, valency for cytokine capture and similarly have one or more valency for target binding. While a single valency allows capture of one copy of the cytokine molecule, designs with more than one valency will allow the capture of up to an equivalent number of copies of the cytokine or offer stronger avid binding of the cytokine molecule.

A variety of techniques including methods based on hybridoma, surface display, and B-cell cloning approaches have made discovery of novel antibodies against desired target antigens in a turnkey approach (Banik, Kushnir, Doranz, and Chambers (2023) Mabs 15 (1), 2273018). A variety of such techniques can be applied to the discovery of anti-cytokine antibodies to obtain antibodies engaging different epitopes on the cytokines. Some of the anti-cytokine antibodies would bind the cytokine and completely block the engagement of the cytokine with its cognate receptor, presenting a truly antagonistic effect. Other anti-cytokine antibodies can bind the cytokine at an epitope, which can still allow the antibody bound cytokine to interact with its cognate receptor in a manner comparable to cytokine by itself, i.e. agonistic antibodies. Other antibodies may engage the cytokine such that they modulate the interaction of the cytokine with its native receptor, i.e are partial/altered agonistic antibodies. These second two classes of antibodies that engage with the cytokine and retain a fully agonistic or partial/altered agonistic effect of the cytokine. The cytokine capture antibodies used in the Amplifier design comprise fully agonistic or partial/altered agonistic antibodies.

Antibodies in the categories of either agonistic or partially agonistic are explored in the context of a bispecific antibody molecule. The bispecific molecule is an engineered protein design comprising one or more binding domains capable of specifically recognizing a second target other than IL-15 (the targeting binding domain), fused to the antibodies targeting IL-15 described above. A number of bispecific molecular formats are known in the literature (Brinkmann U & Kontermann RE (2017) MAbs 9, 182-212). A particular symmetric bispecific design of interest comprises an scFv specifically targeting the second receptor target, fused to the C-terminus of the heavy chains of the anti-IL-15 antibody. An alternate bispecific design comprises heterodimerizing heavy chain mutations such as the Knob-into-Hole mutations (Ridgway J B B, Presta L G, Carter P (1996) Prot Engg Des Sel 9, 617-621; von Kreudenstein T S etal (2013) MAbs 5, 646-654) to achieve asymmetric antibodies comprising one arm engaging IL-15 and the second arm engaging the second target.

In some embodiments, the second arm in bispecific molecule comprises one or more binding domains capable of targeting a receptor of interest commonly expressed on various immune cell subtypes such as PD1, CTLA4, PD-L1, CD25, GITR, CD11b, CSF-1R, CD40, CD44, SIRPa, TIM3, TIGIT, KIR, NKG2D, NKG2A, LAG3, CD8, Vg9Vd2, etc. Some of these second receptors allow for a cis-engagement, i.e. co-engagement of the second receptor and the IL-15 receptors on the same cell (see FIG. 3A). A few others allow trans-engagement, i.e. the second receptor is engaged on a different cell relative to the cell on which the IL-15 receptor is engaged.

Figure 3:
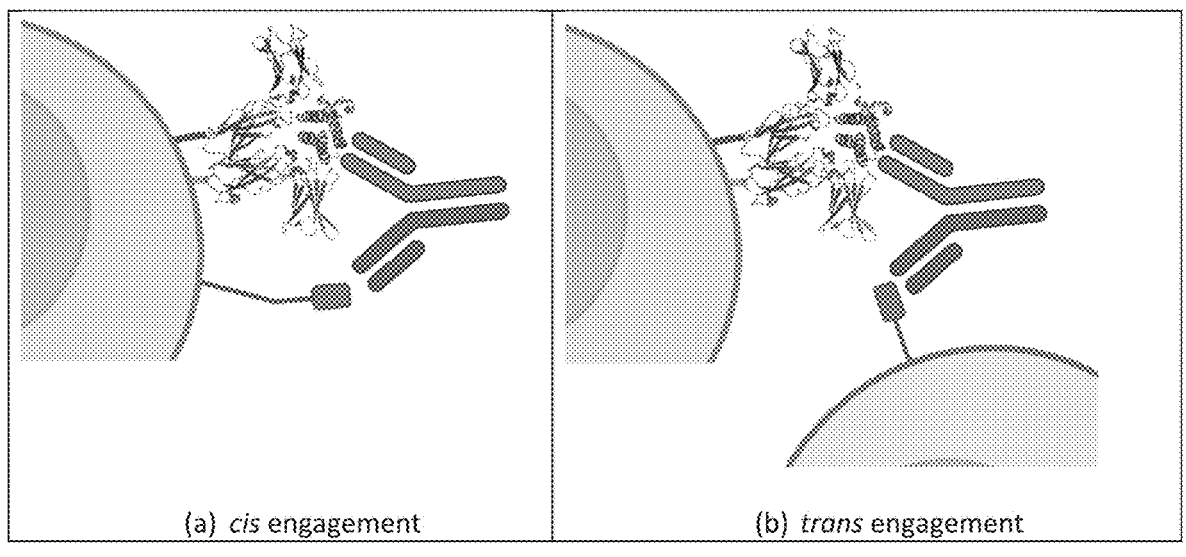
FIGS. 3A and 3B are schematics of the two modes of bispecific engagement by the bispecific amplifier antibody described in FIG. 2. In the cis engagement mode (FIG. 3A), the cognate cytokine receptor and the target receptor are on the same cell surface. In the trans engagement mode (FIG. 3B), the cognate cytokine receptor and target receptor are on two different cells.

In some embodiments, the second arm in the bispecific molecule can comprise one or more binding domains capable of targeting a receptor of interest commonly expressed on various tumor cells, tumor associated stromal cells or the extracellular matrix in the tumor microenvironment (See FIG. 3B). Some of the receptors of interest are cell surface receptors such as PD-L1, CD47, VEGFR, PDGFR, HER2, EGFR, EGFRVIII, IGF1R, PSCA, PSMA, CEA, Claudin 18.2, Mesothelin, MUC1, ROR1, AXL, GPC3, CD133, CD147, Folate receptor, MUC16, CA-IX, CD44, CD49d, ICAM1, etc. Other targets that are related to hematological tumors include CD20, CD19, CD22, CD52, CD38, SLAMF7, CD37, CD98, DKK-1, CD157, CCR4, CXCR4, BAFF-R, CD123, CECAM5, Dyadherin, Tenascin-C, etc.

Many alternatives, modifications, and variations are enabled by the present disclosure. While specific embodiments have been shown and described in detail to illustrate the application of the principles of the present disclosure, it will be understood that the invention may be embodied otherwise without departing from such principles. Accordingly, Applicant intends to embrace all such alternatives, modifications, equivalents, and variations that are within the spirit and scope of the present invention.

All publications and patents cited in this disclosure are incorporated by reference in their entirety. To the extent, the material incorporated by reference contradicts or is inconsistent with this specification, the specification will supersede any such material. The citation of any references herein is not an admission that such references are prior art to the present disclosure. Various terms relating to aspects of the description are used throughout the specification and claims. Such terms are to be given their ordinary meaning in the art unless otherwise indicated. Other specifically defined terms are to be construed in a manner consistent with the definitions provided herein.

The articles "a" and "an" are used herein to refer to one or more than one (e.g., to at least one) of the grammatical object of the article. By way of example, "an element" means one element or more than one element.

The term "about" when referring to a measurable value such as an amount, a temporal duration, and the like, is meant to encompass variations of ±20% or less, or in some instances ±15% or less, or in some instances ±10% or less, or in some instances ±5% or less, or in some instances ±1% or less, or in some instances ±0.1% or less, from the specified value, as such variations are appropriate.

The phrase "and/or" as used herein should be understood to mean "either or both" of the elements so conjoined, e.g., elements that are conjunctively present in some cases and disjunctively present in other cases. Multiple elements listed with "and/or" should be construed in the same fashion, e.g., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

EXAMPLES

Below are examples of certain specific embodiments for making and using the cytokine-binding polypeptide constructs described herein. The examples are offered for illustrative purposes only and are not intended to limit the scope of the disclosure in any way. Efforts have been made to ensure accuracy with respect to numbers used (e.g., amounts, temperatures, etc.), but some experimental error and deviation should, of course, be allowed for.

The constructs and methods described herein may be prepared and carried out employing, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al, Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1: Method for Creating and Characterizing Bispecific Antibodies

Figure 6A:
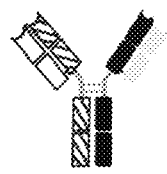
FIGS. 6A-6E show exemplary formats that are IgG1 based, with the PD1 antigen binding domain derived from Pembrolizumab and the IL-15 binding domain derived from DISC0280. The heavy chain in black and the light chain in grey are specific for IL-15, whereas the heavy chain in hatched fill with corresponding light chain in white fill are specific for PD1.
Figure 6B:
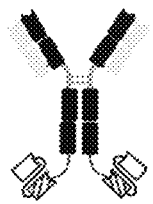
Figure 6C:
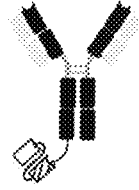
Figure 6D:
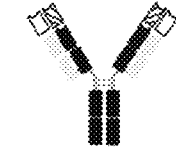
Figure 6E:
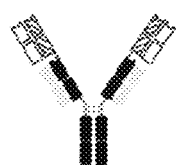

Bispecific antibodies can be produced in a variety of geometries, also referred to as formats (see reference Brinkmann and Kontermann (2017), MABS 9 (2), 182-212 for a description of several such formats). Designing and exploring activity of bispecific molecules in a few different formats can potentially present molecules with slightly different functional and biophysical features. Here, we describe the preparation of bispecific antibodies comprising of binding domains from the anti PD1 antibody, pembrolizumab and the anti IL-15 antibody, DISC0280. The antibodies and controls have been prepared in different formats, and representations of exemplary bispecific formats are shown in FIGS. 6A-6E. All of the formats shown in FIGS. 6A-6E are based on use of an antibody scaffold. Furthermore, the heavy chain in black and the light chain in grey are representative of specificity for IL-15, whereas the heavy chain in hatched fill with corresponding light chain in white fill are representative of specificity for PD1. FIG. 6A depicts the structure of a bispecific antibody in a Fab-Fab format, with one Fab arm specific for PD1 and the other Fab arm specific for IL-15. FIGS. 6B and 6C depict the structure of possible versions of a bispecific antibody in Fab-Fab format with one or two scFvs fused to the C terminus of heavy chains. For these versions, the Fabs are specific for one antigen, whereas the scFvs are specific for the other antigen. FIG. 6D depicts the structure of a bispecific antibody in dual variable domain (DVD) format, where the VH domain with specificity to one antigen is fused to the N terminus of the VH domain with specificity to the other antigen, and the VL domain with specificity to one antigen is fused to the N terminus of the VL domain with specificity to the other antigen. FIG. 6E depicts the structure of a bispecific antibody in dual Fab domain format, where the outermost Fabs are specific for one antigen and the inner Fabs are specific for the other antigen.

The sequences of the following variants are provided in Appendix A following the Examples. CDR regions were identified using IMGT, Kabat and Chothia methods. Regions may vary slightly based on the method used for identification. The Pembrolizumab Fab sequence was generated from the IMGT 2D structure database (IMGT/2Dstructure-DB card for INN 9798). The DISC0280 Fab sequence was generated from the PDB ID 2×QB with the missing N terminal residues in the light chain (L) added from IMGT: IGLV1-47*01 V-LAMBDA (Z73663). Alternately, bispecific antibodies comprising the anti-mouse PD1 sequence F12.3, obtained from the US2019/0263877A1 patent, specifically the VH and L from sequence 12 and sequence 30, respectively may be used. The constant regions were an IgG1 isotype, obtained from Uniprot P0DOX5, that also incorporated the LALAPG Fc null mutations). Fusions of scFvs to the heavy chains (H) of bispecific antibodies in Fab-Fab format (FIG. 6B and FIG. 6C), outer variable domains to inner variable domains in DVD bispecific antibodies (FIG. 6D), as well as within scFvs connecting VH and VL domains used glycine serine linkers. Bispecific antibodies in dual Fab domain format (FIG. 6E) used an inter-Fab hinge obtained/derived from SEQ ID NO. 3 within the WO 2018/178101 A1 patent publication. For bispecific antibodies in a Fab-Fab format (FIG. 5A), Fc heterodimerization used sequence substitutions within the CH3 domain from the US20130195849A1 patent publication (Table A2). Fab preferential H:L pairing (FIG. 6A, FIG. 6E) used sequence substitutions within the CH1, hinge and CL domains from US20190338048A1.

Exemplary bispecific antibodies with different molecular formats were cloned, expressed and purified as follows. The genes encoding the antibody heavy and light chains were constructed via gene synthesis using codons optimized for human/mammalian expression. The final gene products were sub-cloned into the mammalian expression vector PTT5 (NRC-BRI, Canada) and expressed in CHO cells. CHO cells were maintained in a proprietary medium supplemented with 4 mM glutamine (HyClone, catalog #CSH0034.01) and 0.1% Pluronic F-68 (Gibco, Life Technologies catalog #24040-032) in vented Erlenmeyer flasks at 120 rpm, 37° C., 5% CO2 and standard humidified conditions. For protein production, CHO cells were seeded 2 days prior to transfection. On the day of transfection, cells were diluted to a density of 5-6×10^6 cells/ml. Cells were transfected with 1.4 μg DNA per 1 mL of cells using PEI MAX 40 kDa (PEIMAX® from Polyscience, catalog #24765) at a DNA:PEI ratio of 1:7.1 (w/w). The transfected DNA was a mix of plasmids encoding for the recombinant protein of interest (in pTT vector), GFP DNA (in pTT vector), and pSV40-Bcl-XL DNA with a 5.7:1 w/w ratio. 0.075% of Dimethylacetamide (Alta Aesar, catalog #A10924) and 1× antibiotic/antimycotics (HyClone, catalog #SV30079.01) were added to the transfected cells and were returned to incubator at 120 rpm, 37° C., 5%, 24 h post-transfection, cultures were supplemented with anti-Clumping agent (Irvine Scientific, catalog #91150) and moved to a 32° C. humidified incubator (120 rpm, 5% CO2) for 6 more days prior to harvesting. During protein production, cells were fed with Feed 4 (Irvine Scientific, catalog #94134) supplemented with Kolliphor P188 (Sigma-Aldrich, catalog #K4894) and Sodium bicarbonate (Sigma-Aldrich, catalog #S3817), and glucose was added as needed (Sigma-Aldrich, catalog #G7021).

Fusions of 2 scFvs to the Hs of bispecific antibodies in Fab-Fab format (FIG. 6B) and DVD bispecific antibodies (FIG. 6D) were transfected in a H:L ratio of 1:2. For bispecific antibodies in a Fab-Fab format (FIG. 6A), fusion of 1 scFv to a H chain in Fab-Fab format (FIG. 6C), and in dual Fab domain format (FIG. 6E), the DNA was transfected in optimal DNA ratios that allow for heterodimer formation (e.g. fusion of 1 scFv to a H chain in Fab-Fab format H1/H2/L1 ratios=22:8:70 (RV26)). Transfected cells were harvested after 7 days with the culture medium collected after centrifugation at 3800 rpm and clarified using a 0.2 um filter. The clarified culture medium was loaded onto a MabSelect SuRe (Cytiva) protein-A column, antibody eluted with 100 mM Citrate pH 3.0 or a combination of 100 mM citrate and L-Arginine (100 mM citrate pH 3.6+200 mM L-Arginine followed by 100 mM citrate pH 3.0+200 mM L-Arginine) and the pooled fractions containing the antibody neutralized with 10% (v/v) 1M HEPES. For variants where post pA amounts were greater than 1 mg, the protein-A antibody eluates were then either buffer exchanged or further purified by gel filtration (SEC) using DPBS (Cytiva (Hyclone) DPBS/Modified-Calcium-Magnesium) or DPBS+200 mM L-Arginine. For gel filtration, the protein was concentrated using Vivaspin turbo devices and 30 kDa membrane prior to loading onto a Sephadex 200 HiLoad 16/600 200 pg column (Cytiva) via an AKTA system at a flow-rate of 1 mL/min. DPBS or DPBS+200 mM L-Arginine buffer at pH 7.1 was used at a flow-rate of 1 mL/min and fractions corresponding to the purified bispecific antibody were collected. Protein was quantified based on measured absorbance at 280 nm. Endotoxin level was then assessed using a FDA-licensed LAL test cartridge and an Endosafe® PTS™ or MCS™ reader (Charles River Laboratories).

The structure and a brief description of the bispecific variants produced (RV15, RV17, RV18, RV19, RV20, RV21, RV22, RV23, RV24, RV25, RV26, RV29, RV30, RV31, RV32, RV33, RV34, RV35, RV36 and RV37) and the monospecific parent antibodies produced (RV1, RV2, RV3, RV9 and RV10) are provided in FIGS. 24A-24F (Table 1). The clones used to produce each bispecific variant are listed in Table 2.

TABLE 2

| | Variant Construction | | | |
|---|---|---|---|---|
| Variant ID | H1 Clone name | L1 Clone name | H2 Clone name | L2 Clone name |
| RV 1 | RC1 | RC2 | NA | NA |
| RV 2 | RC3 | RC2 | NA | NA |
| RV 3 | RC4 | RC2 | NA | NA |
| RV 9 | RC15 | RC16 | NA | NA |
| RV 10 | RC17 | RC16 | NA | NA |
| RV 15 | RC25 | RC26 | RC27 | RC24 |
| RV 17 | RC30 | RC2 | NA | NA |
| RV 18 | RC31 | RC2 | NA | NA |
| RV 19 | RC32 | RC2 | NA | NA |
| RV 20 | RC33 | RC2 | NA | NA |
| RV 21 | RC34 | RC16 | NA | NA |
| RV 22 | RC35 | RC16 | NA | NA |
| RV 23 | RC36 | RC2 | RC37 | NA |
| RV 24 | RC38 | RC2 | RC37 | NA |
| RV 25 | RC39 | RC2 | RC37 | NA |
| RV 26 | RC40 | RC2 | RC37 | NA |
| RV 29 | RC44 | RC45 | NA | NA |
| RV 30 | RC46 | RC47 | NA | NA |
| RV 31 | RC48 | RC26 | NA | RC24 |
| RV 32 | RC49 | RC26 | NA | RC24 |
| RV 33 | RC50 | RC51 | RC28 | RC24 |

TABLE 2-continued

| Variant ID | H1 Clone name | L1 Clone name | H2 Clone name | L2 Clone name |
|---|---|---|---|---|
| RV 34 | RC52 | RC2 | NA | NA |
| RV 35 | RC53 | RC54 | NA | NA |
| RV 36 | RC55 | RC56 | NA | NA |
| RV 37 | RC57 | RC58 | NA | NA |

*NA = not applicable

Figure 7A:
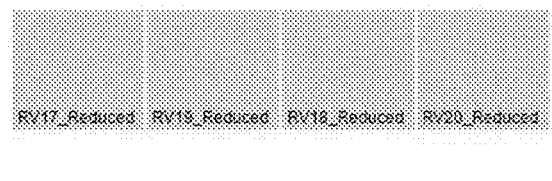
FIGS. 7A and 7B show a reduced capillary electrophoresis sodium dodecyl sulfate (CE-SDS) digital gel image of bispecific antibodies in Fab-Fab format with one (RV17, RV18, RV19, RV20) or two (RV23, RV24, RV25, RV26) anti-PD1 scFvs fused to the C terminus of heavy chains. For RV18, RV20, RV24 and RV26, the anti-PD1 scFv was designed with the VL-linker-VH orientation. For RV17, RV19, RV23 and RV25, the anti-PD1 scFv were designed with the VH-linker-VL orientation. Additionally, for RV19, RV20, RV25 and RV26, the anti-PD1 scFv also was designed with an engineered disulfide present.
Figure 7B:
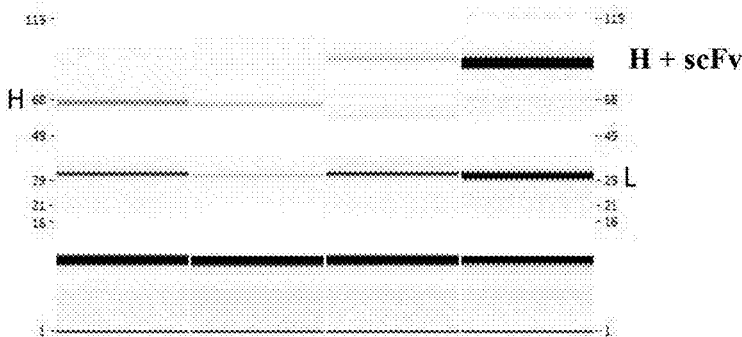
Figure 8A:
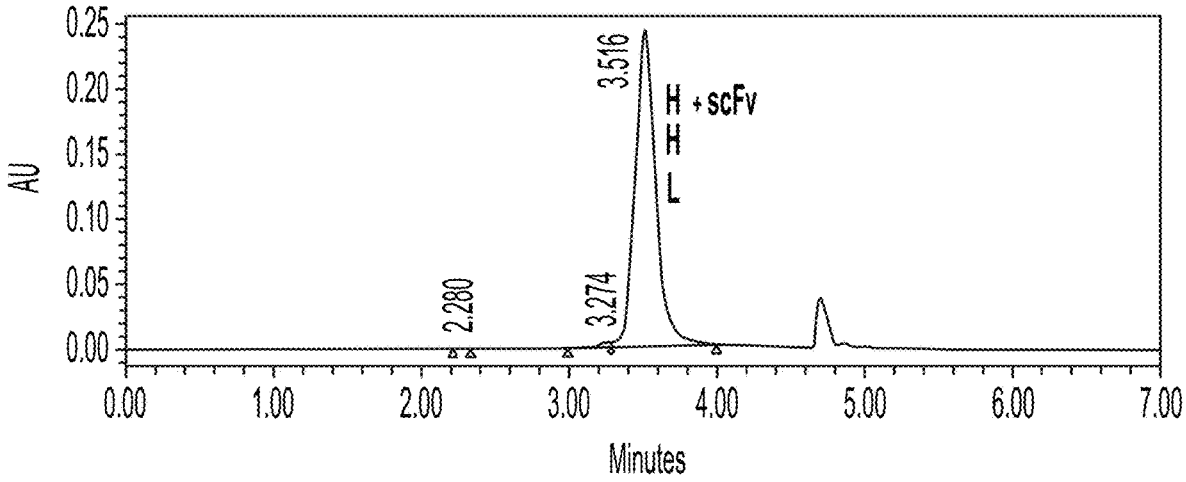
FIGS. 8A-8E show representative UPLC-SEC profiles for the following.
Figures 8B, 8C:
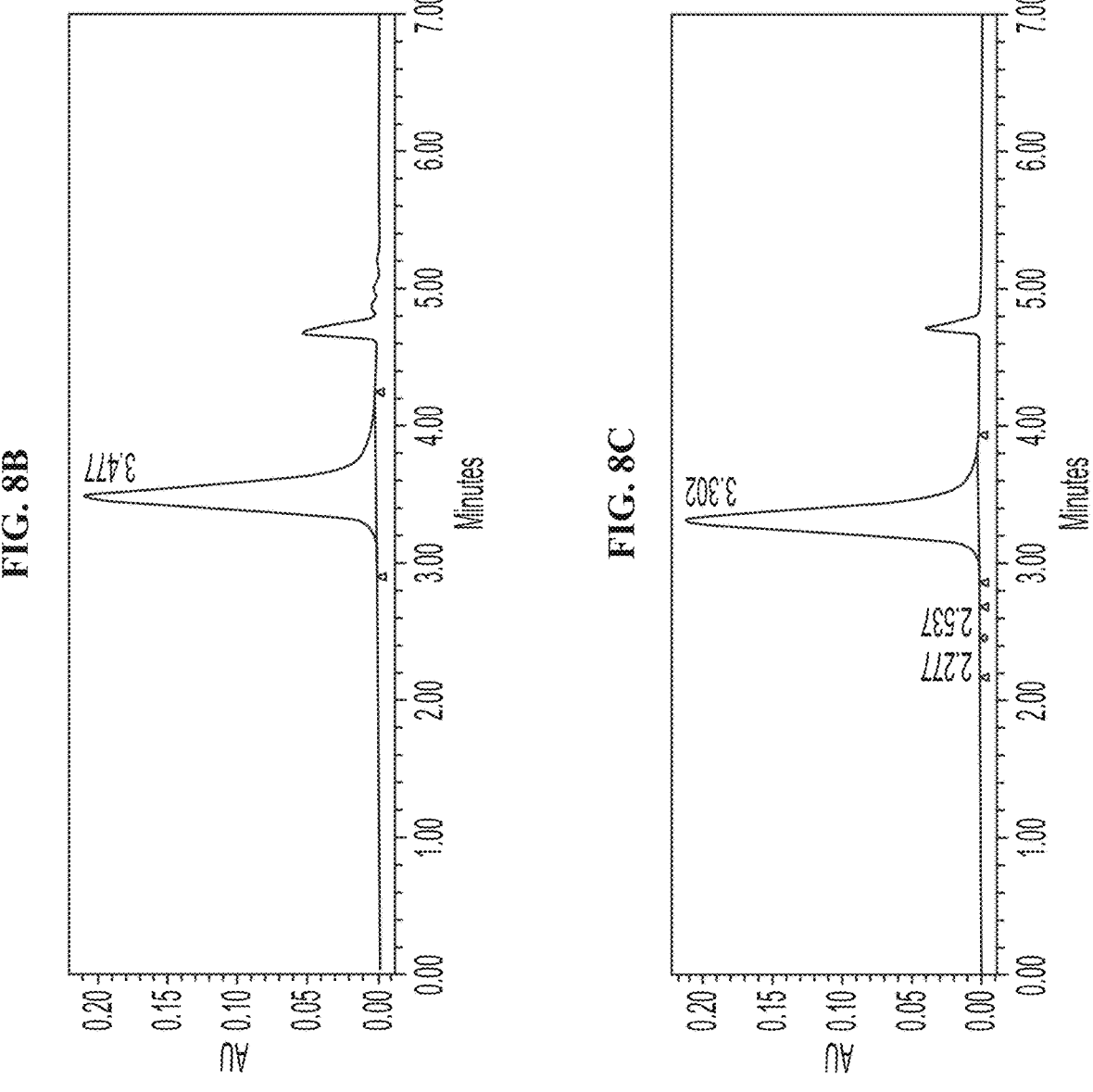
Figures 8D, 8E:
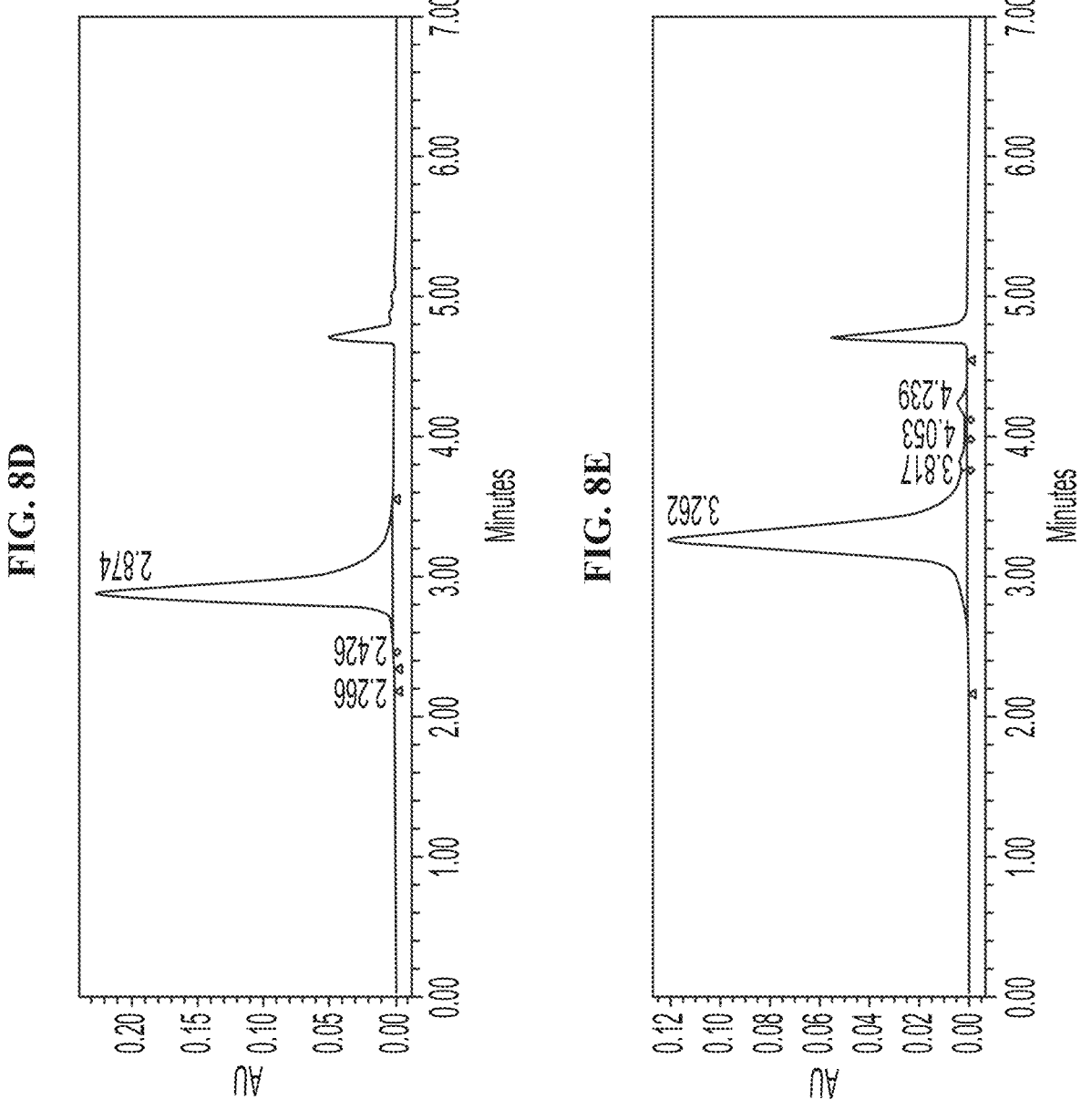
Figure 9A:
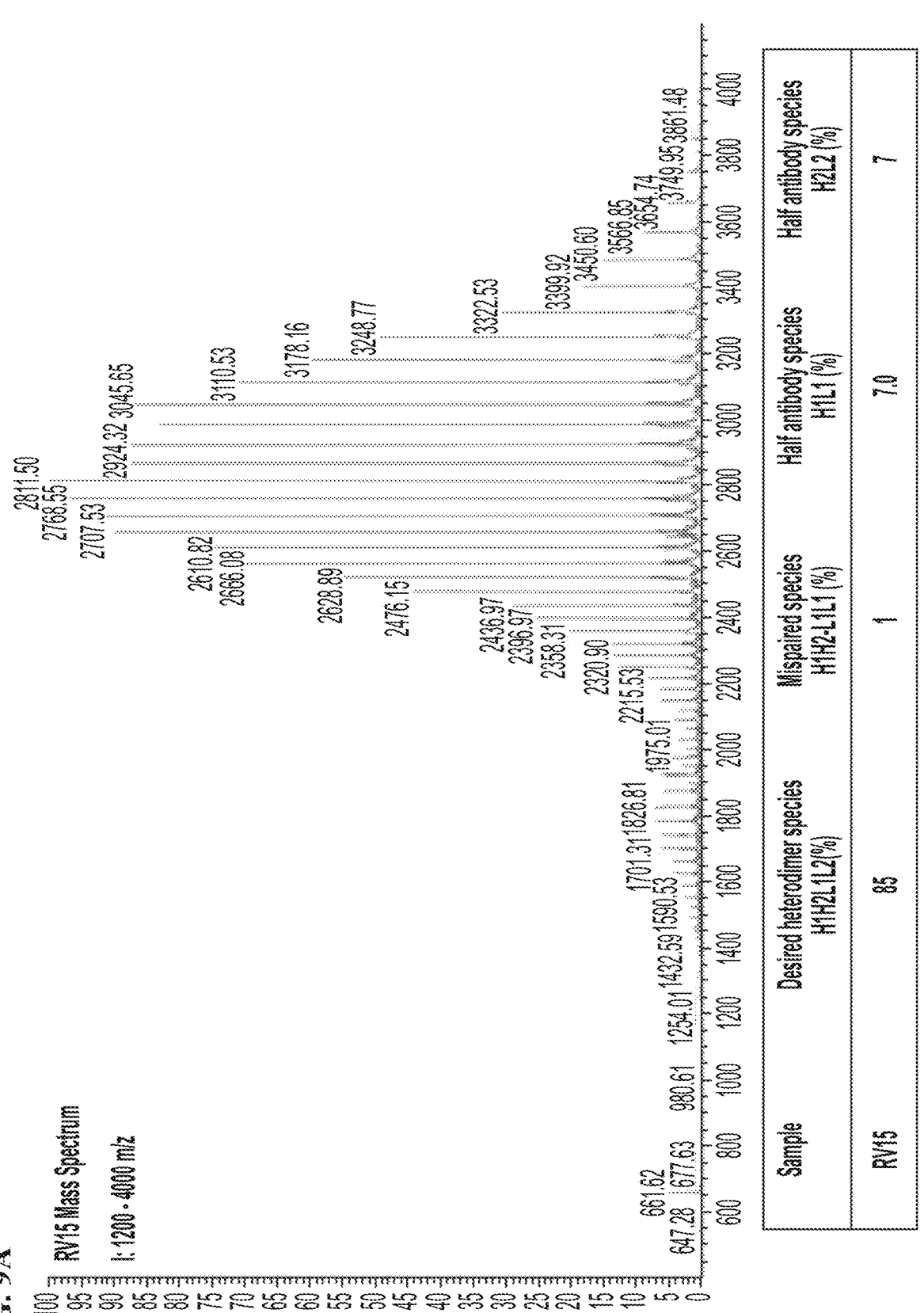
FIGS. 9A-9E depict LCMS analysis of the purity of exemplary bispecific antibodies.
Figure 9B:
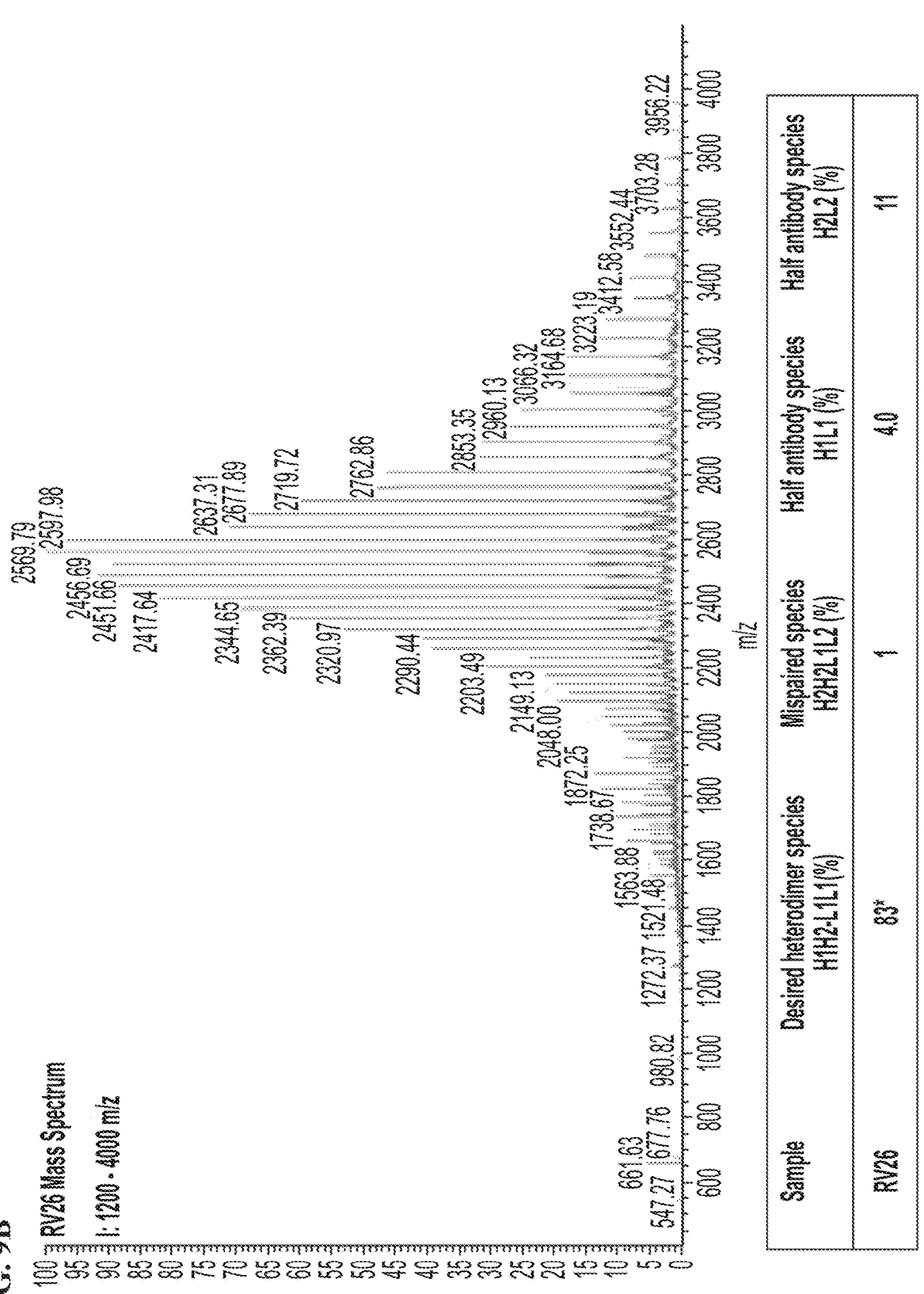
Figure 9C:
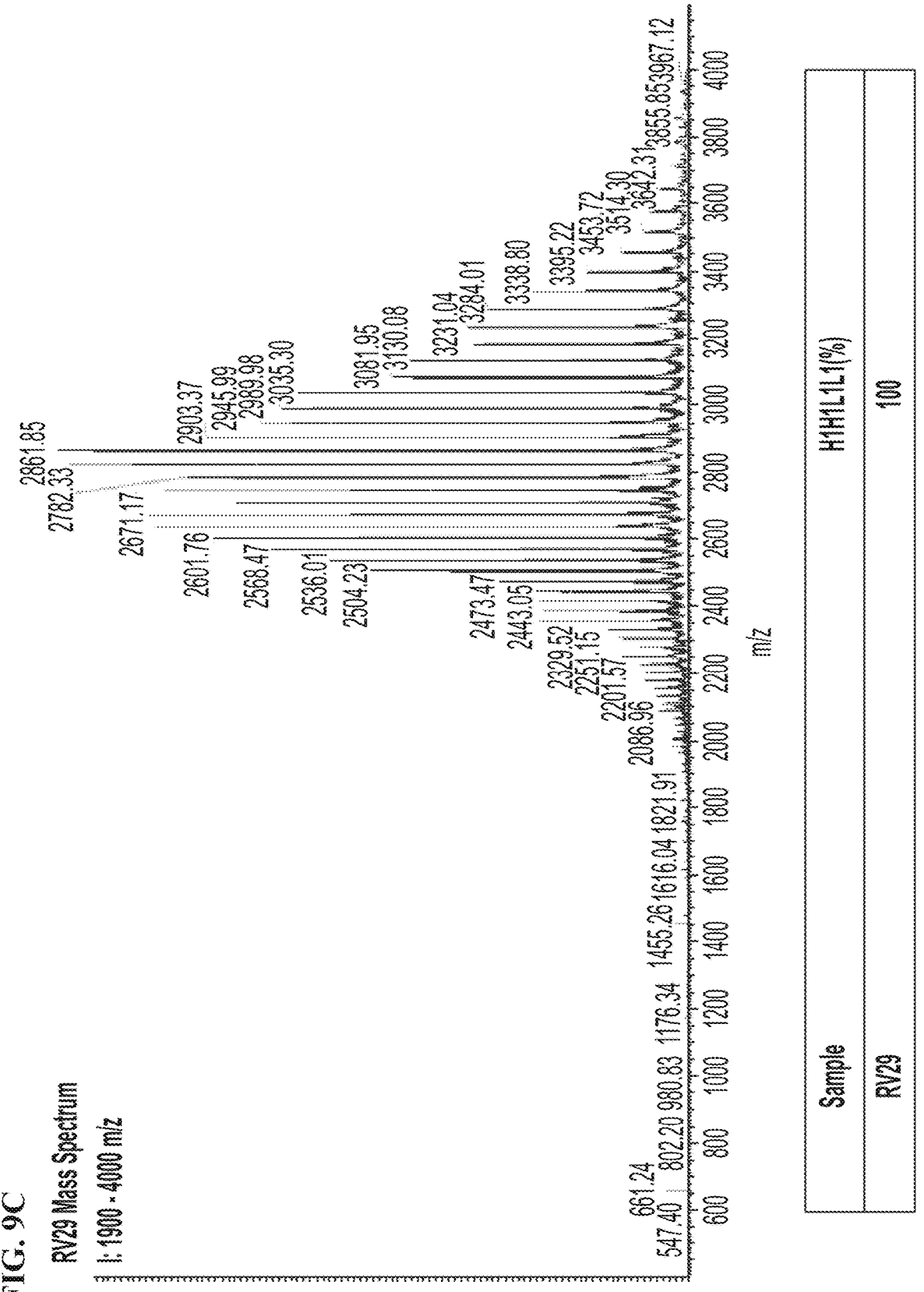
Figure 9D:
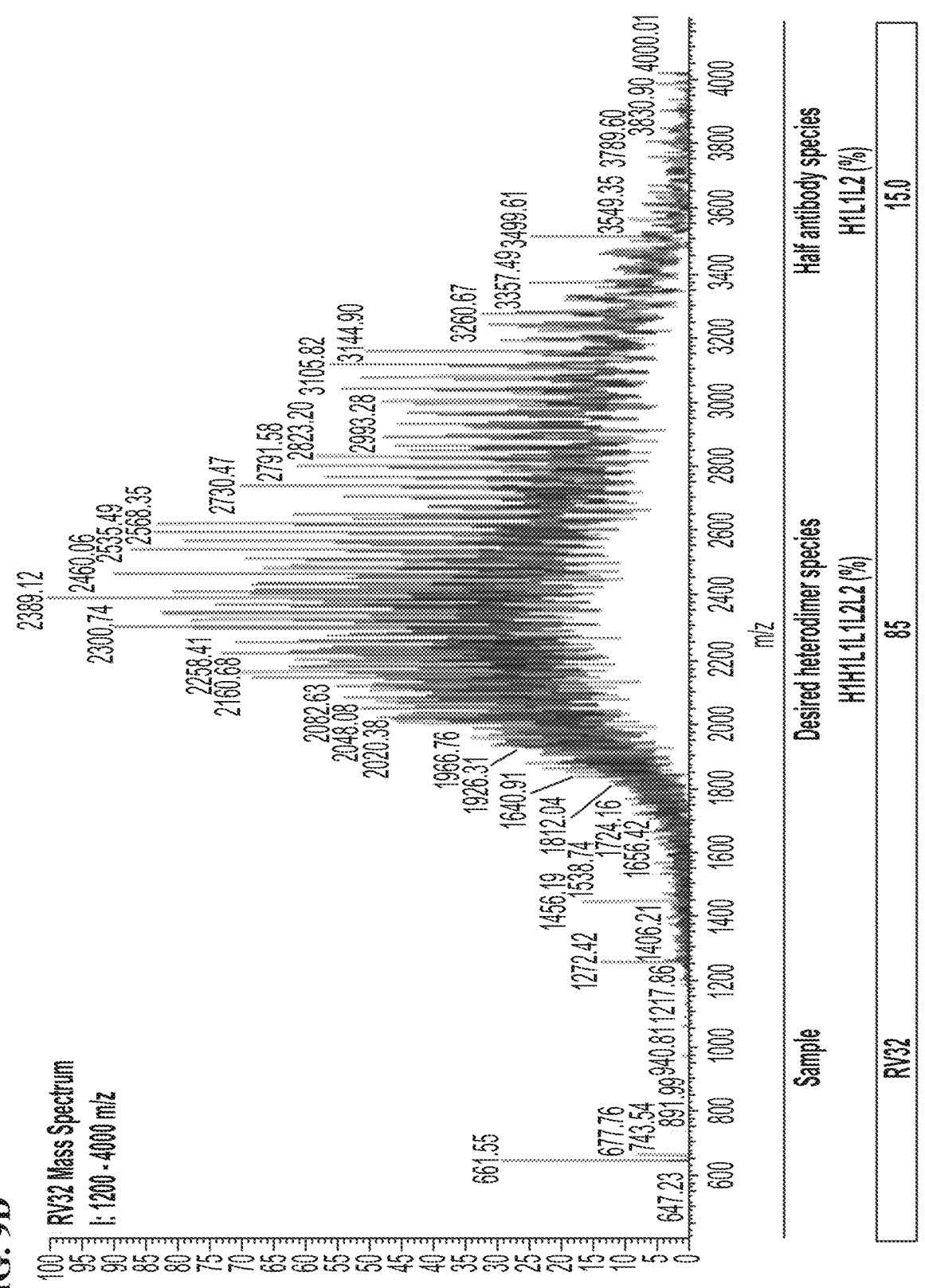
Figure 9E:
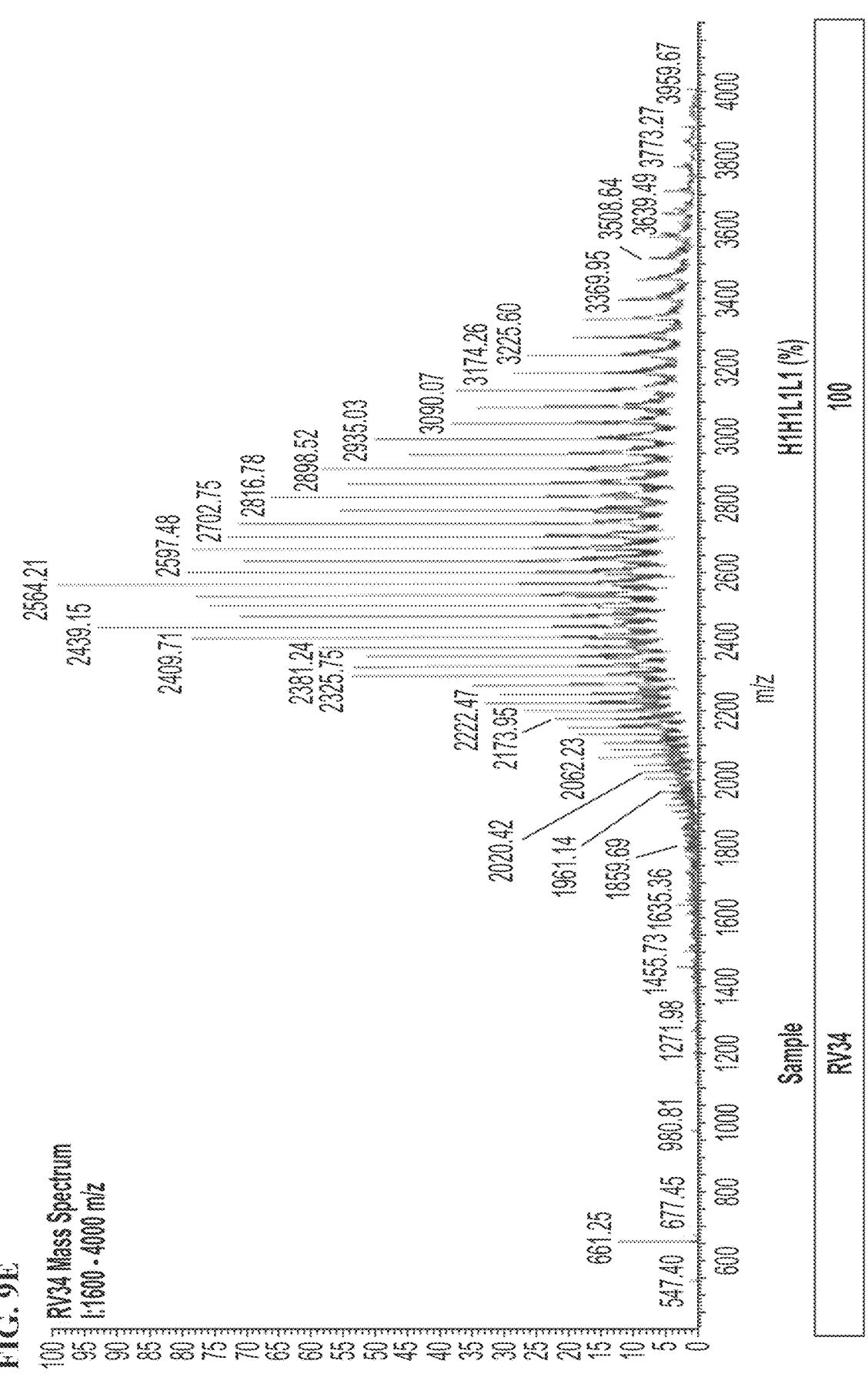

Overall, intact protein was obtained for biophysical characterization for all of the variants except for the following: RV17, RV19, RV21, RV22, RV23 and RV25, which exhibited significant instability issues. RV17, RV19, RV23 and RV25, bispecific antibodies in Fab-Fab format designed with-anti-PD1 scFv (in the VH-linker-VL orientation) fused to the C terminus of the heavy chains, showed complete loss of the scFv, as observed by CE-SDS (FIGS. 7A and 7B). In comparison, bispecific antibodies RV18, RV20, RV24 and RV26 in Fab-Fab format designed with anti-PD1 scFv (in the VL-linker-VH orientation) showed intact constructs, as observed by CE-SDS (FIGS. 7A and 7B). The scFv, in the VH-linker-VL orientation, was likely unstable as intact constructs were observed for similar format variants (RV18, RV20, RV24 and RV26) but with the anti-PD1 scFv in the VL-linker-VH orientation. Furthermore, for the variants with the anti-PD1 scFv designed with the VL-linker-VH orientation (RV20 and RV26), the engineered disulfides seemed to stabilize the scFv, as evidenced by the stronger H+ scFv bands versus variants that lacked the engineered disulfides (RV18, RV24) (FIG. 7). As for RV21 and RV22, bispecific antibodies in Fab-Fab format designed with one anti-IL-15 scFv (each variant with a different scFv orientation) fused to the C terminus of each of the heavy chains, most of the proteins precipitated and therefore were not further characterized. As appreciated in the art, not all conversions from VH-VL of Fab to ScFv result in stable protein. The unstable variants may be stabilized by engineering of the scFv and/or optimization of the transfection and purification processes.

Example 2: Analysis of Bispecific Antibody Purity by UPLC-SEC and LC-MS

The purity and percent aggregation of exemplary bispecific antibodies was determined by UPLC-SEC. UPLC-SEC analysis was performed using a Waters Acquity BEH200 SEC column (2.5 mL, 4.6×150 mm, stainless steel, 1.7 um particles) set to 30° C. and mounted on a Waters Acquity UPLC H-Class Bio system with a photodiode array (PDA) detector. Run times consisted of 7 min with running buffer 0.2 M KPO4, 0.2 M KCl, pH 7+0.02% Tween 20 at 0.4 ml/min. Elution was monitored by UV absorbance in the range 210-500 nm, and chromatograms were extracted at 280 nm. Peak integration was performed using Waters Empower 3 software employing the Apex Track™ and detect shoulders features. FIGS. 8A-8E show UPLC-SEC profiles for representatives of the exemplary bispecific antibodies. Results are in Table 3.

Purity and composition of the exemplary bispecific antibodies were assessed using mass spectrometry after nondenaturing deglycosylation. As the bispecific antibodies contained Fc N-linked glycans, the purified samples were de-glycosylated with PNGaseF (Millipore Sigma) as follows: 0.1 U PNGaseF/μg of antibody in 50 mM Tris-HCl pH 7.0, overnight incubation at 37° C., for a final protein concentration of 0.48 mg/mL. Additionally, as RV31 and RV32 also contained O-glycosylation (likely present in the inter-Fab hinge-like linker), the purified samples were further deglycosylated with O-glycosidase (OglyZOR, Genovis) at 1 U OglyZOR/μg of antibody and sialidases (SialEXO, Genovis) at 0.5 U SialEXO/μg of antibody in 50 mM Tris-HCl pH 7.0 at 37° C. overnight for a final protein concentration of 0.45 mg/ml. The deglycosylated protein samples were analyzed by intact LC-MS using an Ultimate3000 HPLC system coupled to an LTQ-Orbitrap XL mass spectrometer (ThermoFisher Scientific) via an Ion Max electrospray ion source (ThermoFisher Scientific). The samples (5 μg) were injected onto a 2.1×30 mm Poros R2 reverse phase column (ThermoFisher Scientific) and resolved using the following gradient conditions: 0-3 min: 20% solvent B; 3-6 min: 20-90% solvent B; 6-7 min: 90-20% Solvent B; 7-9 min: 20% solvent B. Solvent A was degassed 0.1% formic acid aq. and solvent B was degassed acetonitrile. The flow rate was 3 mL/min. The flow was split post-column to direct 100 μL/min into the electrospray interface. The column was heated to 82.5° C. and solvents were heated pre-column to 80° C. to improve protein peak shape. The LTQ-Orbitrap XL was calibrated using ThermoFisher Scientific's LTQ Positive Ion ESI calibration solution (caffeine, MRFA and Ultramark 1621). The cone voltage (source fragmentation setting) was 40 V, the FT resolution was 7,500 and the scan range was m/z 400-4,000. The LTQ-Orbitrap XL was tuned for optimal detection of larger proteins (>50 kDa) using α-lactalbumin (0.5 mg/mL, Millipore Sigma). The LC-MS system performance was evaluated prior to sample analysis using in-house standards: deglycosylated IgG standard (Waters IgG standard) and a mix of deglycosylated IgG and ~80 kDa protein. For each LC-MS analysis, the mass spectra acquired across the antibody peak were summed and the entire multiply charged ion envelope was deconvoluted into a molecular weight profile using the MaxEnt 1 module of MassLynx data analysis software (Waters) (Parameters: Peak width at half height=1.0, Iterations=10, Minimum intensity ratios Left=60%, Right=60%). The apparent relative amount of each antibody species in each sample was determined from the peak heights in the resulting molecular weight profiles.

Results from LC-MS analysis of the bispecific antibodies and component IL-15 cytokine capture and PD1 receptor targeting monospecific antibodies are shown in Table 4 and LC-MS mass spectra of representative variants are shown in FIGS. 9A-9E. Overall, the data shows the following: correct pairing of H:H and H:L with only trace amounts of mispairing present (<2%) and partial loss of ~195 Da, likely corresponding to the loss of N terminal residues QS from the L chain of the anti-IL-15 binding domain. To address the instability of the anti-IL-15 binding domain L chain, a combination of stability engineering and process optimization can be conducted.

TABLE 3

| Abundance of desired species as determined by UPLC-SEC % main peak | |
|---|---|
| Variant ID | % main peak |
| RV1 | 97.5 |
| RV9 | 99.8 |
| RV10 | 98.5 |
| RV15 | 99.2 |
| RV17 | 66.9 |

TABLE 3-continued

Abundance of desired species as
determined by UPLC-SEC % main peak

| Variant ID | % main peak |
|---|---|
| RV18 | 20.8 |
| RV19 | 85.6 |
| RV20 | 57.7 |
| RV20* | — |
| RV26 | 100 |
| RV29 | 99.9 |
| RV30 | 88.2 |
| RV30* | — |
| RV31 | 83 |
| RV32 | 99.9 |
| RV33 | 93.3 |
| RV34 | 95.7 |
| RV35 | 94.3 |
| RV36 | 99.9 |
| RV37 | 71.4 |

*From additional production

TABLE 4

Abundance of species as determined by LC-MS

| Sample | % main peak (UPLC-SEC) | H1H2L1L2 (%) | H1H1L1L1 (%) | H1H2L1L1 (%) | H2H2L2L2 (%) | H2H2L1L1 (%) |
|---|---|---|---|---|---|---|
| RV1 | 97.5 | | 100* | | | |
| RV9 | 99.8 | | 100* | | | |
| RV29 | 99.9 | | 100* | | | |
| RV36 | 99.9 | | 100* | | | |
| RV34 | 95.7 | | 100* | | | |
| RV35 | 94.3 | | 100* | | | |
| RV15 | 99.2 | 85* | | 1 | | |
| RV26 | 100 | | | 83* | | 1 |
| RV33 | 93.3 | 73* | 1 | | 1 | |
| RV31 | 83.0 | | | | | |
| RV32 | 99.9 | | | | | |

| Sample | H1H1L1 L1L2L2 | H1L1 | H2L2 | H2L1 (%) | H1L1L2 (%) | Correct chain pairing (HH, HL %) |
|---|---|---|---|---|---|---|
| RV1 | (%) | (%) | (%) | | | 100, 100 |
| RV9 | | | | | | 100, 100 |
| RV29 | | | | | | 100, 100 |
| RV36 | | | | | | 100, 100 |
| RV34 | | | | | | 100, 100 |
| RV35 | | | | | | 100, 100 |
| RV15 | | | | | | 100, 99.5 |
| RV26 | | 7.0 | 7 | | | 99, 100 |
| RV33 | | 4.0 | | 11 | | 98, 100 |
| RV31 | | 18.0 | 7 | | | 100, 100 |
| RV32 | 100* | | | | | 100, 100 |
| | 100* | | | | | |

*Desired antibody

Example 3: Thermal Stability of Bispecific Antibodies

Stability of selected bispecific heterodimeric antibodies and wild-type controls was assessed by freeze-thaw (F/T) cycle testing and/or by differential scanning calorimetry (DSC). For the freeze thaw testing, small scale F/T studies included three cycles of freezing to −80° C. for 30 minutes and thawing at Room Temperature (RT ~22-25° C.) for 30 minutes. Samples before and after the F/T cycles were then assessed for integrity and aggregation by CE-SDS and UPLC-SEC, respectively. For DSC, following preparative SEC treatment, 400 μL samples at concentration of 0.4 mg/mL in PBS were used for DSC analysis with a MicroCal VP-Capillary DSC (Malvern Instruments). At the start of each DSC run, 5 buffer blank injections were performed to stabilize the baseline, and a buffer injection was placed before each sample injection for referencing. Each sample was scanned from 20 to 100° C. at a 60° C./hr rate, with low feedback, 8 sec filter, 5 minute preTstat, and 70 psi nitrogen pressure. The resulting thermograms were referenced and analyzed using Origin 7 software.

Figure 10:
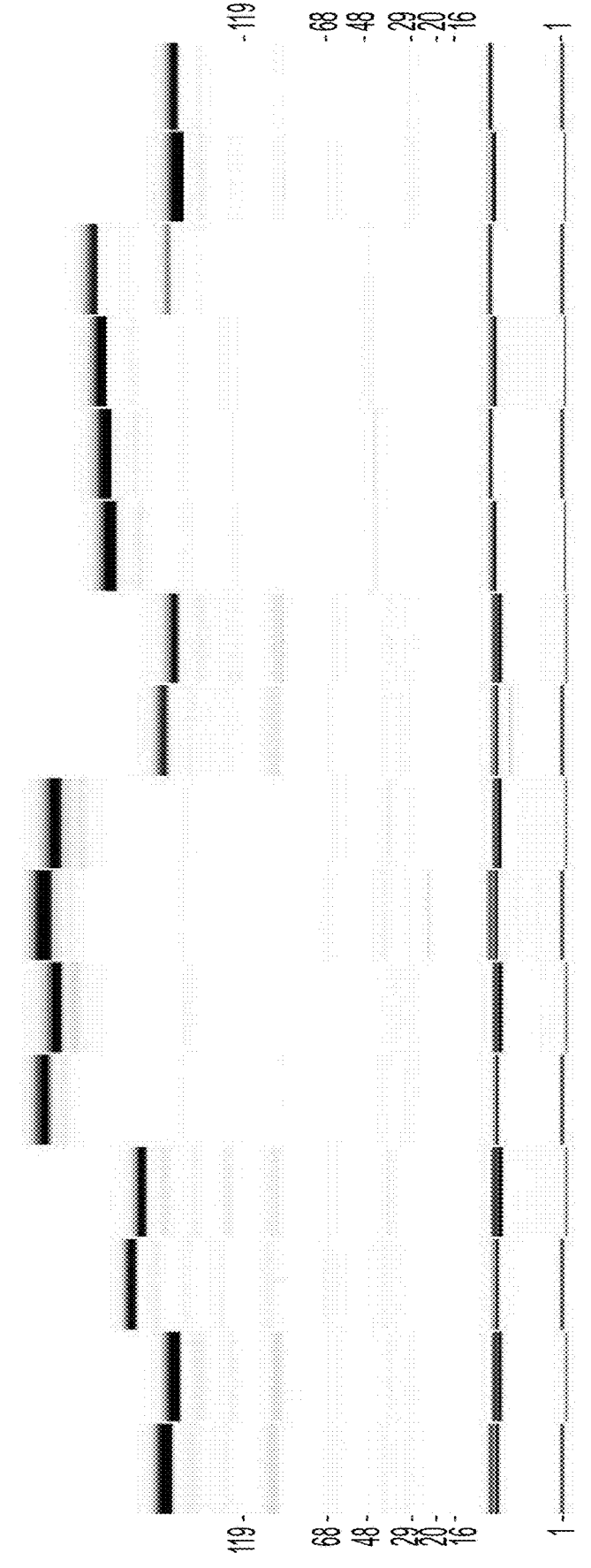
FIG. 10 shows a non-reduced CE-SDS digital gel image of selected variants, before (pre-3×FT) and after (post-3× FT) three cycles of freeze thaw testing. All variants retained structural integrity, except for RV36, where CE-SDS showed partial truncation, which is likely due to loss of the anti-IL-15 outer Fv domain.
Figure 11A:
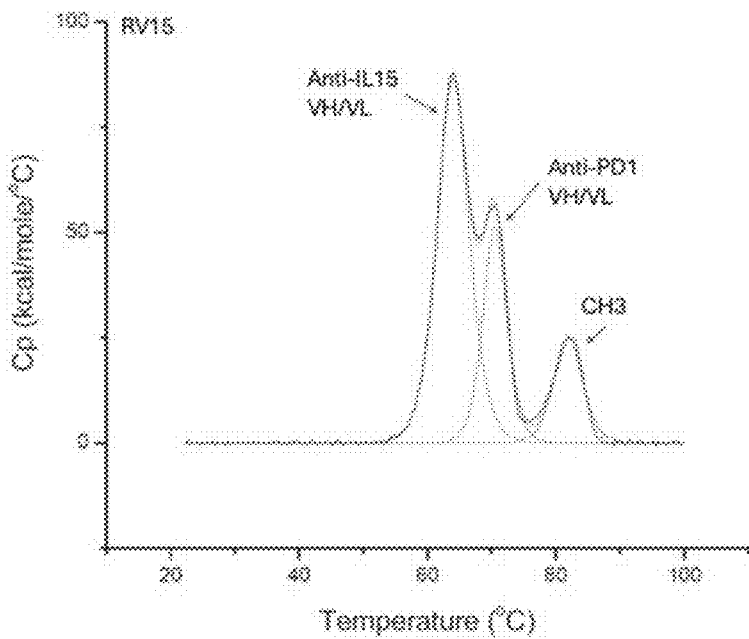
FIGS. 11A-11D show thermal unfolding, measured with differential scanning calorimetry (DSC), of exemplary bispecific antibodies for the following.
Figure 11B:
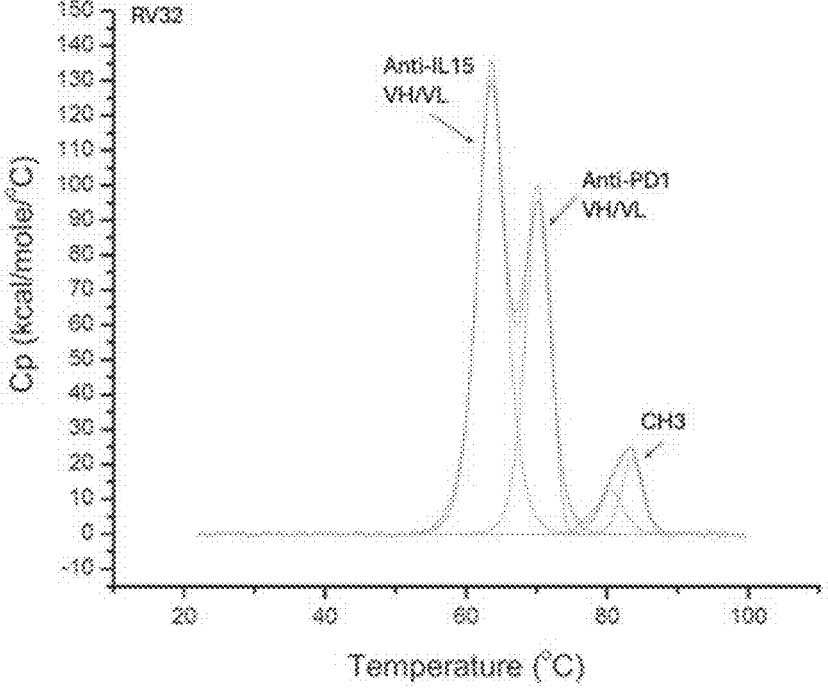
Figure 11C:
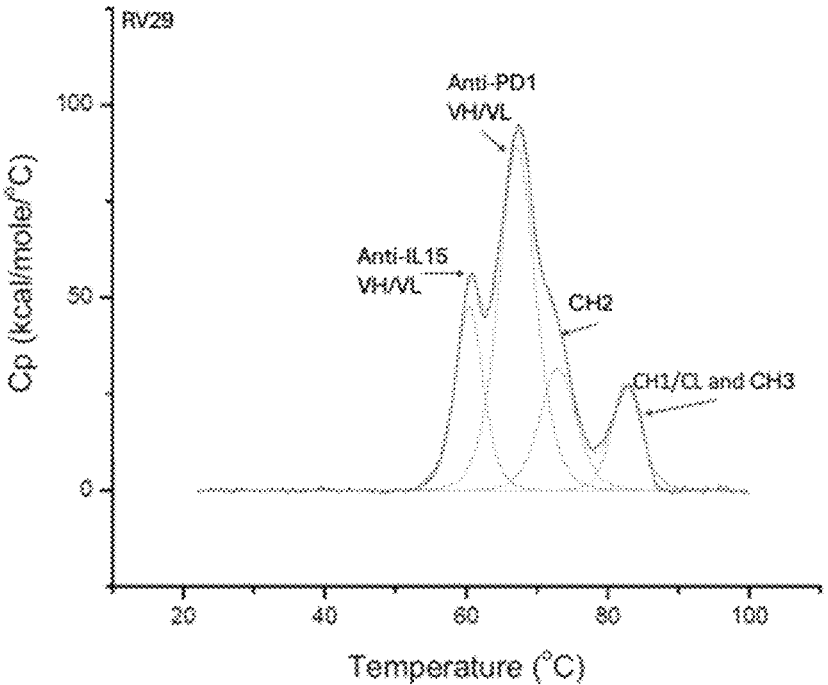
Figure 11D:
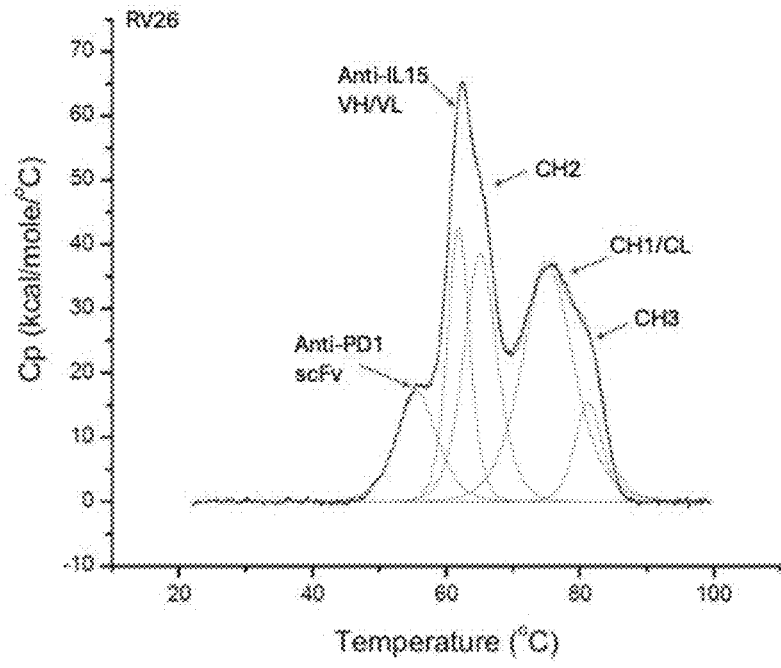

Following FT cycle testing, all variants except RV36 retained structural integrity, as determined by UPLC-SEC % main peak. For RV36, CE-SDS further showed partial truncation, which is likely due to loss of the anti-IL-15 outer Fv domain (FIG. 10). The instability is likely due to the inter-Fv linker, as RV29, which is similar to RV36 except that RV29 has a shorter inter-Fv linker, showed a stable construct. As for stability assessments via DSC (Table 5), the Tm onset showed that most stable bispecific constructs were asymmetric antibodies (RV15, RV33), followed by antibodies in dual Fab domain format (RV31 and RV32), DVDs (RV29 and RV36) and then antibody with scFv (RV26). VH/VL domain stabilities also followed a similar pattern, where variable domains in Fab format showed the highest melting temperatures (TM), followed by the outer Fv domain in the DVD format, and then by scFv format. The thermograms of exemplary bispecific antibodies (RV15, RV32, RV29 and RV26) are shown in FIGS. 11A-11D.

TABLE 5

| Variant | % main peak (UPLC-SEC) pre-3 × FT (ave) | % main peak (UPLC-SEC) post-3 × FT (ave) | DSC (° C.), Tm onset | DSC (° C.) with VH/VL Tms reported (anti-IL-15, anti PD1) |
|---|---|---|---|---|
| | Biophysical characterization (UPLC-SEC, thermal stability) | | | |
| RV1 | 97.5 | 97.2 | 60.81 | 65.8, N/A |
| RV9 | 99.8 | 99.5 | 60.5 | NA, 71.8 |
| RV10 (RV9 with LALAPG in Fc) | 98.5 | 98.4 | 61.6 | NA, 70.2 |
| RV15 | 99.2 | 99.2 | 55.6 | 64.0, 70.5 |
| RV26 | 100 | 99.7 | 48.2 | 61.7, 55.5 |
| RV31 | 83.0 | 87.5 | 53.4 | 62.5, 70.1 |
| RV32 | 99.9 | 99.3 | 55.6 | 63.6, 70.2 |
| RV29 | 99.9 | 99.9 | 54.2 | 60.5, 67.2 |
| RV36 | 99.9 | 70.4 | 49.7 | 57.9, 67.9 |
| RV33 | 93.3 | 92.9 | 55.9 | 63.6, 74.3 |
| RV34 | 95.7 | 93.6 | ND | ND |
| RV35 | 94.3 | 94.5 | ND | ND |

ND = Not Determined
NA = Not Applicable

Example 4: Antigen Affinity Measurements of Bispecific Antibodies and Controls The ability of the bispecific antibodies to present the bound cytokine for functionally relevant activity was assessed to determine whether the antibodies can bind the antigens with high affinity as well as form a complex with the IL-15Rβγ receptor chain heterodimer. The antigen binding affinities were determined by Surface Plasmon Resonance (SPR) as follows.

SPR Biosensor Assays

EDC: 1-ethyl-3-(3-dimethylaminopropyl) carbodiimide hydrochloride; NHS: N-Hydroxysuccinimide; SPR: surface plasmon resonance; EDTA: ethylenediaminetetraacetic acid SPR Supplies Series S Sensor Chip CM5, Biacore amine coupling kit (NHS, EDC and 1 M ethanolamine), and 10 mM sodium acetate buffers were purchased from Cytiva Life Sciences (Marlborough, MA). Premium grade IL-15, IL-15Rβγ protein comprising the human IL-2/IL-15 Rβ chain & common gamma (γ) receptor chain heterodimer and human PD-1 were purchased from Acrobiosystems (Newark, DE). PBS running buffer with 1% Tween20 (PBST) was purchased from Teknova Inc. (Hollister, Calif.). Goat polyclonal anti-human Fc antibody was purchased from Jackson Immuno Research Laboratories Inc. (West Grove, Pa.). EDTA was purchased from Bioshop (Burlington, ON). All SPR assays were carried out using a Biacore T200 Surface Plasmon Resonance instrument (Cytiva Life Sciences, (Marlborough, MA)) with PBST running buffer (with 0.5 M EDTA stock solution added to 3.4 mM final concentration) at a temperature of 25° C. The anti-human Fc capture surface was generated using a Series S Sensor Chip CM5 using the default parameters under the Immobilization Wizard in the Biacore T200 control software which was set to target 3000 resonance units (RUs).

SPR experiments were conducted using two methods: 1) variants and/or IL-15 complexed variants as ligands, with IL-15 or IL-15Rβγ receptor as analytes, respectively; and 2) PD1 antigen, PD1:variant complex and/or PD1:variant: IL-15 as ligand, with variants, IL-15, and IL-15Rβγ as analytes, respectively. Furthermore, SPR experiments were also conducted using IL-15 bound variants for PD1, as well as IL-15 and PD1 bound variants for IL-15Rβγ.

For IL-15 binding, one method involved an indirect capture of the antibody variants onto the anti-human Fc antibody SPR surface followed by the injection of 4 concentrations of IL-15 for kinetic analysis using the single cycle kinetics methodology. Variants were captured onto individual anti-hFc surfaces at 2.5 µg/mL for 30 s at a flow rate of 10 µL/min. In general, this resulted in a capture between approximately 131 to 650 RUs of variant onto the anti-human Fc surface. The first flow cell was left empty to use as a blank control. This capture step was immediately followed by four concentrations of IL-15 (0.104 nM, 0.52 nM, 2.6 nM, and 13 nM) that were sequentially injected over all the four flow cells at 50 µL/min for 150 seconds with a dissociation phase of 900 seconds. The captured antibody surfaces were regenerated twice by 10 mM Glycine pH1.5 for 30 seconds at 30 µL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity ($K_D$) of the interactions under analysis.

The other method used to assess IL-15 binding involved an indirect capture of the antibody variants onto the PD1 flow cell surface followed by injection of 4 concentrations of IL-15 for kinetic analysis using the single cycle kinetics methodology. The PD1 surface was prepared by injection of PD1 at 5 µg/ml pH 4.5, and immobilization via NHS/EDC with the Immobilization Wizard within the Biacore control software set to 500 RUs. Variants were injected at 5 µg/mL over individual flow cells for 30 seconds at a flow rate of 10 µL/min. In general, this resulted in a capture between approximately 500 to 700 RUs onto the PD1 surface. This capture step was immediately followed by four concentrations of IL-15 (0.104 nM, 0.52 nM, 2.6 nM, and 13 nM) that were sequentially injected over all of the four flow cells at 10 µL/min for 180 seconds with a dissociation phase of 900 seconds. The captured antibody surfaces were regenerated twice by 10 mM Glycine pH1.5 for 30 seconds at 10 µL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity ($K_D$) of the interactions under analysis.

For IL-15Rβγ receptor binding, one method involved an indirect capture of the antibody variants onto the anti-human Fc antibody flow cell surface where variants were injected at 2.5 µg/mL over individual flow cells for 30 seconds at a flow rate of 10 µL/min. The first flow cell was left empty to use as a blank control. IL-15 at 20 nM was then injected for 180 seconds at 10 uL/min to form antibody: IL-15 complexes. In general, this resulted in a capture between approximately 360 to 690 RUs. This capture step was immediately followed by four concentrations of IL-15Rβγ receptor (0.24 nM, 1.2 nM, 6 nM, and 30 nM) that were sequentially injected over all of the four flow cells at 20 µL/min for 150 seconds with a dissociation phase of 900 seconds. The captured antibody surfaces were regenerated twice by 10 mM Glycine pH1.5 for 30 seconds at 10 or 30 µL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity ($K_D$) of the interactions under analysis.

The second method used to assess IL-15Rβγ receptor binding involved an indirect capture of the antibody variants onto the PD1 flow cell surface followed by injection of IL-15 at 20 nM and then by the injection of 4 concentrations of IL-15Rbg receptor for kinetic analysis using the single cycle kinetics methodology. The PD1 surface was prepared by injection of PD1 at 5 μg/ml pH 4.5, and immobilization via NHS/EDC with wizard set to 500 RUs. Bispecific variants were injected at 5.0 μg/mL over individual flow cells for 30 seconds at a flow rate of 10 μL/min. IL-15 was then injected at 20 nM for 180 seconds at a flow rate of 10 μL/min to form a variant-IL-15 complex. This capture step was immediately followed by four concentrations of IL-15Rβγ receptor (0.24 nM, 1.2 nM, 6 nM, and 30 nM) that were sequentially injected over all of the four flow cells at 20 μL/min for 150 seconds with a dissociation phase of 900 seconds. The captured antibody surfaces were regenerated twice by 10 mM Glycine pH1.5 for 30 seconds at 10 μL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity ($K_D$) of the interactions under analysis.

For PD1 binding, one method used involved an indirect capture of the antibody variants via the Fc regions onto the flow cell surface followed by the injection of 4 concentrations of PD1 for kinetic analysis using the single cycle kinetics methodology. For the protein A (pA) flow cell surface, variants were injected at 2 μg/mL over individual flow cells for 40 seconds at a flow rate of 5 μL/min. In general, this resulted in a capture between approximately 150 to 935 RUs onto the pA surface. The first flow cell was left empty to use as a blank control. This capture step was immediately followed by four concentrations of PD1 (0.3125 nM, 1.25 nM, 5 nM and 20 nM) that were sequentially injected over all of the four flow cells at 50 μL/min for 150 seconds with a dissociation phase of 900 seconds. The pA surfaces were regenerated by twice 10 mM Glycine pH1.5 for 30 seconds at 10 μL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity ($K_D$) of the interactions under analysis. For the anti-human Fc antibody flow cell surface, variants were injected at 2.5 μg/mL over individual flow cells for 30 seconds at a flow rate of 10 μL/min. In general, this resulted in a capture between approximately 211 to 261 RUs of variant onto the anti-human Fc surface. The first flow cell was left empty to use as a blank control. This capture step was immediately followed by four concentrations of PD1 (0.24 nM, 1.2 nM, 6 nM and 30 nM) that were sequentially injected over all the four flow cells at 20 μL/min for 150 seconds with a dissociation phase of 900 seconds. The captured antibody surfaces were regenerated twice by 10 mM Glycine pH1.5 for 30 seconds at 30 μL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity (KD) of the interactions under analysis.

The other method used to assess PD1 binding involved an injection of 4 concentrations (0.31 nM, 1.25 nM, 5 nM, and 20 nM; or 0.24 nM, 1.2 nM, 6 nM, and 30 nM) of the antibody variants over the PD1 ligand flow cell surface using single cycle kinetics methodology. The PD1 surface was prepared by injection of PD1 at 5 μg/ml pH 4.5, and immobilization via NHS/EDC with wizard set to 500 RUs. The four concentrations of variants were sequentially injected over all of the four flow cells at 10 μL/min for 150 seconds with a dissociation phase of 800 or 900 seconds. The captured antibody surfaces were regenerated twice by 10 mM Glycine pH1.5 for 30 seconds at 10 μL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity ($K_D$) of the interactions under analysis.

For SPR experiments of PD1 binding using IL-15 bound variants, this method involved an indirect capture of the antibody variants onto the anti-human Fc antibody flow cell surface where variants were injected at 2.5 μg/mL over individual flow cells for 30 seconds at a flow rate of 10 L/min. The first flow cell was left empty to use as a blank control. IL-15 at 20 nM was then injected for 180 seconds at 10 uL/min to form antibody: IL-15 complexes. In general, this resulted in a capture between approximately 170 and 190 RUs. This capture step was immediately followed by four concentrations of PD1 (0.24 nM, 1.2 nM, 6 nM and 30 nM) that were sequentially injected over all of the four flow cells at 50 μL/min for 150 seconds with a dissociation phase of 900 seconds. The anti-human Fc surfaces were regenerated twice by 10 mM Glycine pH1.5 for 30 seconds at 10 μL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity (KD) of the interactions under analysis.

For SPR experiments of IL-15Rβγ receptor binding using IL-15 and PD1 bound variants, this method involved an indirect capture of the antibody variants onto the anti-human Fc antibody flow cell surface where variants were injected at 2.5 μg/mL over individual flow cells for 30 seconds at a flow rate of 10 μL/min. The first flow cell was left empty to use as a blank control. IL-15 at 20 nM was then injected for 180 seconds at 10 uL/min to form antibody: IL-15 complexes. Then PD1 at 30 nM was injected for 180 seconds at 10 uL/min to form antibody: IL-15:PD1 complexes. In general, this resulted in a capture between approximately 190 and 235 RUs. This capture step was immediately followed by four concentrations of IL-15bg receptor (0.24 nM, 1.2 nM, 6 nM, and 30 nM) that were sequentially injected over all of the four flow cells at 50 μL/min for 150 seconds with a dissociation phase of 900 seconds. The captured antibody surfaces were regenerated twice by 10 mM Glycine pH1.5 for 30 seconds at 30 μL/min. Buffer injections were performed for each analyte injection to be used for referencing. The resulting single cycle kinetics sensorgrams were double referenced and fit to the 1:1 binding model using Biacore T200 BiaEvaluation software to derive the rate constants and affinity (KD) of the interactions under analysis.

Overall, antigen affinities of the heterodimeric antibodies were assessed with reference to the respective wild-type controls, Mab for RV1 for IL-15 binding and RV9 for PD1 binding. Altogether, variants bind PD1 and IL-15 with high affinities similar to the wild type controls (see Table 6), with the following caveats/exceptions: 1) some variants exhibited lower purity (<95%), as determined by UPLC-SEC peak profiles, resulting in KDs that are likely affected by the impurities present; 2) impaired accessibility to some variants (e.g. RV18, RV20) due to attachment on chip is observed, resulting in seemingly lowered affinities for PD1; 3) where variants with two anti-PD1 domains are analytes, the KDs obtained likely reflect KDs that show avidity as well as affinity; and 4) RV17 and RV19 showed truncations consistent with loss of anti PD1 scFvs (FIGS. 7A and 7B), thereby resulting in no binding to PD1, as expected.

Figure 12A:
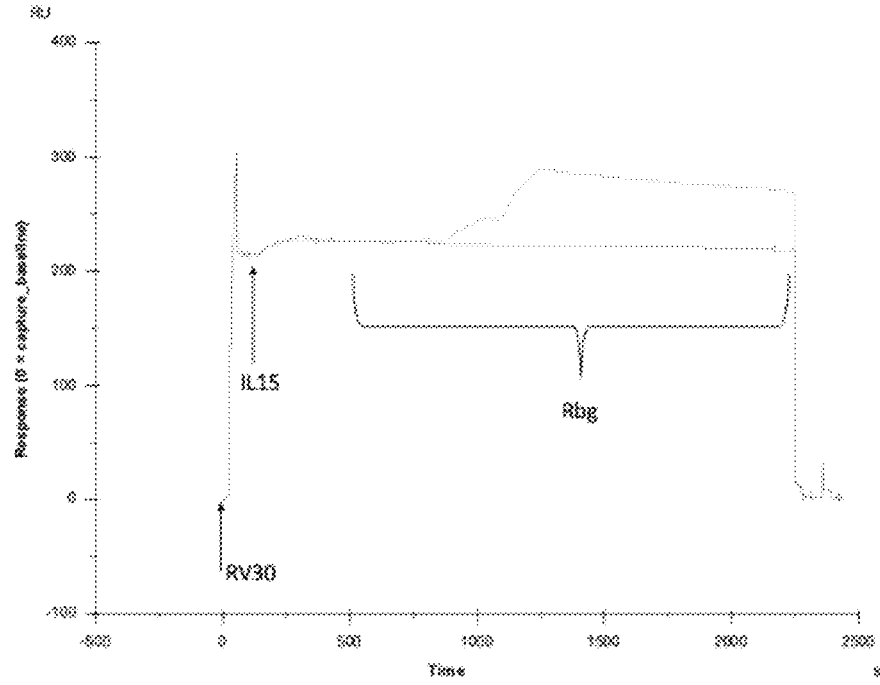
FIGS. 12A and 12B show representative adjusted SPR sensorgrams of the formation of RV:PD1:IL-15:IL-15βγ receptor complex, using RV30.
Figure 12B:
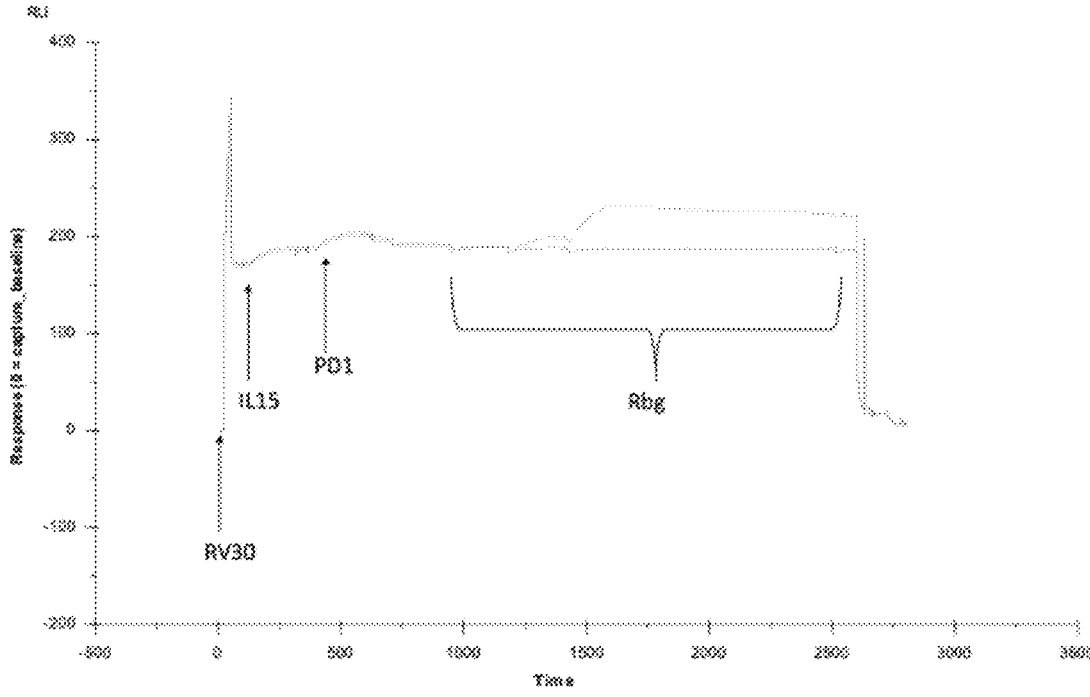

Furthermore, the variants can form the desired IL-15:PD1:IL-15Rβγ receptor complexes as shown by SPR experiments assessing IL-15Rβγ receptor affinity using a PD1 capture surface (Table 6, FIG. 12A) as well as SPR experiments assessing IL-15Rβγ receptor binding of IL-15 and PD1 bound variants using an anti-human Fc capture surface (Table 7, FIG. 12B). For the PD1 capture surface, the RVs are first captured by the anti-PD1 binding domain(s), followed by capture of IL-15 by the anti-IL-15 domain(s) and subsequently by capture of the IL-15βγ receptor(s) by the IL-15 bound anti-IL-15 domain(s). For the anti-human Fc capture surface, RVs are first captured, followed by capture of IL-15 by the anti-IL-15 domain(s), then by capture of PD1 by the anti-PD1 domain(s) and subsequently by capture of the IL-15 βγ receptor(s) by the IL-15 bound anti-IL-15 domain(s). For RV30 and RV37, PD1 binding affinities were similar for variants with (Table 7) or without (Table 6) bound IL-15. Also, IL-15Rβγ receptor affinities were similar for IL-15 bound variants with or without bound PD1 (Table 6 and Table 7).

Example 5: Anti-IL-15 Antibodies Induce In Vivo Expansion of IL-15 Responsive Lymphocytes (CD8+ T, NK and NKT Cells)

The in vivo effects of an exemplary anti-IL-15 antibody were evaluated in C57BL/6 mice. The anti-IL-15 antibody does not bind murine IL-15, thus mice were treated intraperitoneally with 10 mg of GMP grade human IL-15 (Acro Biosystems) (functionally active in mice). Concurrently, mice were treated subcutaneously with 100 mg of anti IL-15 antibody (RV1) or an IgG1 isotype control (anti-RSV). Mice were monitored for 7 days; the capture antibody was well tolerated as monitored by body weight and clinical observations. The effect of the anti-IL-15 antibody on immune cell populations was evaluated in the peripheral blood 4 days post treatment and in the spleen at sacrifice on day 7. Lymphocyte subsets were evaluated by flow cytometry.

Figure 13:
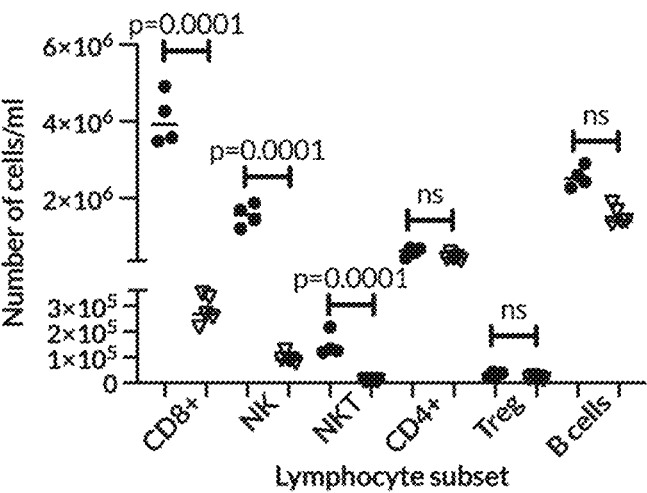
FIG. 13 shows the significant in vivo expansion of CD8+ T cells, NK cells and NKT cells in the peripheral blood of C57BL/6 mice 4 days after treatment with 100 mg of anti-IL-15 antibody (RV1) and 10 mg of human IL-15 versus 100 mg of isotype control antibody (anti-RSV) and 10 mg of human IL-15.

Compared to the isotype control group, administration of the anti-IL-15 antibody resulted in an increase in lymphocyte subsets known to be responsive to IL-15 on day 4. The number of CD8+ T cells, NK cells and NKT cells were significantly higher in the peripheral blood ($p=0.0001$ two-way ANNOVA with Tukey's multiple comparison test) but not CD4+ T cells, CD4+ Treg cells or B cells (FIG. 13). In addition, on day 7, analysis of the spleen showed a significantly increased proportion of CD3+ T cells being CD8+ in the presence of the anti-IL-15 antibody versus isotype

TABLE 6

Affinities of variants as characterized by SPR

| Variant ID | % main peak (UPLC-SEC) | KD (IL-15) (M) Using capture surface anti-human Fc/PD1 | KD (IL-15βγ) (M) Using capture surface anti-human Fc/PD1 | KD (PD1) (M) Using capture surface anti-human Fc/pA/PD1 |
|---|---|---|---|---|
| RV1 | 97.50 | 3.49E−10/NA | 7.05E−10/ND | N/A |
| RV9 | 99.8 | N/A | N/A | ND/4.81E−09/3.32E−13 |
| RV15 | 99.2 | 1.08E−10/ND | 8.04E−10/7.22E−10 | ND/ND/3.62E−09 |
| RV26 | 100 | 3.96E−10/ND | 1.36E−09/1.53E−09 | ND/ND/2.19E−09 |
| RV31 | 83 | 1.80E−10/7.17E−10 | 9.79E−10/9.81E−10 | ND/ND/1.63E−10 |
| RV32 | 99.9 | 1.08E−10/3.52E−10 | 7.42E−10/1.45E−09 | ND/ND/6.78E−11 |
| RV17 | 66.9 | 1.06E−10/ND | 9.90E−10/ND | ND/NB/NB |
| RV18 | 20.8 | 7.69E−11/ND | 1.02E−09/2.39E−10 | ND/1.3E−08/2.15E−10 |
| RV19 | 85.6 | 8.47E−11/ND | 1.17E−09/ND | ND/NB/ND |
| RV20 | 57.7 | 5.19E−11/ND | 8.52E−10/6.67E−10 | ND/2.69E−07/1.72E−08 |
| RV20* | 96.5 | 5.31E−11/1.69E−10 | ND/7.26E−10 | 3.99E−09/ND/ND |
| RV29 | 99.9 | 1.14E−10/3.39E−10 | 7.32E−10/7.20E−10 | ND/NB/2.35E−09 |
| RV30 | 88.2 | 7.70E−11/4.52E−10 | 8.49E−10/8.28E−10 | ND/6.48E−09/3.74E−11 |
| RV30* | 97.4 | 6.64E−11/8.50E−10 | ND/6.65E−10 | 4.90E−09/ND/ND |
| RV36 | 99.9 | 1.16E−10/1.11E−10 | 7.71E−10/1.07E−09 | ND/9.70E−08/2.43E−10 |
| RV37 | 71.4 | 6.64E−11/2.27E−10 | 9.86E−10/6.93E−10 | ND/7.15E−09/4.88E−11 |

ND = Not Determined
NB = No Binding
NA = Not Applicable
*from additional production

TABLE 7

Affinities of IL-15 bound variants as characterized by SPR

Figure 14:
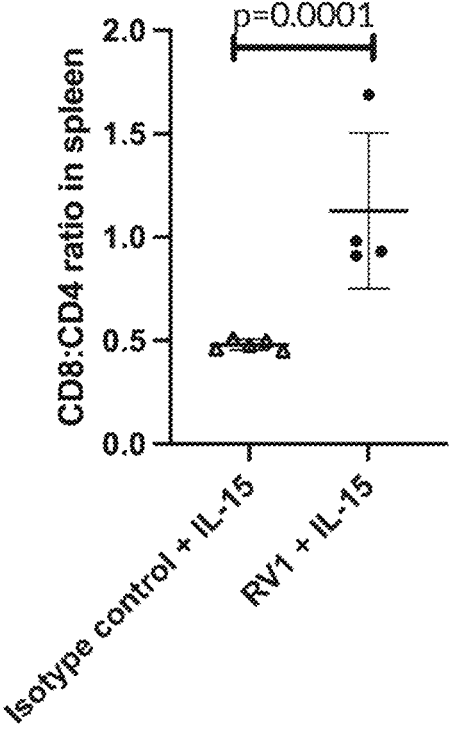
FIG. 14 shows the significant increase in the ratio of CD8+:CD4+ T cells in the spleens of C57BL/6 mice 7 days after treatment with 100 mg of anti-IL-15 antibody (RV1) and 10 mg of human IL-15 or 100 mg of isotype control antibody (anti-RSV) and 10 mg of human IL-15.

| Variant ID | % main peak (UPLC-SEC) | KD (IL-15bg) (M) Using capture surface anti-human Fc | KD (PD1) (M) Using capture surface anti-human Fc |
|---|---|---|---|
| RV30 (IL-15 bound) | 88.2 | 7.06E−10 | 6.57E−09 |
| RV37 (IL-15 bound) | 71.4 | 8.48E−10 | 6.88E−09 | control, ($p=0.0001$ two-way ANNOVA with Tukey's multiple comparison test (FIG. 14)). These results suggest that the anti-IL-15 antibody is able to bind and present IL-15 to IL-15Rβγ receptor expressing cells in vivo.

Example 6: Anti-IL-15 Antibodies Induce Cytokine Production in In Vitro Cultures of PBMC The effect of an exemplary anti-IL-15 antibody (RV1) on cytokine production was evaluated in human peripheral blood mononuclear cells (PBMC). Frozen PBMC were purchased from AllCells Inc. (Alameda, CA), cells were thawed just prior to the experiment. Cells were cultured in duplicate in 96 well U bottomed plates (200,000 cells per well) for 4 days with the indicated concentration of test samples. After 4 days the level of cytokines secreted by cells and present in the culture supernatant was determined by MSD (Meso Scale Dynamics) analysis. Two experiments were performed. In the first experiment, two forms of the anti-IL-15 antibody (Fc active, RV1 and Fc null, RV2) and an isotype control (anti-RSV, Fc active) were cultured in duplicate at 10 mg/ml in the absence or presence of human IL-15 (50 pM or 1 nM) for 4 days. GM-CSF was detected in the culture supernatants of the anti-IL-15 antibody with an active Fc (RV1), but not with a silenced Fc (RV2) (FIG. 15A), both in the presence of exogenously added IL-15 (50 pM and 1 nM) and with endogenous IL-15 levels (no IL-15 added to the culture). Similarly, significantly increased levels of TNF-α were present in cultures containing the anti-IL-15 antibody with an active Fc and 1 nM of IL-15 (p=0.0001 two-way ANNOVA (FIG. 15B) along with increased levels of TNF-α with 50 pM and endogenous levels of IL-15 with RV1 versus RV2 and the isotype control. Additional cytokines (IL-2, IFN-g, granzyme A/B and perforin) were not detected above background levels in this assay. These data suggest that the Fc active format of the anti-IL-15 antibody RV1 can bind to endogenous and exogenous IL-15 and enhance its activity. In the second experiment, the Fc active IL-15 capture antibody was either precomplexed with IL-15 (by overnight incubation at an equimolar concentration at 4° C. in a low protein binding polypropylene 96-well U bottom plate) or allowed to form a complex with IL-15 in the assay. Human PBMC (AllCells Inc., Alameda, CA) were cultured in duplicate for 4 days in 96-well U bottom plates in the presence 100 nM, 10 nM or 1 nM of RV1 precomplexed with IL-15, or with RV1 and free IL-15 (equimolar concentrations), controls of IL-15 alone, media alone and IL-15 precomplexed with IL-15Rα-Fc (IL-15Rα-Fc fusion protein, ACROBiosystems) were included. After 4 days the culture supernatant was analyzed by MSD for the presence of IL-2, IFN-γ, Granzyme A, Granzyme B, Perforin, GM-CSF and TNF-α (FIGS. 16A-G). There was a dose dependent increase observed for all cytokines when PBMC were cultured with RV1 precomplexed with IL-15, RV1 with free IL-15 and IL-15Rα-Fc precomplexed with IL-15. In contrast, IL-15 alone did not result in TNF-α levels above the negative control and only a small increase in GM-CSF. These data suggest that production of both GM-CSF and TNF-α is enhanced by the active Fc in the RV1 and IL-15Rα-Fc constructs, it also demonstrates that RV1 binding to IL-15 in the assay results in functional antibody-IL-15 complex formation and enhanced GM-CSF and TNF-α production, likely by Fc mediated activation of monocytes and macrophages with the culture of PBMC (typically 10% of PBMC). For the remaining cytokines, the anti-IL-15 antibody when precomplexed with IL-15 or when cultured with free IL-15 to allow complex formation in vitro, can stimulate the release of cytokines by PBMC in a manner similar to both free IL-15 and IL-15 bound to IL-15Rα-Fc, confirming that complexes formed between the anti-IL-15 antibody (RV1) and IL-15 are functional.

Figure 17A:
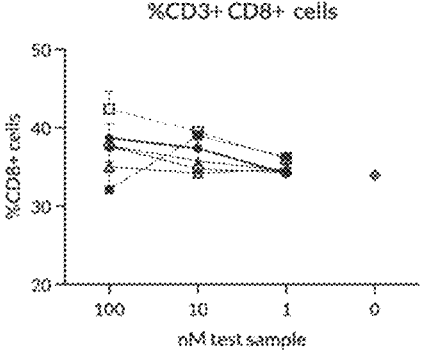
FIGS. 17A-17C show the frequency of CD3+CD8+ (FIG. 17A), CD3+CD4+ (FIG. 17B), and CD56+ NK (FIG. 17C) cells in human PBMC after 4 days of in vitro culture with 100 nM, 10 nM or 1 nM of IL-15 precomplexed with either RV1, RV2, RV29, RV32 or IL-15Rα-Fc, IL-15 alone or no treatment.
Figure 17B:
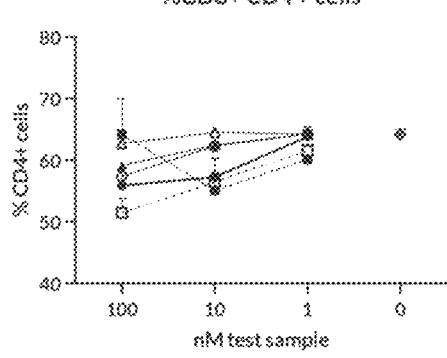
Figure 17C:
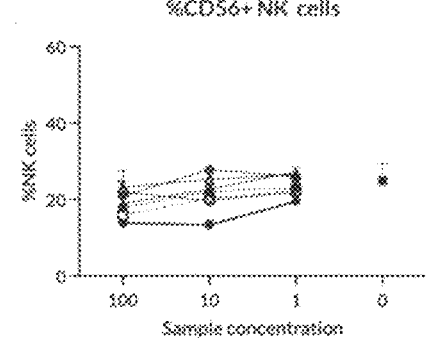

Example 7: Anti-IL-15 Antibodies Stimulate Phosphor STAT5 (pSTAT5) Signaling in NK Cells The effect of exemplary bispecific and monospecific anti-IL-15 antibodies on the proliferation of T and NK cell in in vitro cultures of PBMC was studied by flow cytometry using the cellular proliferation marker Ki-67. The Ki-67 antigen is a well-established marker for the proliferation of cells and can be combined with extracellular markers of cell subsets to identify proliferating cells within a mixed culture of cells using flow cytometry (Kim and Sederstrom (2015) Curr Protoc Mol Biol 111, 28.6.1). Cryopreserved PBMC (StemCell Technologies, Vancouver, BC) were thawed and 200,000 cells cultured per well in 96-well U bottomed plates in the presence of 100 nM, 10 nM, or 1 nM of monoclonal anti-IL-15 antibodies (RV1 and RV2), bispecific anti-PD-1× anti-IL-15 antibodies (RV29 and RV32) or IL-15Rα-Fc all pre-complexed with an equimolar concentration of IL-15 (overnight at 4° C. in low protein binding polypropylene plates). IL-15 alone and media served as a positive and negative control respectively, and each condition was performed in duplicate. After 4 days of culture, supernatant was harvested and remaining cells were surface stained for CD3, CD4, CD8, CD16 and CD56 (BioLegend, CA, USA), to allow identification of T and NK cell subsets. Following surface staining, cells were fixed and permeabilized using a transcription factor staining kit (Thermo Fisher Scientific, MA, USA) and intracellular staining was performed for Ki-67 (BioLegend, CA, USA). Flow cytometry of the fixed cells was performed on a CytoFLEX (Beckman Coulter, IN, USA) and the % of individual cell populations was determined by analysis using FlowJo (BD BioSciences, NJ, USA). Analysis of the surface staining demonstrated a treatment related dose dependent increase in the fraction of CD8+ T cells within the CD3+ T cell subset and corresponding decrease in the frequency of CD4+ T cells with all treatment conditions over the negative control (FIG. 17A and FIG. 17B, respectively), consistent with an IL-15 dependent stimulation of CD8 T cell over CD4 T cells. There was no dose dependent alteration in the frequency of NK cells when the NK cell marker, CD56, was analyzed (FIG. 17C). Consistent with the increased frequency of CD8 vs CD4 T cells, the levels of the proliferation marker Ki-67 correlated with IL-15 in a dose dependent manner, in particular within CD8+ T cells (FIG. 18A) for all conditions tested. This was more pronounced with the anti-IL-15 antibodies compared to IL-15 alone or IL-15 complexed with IL-15Rα-Fc. As expected, the frequency of Ki-67 expressing CD4+ T cells was less than that observed for CD8+ T cells (FIG. 18B) given our observations that IL-15 preferentially stimulated CD8 cells, however, there was still a treatment dose dependent increase in Ki-67 positive CD4+ T cells. There was no dose dependent effect in NK cells with IL-15, IL-15Rα-Fc precomplexed with IL-15 or RV1 precomplexed with IL-15, suggesting the lowest dose of these test samples was saturating. In particular, within CD8 cells, a dose dependent effect was observed with IL-15 precomplexed with RV2 (Fc null) and the bispecific anti-PD-1×anti-IL-15 antibodies RV29 and RV32 suggesting a lower potency in this assay where on primary PBMC PD-1 levels may be low. NK cells were further subdivided into the CD56 bright (CD16−) and CD56dimCD16+ subsets (FIG. 19A and FIG. 19B). Again, no dose dependent Ki-67 staining was observed for IL-15, IL-15Rα-Fc precomplexed with IL-15 or RV1 precomplexed with IL-15. In both NK subsets there was a dose dependent effect of the bispecific antibodies (RV29 and RV32) and in the CD56dimCD16+ subset there was also a dose dependent effect of RV2. This observation with RV2 is consistent with an increased potency via Fc based presentation of IL-15 by RV1 and IL-15Rα-Fc via CD16 in the CD56dimCD16+ subset of NK cells. In conclusion, this example demonstrates that monoclonal anti-IL-15 antibodies (RV1 or RV2) and bispecific anti-PD-1×anti-IL-15 antibodies (RV29 and RV32) can form functional complexes with IL-15 that results in the proliferation of both CD8+ T cells and NK cell more so than CD4+ T cells.

Figure 15A:
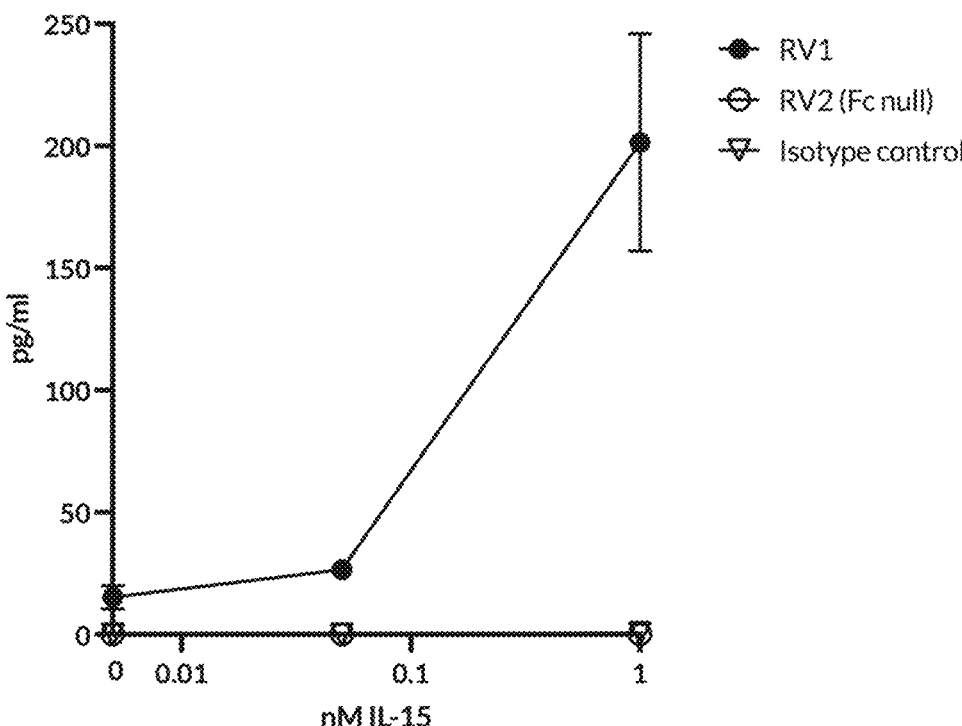
FIGS. 15A and 15B show the levels of GM-CSF (FIG. 15A) and TNF-a (FIG. 15B) in the supernatant of human PBMC after 4 days of in vitro culture in the presence of human IL-15 (50 pM or 1 nM) or absence of IL-15 plus RV1, RV2, or isotope control (anti-RSV) antibody.
Figure 15B:
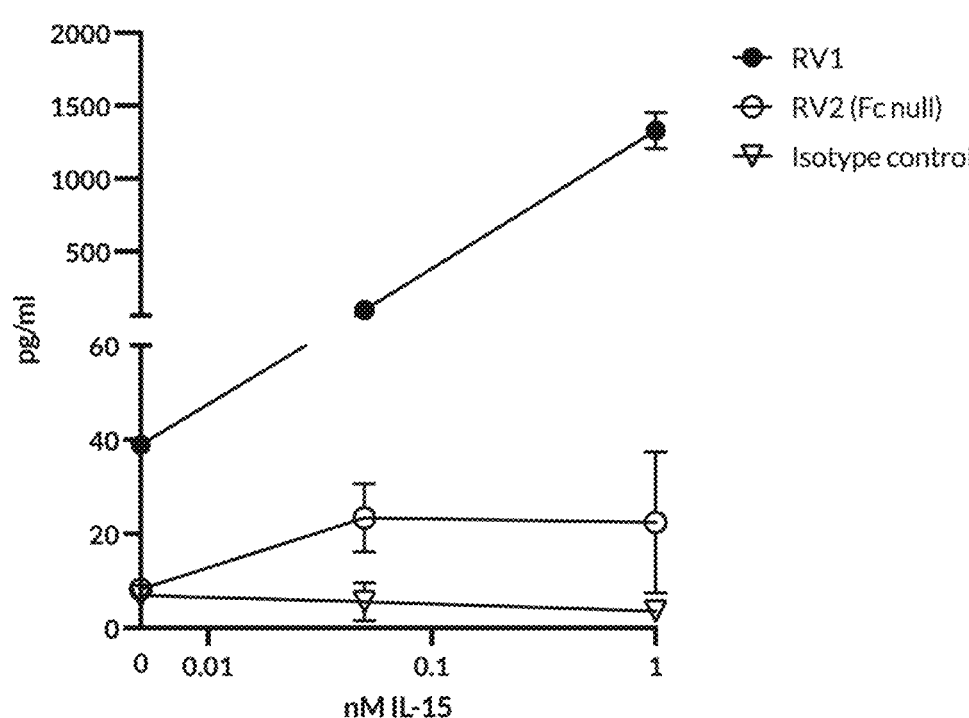
Figure 16A:
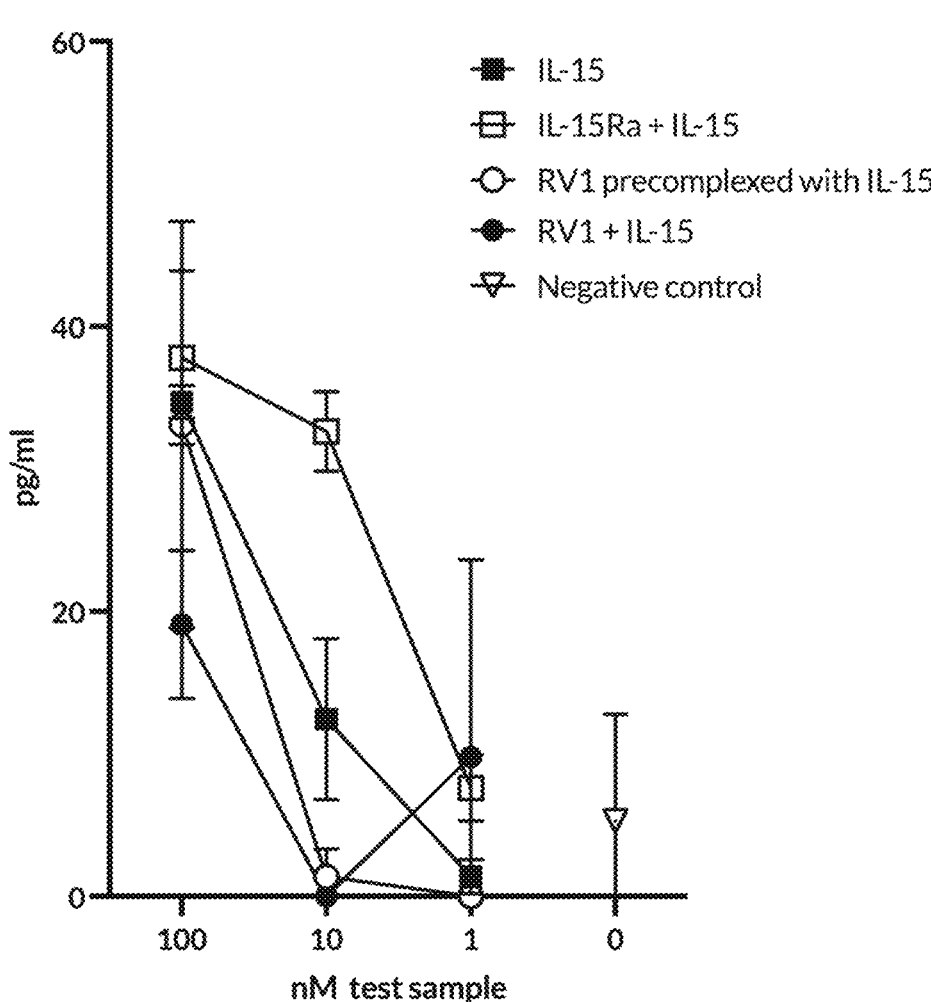
FIGS. 16A-16G show the levels of IL-2 (FIG. 16A), IFN-γ (FIG. 16B), Granzyme A (FIG. 16C), Granzyme B (FIG. 16D), Perforin (FIG. 16E), GM-CSF (FIG. 16F) or TNF-α (FIG. 16G), in the supernatant of human PBMC after 4 days of in vitro culture with 100 nM, 10 nM or 1 nM of RV1 precomplexed with IL-15, RV1 with free IL-15, IL-15Rα precomplexed with IL-15, IL-15 alone, or no treatment. * Signifies interpolated sample concentration was at or above the upper limit of detection in the MSD assay.
Figure 16B:
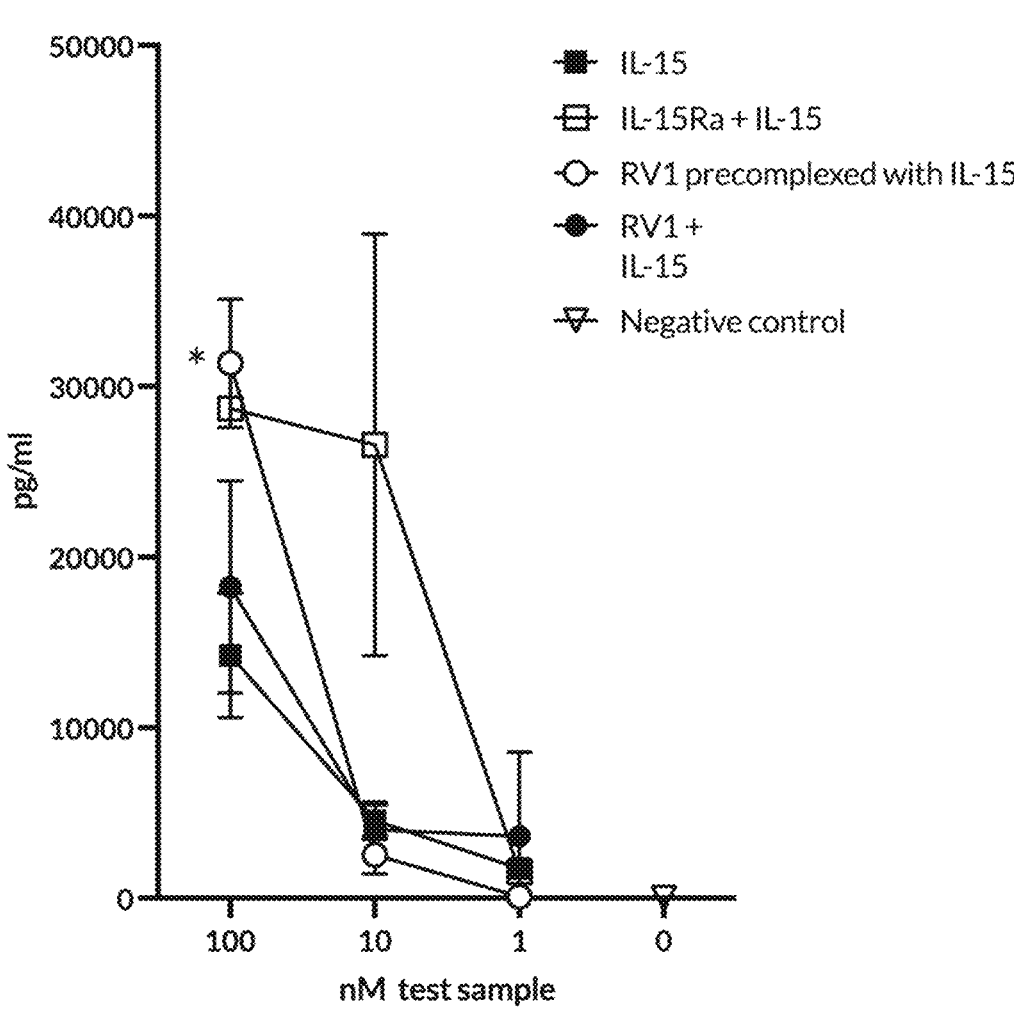
Figure 16C:
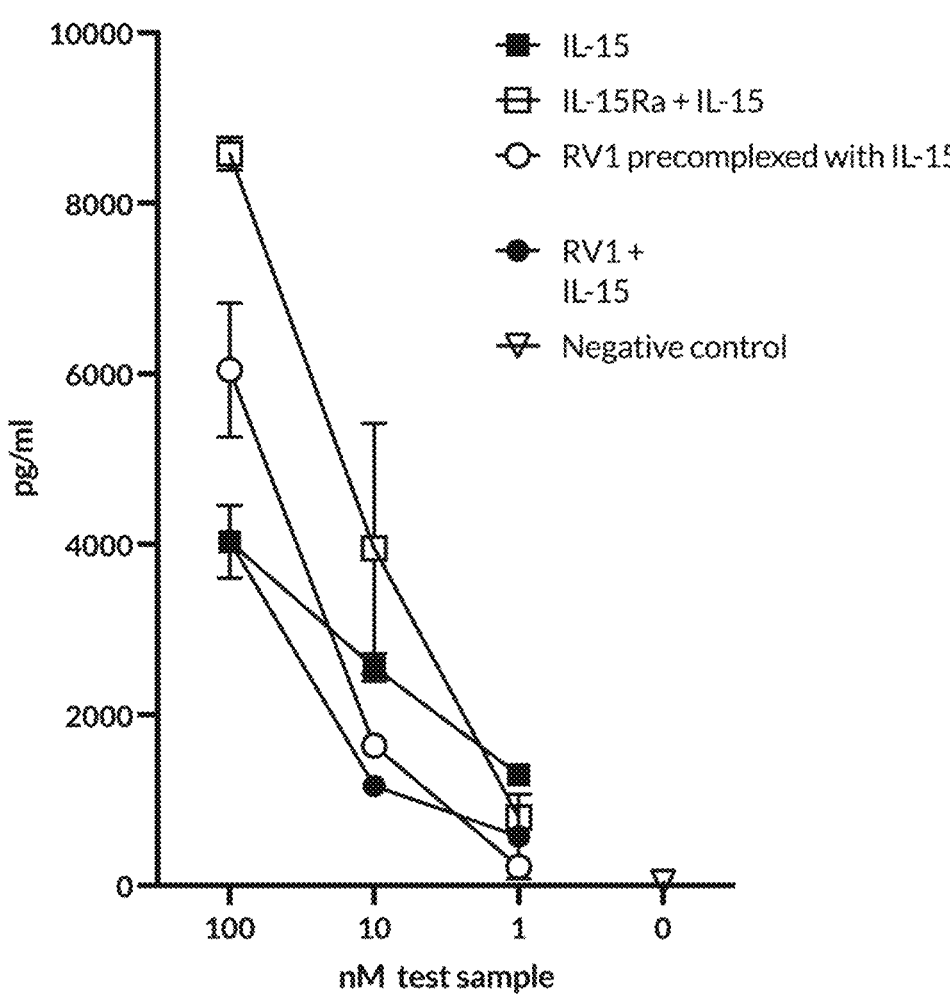
Figure 16D:
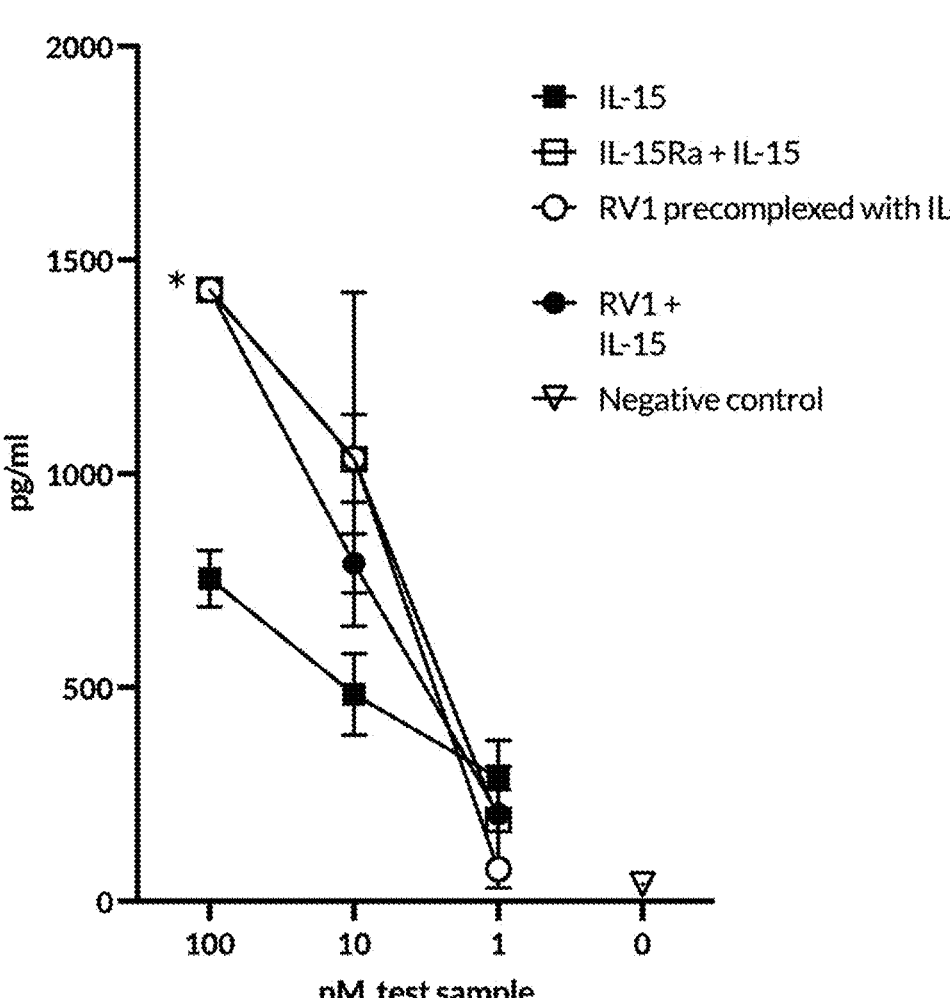
Figure 16E:
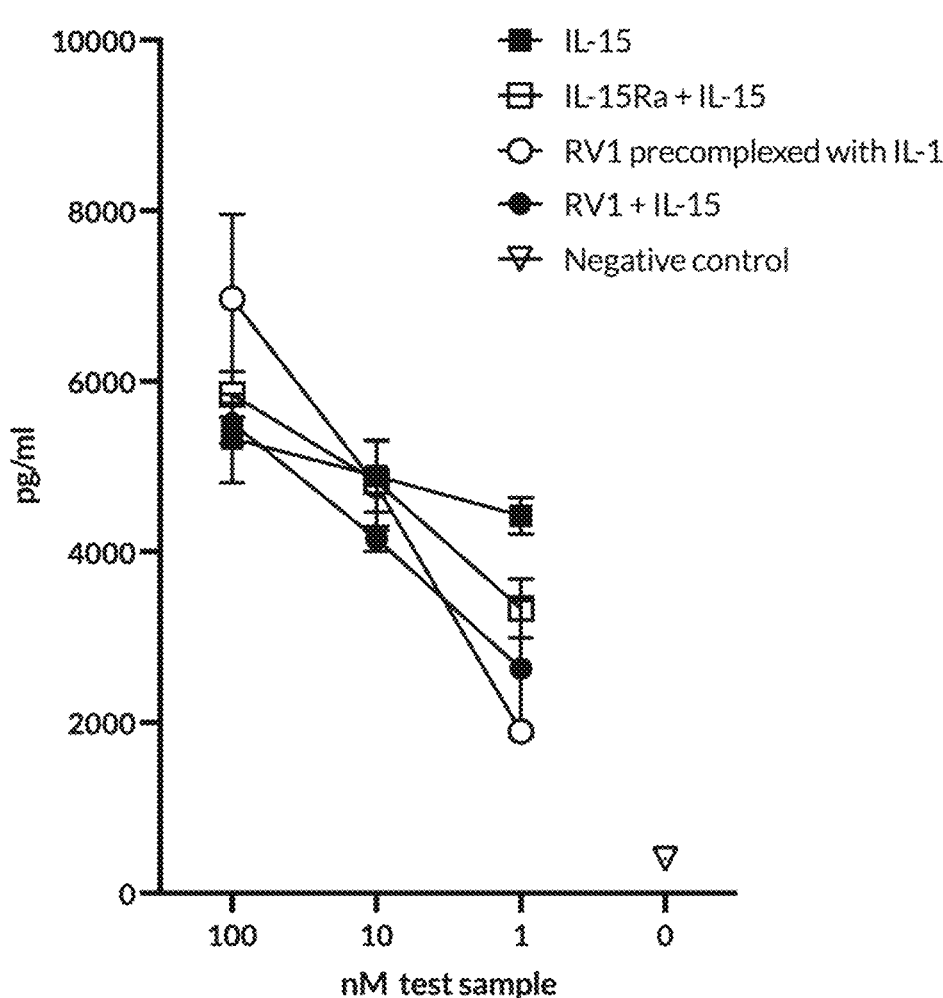
Figure 16F:
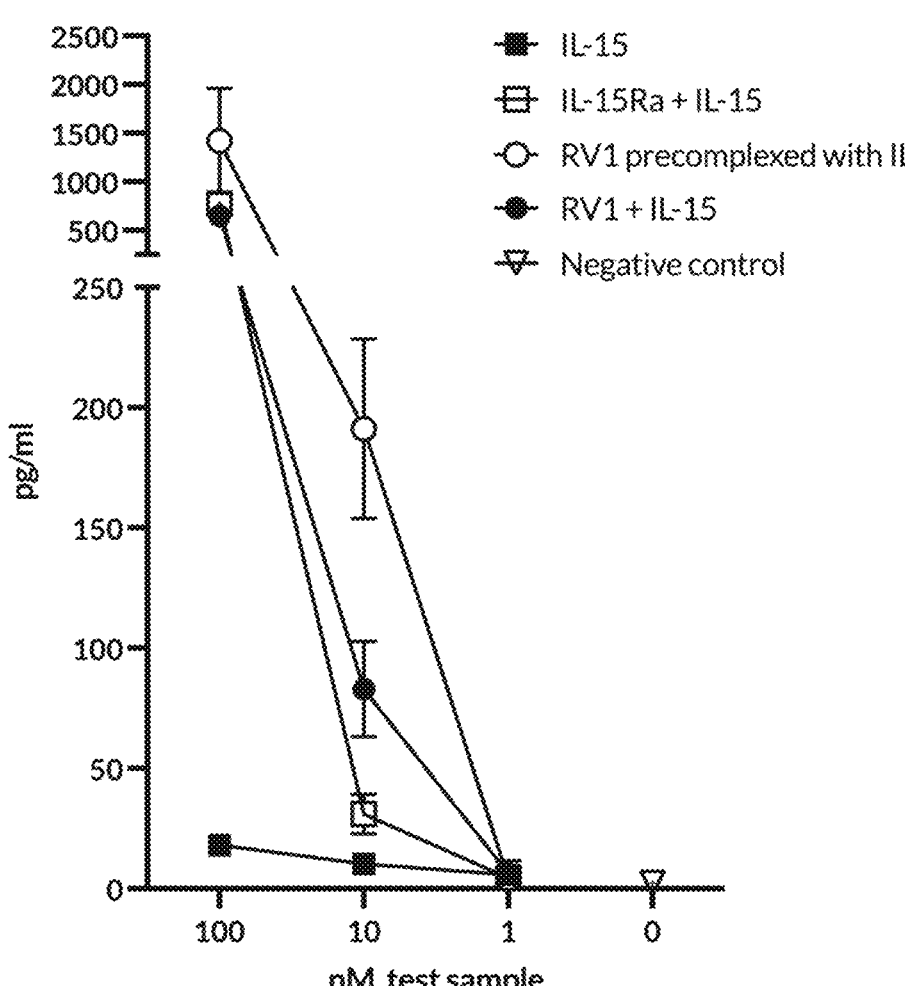
Figure 16G:
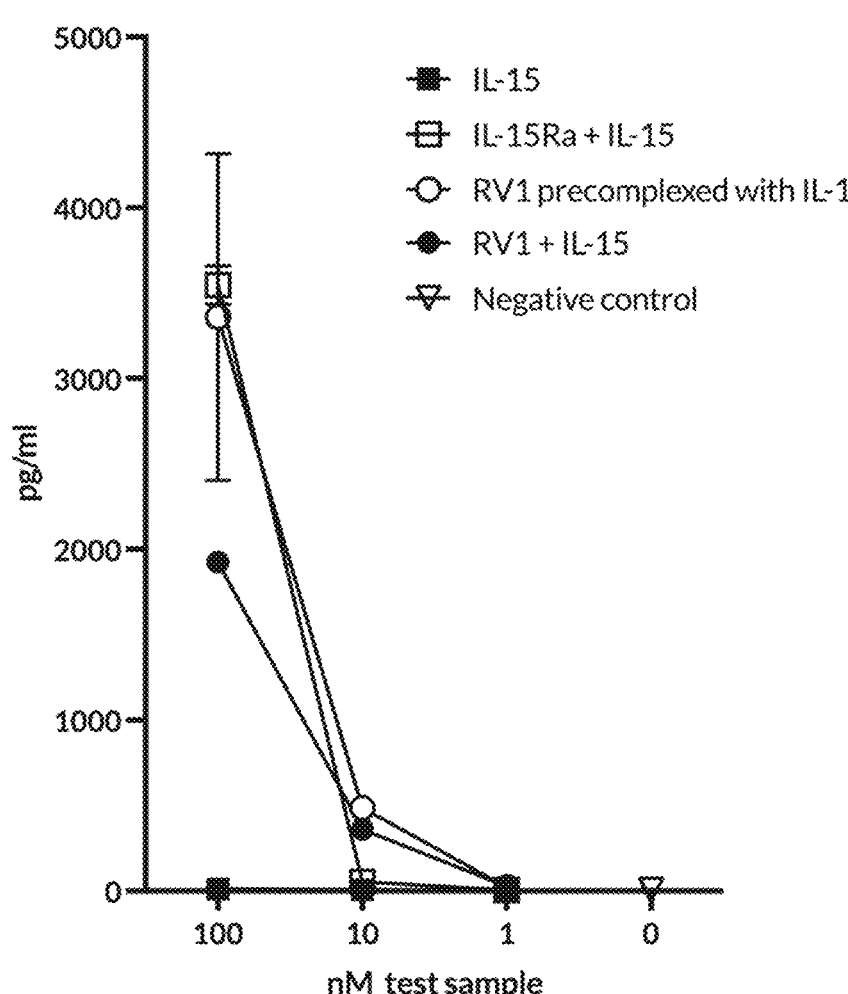

The cell culture supernatant collected from the cells was analyzed by MSD for the presence of IL-2, IFN-γ, Granzyme A, Granzyme B, Perforin, GM-CSF and TNF-α (FIGS. 20A-20G). Despite variability between the duplicate samples in some cases, a dose dependent cytokine response was observed with the majority test samples. In particular IFN-γ, granzyme A and B, perforin and GM-CSF (FIGS. 20B-20F) showed dose dependent increases with IL-15 and IL-15 precomplexed with either IL-15Rα-Fc or RV1 resulting in the highest levels of cytokines. The Fc null anti-IL-15 antibody (RV2) and the bispecific anti-PD-1×anti-IL-15 antibodies (RV29 and RV32) resulted in lower levels of cytokines consistent with observed lower levels of T and NK cell proliferation. As also shown in FIG. 15A and FIG. 16F, RV1 stimulated the greatest levels of GM-CSF and was the only test sample to stimulate high levels of TNF-α (FIG. 20F and FIG. 20G) supporting the previous observation of Fc enhanced production of these cytokines. Levels of IL-2 were high in the negative control culture of cells alone (FIG. 20A) making interpretation for IL-2 difficult. These data demonstrate that the anti-IL-15 antibody containing bispecific constructs are able to bind IL-15 and present it in a way to stimulate both cytokine production and proliferation of cells in vitro.

Example 8: Bispecific Anti-IL-15 Antibodies Stimulate In Vitro Proliferation of Exhausted T Cells Expressing PD-1

Figure 18A:
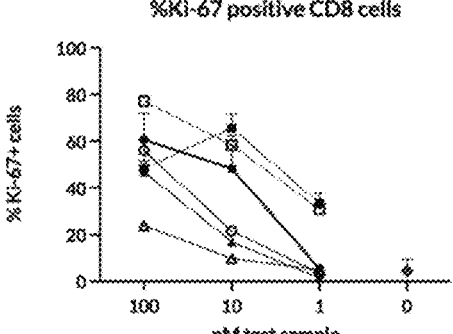
FIGS. 18A-18C show the frequency of Ki-67 positive CD3+CD8+ (FIG. 18A), CD3+CD4+ (FIG. 18B) and CD56+ NK (FIG. 18C) cells in human PBMC after 4 days of in vitro culture with 100 nM, 10 nM, or 1 nM of IL-15 precomplexed with either RV1, RV2, RV29, RV32 or IL-15Rα-Fc, IL-15 alone or no treatment.
Figure 18B:
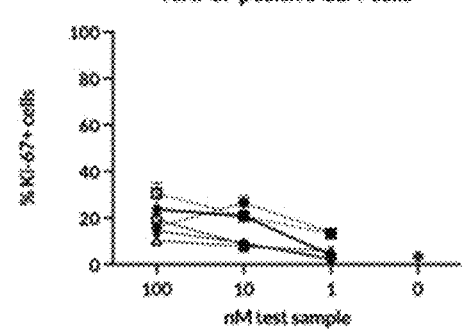
Figure 18C:
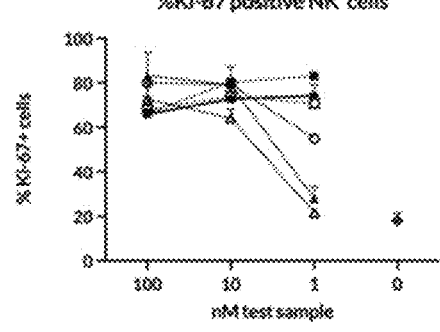
Figure 20A:
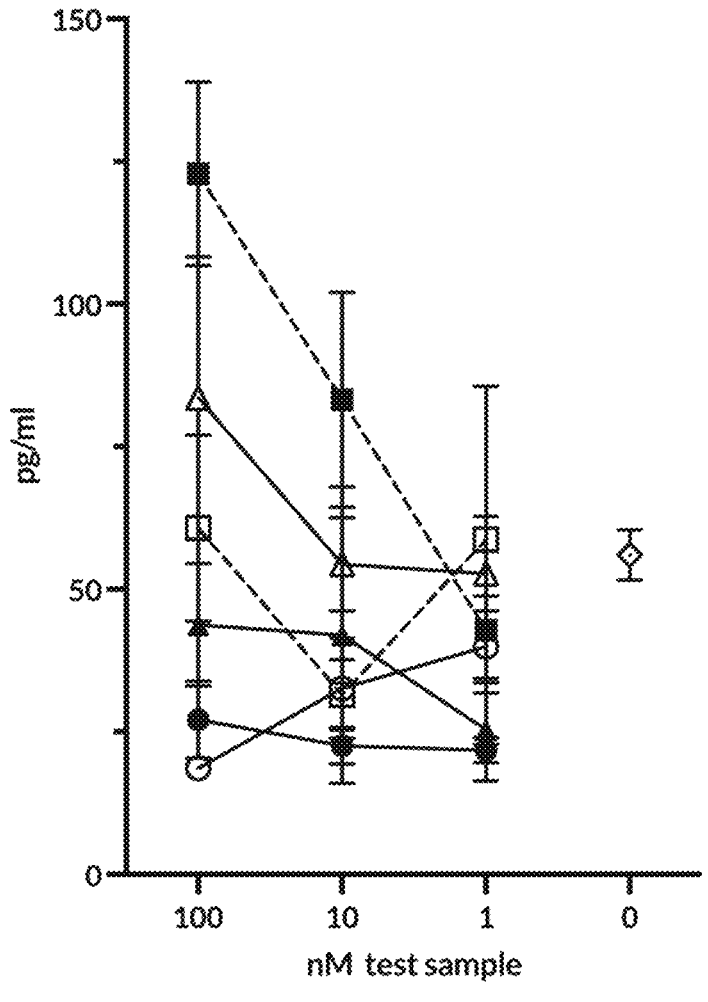
FIGS. 20A-20G show the levels of IL-2 (FIG. 20A), IFN-γ (FIG. 20B), Granzyme A (FIG. 20C), Granzyme B (FIG. 20D), Perforin (FIG. 20E), GM-CSF (FIG. 20F) or TNF-a (FIG. 20G), in the supernatant of human PBMC after 4 days of in vitro culture with 100 nM, 10 nM, or 1 nM of IL-15 precomplexed with either RV1, RV2, RV29, RV32 or IL-15Ra-Fc, IL-15 alone or no treatment. * Signifies interpolated sample concentration was at or above the upper limit of detection in the MSD assay.
Figure 20B:
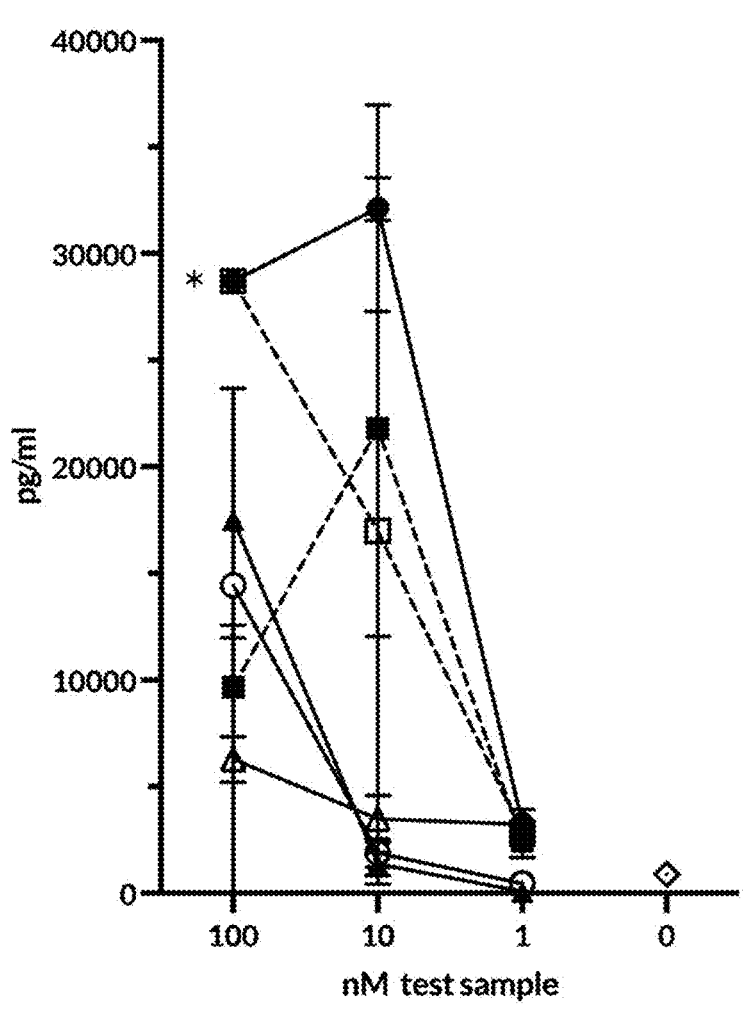
Figure 20C:
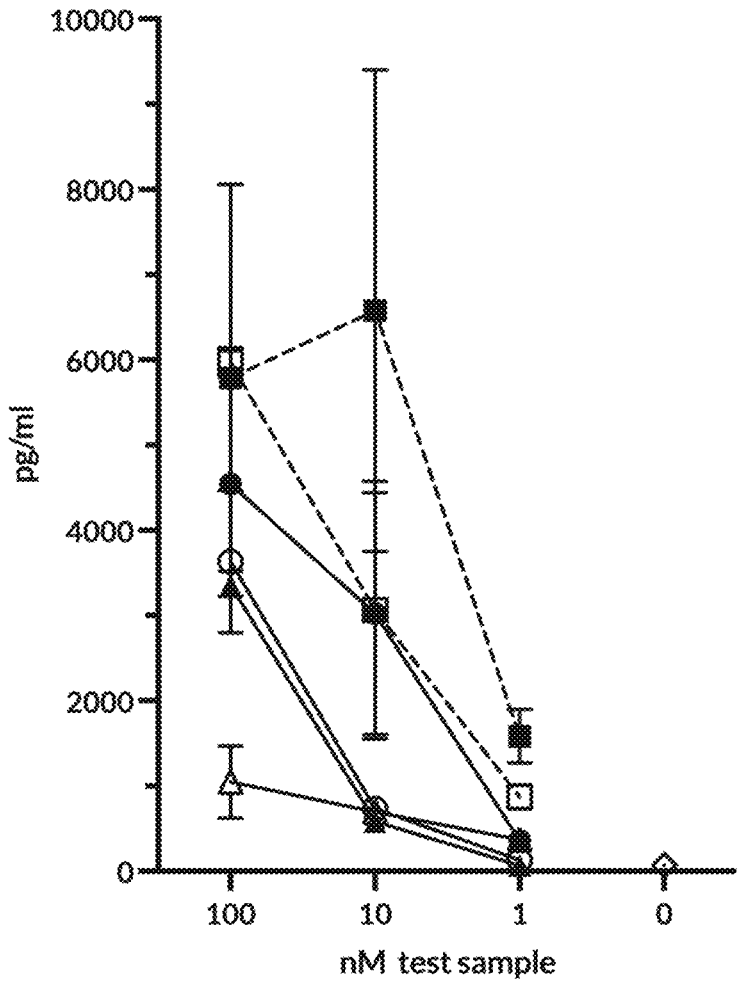
Figure 20D:
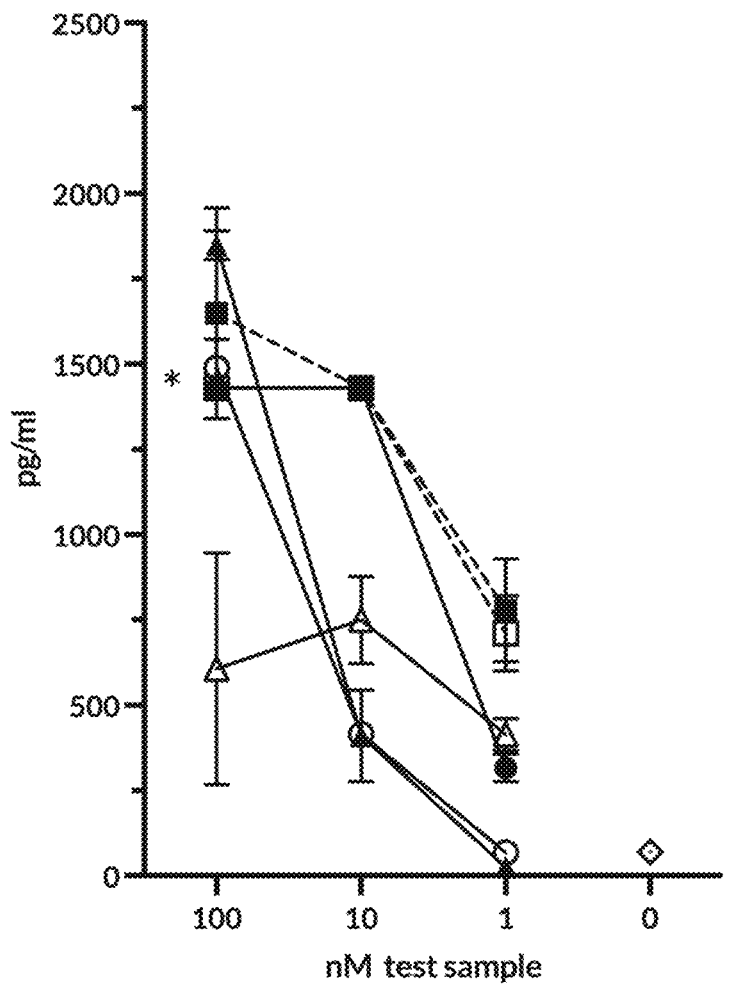
Figure 20E:
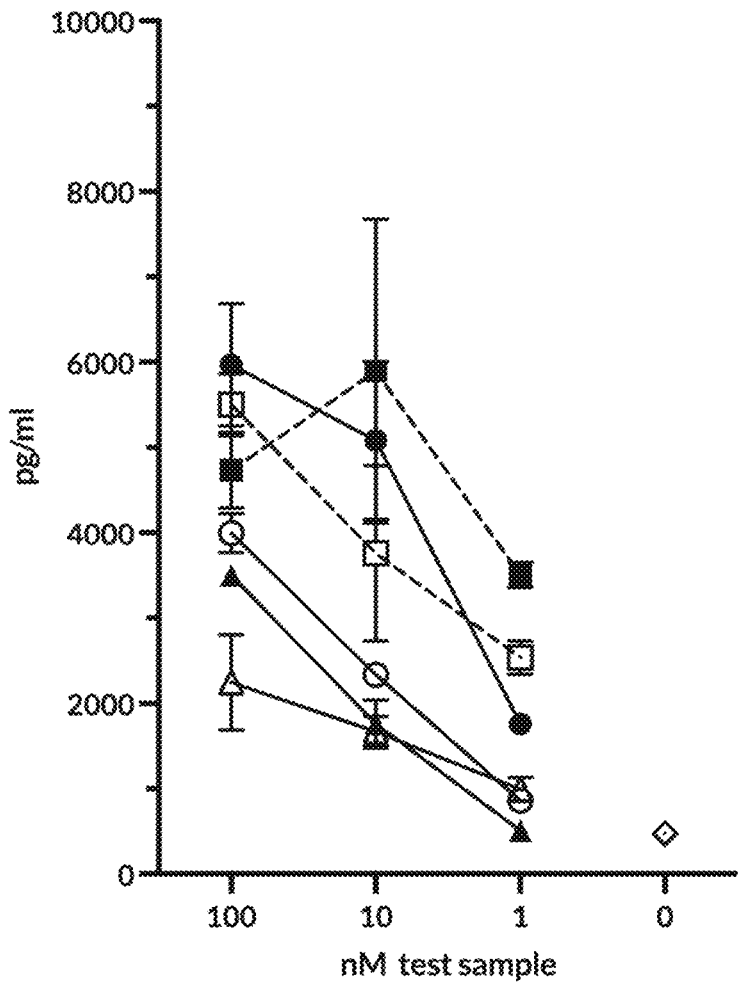
Figure 20F:
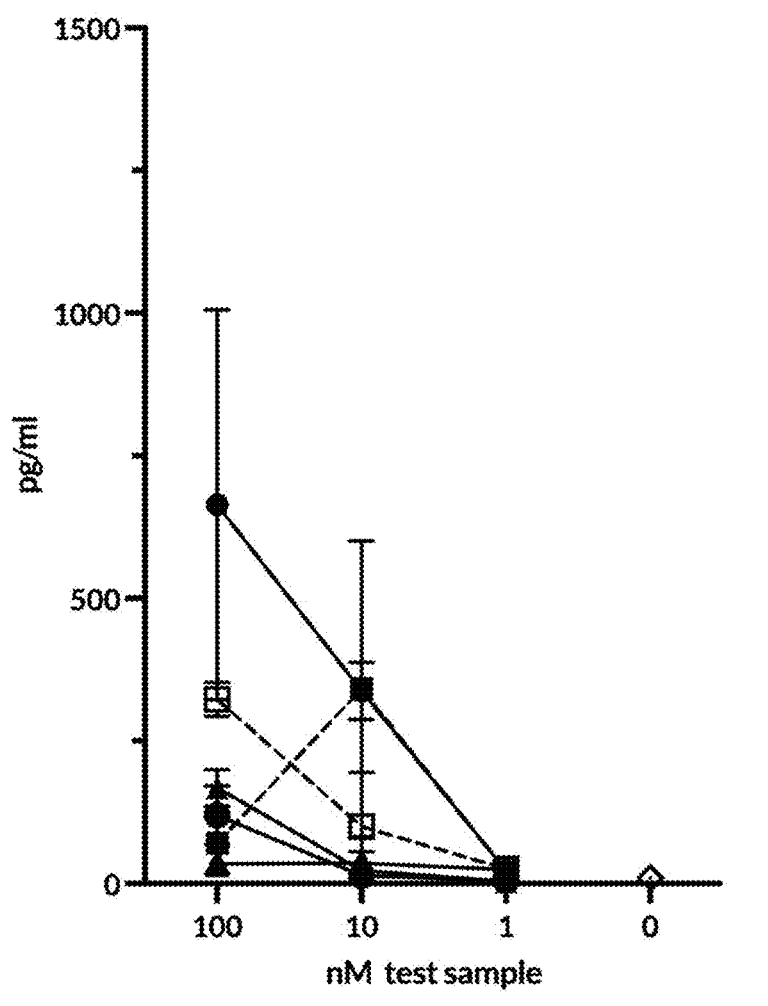
Figure 20G:
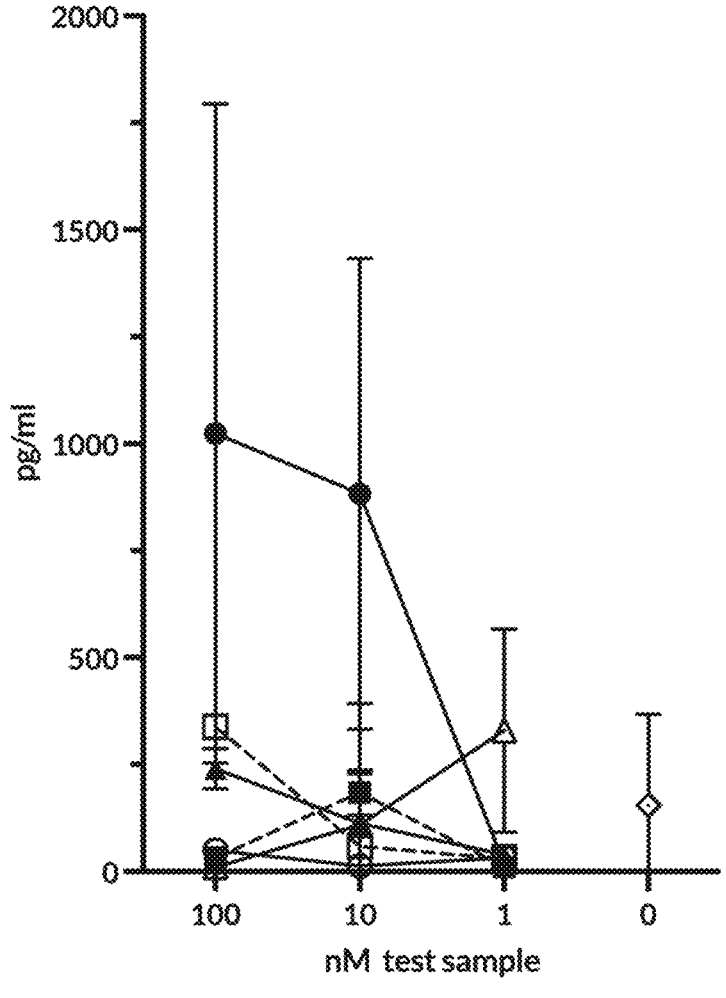

To test the ability of the anti-IL-15 antibody containing bispecific constructs to bind to a second target and present IL-15, exemplary anti-PD-1×anti-IL-15 bispecific antibodies were evaluated for their ability to induce proliferation in PD-1 expressing, exhausted primary human T cells. CD3+ T cells were negatively selected using magnetic beads (Miltenyi Biotec, Germany) from cryopreserved PBMC (AllCells Inc, Alameda, CA) and cultured in flasks precoated with anti-CD3 antibody (OKT3 5 mg/ml) and soluble anti-CD28 (2 mg/ml), after 24 hours 20 IU/ml of recombinant human IL-2 was added. Cells were diluted to 2.5 million cells/ml on day 3 and supplemented with fresh IL-2 at 20 IU/ml, IL-2 was replenished on day 6 at 20 IU/ml. After 7 days an aliquot of cells was stained for CD3, CD4 and PD-1 expression (>90% of CD3+ cells expressed PD-1) and the remaining cells cryopreserved. Subsequently cells were thawed and cultured in 96-well U bottom plates in the presence of IL-15 or test samples (IL-15Rα-Fc, RV1, RV2, RV29, RV32) precomplexed with an equimolar concentration of IL-15 (overnight at 4° C. in low protein binding polypropylene plates). Samples were added in duplicated at 100 nM, 10 nM, and 1 nM concentrations and a negative (media only) control was included. After 4 days the cells were surface stained for CD3, CD4, CD8 and PD-1 (BioLegend, CA, USA), to allow identification of PD-1 expressing on T cell subsets. Following surface staining, cells were fixed and permeabilized using a transcription factor staining kit (Thermo Fisher Scientific, MA, USA) and intracellular staining was performed for Ki-67 (BioLegend, CA, USA). Flow cytometry of the fixed cells was performed on a CytoFLEX (Beckman Coulter, IN, USA) and the % of individual cell populations was determined by analysis using FlowJo (BD BioSciences, NJ, USA). The majority of CD8+CD3+ and CD4+CD3+ cells expressed Ki-67 indicating proliferation of both T cell subsets with all test samples (FIGS. 21A and 21B). The frequency of Ki-67 positive CD8 cells was higher than CD4, consistent with our previous observations that IL-15 alone or complexed with anti-IL-15 antibodies preferentially stimulates CD8 cells. In addition, the potency of the bispecific anti-PD-1×anti-IL-15 constructs (RV29 and RV32) was similar to that of the monoclonal anti-IL-15 antibodies (RV1 and RV2), in particular for CD8+ T cells suggesting bispecific binding to PD-1 enhances engagement of IL-15 to the IL-15Rβγ complex, in contrast to observations in PBMC (FIG. 18A). In addition, further evidence that RV29 and RV32 were binding to PD-1 is shown in Table 8. The MFI (Median fluorescence intensity) of PD-1 staining in Ki-67 positive cells treated with IL-15 or IL-15 precomplexed with IL-15Rα-Fc, RV1 or RV2 was similar across treatments for CD8+ cells (MFI range 1693-3224, ave=2186) and CD4+ cells (MFI range 4099-6551, ave=4828). However, a decreased MFI of PD-1 staining was detectable in Ki-67 positive cells treated with bispecific constructs RV29 and RV32 (Table 8) for both CD8+ cells (MFI range 2025-999, ave=1456) and CD4+ cells (MFI range 3898-2336, ave=3092) indicating that the bispecific constructs had bound to PD-1 and blocked detection of PD-1, additionally the MFI of PD-1 was lower for cells treated with RV32 vs RV29 consistent with RV32 having higher affinity for PD-1 as demonstrated by SPR (Table 6). This failure to detect PD-1 was anticipated since the anti-PD-1 arm of the bispecific and the PD-1 detection antibody (clone EH12.2H7) have overlapping epitopes. These data show that IL-15 was functionally redirected towards PD-1 expressing in vitro activated T cells by the bispecific anti-PD-1×anti-IL-15 constructs (RV29 and RV32), resulting in increased potency on PD-1 expressing T cells compared to PBMC.

TABLE 8

| Median fluorescence intensity of PD-1 staining in in vitro activated Ki-67 positive CD8+ and CD4+ T cells | | | |
| --- | --- | --- | --- |
| Test sample | Concentration in assay | MFI of PD-1 in Ki-67 positive CD8+ T cells | MFI of PD-1 in Ki-67 positive CD4+ T cells |
| IL-15 | 100 nM | 3224 | 6551.5 |
| | 10 nM | 3189.5 | 6439.5 |
| | 1 nM | 2045.5 | 4873.5 |
| RV1 | 100 nM | 2367.5 | 4832 |
| | 10 nM | 1888.5 | 4621.5 |
| | 1 nM | 1870.5 | 4099.5 |
| RV2 | 100 nM | 2817 | 5842.5 |
| | 10 nM | 2023 | 5073 |
| | 1 nM | 1920.5 | 4198 |
| RV29 | 100 nM | 1843 | 3561 |
| | 10 nM | 1461.5 | 3322.5 |
| | 1 nM | 2025 | 3898 |
| RV32 | 100 nM | 1145 | 2830 |
| | 10 nM | 999 | 2336 |
| | 1 nM | 1262 | 2605 |
| IL-15Rα-Fc | 100 nM | 2111 | 4379 |
| | 10 nM | 2120 | 4475.5 |
| | 1 nM | 1693 | 4276.5 |
| Negative control | — | 2249.5 | 4015.5 |

Example 9: Anti-IL-15 Antibodies Stimulate Phosphor STAT5 (pSTAT5) Signaling in NK Cells The effect of an exemplary anti-IL-15 antibody on the earliest stage of cytokine signaling (i.e., phosphorylation of the intracellular signaling molecule STAT5) upon binding of IL-15 to the IL-15Rβγ was examined. PBMC from 3 independent donors were incubated, in duplicate, in the presence of IL-15, IL-15 complexed with IL-15Rα-Fc, IL-15 complexed with anti-IL-15 antibody RV1 (IgG1 isotype), and RV3 (IgG4 isotype) or an IgG1 isotype control (anti-RSV). After 20 minutes cells were stained for CD3, CD4, CD8, CD56 and CD16 followed by intracellular staining for pSTAT5 (BD Biosciences, CA, USA). Cells were analyzed by flow cytometry (using a CytoFLEX, Beckman Coulter, IN, USA) and the average percent (and SD) of cells expressing pSTAT5 determined for CD8+ T cells, CD4+ T cells, CD56 bright NK cells and CD56+CD16+ NK cells by analysis using FlowJo (BD BioSciences, NJ, USA) (FIGS. 22A-22D). EC50 values were derived for each treatment and cell subset and shown in Table 9. IL-15, IL-15 complexed with IL-15Rα-Fc and the isotype control (i.e., free IL-15) resulted in dose dependent pSTAT5 in all 4 cell subsets. IL-15 complexed with both formats of the anti-IL-15 antibody stimulated dose dependent pSTAT5 in CD56 bright NK cells (FIG. 22C) and CD56+CD16+ NK cells (FIG. 22D). However, the IgG1 format anti-IL-15 antibody (RV1) was more efficient at pSTAT5 induction compared to the IgG4 format (RV3), as evidenced by the lower EC50 values, and consistent with the observation that the IgG1 Fc of RV1 has enhanced binding to CD16 (FcγRIII) on NK cells and subsequent increased pSTAT5 activity versus the IgG4 isotype (RV3) which does not interact with CD16. The data suggests that a secondary presentation (Fc based in this case) contributes to the increased IL-15 activity upon presentation by the IL-15 capture antibody.

TABLE 9

| Mean pSTAT5 EC50 values (log[M]) | | | |
| --- | --- | --- | --- |
| | CD8+ T cells | CD4+ T cells | CD56 bright NK cells | CD56+ CD16+ NK cells |
| IL-15 | −9.73 | −9.82 | −11.03 | −10.44 |
| IL-15 + IL-15Ra | −9.38 | −9.14 | −10.55 | −10.19 |
| IL-15 + RV1 | * | * | −9.49 | −9.35 |
| IL-15 + RV3 | * | * | −9.16 | −8.75 |
| IL-15 + Isotype control | −9.35 | −9.82 | −10.87 | −10.23 |

* Poor curve fit, EC50 not determined.

Example 10. Structural Modeling of Non-Blocking Epitopes on IL-15 Cytokine

Structural modeling of the quaternary crystal structure of IL-15 bound to its receptors IL-15Rα, IL-15Rβ and common gamma chains was performed using the structure in pdb (id 4gs7). A 2D representation of the structure is shown in FIG. 5A, the cytokine presented as space fill with the IL-15Rβ and common gamma chain shown as a wire frame and the IL-15Rα chain as a ribbon. The IL-15Rβ and common gamma receptor chains which are present on effector cells such as T and NK cells of the immune system transduce activating signal following IL-15 binding. The IL-15Rα plays a role in the presentation of IL-15 to the beta gamma receptor heterodimer (IL-15Rβγ). Hence, in order to achieve a non-blocking or partially blocking engagement of IL-15 which would not inhibit binding of IL-15 to the IL-15Rβγ heterodimer, capturing IL-15 on an epitope close to its interface with the IL-15Rα chain should allow for productive engagement with IL-15Rβγ. A number of anti-IL-15 antibodies that can bind IL-15 are known in the literature including DISC0280 (Finch et al. (2011) British Journal of Pharmacology 162, 480), B-E29, MOB-1254Z, PABZ-081, MOB-0784CT, HPAB-0238-YC, HPAB-0359-

WJ, MOM-18387, 04H04 (Sestak et al. (2018) Front Immunol 9, 1603), AMG714/Ordesekimab (Wei et al. (2022) Journal of Immunotoxicology 19, 109) and CALY-002 (Vicari et al (2017) Mabs 9, 927). While a number of these antibodies bind IL-15 to block its interaction with IL-15Rβ and the common gamma chain, DISC0280 binds an epitope on IL-15 that competes for the Il-15Rα binding. FIG. 5B shows a 2D representation of the crystal structure of IL-15 bound to DISC0280 based on pdb id 2xqb, which was an antibody developed with the goal of blocking IL-15 activity. We modelled a co-complex structure of antibody bound IL-15 with the Il-15Rβγ receptor heterodimer by fitting the structure of IL-15 in the two independent crystal structure 4gs7 and 2xqb. The model structure is shown in FIG. 5C and conveys that the antibody can potentially bind IL-15 and allow the interaction of the bound cytokine with the IL-15Rβγ heterodimeric receptor complex. This modelling exercise provides insight into the nature of cytokine binding domains and their epitopes on the cytokine that can potentially agonize its cognate receptor in spite of the cytokine being engaged by its binding domain.

Figure 23A:
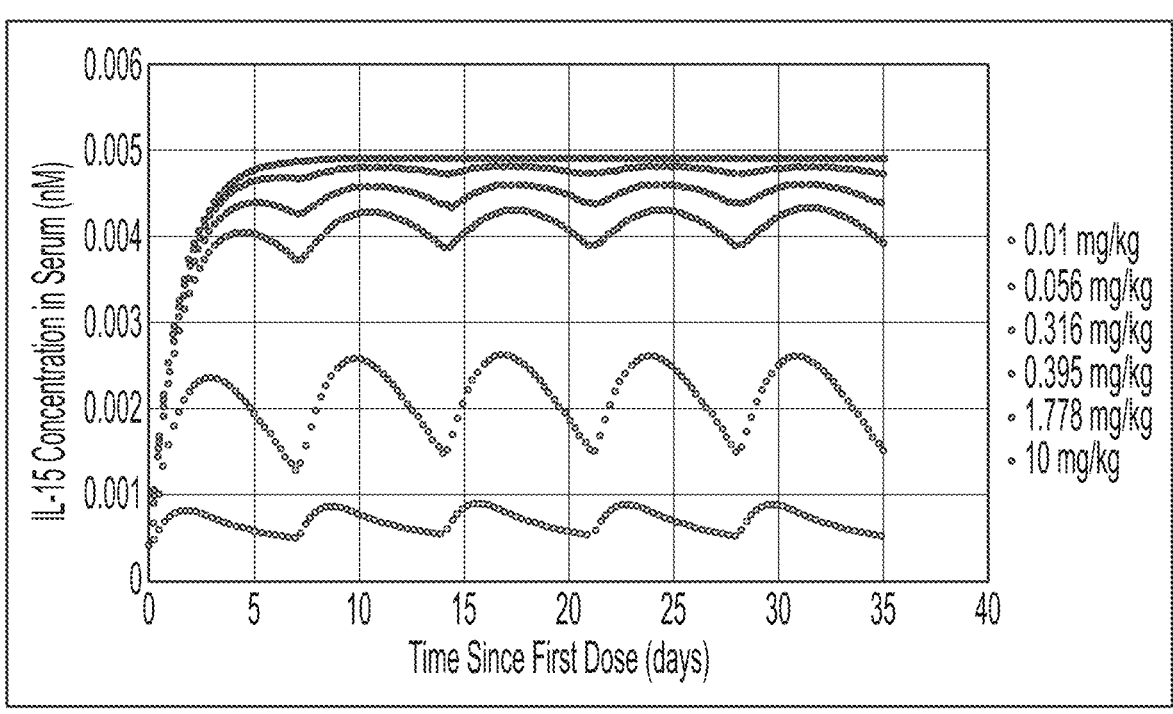
FIGS. 23A-23C show stimulation output predicting the change in concentration of IL-15 (ligand) bound to IL-15 capture antibody under different conditions of treatment.
Figure 23B:
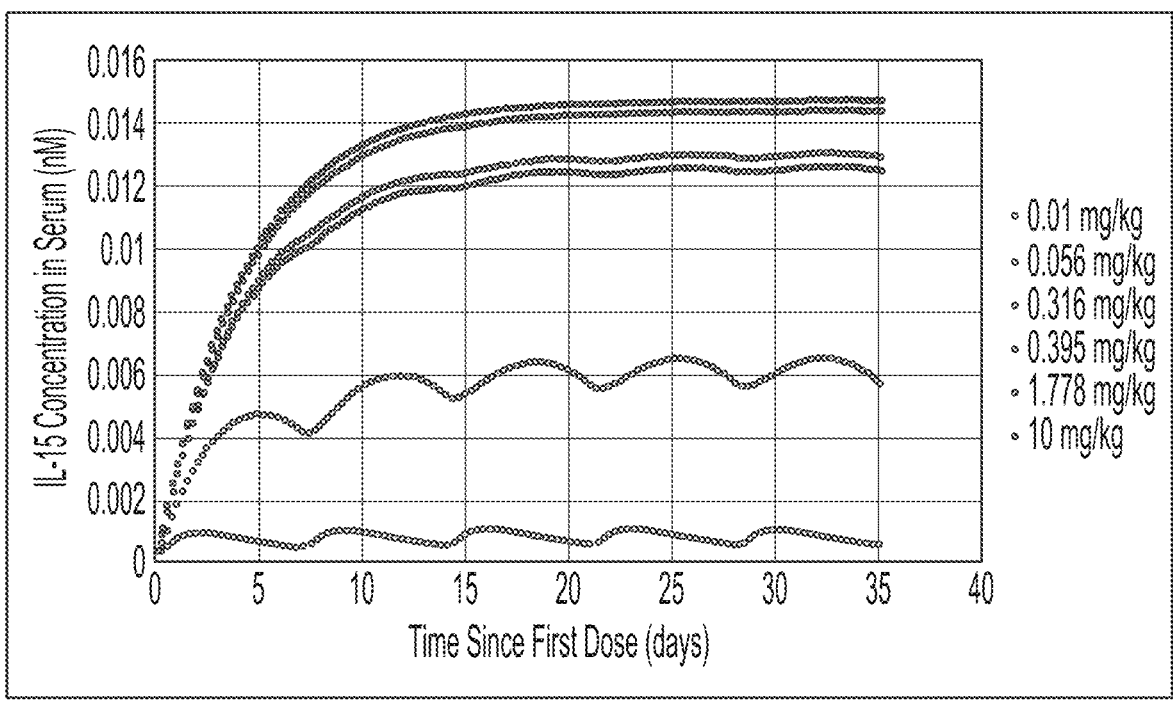
Figure 23C:
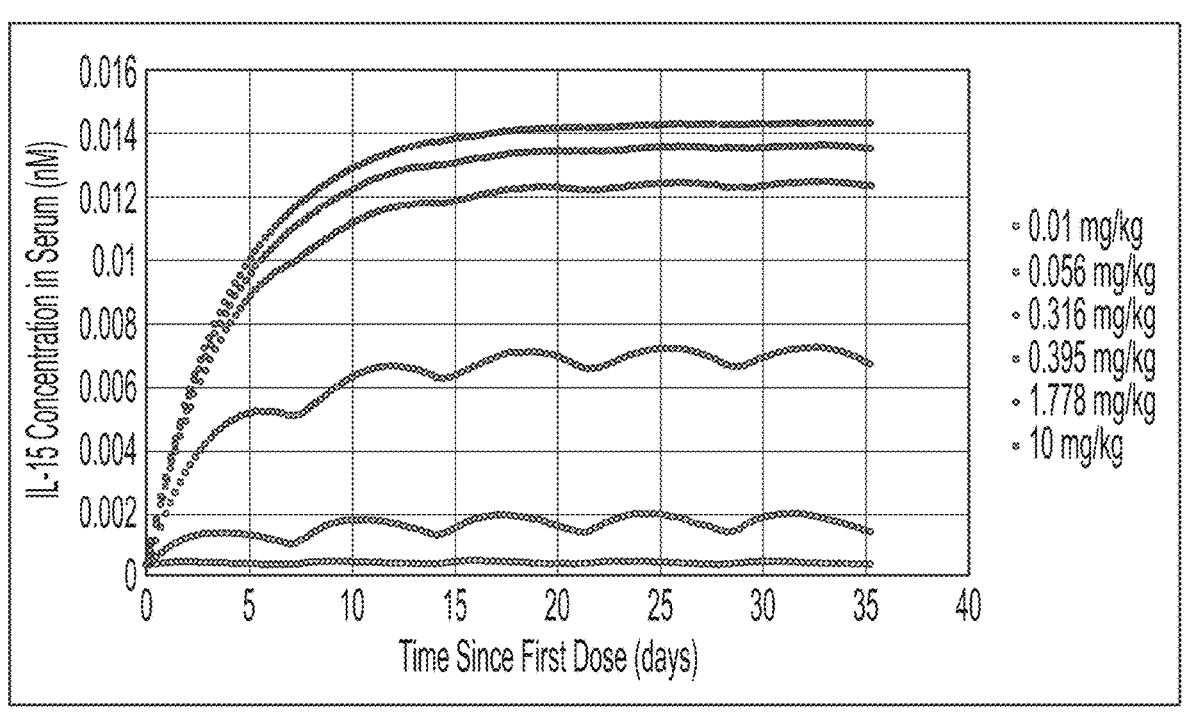

Example 11. Modeling the Pharmacology of IL-15 in Presence of IL-15 Capture Antibody Exploratory modeling of the effect of an antibody comprising a cytokine binding domain on the pharmacological aspects of cytokine exposure in the system using the Access tool developed by Applied Biomath (Grant et al., 2023, Mabs, 15, 2192251). The model provides a mathematical description of key mechanisms such as drug targeting, distribution, and elimination based on biophysical features of the protein therapeutic and is able to link the pharmacokinetic and pharmacodynamic aspects of drug action to these properties. Features such as affinity of the binding domain for the ligand (cytokine), dosing frequency, half-life of the drug, half-life of the ligand, concentration of the ligand, blood distribution volume, etc. among many other features are critical for model performance. The tool can take as input exploratory values of certain feature parameter values and scan other properties as dependent variables. Starting with an IL-15 concentration of 5 pg/ml i.e. about 0.0004 nM concentration and a half-life of 2 hours, FIG. 23A shows the modelled change in concentration of IL-15 in the presence of an IL-15 capture antibody with an affinity (KD) of 0.1 nM for IL-15, that increase the half-life of IL-15 to 1 day (24 hours) and being dosed every 7 days. The curves show how the persistence and hence concentration of IL-15 changes at different doses of the antibody. The legend on the right shows that dose range of the antibody changes from 0.01 mg/kg to 10 mg/kg. The model predicts that in this situation the concentration of IL-15 goes up by about 10 fold (to about 0.004 nM) following weekly dosing of 0.316 mg/kg of the cytokine capture antibody with the cytokine binding domain. FIG. 23B shows results from a simulation with a similar antibody, but with a half-life extension to 3 days. The results here suggest that the concentration of IL-15 can increase to about 30-fold at the same dose level relative to simulation in FIG. 23A. FIG. 23C presents simulation results when the affinity of the cytokine binding domain is changed to 1 nM affinity (KD). Such models can be further expanded to account for other parameters that may be critical for the action of the drug.

Appendix A: Sequences

TABLE A1

Domain Definitions

| SEQ ID NO: | Type | Domain | Clones | Sequence |
|---|---|---|---|---|
| 1 | DISC0280 | VL | RC2, RC24, RC45, RC47, RC54, RC56, RC58 | QSVLTQPPSASGTPGQRVTISCS GSTSNLKRNYVYWYQQLPGTA PKLLIYRDRRRPSGVPDRFSGSK SGTSASLAISGLRSEDEADYYC AWYDRELSEWVFGGGTKLTVL |
| 2 | DISC0280 | VL | RC34, RC35, | QSVLTQPPSASGTPGQRVTISCS GSTSNLKRNYVYWYQQLPGTA PKLLIYRDRRRPSGVPDRFSGSK SGTSASLAISGLRSEDEADYYC AWYDRELSEWVFG<u>C</u>GTKLTVL |
| 3 | DISC0280 | CL | RC2, RC47, RC58 | QPKAAPSVTLFPPSSEELQANK ATLVCLISDFYPGAVTVAWKA DSSPVKAGVETTTPSKQSNNKY AASSYLSLTPEQWKSHRSYSCQ VTHEGSTVEKTVAPTECS |
| 4 | DISC0280 | CL | RC24 | QPKAAPSVTLFPPSDEELQANT ATLVCLISDFYPGA<u>V</u>TVAWKA DSSPVKAGVETTTPSKQSNNKY AAESELSLTPEQWKSHRSYSCQ VT<u>H</u>EGSTVEKTVAPTECS |
| 5 | Pembrolizumab | VL | RC16, RC26, RC31, RC38, RC45, RC47, RC56, RC58 | EIVLTQSPATLSLSPGERATLSCRA SKGVSTSGYSYLHWYQQKPGQA PRLLIYLASYLESGVPARFSGSGS GTDFTLTISSLEPEDFAVYYCQHS RDLPLTFGGGTKVEIK |
| 6 | Pembrolizumab | VL | RC30, RC36, | EIVLTQSPATLSLSPGERATLSCRA SKGVSTSGYSYLHWYQQKPGQA PRLLIYLASYLESGVPARFSGSGS GTDFTLTISSLEPEDFAVYYCQHS RDLPLTFGGGTKVEI |
| 7 | Pembrolizumab | VI | RC33, RC40, | EIVLTQSPATLSLSPGERATLSCRA SKGVSTSGYSYLHWYQQKPGQA PRLLIYLASYLESGVPARFSGSGS GTDFTLTISSLEPEDFAVYYCQHS RDLPLTFG<u>C</u>GTKVEIK |
| 8 | Pembrolizumab | VL | RC32, RC39, | EIVLTQSPATLSLSPGERATLSCRA SKGVSTSGYSYLHWYQQKPGQA PRLLIYLASYLESGVPARFSGSGS GTDFTLTISSLEPEDFAVYYCQHS RDLPLTFG<u>C</u>GTKVEI |
| 9 | Pembrolizumab | CL | RC26 | RTVAAPSVFIFPPKDERLKSGTAS VVCLLNNFYPREA<u>K</u>VQ<u>W</u>KVDNA LQSGNSQESVTEQDSKDSTYSLSS RLTLSKADYEKHKVYACEVTHQ <u>G</u>LSSPVTKSFNRGEC |
| 10 | Pembrolizumab | CL | RC16, RC45, RC56 | RTVAAPSVFIFPPSDEQLKSGTASV VCLLNNFYPREAKVQWKVDNAL QSGNSQESVTEQDSKDSTYSLSST LTLSKADYEKHKVYACEVTHQGL SSPVTKSFNRGEC |
| 11 | F12.3 | VL | RC51, RC54, | DIVMTQSPSSLSVSAGDKVTMSCR ASQGISSWLAWYQQKPWQPPKLL IYKASTLESGVPDRFTGSGSGTDF TLTISSVQAEDLAVYYCQQSYSTP WTFGGGTKLEIK |
| 12 | F12.3 | VL | RC52, | DIVMTQSPSSLSVSAGDKVTMSCR ASQGISSWLAWYQQKPWQPPKLL IYKASTLESGVPDRFTGSGSGTDF TLTISSVQAEDLAVYYCQQSYSTP WTFG<u>C</u>GTKLEI |

TABLE A1-continued

| | | Domain Definitions | | |
|---|---|---|---|---|
| SEQ ID NO: | Type | Domain | Clones | Sequence |
| 13 | F12.3 | CL | RC54, | GTVAAPSVFIFPPSDEQLKSGTASV VCLLNNFYPREAKVQWKVDNAL QSGNSQESVTEQDSKDSTYSLSST LTLSKADYEKHKVYACEVTHQGL SSPVTKSFNRGEC |
| 14 | F12.3 | CL | RC51 | GTVAAPSVFIFPPKDERLKSGTAS VVCLLNNFYPREAKVQWKVDNA LQSGNSQESVTEQDSKDSTYSLSS RLTLSKADYEKHKVYACEVTHQG LSSPVTKSFNRGEC |
| 15 | F12.3 | VH | RC52, | EVQLVESGGGLVKPGGSLELSCA ASGFTFSSYWMSWVRQAPEKCLE WVAAISPSGGSTYYADSVKGRFTI SRDNAKNTLFLQMTSLRSEDTAM YYCAKESWGAYYDLWGQGTTVT VSS |
| 16 | F12.3 | VH | RC50, RC53, | EVQLVESGGGLVKPGGSLELSCA ASGFTFSSYWMSWVRQAPEKGLE WVAAISPSGGSTYYADSVKGRFTI SRDNAKNTLFLQMTSLRSEDTAM YYCAKESWGAYYDLWGQGTTVT VSS |
| 17 | DISCO280 | VH | RC1, RC3, RC4, RC27, RC28, RC30, RC31, RC32, RC33, RC36, RC37, RC38, RC39, RC40, RC44, RC46, RC48, RC49, RC52, RC53, RC55, RC57, | QVQLVQSGAEVKKPGASVKVSCK ASGYSFSSFGISWVRQAPGQGLEW LGWISAFNGYTKYAQKFQDRVTM TTDTSTSTAYMELRSLRSDDTAVY YCARDPAAWPLQQSLAWFDPWG QGTMVTVSS |
| 18 | DISCO280 | VH | RC34, RC35, | QVQLVQSGAEVKKPGASVKVSCK ASGYSFSSFGISWVRQAPGQCLE WLGWISAFNGYTKYAQKFQDRV TMTTDTSTSTAYMELRSLRSDDT AVYYCARDPAAWPLQQSLAWFD PWGQGTMVTVSS |
| 19 | Pembrolizumab | VH | RC15, RC17, RC25, RC30, RC31, RC34, RC35, RC36, RC38, RC44, RC46, RC48, RC49, RC55, RC57, | QVQLVQSGVEVKKPGASVKV SCKASGYTFTNYYMYWVRQ APGQGLEWMGGINPSNGGTN FNEKFKNRVTLTTDSSTTTAY MELKSLQFDDTAVYYCARRD YRFDMGFDYWGQGTTVTVSS |
| 20 | Pembrolizumab | VH | RC32, RC33, RC39, RC40, | QVQLVQSGVEVKKPGASVKV SCKASGYTFTNYYMYWVRQ APGQCLEWMGGINPSNGGTN FNEKFKNRVTLTTDSSTTTAY MELKSLQFDDTAVYYCARRD YRFDMGFDYWGQGTTVTVSS |
| 21 | DISCO280 | CH1 | RC27, RC28, RC48, RC49 | ASTKGPSVFPLRPSSKSTSGGTAAL GCLVKDYFPEPVTVSWNSGALTS GVHTFPAVLQSSGLYSLKSVVTVP SSSLGTQTYICNVNHKPSNTKVDK KV |
| 22 | DISCO280/ Pembrolizumab /F12.3 | CH1 | RC1, RC3, RC17, RC30, RC31, RC32, RC33, RC34, RC35, | ASTKGPSVFPLAPSSKSTSGGTAAL GCLVKDYFPEPVTVSWNSGALTS GVHTFPAVLQSSGLYSLSSVVTVP SSSLGTQTYICNVNHKPSNTKVDK KV |

TABLE A1-continued

| SEQ ID NO: | Type | Domain | Clones | Sequence |
|---|---|---|---|---|
| | | | RC36, RC37, RC38, RC39, RC40, RC44, RC46, RC52, RC53, RC55, RC57, | |
| 23 | Pembrolizumab/ F12.3 | CH1 | RC25, RC48, RC49, RC50, | ASTKGPSVFPLAPSSKSTSGGTAAL GCEVTDYFPEPVTVSWNSGALTS GVHTFPAVLESSGLYSLSSVVTVP SSSLGTQTYICNVNHKPSNTKVDK KV |
| 24 | Pembrolizumab | CH1 | R4, RC15 | ASTKGPSVFPLAPCSRSTSESTAAL GCLVKDYFPEPVTVSWNSGALTSG VHTFPAVLQSSGLYSLSSVVTVPSS SLGTKTYTCNVDHKPSNTKVDKR V |
| 25 | DISC0280/ Pembrolizumab/ F12.3 | CH2 | RC3, RC17, RC25, RC27, RC28, RC30, RC31, RC32, RC33, RC34, RC35, RC36, RC37, RC38, RC39, RC40, RC44, RC46, RC48, RC49, RC50, RC52, RC53, RC55, RC57, | APEAAGGPSVFLFPPPKPKDTLMIS RTPEVTCVVVDVSHEDPEVKFN WYVDGVEVHNAKTKPREEQYNS TYRVVSVLTVLHQDWLNGKEYK CKVSNKALGAPIEKTISKAK |
| 26 | DISC0280 | CH2 | RC1, | APELLGGPSVFLFPPPKPKDTLMIS RTPEVTCVVVDVSHEDPEVKFNW YVDGVEVHNAKTKPREEQYNST YRVVSVLTVLHQDWLNGKEYKC KVSNKALPAPIEKTISKAK |
| 27 | Pembrolizumab | CH2 | RC4, RC15 | APEFLGGPSVFLFPPPKPKDTLMISR TPEVTCVVVDVSQEDPEVQFNWY VDGVEVHNAKTKPREEQFNSTYR VVSVLTVLHQDWLNGKEYKCKV SNKGLPSSIEKTISKAK |
| 28 | Pembrolizumab/ F12.3 | Hinge | RC25, RC48, RC50, | EPDSCDKTHTCPPCP |
| 29 | Pembro/ DISC0280/ F12.3 | Hinge | RC1, RC3, RC17, RC27, RC28, RC30, RC31, RC32, RC33, RC34, RC35, RC36, RC37, RC38, RC39, RC40, RC44, RC46, RC49, RC52, RC53, RC55, RC57, | EPKSCDKTHTCPPCP |
| 30 | Pembrolizumab | Hinge | RC4, RC15 | ESKYGPPCPPCP |
| 31 | Pembrolizumab/ DISC0280 | CH3 | RC30, RC31, RC32, RC33, RC34, RC35, RC52 | GQPREPQVYTLPPSRDELTKNQV SLTCLVKGFYPSDIAVEWESNGQ PENNYKTTPPVLDSDGSFFLYSKL TVDKSRWQQGNVFSCSVMHEAL HNHYTQKSLSLSPGK |
| 32 | Pembrolizumab/ DISC0280/ F12.3 | CH3 | RC1, RC3, RC17, RC44, RC46, RC48, RC49, RC53, RC55, RC57, | GQPREPQVYTLPPSRDELTKNQV SLTCLVKGFYPSDIAVEWESNGQ PENNYKTTPPVLDSDGSFFLYSKL TVDKSRWQQGNVFSCSVMHEAL HNHYTQKSLSLSPG |

TABLE A1-continued

| | | Domain Definitions | | |
|---|---|---|---|---|
| SEQ ID NO: | Type | Domain | Clones | Sequence |
| 33 | Pembrolizumab/ DISC0280 | CH3 | RC25, RC28 | GQPREPQVYVYPPSRDELTKNQV SLTCLVKGFYPSDIAVEWESNGQ PENNYKTTPPVLDSDGSFALVSK LTVDKSRWQQGNVFSCSVMHEA LHNHYTQKSLSLSPG |
| 34 | DISC0280 | CH3 | RC36, RC38, RC39, RC40, | GQPREPQVYVYPPSRDELTKNQV SLTCLVKGFYPSDIAVEWESNGQ PENNYKTTPPVLDSDGSFALVSK LTVDKSRWQQGNVFSCSVMHEA LHNHYTQKSLSLSPGK |
| 35 | DISC0280/ F12.3 | CH3 | RC27, RC37, RC50, | GQPREPQVYVLPPSRDELTKNQV SLLCLVKGFYPSDIAVEWESNGQ PENNYLTWPPVLDSDGSFFLYSK LTVDKSRWQQGNVFSCSVMHEA LHNHYTQKSLSLSPG |
| 36 | Pembrolizumab | CH3 | RC4, RC15 | GQPREPQVYTLPPSQEEMTKNQV SLTCLVKGFYPSDIAVEWESNGQ PENNYKTTPPVLDSDGSFFLYSRL TVDKSRWQEGNVFSCSVMHEAL HNHYTQKSLSLSLG |
| 37 | | Linker | RC30, RC31, RC32, RC33, RC34, RC35, RC36, RC38, RC39, RC40, RC52, RC55, RC56, RC57, RC58 | GGGGSGGGGSGGGGSGGGGS |
| 38 | | Linker | RC30, RC31, RC32, RC33, RC34, RC35, RC36, RC38, RC39, RC40, RC52, | GGSGGGSGGGSGGGSGGGSG |
| 39 | | Linker | RC44, RC45, RC46, RC47, RC53, RC54, | GGGGSGGGGS |
| 40 | | Linker | RC49 | EPDSCDKTHTSPPAPAPELLGGPA APPAPAPAGG |
| 41 | | Linker | RC48 | EPKSCDKTHTSPPAPAPELLGGPA APPAPAPAGG |

TABLE A2

| | | | Sequence Substitutions | |
|---|---|---|---|---|
| Type | Domain | Clones | Sequence Substitutions (Kabat numbering) | Reference |
| Fc Heterodimerization | CH3 | RC25, RC28, RC36, RC38, RC39, RC40, | T371V_L372Y_F436A_Y438V | US20130195849A1 |
| Fc Heterodimerization | CH3 | RC37, RC27, RC50, | T371V_T389L_K420L_T422W | US20130195849A1 |
| Fab preferential pairing | CH1 | RC27, RC28, RC48, RC49 | A125R_S188K | US20190338048A1 |
| Fab preferential pairing | CL (lambda) | RC24 | S122D_K129T_S176E_Y178E | US20190338048A1 |
| Fab preferential pairing | CH1 and hinge | RC25, RC48, RC49, RC50, | L143E_K145T_Q179E_K228D | US20190338048A1 |

TABLE A2-continued

| | | | Sequence Substitutions | |
|---|---|---|---|---|
| Type | Domain | Clones | Sequence Substitutions (Kabat numbering) | Reference |
| Fab preferential pairing | CL (kappa) | RC26, RC51 | S121K_Q124R_T178R | US20190338048A1 |
| Fc silencing mutations | CH2 | RC3, RC17, RC25, RC27, RC28, RC30, RC31, RC32, RC33, RC34, RC35, RC36, RC37, RC38, RC39, RC40, RC44, RC46, RC48, RC49, RC50, RC52, RC53, RC55, RC57, | L247A_L248A_P348G | Schlothauer T, Herter S, Koller C F, Grau-Richards S, Steinhart V, Spick C, Kubbies M, Klein C, Umaña P, Mössner E. Novel human IgG1 and IgG4 Fc-engineered antibodies with completely abolished immune effector functions. Protein Eng Des Sel. 2016 October; 29(10): 457-466. doi: 10.1093/protein/gzw040. Epub 2016 Aug. 29. PMID: 27578889. |
| scFv stabilization | VH | RC32, RC33, RC34, RC35, RC39, RC40, RC52 | G44C | Geddie M L, Kirpotin D B, Kohli N, Kornaga T, Boll B, Razlog M, Drummond D C, Lugovskoy A A. Development of disulfide-stabilized Fabs for targeting of antibody-directed nanotherapeutics. MAbs. 2022 January-December; 14(1): 2083466. doi: 10.1080/19420862.2022.2083466. PMID: 35708974; PMCID: PMC9225506. |
| scFv stabilization | VL | RC32, RC33, RC34, RC35, RC39, RC40, RC52 | G100C | Geddie M L, Kirpotin D B, Kohli N, Kornaga T, Boll B, Razlog M, Drummond D C, Lugovskoy A A. Development of disulfide-stabilized Fabs for targeting of antibody-directed nanotherapeutics. MAbs. 2022 January-December; 14(1): 2083466. doi: 10.1080/19420862.2022.2083466. PMID: 35708974; PMCID: PMC9225506. |
| IgG4 stabilization | Hinge | RC4, RC15 | S241P | Angal S, King D J, Bodmer M W, Turner A, Lawson A D, Roberts G, Pedley B, Adair J R. A single amino acid substitution abolishes the heterogeneity of chimeric mouse/human (IgG4) antibody. Mol Immunol. 1993 January; 30(1): 105-8. doi: 10.1016/0161-5890(93)90432-b. PMID: 8417368. |

TABLE A3

| SEQ ID NO: | Type | Chain | CDR | IMGT* | Kabat** | Chothia |
|---|---|---|---|---|---|---|
| | | | | CDR Definitions | | |
| 52 | DISC0280 | HC | 1 | GYSFSSF | | |
| 53 | DISC0280 | HC | 1 | | SFGIS | |
| 54 | DISC0280 | HC | 1 | | | GYSFSSF |
| 55 | DISC0280 | HC | 2 | ISAFNGYT | | |
| 56 | DISC0280 | HC | 2 | | WISAFNGYTK YAQKFQD | |
| 57 | DISC0280 | HC | 2 | | | SAFNGY |
| 58 | DISC0280 | HC | 3 | ARDPAA WPLQQSL AWFDP | | |
| 59 | DISC0280 | HC | 3 | | DPAAWPLQQS LAWFDP | |
| 60 | DISC0280 | HC | 3 | | | DPAAWPLQQ SLAWFDP |
| 61 | DISC0280 | LC | 1 | TSNLKRN Y | | |
| 62 | DISC0280 | LC | 1 | | SGSTSNLKRN YVY | |
| 63 | DISC0280 | LC | 1 | | | SGSTSNLKR NYVY |
| 64 | DISC0280 | LC | 2 | RDR | | |
| 65 | DISC0280 | LC | 2 | | RDRRRPS | |
| 66 | DISC0280 | LC | 2 | | | RDRRRPS |
| 67 | DISC0280 | LC | 3 | AWYDRE LSEWV | | |
| 68 | DISC0280 | LC | 3 | | AWYDRELSE WV | |
| 69 | DISC0280 | LC | 3 | | | AWYDRELSE WV |
| 70 | Pembrolizumab | HC | 1 | GYTFTN YY | | |
| 71 | Pembrolizumab | HC | 1 | | NYYMY | |
| 72 | Pembrolizumab | HC | 1 | | | GYTFTNY |
| 73 | Pembrolizumab | HC | 2 | INPSNGG T | | |
| 74 | Pembrolizumab | HC | 2 | | GINPSNG GTNFNEK FKN | |
| 75 | Pembrolizumab | HC | 2 | | | NPSNGG |
| 76 | Pembrolizumab | HC | 3 | ARRDYR FDMGFD Y | | |
| 77 | Pembrolizumab | HC | 3 | | RDYRFD MGFDY | |
| 78 | Pembrolizumab | HC | 3 | | | RDYRFDMGF DY |

TABLE A3-continued

| | | | | CDR Definitions | | |
|---|---|---|---|---|---|---|
| SEQ ID NO: | Type | Chain | CDR | IMGT* | Kabat** | Chothia |
| 79 | Pembrolizumab | LC | 1 | KGVSTS GYSY | | |
| 80 | Pembrolizumab | LC | 1 | | RASKGVS TSGYSYL H | |
| 81 | Pembrolizumab | LC | 1 | | | RASKGVSTS GYSYLH |
| 82 | Pembrolizumab | LC | 2 | LAS | | |
| 83 | Pembrolizumab | LC | 2 | | LASYLES | LASYLES |
| 84 | Pembrolizumab | LC | 2 | | | LASYLES |
| 85 | Pembrolizumab | LC | 3 | QHSRDL PLT | | |
| 86 | Pembrolizumab | LC | 3 | | QHSRDLP LT | |
| 87 | Pembrolizumab | LC | 3 | | | QHSRDLPLT |

*IMGT/DomainGapAlign

**For CDRs (Kabat and Chothia), used http://www.abysis.org/abysis/sequence_input/key_annotation/key_annotation.cgi

TABLE A4

| | | FASTA sequences (protein and corresponding DNA) |
|---|---|---|
| SEQ ID NO. | NAME | SEQUENCE |
| 88 | RC1 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCPAP ELLGGPSVFLFPPKPKDTLMISRTPEVTCVVVDVSHEDPE VKFNWYVDGVEVHNAKTKPREEQYNSTYRVVSVLTVLHQD WLNGKEYKCKVSNKALPAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HNHYTQKSLSLSPG |
| 90 | RC2 Protein | QSVLTQPPSASGTPGQRVTISCSGSTSNLKRNYVYWYQQL PGTAPKLLIYRDRRRPSGVPDRFSGSKSGTSASLAISGLR SEDEADYYCAWYDRELSEWVFGGGTKLTVLQPKAAPSVTL FPPSSEELQANKATLVCLISDFYPGAVTVAWKADSSPVKA GVETTTPSKQSNNKYAASSYLSLTPEQWKSHRSYSCQVTH EGSTVEKTVAPTECS |
| 92 | RC3 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCPAP EAAGGPSVFLFPPKPKDTLMISRTPEVTCVVVDVSHEDPE VKFNWYVDGVEVHNAKTKPREEQYNSTYRVVSVLTVLHQD WLNGKEYKCKVSNKALGAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HNHYTQKSLSLSPG |
| 94 | RC4 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSASTKGPSVFPLAPCSRSTSESTAALGCLVKDYFPE PVTVSWNSGALTSGVHTFPAVLQSSGLYSLSSVVTVPSSS LGTKTYTCNVDHKPSNTKVDKRVESKYGPPCPPCPAPEFL |

TABLE A4-continued

| | | FASTA sequences (protein and corresponding DNA) |
|---|---|---|
| SEQ ID NO. | NAME | SEQUENCE |

|  |  | GGPSVFLFPPKPKDTLMISRTPEVTCVVVDVSQEDPEVQF<br>NWYVDGVEVHNAKTKPREEQFNSTYRVVSVLTVLHQDWLN<br>GKEYKCKVSNKGLPSSIEKTISKAKGQPREPQVYTLPPSQ<br>EEMTKNQVSLTCLVKGFYPSDIAVEWESNGQPENNYKTTP<br>PVLDSDGSFFLYSRLTVDKSRWQEGNVFSCSVMHEALHNH<br>YTQKSLSLSLG |
| 96 | RC15 Protein | QVQLVQSGVEVKKPGASVKVSCKASGYTFTNYYMYWVRQA<br>PGQGLEWMGGINPSNGGTNFNEKFKNRVTLTTDSSTTTAY<br>MELKSLQFDDTAVYYCARRDYRFDMGFDYWGQGTTVTVSS<br>ASTKGPSVFPLAPCSRSTSESTAALGCLVKDYFPEPVTVS<br>WNSGALTSGVHTFPAVLQSSGLYSLSSVVTVPSSSLGTKT<br>YTCNVDHKPSNTKVDKRVESKYGPPCPPCPAPEFLGGPSV<br>FLFPPKPKDTLMISRTPEVTCVVVDVSQEDPEVQFNWYVD<br>GVEVHNAKTKPREEQFNSTYRVVSVLTVLHQDWLNGKEYK<br>CKVSNKGLPSSIEKTISKAKGQPREPQVYTLPPSQEEMTK<br>NQVSLTCLVKGFYPSDIAVEWESNGQPENNYKTTPPVLDS<br>DGSFFLYSRLTVDKSRWQEGNVFSCSVMHEALHNHYTQKS<br>LSLSLG |
| 98 | RC16 Protein | EIVLTQSPATLSLSPGERATLSCRASKGVSTSGYSYLHWY<br>QQKPGQAPRLLIYLASYLESGVPARFSGSGSGTDFTLTIS<br>SLEPEDFAVYYCQHSRDLPLTFGGGTKVEIKRTVAAPSVF<br>IFPPSDEQLKSGTASVVCLLNNFYPREAKVQWKVDNALQS<br>GNSQESVTEQDSKDSTYSLSSTLTLSKADYEKHKVYACEV<br>THQGLSSPVTKSFNRGEC |
| 100 | RC17 Protein | QVQLVQSGVEVKKPGASVKVSCKASGYTFTNYYMYWVRQA<br>PGQGLEWMGGINPSNGGTNFNEKFKNRVTLTTDSSTTTAY<br>MELKSLQFDDTAVYYCARRDYRFDMGFDYWGQGTTVTVSS<br>ASTKGPSVFPLAPSSKSTSGGTAALGCLVKDYFPEPV<br>TVSWNSGALTSGVHTFPAVLQSSGLYSLSSVVTVPSSSLG<br>TQTYICNVNHKPSNTKVDKKVEPKSCDKTHTCPPCPAPEA<br>AGGPSVFLFPPKPKDTLMISRTPEVTCVVVDVSHEDPEVK<br>FNWYVDGVEVHNAKTKPREEQYNSTYRVVSVLTVLHQDWL<br>NGKEYKCKVSNKALGAPIEKTISKAKGQPREPQVYTLPPS<br>RDELTKNQVSLTCLVKGFYPSDIAVEWESNGQPENNYKTT<br>PPVLDSDGSFFLYSKLTVDKSRWQQGNVFSCSVMHEALHN<br>HYTQKSLSLSPG |
| 102 | RC24 Protein | QSVLTQPPSASGTPGQRVTISCSGSTSNLKRNYVYWYQQL<br>PGTAPKLLIYRDRRRPSGVPDRFSGSKSGTSASLAISGLR<br>SEDEADYYCAWYDRELSEWVFGGGTKLTVLQPKAAPSVTL<br>FPPSDEELQANTATLVCLISDFYPGAVTVAWKADSSPVKA<br>GVETTTPSKQSNNKYAAESELSLTPEQWKSHRSYSCQVTH<br>EGSTVEKTVAPTECS |
| 104 | RC25 Protein | QVQLVQSGVEVKKPGASVKVSCKASGYTFTNYYMYWVRQA<br>PGQGLEWMGGINPSNGGTNFNEKFKNRVTLTTDSSTTTAY<br>MELKSLQFDDTAVYYCARRDYRFDMGFDYWGQGTTVTVSS<br>ASTKGPSVFPLAPSSKSTSGGTAALGCEVTDYFPEPVTVS<br>WNSGALTSGVHTFPAVLESSGLYSLSSVVTVPSSSLGTQT<br>YICNVNHKPSNTKVDKKVEPDSCDKTHTCPPCPAPEAAGG<br>PSVFLFPPKPKDTLMISRTPEVTCVVVDVSHEDPEVKFNW<br>YVDGVEVHNAKTKPREEQYNSTYRVVSVLTVLHQDWLNGK<br>EYKCKVSNKALGAPIEKTISKAKGQPREPQVYVPPSRDE<br>LTKNQVSLTCLVKGFYPSDIAVEWESNGQPENNYKTTPPV<br>LDSDGSFALVSKLTVDKSRWQQGNVFSCSVMHEALHNHYT<br>QKSLSLSPG |
| 106 | RC26 Protein | EIVLTQSPATLSLSPGERATLSCRASKGVSTSGYSYLHWY<br>QQKPGQAPRLLIYLASYLESGVPARFSGSGSGTDFTLTIS<br>SLEPEDFAVYYCQHSRDLPLTFGGGTKVEIKRTVAAPSVF<br>IFPPKDERLKSGTASVVCLLNNFYPREAKVQWKVDNALQS<br>GNSQESVTEQDSKDSTYSLSSRLTLSKADYEKHKVYACEV<br>THQGLSSPVTKSFNRGEC |
| 108 | RC27 Protein | QVQLVQSGAEVKKPGASVKVSCKASGYSFSSFGISWVRQA<br>PGQGLEWLGWISAFNGYTKYAQKFQDRVTMTTDTSTSTAY<br>MELRSLRSDDTAVYYCARDPAAWPLQQSLAWFDPWGQGTM<br>VTVSSASTKGPSVFPLRPSSKSTSGGTAALGCLVKDYFPE<br>PVTVSWNSGALTSGVHTFPAVLQSSGLYSLKSVVTVPSSS<br>LGTQTYICNVNHKPSNTKVDKKVEPKSCDKTHTCPPCPAP<br>EAAGGPSVFLFPPKPKDTLMISRTPEVTCVVVDVSHEDPE<br>VKFNWYVDGVEVHNAKTKPREEQYNSTYRVVSVLTVLHQD<br>WLNGKEYKCKVSNKALGAPIEKTISKAKGQPREPQVYVLP |

TABLE A4-continued

| | FASTA sequences (protein and corresponding DNA) | |
|---|---|---|
| SEQ ID NO. | NAME | SEQUENCE |

| SEQ ID NO. | NAME | SEQUENCE |
|---|---|---|
| | | PSRDELTKNQVSLLCLVKGFYPSDIAVEWESNGQPENNYL TWPPVLDSDGSFFLYSKLTVDKSRWQQGNVFSCSVMHEAL HNHYTQKSLSLSPG |
| 110 | RC28 Protein | QVQLVQSGAEVKKPGASVKVSCKASGYSFSSFGISWVRQA PGQGLEWLGWISAFNGYTKYAQKFQDRVTMTTDTSTS TAYMELRSLRSDDTAVYYCARDPAAWPLQQSLAWFDPWGQ GTMVTVSSASTKGPSVFPLRPSSKSTSGGTAALGCLVKDY FPEPVTVSWNSGALTSGVHTFPAVLQSSGLYSLKSVVTVP SSSLGTQTYICNVNHKPSNTKVDKKVEPKSCDKTHTCPPC PAPEAAGGPSVFLFPPKPKDTLMISRTPEVTCVVVDVSHE DPEVKFNWYVDGVEVHNAKTKPREEQYNSTYRVVSVLTVL HQDWLNGKEYKCKVSNKALGAPIEKTISKAKGQPREPQVY VYPPSRDELTKNQVSLTCLVKGFYPSDIAVEWESNGQPEN NYKTTPPVLDSDGSFALVSKLTVDKSRWQQGNVFSCSVMH EALHNHYTQKSLSLSPG |
| 112 | RC30 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCPAP EAAGGPSVFLFPPKPKDTLMISRTPEVTCVVVDVSHEDPE VKFNWYVDGVEVHNAKTKPREEQYNSTYRVVSVLTVLHQD WLNGKEYKCKVSNKALGAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HNHYTQKSLSLSPGKGGGGSGGGGSGGGGSGGGGSQVQLV QSGVEVKKPGASVKVSCKASGYTFTNYYMYWVRQAPGQGL EWMGGINPSNGGTNFNEKFKNRVTLTTDSSTTTAYMELKS LQFDDTAVYYCARRDYRFDMGFDYWGQGTTVTVSSGGSGG GSGGGGSGGGGSGGGSGEIVLTQSPATLSLSPGERATLSCRA SKGVSTSGYSYLHWYQQKPGQAPRLLIYLASYLESGVPAR FSGSGSGTDFTLTISSLEPEDFAVYYCQHSRDLPLTFGGG TKVEI |
| 114 | RC31 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCPAP EAAGGPSVFLFPPKPKDTLMISRTPEVTCVVVDVSHEDPE VKFNWYVDGVEVHNAKTKPREEQYNSTYRVVSVLTVLHQD WLNGKEYKCKVSNKALGAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HNHYTQKSLSLSPGKGGGGSGGGGSGGGGSGGGGSEIVLT QSPATLSLSPGERATLSCRASKGVSTSGYSYLHWYQQKPG QAPRLLIYLASYLESGVPARFSGSGSGTDFTLTISSLEPE DFAVYYCQHSRDLPLTFGGGTKVEIKGGSGGGSGGGSGGG SGGGSGQVQLVQSGVEVKKPGASVKVSCKASGYTFTNYYM YWVRQAPGQGLEWMGGINPSNGGTNFNEKFKNRVTLTTDS STTTAYMELKSLQFDDTAVYYCARRDYRFDMGFDYWGQGT TVTVSS |
| 116 | RC32 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCPAP EAAGGPSVFLFPPKPKDTLMISRTPEVTCVVVDVSHEDPE VKFNWYVDGVEVHNAKTKPREEQYNSTYRVVSVLTVLHQD WLNGKEYKCKVSNKALGAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HNHYTQKSLSLSPGKGGGGSGGGGSGGGGSGGGGSQVQLV QSGVEVKKPGASVKVSCKASGYTFTNYYMYWVRQAPGQCL EWMGGINPSNGGTNFNEKFKNRVTLTTDSSTTTAYMELKS LQFDDTAVYYCARRDYRFDMGFDYWGQGTTVTVSSGGSGG GSGGGGSGGGGSGGGSGEIVLTQSPATLSLSPGERATLSCRA SKGVSTSGYSYLHWYQQKPGQAPRLLIYLASYLESGVPAR FSGSGSGTDFTLTISSLEPEDFAVYYCQHSRDLPLTFGCG TKVEI |

TABLE A4-continued

| | | FASTA sequences (protein and corresponding DNA) |
|---|---|---|
| SEQ ID NO. | NAME | SEQUENCE |

| 118 | RC33 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCPAP EAAGGPSVFLFPPKPKDTLMISRTPEVTCVVVDVSHEDPE VKFNWYVDGVEVHNAKTKPREEQYNSTYRVVSVLTVLHQD WLNGKEYKCKVSNKALGAPIEKTISKAKGQPREPQVYTLP PSRDELTKNQVSLTCLVKGFYPSDIAVEWESNGQPENNYK TTPPVLDSDGSFFLYSKLTVDKSRWQQGNVFSCSVMHEAL HNHYTQKSLSLSPGKGGGGSGGGGSGGGGSGGGGSEIVLT QSPATLSLSPGERATLSCRASKGVSTSGYSYLHWYQQKPG QAPRLLIYLASYLESGVPARFSGSGSGTDFTLTISSLEPE DFAVYYCQHSRDLPLTFGCGTKVEIKGGSGGGSGGGSGGG SGGGSGQVQLVQSGVEVKKPGASVKVSCKASGYTFTNYYM YWVRQAPGQCLEWMGGINPSNGGTNFNEKFKNRVTLTTDS STTTAYMELKSLQFDDTAVYYCARRDYRFDMGFDYWGQGT TVTVSS |
| 120 | RC34 Protein | QVQLVQSGVEVKKPGASVKVSCKASGYTFTNYYMYWVRQA PGQGLEWMGGINPSNGGTNFNEKFKNRVTLTTDSSTTTAY MELKSLQFDDTAVYYCARRDYRFDMGFDYWGQGTTVTVSS ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALGAPIEKTISKAKGQPREPQVYTLPPSRDE LTKNQVSLTCLVKGFYPSDIAVEWESNGQPENNYKTT PPVLDSDGSFFLYSKLTVDKSRWQQGNVFSCSVMHEALHN HYTQKSLSLSPGKGGGGSGGGGSGGGGSGGGGSQVQLVQS GAEVKKPGASVKVSCKASGYSFSSFGISWVRQAPGQCLEW LGWISAFNGYTKYAQKFQDRVTMTTDTSTSTAYMELRSLR SDDTAVYYCARDPAAWPLQQSLAWFDPWGQGTMVTVSSGG SGGGSGGGSGGGSGGGSGQSVLTQPPSASGTPGQRVTISC SGSTSNLKRNYVYWYQQLPGTAPKLLIYRDRRRPSGVPDR FSGSKSGTSASLAISGLRSEDEADYYCAWYDRELSEWVFG CGTKLTVL |
| 122 | RC35 Protein | QVQLVQSGVEVKKPGASVKVSCKASGYTFTNYYMYWVRQA PGQGLEWMGGINPSNGGTNFNEKFKNRVTLTTDSSTTTAY MELKSLQFDDTAVYYCARRDYRFDMGFDYWGQGTTVTVSS ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALGAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHYT QKSLSLSPGKGGGGSGGGGSGGGGSGGGGSQSVLTQPPSA SGTPGQRVTISCSGSTSNLKRNYVYWYQQLPGTAPKLLIY RDRRRPSGVPDRFSGSKSGTSASLAISGLRSEDEADYYCA WYDRELSEWVFGCGTKLTVLGGSGGGSGGGSGGGSGGGSG QVQLVQSGAEVKKPGASVKVSCKASGYSFSSFGISWVRQA PGQCLEWLGWISAFNGYTKYAQKFQDRVTMTTDTSTSTAY MELRSLRSDDTAVYYCARDPAAWPLQQSLAWFDPWGQGTM VTVSS |
| 124 | RC36 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKKVEPKSCDKTHTCPPCPAP EAAGGPSVFLFPPKPKDTLMISRTPEVTCVVVDVSHEDPE VKFNWYVDGVEVHNAKTKPREEQYNSTYRVVSVLTVLHQD WLNGKEYKCKVSNKALGAPIEKTISKAKGQPREPQVYVYP PSRDELTKNQVSLTCLVKGFYPSDIAVEWESNGQPENNYK TTPPVLDSDGSFALVSKLTVDKSRWQQGNVFSCSVMHEAL HNHYTQKSLSLSPGKGGGGSGGGGSGGGGSGGGGSQVQLV QSGVEVKKPGASVKVSCKASGYTFTNYYMYWVRQAPGQGL EWMGGINPSNGGTNFNEKFKNRVTLTTDSSTTTAYMELKS LQFDDTAVYYCARRDYRFDMGFDYWGQGTTVTVSSGGSGG |

TABLE A4-continued

| FASTA sequences (protein and corresponding DNA) | | |
|---|---|---|
| SEQ ID NO. | NAME | SEQUENCE |
| | | GSGGGSGGGSGGGSGGGSGEIVLTQSPATLSLSPGERATLSCRA |
| | | SKGVSTSGYSYLHWYQQKPGQAPRLLIYLASYLESGVPAR |
| | | FSGSGSGTDFTLTISSLEPEDFAVYYCQHSRDLPLTFGGG |
| | | TKVEI |
| 126 | RC37 Protein | QVQLVQSGAEVKKPGASVKVSCKASGYSFSSFGISWVRQA |
| | | PGQGLEWLGWISAFNGYTKYAQKFQDRVTMTTDTSTSTAY |
| | | MELRSLRSDDTAVYYCARDPAAWPLQQSLAWFDPWGQGTM |
| | | VTVSSASTKGPSVFPLAPSSKSTSGGTAALGCLVKDYFPE |
| | | PVTVSWNSGALTSGVHTFPAVLQSSGLYSLSSVVTVPSSS |
| | | LGTQTYICNVNHKPSNTKVDKKVEPKSCDKTHTCPPCPAP |
| | | EAAGGPSVFLFPPKPKDTLMISRTPEVTCVVVDVSHEDPE |
| | | VKFNWYVDGVEVHNAKTKPREEQYNSTYRVVSVLTVLHQD |
| | | WLNGKEYKCKVSNKALGAPIEKTISKAKGQPREPQVYVLP |
| | | PSRDELTKNQVSLLCLVKGFYPSDIAVEWESNGQPENNYL |
| | | TWPPVLDSDGSFFLYSKLTVDKSRWQQGNVFSCSVMHEAL |
| | | HNHYTQKSLSLSPG |
| 128 | RC38 Protein | QVQLVQSGAEVKKPGASVKVSCKASGYSFSSFGISWVRQA |
| | | PGQGLEWLGWISAFNGYTKYAQKFQDRVTMTTDTSTSTAY |
| | | MELRSLRSDDTAVYYCARDPAAWPLQQSLAWFDPWGQGTM |
| | | VTVSSASTKGPSVFPLAPSSKSTSGGTAALGCLVKDYFPE |
| | | PVTVSWNSGALTSGVHTFPAVLQSSGLYSLSSVVTVPSSS |
| | | LGTQTYICNVNHKPSNTKVDKKVEPKSCDKTHTCPPCPAP |
| | | EAAGGPSVFLFPPKPKDTLMISRTPEVTCVVVDVSHEDPE |
| | | VKFNWYVDGVEVHNAKTKPREEQYNSTYRVVSVLTVLHQD |
| | | WLNGKEYKCKVSNKALGAPIEKTISKAKGQPREPQVYVYP |
| | | PSRDELTKNQVSLTCLVKGFYPSDIAVEWESNGQPENNYK |
| | | TTPPVLDSDGSFALVSKLTVDKSRWQQGNVFSCSVMHEAL |
| | | HNHYTQKSLSLSPGKGGGGSGGGGSGGGGSGGGGSEIVLT |
| | | QSPATLSLSPGERATLSCRASKGVSTSGYSYLHWYQQKPG |
| | | QAPRLLIYLASYLESGVPARFSGSGSGTDFTLTISSLEPE |
| | | DFAVYYCQHSRDLPLTFGGGTKVEIKGGSGGGSGGGSGGG |
| | | SGGGGSGQVQLVQSGVEVKKPGASVKVSCKASGYTFTNYYM |
| | | YWVRQAPGQGLEWMGGINPSNGGTNFNEKFKNRVTLTTDS |
| | | STTTAYMELKSLQFDDTAVYYCARRDYRFDMGFDYWGQGT |
| | | TVTVSS |
| 130 | RC39 Protein | QVQLVQSGAEVKKPGASVKVSCKASGYSFSSFGISWVRQA |
| | | PGQGLEWLGWISAFNGYTKYAQKFQDRVTMTTDTSTSTAY |
| | | MELRSLRSDDTAVYYCARDPAAWPLQQSLAWFDPWGQGTM |
| | | VTVSSASTKGPSVFPLAPSSKSTSGGTAALGCLVKDYFPE |
| | | PVTVSWNSGALTSGVHTFPAVLQSSGLYSLSSVVTVPSSS |
| | | LGTQTYICNVNHKPSNTKVDKKVEPKSCDKTHTCPPCPAP |
| | | EAAGGPSVFLFPPKPKDTLMISRTPEVTCVVVDVSHEDPE |
| | | VKFNWYVDGVEVHNAKTKPREEQYNSTYRVVSVLTVLHQD |
| | | WLNGKEYKCKVSNKALGAPIEKTISKAKGQPREPQVYVYP |
| | | PSRDELTKNQVSLTCLVKGFYPSDIAVEWESNGQPENNYK |
| | | TTPPVLDSDGSFALVSKLTVDKSRWQQGNVFSCSVMHEAL |
| | | HNHYTQKSLSLSPGKGGGGSGGGGSGGGGSGGGGSQVQLV |
| | | QSGVEVKKPGASVKVSCKASGYTFTNYYMYWVRQAPGQCL |
| | | EWMGGINPSNGGTNFNEKFKNRVTLTTDSSTTTAYMELKS |
| | | LQFDDTAVYYCARRDYRFDMGFDYWGQGTTVTVSSGGSGG |
| | | GSGGGSGGGSGGGSGEIVLTQSPATLSLSPGERATLSCRA |
| | | SKGVSTSGYSYLHWYQQKPGQAPRLLIYLASYLESGVPAR |
| | | FSGSGSGTDFTLTISSLEPEDFAVYYCQHSRDLPLTFGCG |
| | | TKVEI |
| 132 | RC40 Protein | QVQLVQSGAEVKKPGASVKVSCKASGYSFSSFGISWVRQA |
| | | PGQGLEWLGWISAFNGYTKYAQKFQDRVTMTTDTSTSTAY |
| | | MELRSLRSDDTAVYYCARDPAAWPLQQSLAWFDPWGQGTM |
| | | VTVSSASTKGPSVFPLAPSSKSTSGGTAALGCLVKDYFPE |
| | | PVTVSWNSGALTSGVHTFPAVLQSSGLYSLSSVVTVPSSS |
| | | LGTQTYICNVNHKPSNTKVDKKVEPKSCDKTHTCPPCPAP |
| | | EAAGGPSVFLFPPKPKDTLMISRTPEVTCVVVDVSHEDPE |
| | | VKFNWYVDGVEVHNAKTKPREEQYNSTYRVVSVLTVLHQD |
| | | WLNGKEYKCKVSNKALGAPIEKTISKAKGQPREPQVYVYP |
| | | PSRDELTKNQVSLTCLVKGFYPSDIAVEWESNGQPENNYK |
| | | TTPPVLDSDGSFALVSKLTVDKSRWQQGNVFSCSVMHEAL |
| | | HNHYTQKSLSLSPGKGGGGSGGGGSGGGGSGGGGSEIVLT |
| | | QSPATLSLSPGERATLSCRASKGVSTSGYSYLHWYQQKPG |
| | | QAPRLLIYLASYLESGVPARFSGSGSGTDFTLTISSLEPE |
| | | DFAVYYCQHSRDLPLTFGCGTKVEIKGGSGGGSGGGSGGG |

TABLE A4-continued

| FASTA sequences (protein and corresponding DNA) | | |
| --- | --- | --- |
| SEQ ID NO. | NAME | SEQUENCE |

| | | SGGGSGQVQLVQSGVEVKKPGASVKVSCKASGYTFTNYYM |
| | | YWVRQAPGQCLEWMGGINPSNGGTNFNEKFKNRVTLTTDS |
| | | STTTAYMELKSLQFDDTAVYYCARRDYRFDMGFDYWGQGT |
| | | TVTVSS |
| 134 | RC44 Protein | QVQLVQSGAEVKKPGASVKVSCKASGYSFSSFGISWVRQA |
| | | PGQGLEWLGWISAFNGYTKYAQKFQDRVTMTTDTSTSTAY |
| | | MELRSLRSDDTAVYYCARDPAAWPLQQSLAWFDPWGQGTM |
| | | VTVSSGGGGSGGGGSQVQLVQSGVEVKKPGASVKVSCKAS |
| | | GYTFTNYYMYWVRQAPGQGLEWMGGINPSNGGTNFNEKFK |
| | | NRVTLTTDSSTTTAYMELKSLQFDDTAVYYCARRDYRFDM |
| | | GFDYWGQGTTVTVSSASTKGPSVFPLAPSSKSTSGGTAAL |
| | | GCLVKDYFPEPVTVSWNSGALTSGVHTFPAVLQSSGLYSL |
| | | SSVVTVPSSSLGTQTYICNVNHKPSNTKVDKKVEPKSCDK |
| | | THTCPPCPAPEAAGGPSVFLFPPKPKDTLMISRTPEVTCV |
| | | VVDVSHEDPEVKFNWYVDGVEVHNAKTKPREEQYNSTYRV |
| | | VSVLTVLHQDWLNGKEYKCKVSNKALGAPIEKTISKAKGQ |
| | | PREPQVYTLPPSRDELTKNQVSLTCLVKGFYPSDIAVEWE |
| | | SNGQPENNYKTTPPVLDSDGSFFLYSKLTVDKSRWQQGNV |
| | | FSCSVMHEALHNHYTQKSLSLSPG |
| 136 | RC45 Protein | QSVLTQPPSASGTPGQRVTISCSGSTSNLKRNYVYWYQQL |
| | | PGTAPKLLIYRDRRPSGVPDRFSGSKSGTSASLAISGLR |
| | | SEDEADYYCAWYDRELSEWVFGGGTKLTVLGGGGSGGGGS |
| | | EIVLTQSPATLSLSPGERATLSCRASKGVSTSGYSYLHWY |
| | | QQKPGQAPRLLIYLASYLESGVPARFSGSGSGTDFTLTIS |
| | | SLEPEDFAVYYCQHSRDLPLTFGGGTKVEIKRTVAAPSVF |
| | | IFPPSDEQLKSGTASVVCLLNNFYPREAKVQWKVDNALQS |
| | | GNSQESVTEQDSKDSTYSLSSTLTLSKADYEKHKVYACEV |
| | | THQGLSSPVTKSFNRGEC |
| 138 | RC46 Protein | QVQLVQSGVEVKKPGASVKVSCKASGYTFTNYYMYWVRQA |
| | | PGQGLEWMGGINPSNGGTNFNEKFKNRVTLTTDSSTT |
| | | TAYMELKSLQFDDTAVYYCARRDYRFDMGFDYWGQGTTVT |
| | | VSSGGGGSGGGGSQVQLVQSGAEVKKPGASVKVSCKASGY |
| | | SFSSFGISWVRQAPGQGLEWLGWISAFNGYTKYAQKFQDR |
| | | VTMTTDTSTSTAYMELRSLRSDDTAVYYCARDPAAWPLQQ |
| | | SLAWFDPWGQGTMVTVSSASTKGPSVFPLAPSSKSTSGGT |
| | | AALGCLVKDYFPEPVTVSWNSGALTSGVHTFPAVLQSSGL |
| | | YSLSSVVTVPSSSLGTQTYICNVNHKPSNTKVDKKVEPKS |
| | | CDKTHTCPPCPAPEAAGGPSVFLFPPKPKDTLMISRTPEV |
| | | TCVVVDVSHEDPEVKFNWYVDGVEVHNAKTKPREEQYNST |
| | | YRVVSVLTVLHQDWLNGKEYKCKVSNKALGAPIEKTISKA |
| | | KGQPREPQVYTLPPSRDELTKNQVSLTCLVKGFYPSDIAV |
| | | EWESNGQPENNYKTTPPVLDSDGSFFLYSKLTVDKSRWQQ |
| | | GNVFSCSVMHEALHNHYTQKSLSLSPG |
| 140 | RC47 Protein | EIVLTQSPATLSLSPGERATLSCRASKGVSTSGYSYLHWY |
| | | QQKPGQAPRLLIYLASYLESGVPARFSGSGSGTDFTLTIS |
| | | SLEPEDFAVYYCQHSRDLPLTFGGGTKVEIKGGGGSGGGG |
| | | SQSVLTQPPSASGTPGQRVTISCSGSTSNLKRNYVYWYQQ |
| | | LPGTAPKLLIYRDRRPSGVPDRFSGSKSGTSASLAISGL |
| | | RSEDEADYYCAWYDRELSEWVFGGGTKLTVLQPKAAPSVT |
| | | LFPPSSEELQANKATLVCLISDFYPGAVTVAWKADSSPVK |
| | | AGVETTTPSKQSNNKYAASSYLSLTPEQWKSHRSYSCQVT |
| | | HEGSTVEKTVAPTECS |
| 142 | RC48 Protein | QVQLVQSGAEVKKPGASVKVSCKASGYSFSSFGISWVRQA |
| | | PGQGLEWLGWISAFNGYTKYAQKFQDRVTMTTDTSTSTAY |
| | | MELRSLRSDDTAVYYCARDPAAWPLQQSLAWFDPWGQGTM |
| | | VTVSSASTKGPSVFPLRPSSKSTSGGTAALGCLVKDYFPE |
| | | PVTVSWNSGALTSGVHTFPAVLQSSGLYSLKSVVTVPSSS |
| | | LGTQTYICNVNHKPSNTKVDKKVEPKSCDKTHTSPPAPAP |
| | | ELLGGPAAPPAPAPAGGQVQLVQSGVEVKKPGASVKVSCK |
| | | ASGYTFTNYYMYWVRQAPGQGLEWMGGINPSNGGTNFNEK |
| | | FKNRVTLTTDSSTTTAYMELKSLQFDDTAVYYCARRDYRF |
| | | DMGFDYWGQGTTVTVSSASTKGPSVFPLAPSSKSTSGGTA |
| | | ALGCEVTDYFPEPVTVSWNSGALTSGVHTFPAVLESSGLY |
| | | SLSSVVTVPSSSLGTQTYICNVNHKPSNTKVDKKVEPDSC |
| | | DKTHTCPPCPAPEAAGGPSVFLFPPKPKDTLMISRTPEVT |
| | | CVVVDVSHEDPEVKFNWYVDGVEVHNAKTKPREEQYNSTY |
| | | RVVSVLTVLHQDWLNGKEYKCKVSNKALGAPIEKTISKAK |
| | | GQPREPQVYTLPPSRDELTKNQVSLTCLVKGFYPSDIAVE |
| | | WESNGQPENNYKTTPPVLDSDGSFFLYSKLTVDKSRWQQG |
| | | NVFSCSVMHEALHNHYTQKSLSLSPG |

TABLE A4-continued

| | | FASTA sequences (protein and corresponding DNA) |
|---|---|---|
| SEQ ID NO. | NAME | SEQUENCE |

| 144 | RC49 Protein | QVQLVQSGVEVKKPGASVKVSCKASGYTFTNYYMYWVRQA |
| | | PGQGLEWMGGINPSNGGTNFNEKFKNRVTLTTDSSTTTAY |
| | | MELKSLQFDDTAVYYCARRDYRFDMGFDYWGQGTTVTVSS |
| | | ASTKGPSVFPLAPSSKSTSGGTAALGCEVTDYFPEPVTVS |
| | | WNSGALTSGVHTFPAVLESSGLYSLSSVVTVPSSSLG |
| | | TQTYICNVNHKPSNTKVDKKVEPDSCDKTHTSPPAPAPEL |
| | | LGGPAAPPAPAPAGGQVQLVQSGAEVKKPGASVKVSCKAS |
| | | GYSFSSFGISWVRQAPGQGLEWLGWISAFNGYTKYAQKFQ |
| | | DRVTMTTDTSTSTAYMELRSLRSDDTAVYYCARDPAAWPL |
| | | QQSLAWFDPWGQGTMVTVSSASTKGPSVFPLRPSSKSTSG |
| | | GTAALGCLVKDYFPEPVTVSWNSGALTSGVHTFPAVLQSS |
| | | GLYSLKSVVTVPSSSLGTQTYICNVNHKPSNTKVDKKVEP |
| | | KSCDKTHTCPPCPAPEAAGGPSVFLFPPKPKDTLMISRTP |
| | | EVTCVVVDVSHEDPEVKFNWYVDGVEVHNAKTKPREEQYN |
| | | STYRVVSVLTVLHQDWLNGKEYKCKVSNKALGAPIEKTIS |
| | | KAKGQPREPQVYTLPPSRDELTKNQVSLTCLVKGFYPSDI |
| | | AVEWESNGQPENNYKTTPPVLDSDGSFFLYSKLTVDKSRW |
| | | QQGNVFSCSVMHEALHNHYTQKSLSLSPG |

| 146 | RC50 Protein | EVQLVESGGGLVKPGGSLELSCAASGFTFSSYWMSWVRQA |
| | | PEKGLEWVAAISPSGGSTYYADSVKGRFTISRDNAKNTLF |
| | | LQMTSLRSEDTAMYYCAKESWGAYYDLWGQGTTVTVSSAS |
| | | TKGPSVFPLAPSSKSTSGGTAALGCEVTDYFPEPVTVSWN |
| | | SGALTSGVHTFPAVLESSGLYSLSSVVTVPSSSLGTQTYI |
| | | CNVNHKPSNTKVDKKVEPDSCDKTHTCPPCPAPEAAGGPS |
| | | VFLFPPKPKDTLMISRTPEVTCVVVDVSHEDPEVKFNWYV |
| | | DGVEVHNAKTKPREEQYNSTYRVVSVLTVLHQDWLNGKEY |
| | | KCKVSNKALGAPIEKTISKAKGQPREPQVYVLPPSRDELT |
| | | KNQVSLLCLVKGFYPSDIAVEWESNGQPENNYLTWPPVLD |
| | | SDGSFFLYSKLTVDKSRWQQGNVFSCSVMHEALHNHYTQK |
| | | SLSLSPG |

| 148 | RC51 Protein | DIVMTQSPSSLSVSAGDKVTMSCRASQGISSWLAWYQQKP |
| | | WQPPKLLIYKASTLESGVPDRFTGSGSGTDFTLTISSVQA |
| | | EDLAVYYCQQSYSTPWTFGGGTKLEIKGTVAAPSVFIFPP |
| | | KDERLKSGTASVVCLLNNFYPREAKVQWKVDNALQSGNSQ |
| | | ESVTEQDSKDSTYSLSSRLTLSKADYEKHKVYACEVTHQG |
| | | LSSPVTKSFNRGEC |

| 150 | RC52 Protein | QVQLVQSGAEVKKPGASVKVSCKASGYSFSSFGISWVRQA |
| | | PGQGLEWLGWISAFNGYTKYAQKFQDRVTMTTDTSTSTAY |
| | | MELRSLRSDDTAVYYCARDPAAWPLQQSLAWFDPWGQGTM |
| | | VTVSSASTKGPSVFPLAPSSKSTSGGTAALGCLVKDYFPE |
| | | PVTVSWNSGALTSGVHTFPAVLQSSGLYSLSSVVTVPSSS |
| | | LGTQTYICNVNHKPSNTKVDKKVEPKSCDKTHTCPPCPAP |
| | | EAAGGPSVFLFPPKPKDTLMISRTPEVTCVVVDVSHEDPE |
| | | VKFNWYVDGVEVHNAKTKPREEQYNSTYRVVSVLTVLHQD |
| | | WLNGKEYKCKVSNKALGAPIEKTISKAKGQPREPQVYTLP |
| | | PSRDELTKNQVSLTCLVKGFYPSDIAVEWESNGQPENNYK |
| | | TTPPVLDSDGSFFLYSKLTVDKSRWQQGNVFSCSVMHEAL |
| | | HNHYTQKSLSLSPGKGGGGSGGGGSGGGGSGGGGSEVQLV |
| | | ESGGGLVKPGGSLELSCAASGFTFSSYWMSWVRQAPEKCL |
| | | EWVAAISPSGGSTYYADSVKGRFTISRDNAKNTLFLQMTS |
| | | LRSEDTAMYYCAKESWGAYYDLWGQGTTVTVSSGGSGGGS |
| | | GGGSGGGSGGGSGDIVMTQSPSSLSVSAGDKVTMSCR |
| | | ASQGISSWLAWYQQKPWQPPKLLIYKASTLESGVPDRFTG |
| | | SGSGTDFTLTISSVQAEDLAVYYCQQSYSTPWTFGCGTKL |
| | | EI |

| 152 | RC53 Protein | QVQLVQSGAEVKKPGASVKVSCKASGYSFSSFGISWVRQA |
| | | PGQGLEWLGWISAFNGYTKYAQKFQDRVTMTTDTSTSTAY |
| | | MELRSLRSDDTAVYYCARDPAAWPLQQSLAWFDPWGQGTM |
| | | VTVSSGGGGSGGGGSEVQLVESGGGLVKPGGSLELSCAAS |
| | | GFTFSSYWMSWVRQAPEKGLEWVAAISPSGGSTYYADSVK |
| | | GRFTISRDNAKNTLFLQMTSLRSEDTAMYYCAKESWGAYY |
| | | DLWGQGTTVTVSSASTKGPSVFPLAPSSKSTSGGTAALGC |
| | | LVKDYFPEPVTVSWNSGALTSGVHTFPAVLQSSGLYSLSS |
| | | VVTVPSSSLGTQTYICNVNHKPSNTKVDKKVEPKSCDKTH |
| | | TCPPCPAPEAAGGPSVFLFPPKPKDTLMISRTPEVTCVVV |
| | | DVSHEDPEVKFNWYVDGVEVHNAKTKPREEQYNSTYRVVS |
| | | VLTVLHQDWLNGKEYKCKVSNKALGAPIEKTISKAKGQPR |
| | | EPQVYTLPPSRDELTKNQVSLTCLVKGFYPSDIAVEWESN |
| | | GQPENNYKTTPPVLDSDGSFFLYSKLTVDKSRWQQGNVFS |
| | | CSVMHEALHNHYTQKSLSLSPG |

TABLE A4-continued

| FASTA sequences (protein and corresponding DNA) | | |
|---|---|---|
| SEQ ID NO. | NAME | SEQUENCE |
| 154 | RC54 Protein | QSVLTQPPSASGTPGQRVTISCSGSTSNLKRNYVYWYQQL PGTAPKLLIYRDRRRPSGVPDRFSGSKSGTSASLAISGLR SEDEADYYCAWYDRELSEWVFGGGTKLTVLGGGGSGGGGS DIVMTQSPSSLSVSAGDKVTMSCRASQGISSWLAWYQQKP WQPPKLLIYKASTLESGVPDRFTGSGSGTDFTLTISSVQA EDLAVYYCQQSYSTPWTFGGGTKLEIKGTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| 156 | RC55 Protein | QVQLVQSGAEVKKPGASVKVSCKASGYSFSSFGISWVRQA PGQGLEWLGWISAFNGYTKYAQKFQDRVTMTTDTSTSTAY MELRSLRSDDTAVYYCARDPAAWPLQQSLAWFDPWGQGTM VTVSSGGGGSGGGGSGGGGSGGGGSQVQLVQSGVEVKKPG ASVKVSCKASGYTFTNYYMYWVRQAPGQGLEWMGGINPSN GGTNFNEKFKNRVTLTTDSSTTTAYMELKSLQFDDTAVYY CARRDYRFDMGFDYWGQGTTVTVSSASTKGPSVFPLAPSS KSTSGGTAALGCLVKDYFPEPVTVSWNSGALTSGVHTFPA VLQSSGLYSLSSVVTVPSSSLGTQTYICNVNHKPSNTKVD KKVEPKSCDKTHTCPPCPAPEAAGGPSVFLFPPKPKDTLM ISRTPEVTCVVVDVSHEDPEVKFNWYVDGVEVHNAKTKPR EEQYNSTYRVVSVLTVLHQDWLNGKEYKCKVSNKALGAPI EKTISKAKGQPREPQVYTLPPSRDELTKNQVSLTCLVKGF YPSDIAVEWESNGQPENNYKTTPPVLDSDGSFFLYSKLTV DKSRWQQGNVFSCSVMHEALHNHYTQKSLSLSPG |
| 158 | RC56 Protein | QSVLTQPPSASGTPGQRVTISCSGSTSNLKRNYVYWYQQL PGTAPKLLIYRDRRRPSGVPDRFSGSKSGTSASLAISGLR SEDEADYYCAWYDRELSEWVFGGGTKLTVLGGGGSGGGGS GGGGSGGGGSEIVLTQSPATLSLSPGERATLSCRASK GVSTSGYSYLHWYQQKPGQAPRLLIYLASYLESGVPARFS GSGSGTDFTLTISSLEPEDFAVYYCQHSRDLPLTFGGGTK VEIKRTVAAPSVFIFPPSDEQLKSGTASVVCLLNNFYPRE AKVQWKVDNALQSGNSQESVTEQDSKDSTYSLSSTLTLSK ADYEKHKVYACEVTHQGLSSPVTKSFNRGEC |
| 160 | RC57 Protein | QVQLVQSGVEVKKPGASVKVSCKASGYTFTNYYMYWVRQA PGQGLEWMGGINPSNGGTNFNEKFKNRVTLTTDSSTTTAY MELKSLQFDDTAVYYCARRDYRFDMGFDYWGQGTTVTVSS GGGGSGGGGSGGGGSGGGGSQVQLVQSGAEVKKPGASVKV SCKASGYSFSSFGISWVRQAPGQGLEWLGWISAFNGYTKY AQKFQDRVTMTTDTSTSTAYMELRSLRSDDTAVYYCARDP AAWPLQQSLAWFDPWGQGTMVTVSSASTKGPSVFPLAPSS KSTSGGTAALGCLVKDYFPEPVTVSWNSGALTSGVHTFPA VLQSSGLYSLSSVVTVPSSSLGTQTYICNVNHKPSNTKVD KKVEPKSCDKTHTCPPCPAPEAAGGPSVFLFPPKPKDTLM ISRTPEVTCVVVDVSHEDPEVKFNWYVDGVEVHNAKTKPR EEQYNSTYRVVSVLTVLHQDWLNGKEYKCKVSNKALGAPI EKTISKAKGQPREPQVYTLPPSRDELTKNQVSLTCLVKGF YPSDIAVEWESNGQPENNYKTTPPVLDSDGSFFLYSKLTV DKSRWQQGNVFSCSVMHEALHNHYTQKSLSLSPG |
| 162 | RC58 Protein | EIVLTQSPATLSLSPGERATLSCRASKGVSTSGYSYLHWY QQKPGQAPRLLIYLASYLESGVPARFSGSGSGTDFTLTIS SLEPEDFAVYYCQHSRDLPLTFGGGTKVEIKGGGGSGGGG SGGGGSGGGGSQSVLTQPPSASGTPGQRVTISCSGSTSNL KRNYVYWYQQLPGTAPKLLIYRDRRRPSGVPDRFSGSKSG TSASLAISGLRSEDEADYYCAWYDRELSEWVFGGGTKLTV LQPKAAPSVTLFPPSSEELQANKATLVCLISDFYPGAVTV AWKADSSPVKAGVETTTPSKQSNNKYAASSYLSLTPEQWK SHRSYSCQVTHEGSTVEKTVAPTECS |

REFERENCES

1. Li & Lim (2020) Science 370, 1034
2. Waldmann et al. (2020)) Front Immunol 11,10.3389/ fimmu.2020.00868
3. Schwartz et al. (2002) Oncology 16, 11
4. Werkmeister et al. (2005) Oncology Reports 13, 449
5. Xu et al. (2021) Cancer Immunology Research 9, 1141
6. Martomo et al. (2021) Molecular Cancer Therapeutics 20, 347
7. Santollani et al. (2023) Immunological Reviews 320, 10
8. Kohler et al., Nature 256:495 (1975)
9. Clackson et al., Nature 352:624-628 (1991)
10. Marks et al., J. Mol. Biol. 222:581-597 (1991)
11. Morrison et al., Proc. Natl. Acad. Sci. USA 81:6851- 6855 (1984)
12. Liljeblad et al, Glyco J 17, 323-329 (2000)
13. Heeley, Endocr Res 28, 217-229 (2002)
14. Banik, Kushnir, Doranz, and Chambers (2023) Mabs 15 (1), 2273018

15. Brinkmann U & Kontermann R E (2017) MAbs 9, 182-212
16. Ridgway J B B, Presta L G, Carter P (1996) Prot Engg Des Sel 9, 617-621
17. von Kreudenstein T S etal (2013) MAbs 5, 646-654
18. E. Creighton, Proteins: Structures and Molecular Properties (W.H. Freeman and Company, 1993)
19. A. L. Lehninger, Biochemistry (Worth Publishers, Inc., current addition)
20. Sambrook, et al, Molecular Cloning: A Laboratory Manual (2nd Edition, 1989)
21. Methods In Enzymology (S. Colowick and N. Kaplan eds., Academic Press, Inc.)

22. Remington's Pharmaceutical Sciences, 18th Edition (Easton, Pennsylvania: Mack Publishing Company, 1990)
23. Carey and Sundberg Advanced Organic Chemistry 3rd Ed. (Plenum Press) Vols A and B (1992)
24. Brinkmann and Kontermann (2017), MABS 9 (2), 182-212
25. Finch et al. (2011) British Journal of Pharmacology 162, 480
26. Sestak et al. (2018) Front Immunol 9, 1603
27. Wei et al. (2022) Journal of Immunotoxicology 19, 109
28. Vicari et al (2017) Mabs 9, 927
29. Grant et al., 2023, Mabs, 15, 2192251

What is claimed is:

1. A method for developing a multi-specific binding molecule that redirects an active form of a cytokine to a target cell or a target tissue of interest, the method comprising:

(a) providing a panel that comprises a plurality of cytokine-binding domains that bind to the cytokine and a plurality of target-binding domains that bind to a target molecule, wherein the target molecule is a marker on the target cell in the target tissue;

(b) screening the panel using an assay that measures the ability of the cytokine, when complexed with at least one cytokine-binding domain, to bind to and/or agonize its cognate receptor compared to the ability of an unbound cytokine to bind to and/or agonize its cognate receptor;

(c) screening the plurality of target-binding domains for binding to the target molecule;

(d) selecting at least one cytokine-binding domain among the panel that does not block or only partially blocks the ability of the cytokine to bind to and/or agonize its cognate receptor;

(e) generating a panel of multi-specific binding molecules, wherein the panel of multispecific binding molecules comprise the at least one cytokine-binding domain selected in (d) and at least one target-binding domain selected in (c); and (f) screening the panel of multi-specific binding molecules in an in vitro cell-based assay that measures the ability of the cytokine to bind to and agonize its cognate receptor in the presence of varying amounts of the multi-specific binding molecules.

2. The method of claim 1, further comprising screening the panel of multi-specific binding molecules in an in vivo assay in a non-human subject that measures the ability of the cytokine to bind to and agonize its cognate receptor when administered to the subject.

3. The method of claim 1, further comprising performing an epitope binning assay in conjunction with the screening of the panel of cytokine-binding domains to identify a region or regions on the cytokine that, when bound to the cytokine-binding domain, retain or partially retain the ability of the cytokine to bind to and agonize its cognate receptor.

4. The method of claim 1, wherein a multi-specific binding molecule of the panel of multi-specific binding molecules comprises:

(a) one cytokine-binding domain and one target-binding domain;

(b) one cytokine-binding domain and two target-binding domains;

(c) two cytokine-binding domains and one target-binding domain; or (d) two identical or non-identical cytokine-binding domains and two identical or non-identical target-binding domains.

5. The method of claim 1, wherein the multi-specific binding molecule comprises a cytokine-binding domain that specifically binds to a human interleukin.

6. The method of claim 5, wherein the human interleukin is human: IL-1, IL-2, IL-4, IL-5, Il-6, IL-8 IL-12, IL-18, or IL-23.

7. The method of claim 1, wherein the multi-specific binding molecule comprises a cytokine-binding domain that specifically binds to IL-15 or to IL-15 complexed with IL-15 receptor alpha.

8. The method of claim 7, wherein the cytokine-binding domain binds to an IL-15 or to IL-15-IL:15 receptor alpha complex with an affinity of less than 100 nM as measured by surface plasmon resonance (SPR).

9. The method of claim 7, wherein the cytokine-binding domain binds to an IL-15 or to IL-15-IL:15 receptor alpha complex with an affinity of less than 0.1 nM as measured by surface plasmon resonance (SPR).

10. The method of claim 1, wherein a multi-specific binding molecule of the panel of multi-specific binding molecules comprises a target-binding domain that specifically binds to a protein expressed in a tumor microenvironment (TME).

11. The method of claim 1, wherein a multi-specific binding molecule of the panel of multi-specific binding molecules comprises a target-binding domain that specifically binds to a tumor-associated antigen (TAA) expressed on the surface of a tumor cell, and wherein the cytokine is redirected to the location of the tumor cell.

12. The method of claim 1, wherein a multi-specific binding molecule of the panel of multi-specific binding molecules comprises a target-binding domain that specifically binds to a receptor on an immune cell.

13. The method of claim 12, wherein the immune cell is a T cell.

14. The method of claim 12, wherein the immune cell is a macrophage.

15. The method of claim 12, wherein the immune cell is an NK-cell.

16. The method of claim 1, wherein a multi-specific binding molecule of the panel of multi-specific binding molecules comprises a cytokine-binding domain and a target-binding domain that bind a cognate cytokine receptor and a target that are on the same cell.

17. The method of claim 1, wherein a multi-specific binding molecule of the panel of multi-specific binding molecules comprises a cytokine-binding domain and a target-binding domain that bind to a cognate cytokine receptor and a target that are on different cells.

18. The method of claim 1, wherein a multi-specific binding molecule of the panel of multi-specific binding molecules comprises a scaffold.

19. The method of claim 18, wherein the scaffold is an albumin-based scaffold, a fibronectin-based scaffold or an immunoglobin-based scaffold.

20. The method of claim 19, wherein the scaffold is an immunoglobulin-based scaffold, and wherein the immunoglobulin-based scaffold is derived from an IgG1, an IgG2, an IgG4, an IgM, or an IgA.

21. The method of claim 19, wherein the scaffold is an albumin-based scaffold or an immunoglobulin-based scaffold, and wherein the albumin-based or the immunoglobulin-based scaffold is capable of binding to a neonatal Fc receptor (FcRn).

22. The method of claim 1, wherein a multi-specific binding molecule of the panel of multi-specific binding molecules is a bi-specific antibody comprising a binding domain that specifically binds to an epitope on the active form of the cytokine and a binding domain that specifically binds to an epitope on a molecule that is not a cytokine receptor on the target cell or tissue.

23. The method of claim 1, wherein the multi-specific binding molecule treats a disease when administered to a subject in need thereof.

* * * * *